(12) United States Patent
Bayever et al.

(10) Patent No.: US 11,369,597 B2
(45) Date of Patent: *Jun. 28, 2022

(54) METHODS FOR TREATING PANCREATIC CANCER USING COMBINATION THERAPIES

(71) Applicant: Ipsen Biopharm Ltd., Wrexham (GB)

(72) Inventors: Eliel Bayever, New York, NY (US); Navreet Dhindsa, Boston, MA (US); Jonathan Basil Fitzgerald, Arlington, MA (US); Peter Laivins, Rowayton, CT (US); Victor Moyo, Ringoes, NJ (US); Clet Niyikiza, Gulph Mills, PA (US); Jaeyeon Kim, Lexington, MA (US)

(73) Assignee: Ipsen Biopharm Ltd.

( * ) Notice: Subject to any disclaimer, the term of this patent is extended or adjusted under 35 U.S.C. 154(b) by 0 days.

This patent is subject to a terminal disclaimer.

(21) Appl. No.: 16/012,372

(22) Filed: Jun. 19, 2018

(65) Prior Publication Data

US 2019/0117644 A1 Apr. 25, 2019

Related U.S. Application Data

(63) Continuation of application No. 15/664,930, filed on Jul. 31, 2017, now abandoned, which is a continuation of application No. 15/241,128, filed on Aug. 19, 2016, now Pat. No. 9,717,724, which is a continuation-in-part of application No. 14/406,776, filed as application No. PCT/US2013/045495 on Jun. 12, 2013, now Pat. No. 9,452,162.

(60) Provisional application No. 61/784,382, filed on Mar. 14, 2013, provisional application No. 61/659,211, filed on Jun. 13, 2012.

(51) Int. Cl.
| | |
|---|---|
| A61K 31/4745 | (2006.01) |
| A61K 9/00 | (2006.01) |
| A61K 9/127 | (2006.01) |
| A61K 31/513 | (2006.01) |
| A61K 31/519 | (2006.01) |
| A61K 47/24 | (2006.01) |
| A61K 47/26 | (2006.01) |
| A61K 47/28 | (2006.01) |

(52) U.S. Cl.
CPC ........ *A61K 31/4745* (2013.01); *A61K 9/0019* (2013.01); *A61K 9/127* (2013.01); *A61K 9/1271* (2013.01); *A61K 31/513* (2013.01); *A61K 31/519* (2013.01); *A61K 47/24* (2013.01); *A61K 47/26* (2013.01); *A61K 47/28* (2013.01)

(58) Field of Classification Search
CPC .............................................. A61K 31/4745
See application file for complete search history.

(56) References Cited

U.S. PATENT DOCUMENTS

| | | |
|---|---|---|
| 4,604,463 A | 8/1986 | Miyasaka et al. |
| 5,013,556 A | 5/1991 | Woodle et al. |
| 5,077,056 A | 12/1991 | Bally et al. |
| 5,192,549 A | 3/1993 | Barenolz et al. |
| 5,316,771 A | 5/1994 | Barenholz et al. |
| 5,538,954 A | 7/1996 | Koch et al. |
| 5,543,152 A | 8/1996 | Webb et al. |
| 5,593,622 A | 1/1997 | Yoshioka et al. |
| 5,676,971 A | 10/1997 | Yoshioka et al. |
| 5,783,568 A | 7/1998 | Schlessinger et al. |
| 5,785,987 A | 7/1998 | Hope et al. |
| 5,846,458 A | 12/1998 | Yoshioka et al. |
| 6,110,491 A | 8/2000 | Kirpotin |
| 6,210,707 B1 | 4/2001 | Papahadjopoulos et al. |
| 6,214,388 B1 | 4/2001 | Benz et al. |
| 6,241,999 B1 | 6/2001 | Ye et al. |
| 6,355,268 B1 | 3/2002 | Slater et al. |
| 6,403,569 B1 | 6/2002 | Achterrath |
| 6,465,008 B1 | 10/2002 | Slater et al. |
| 6,511,676 B1 | 1/2003 | Boulikas |
| 6,545,010 B2 | 4/2003 | Bissery |
| 6,720,001 B2 | 4/2004 | Chen et al. |
| 6,787,132 B1 | 9/2004 | Gabizon et al. |
| 6,794,370 B2 | 9/2004 | Achterrath |
| 7,022,336 B2 | 4/2006 | Papahadjopoulos et al. |
| 7,060,828 B2 | 6/2006 | Madden et al. |
| 7,135,177 B2 | 11/2006 | Benz et al. |
| 7,219,016 B2 | 5/2007 | Rimm et al. |
| 7,244,448 B2 | 7/2007 | Madden et al. |
| 7,244,826 B1 | 7/2007 | Marks et al. |
| 7,507,407 B2 | 3/2009 | Benz et al. |
| 7,829,113 B2 | 11/2010 | Okada et al. |
| 7,842,676 B2 | 11/2010 | Janoff et al. |
| 7,846,440 B2 | 12/2010 | Schoeberl et al. |

(Continued)

FOREIGN PATENT DOCUMENTS

| | | |
|---|---|---|
| CA | 2412790 A1 | 1/2002 |
| CN | 1829741 A | 9/2006 |

(Continued)

OTHER PUBLICATIONS

U.S. Appl. No. 15/363,978: Feb. 7, 2017 Nonfinal Office Action, 16 pages.
U.S. Appl. No. 15/363,978: Aug. 21, 2017 Final Office Action, 19 pages.
U.S. Appl. No. 15/363,978: Dec. 14, 2017 Examiner Interview Summary, 3 pages.
U.S. Appl. No. 15/364,021: Mar. 9, 2017 Nonfinal Office Action, 18 pages.
U.S. Appl. No. 15/364,021: Oct. 4, 2017 Final Office Action, 20 pages.

(Continued)

*Primary Examiner* — Heidi Reese
(74) *Attorney, Agent, or Firm* — McNeill Baur PLLC

(57) ABSTRACT

Provided are methods for treating pancreatic cancer in a patient by administering liposomal irinotecan (MM-398) alone or in combination with additional therapeutic agents. In one embodiment, the liposomal irinotecan (MM-398) is co-administered with 5-fluorouracil and leucovorin.

13 Claims, 34 Drawing Sheets

(56) References Cited

U.S. PATENT DOCUMENTS

| | | |
|---|---|---|
| 7,846,473 B2 | 12/2010 | Yoshino et al. |
| 7,850,990 B2 | 12/2010 | Tardi et al. |
| 7,871,620 B2 | 1/2011 | Benz et al. |
| 7,892,554 B2 | 2/2011 | Marks et al. |
| 8,067,432 B2 | 11/2011 | Anderson et al. |
| 8,147,867 B2 | 4/2012 | Hong et al. |
| 8,329,213 B2 | 12/2012 | Hong et al. |
| 8,496,961 B2 | 7/2013 | Hong et al. |
| 8,658,203 B2 | 2/2014 | Drummond et al. |
| 8,703,181 B2 | 4/2014 | Hong et al. |
| 8,992,970 B2 | 3/2015 | Hong et al. |
| 9,339,497 B2 | 5/2016 | Bayever et al. |
| 9,364,473 B2 | 6/2016 | Bayever et al. |
| 9,452,162 B2 | 9/2016 | Bayever et al. |
| 9,492,442 B2 | 11/2016 | Bayever et al. |
| 9,511,155 B2 | 12/2016 | Drummond et al. |
| 9,616,081 B2 | 4/2017 | Okabe |
| 9,717,723 B2 | 8/2017 | Hong et al. |
| 9,717,724 B2 | 8/2017 | Bayever et al. |
| 9,724,303 B2 | 8/2017 | Hong et al. |
| 9,730,891 B2 | 8/2017 | Hong et al. |
| 9,737,528 B2 | 8/2017 | Drummond et al. |
| 9,782,349 B2 | 10/2017 | Hong et al. |
| 9,895,365 B2 | 2/2018 | Blanchette et al. |
| 10,350,201 B2 | 7/2019 | Hong et al. |
| 10,413,510 B2 | 9/2019 | Hong et al. |
| 10,456,360 B2 | 10/2019 | Drummond et al. |
| 10,478,428 B2 | 11/2019 | Blanchette et al. |
| 10,722,508 B2 | 7/2020 | Hong et al. |
| 10,980,795 B2 | 4/2021 | Bayever et al. |
| 10,993,914 B2 | 5/2021 | Drummond et al. |
| 11,052,079 B2 | 7/2021 | Hong et al. |
| 11,071,726 B2 | 7/2021 | Fitzgerald et al. |
| 2002/0035091 A1 | 3/2002 | Govindarajan et al. |
| 2002/0102298 A1 | 8/2002 | Needham |
| 2002/0146450 A1 | 10/2002 | Slater et al. |
| 2002/0192275 A1 | 12/2002 | Zalipsky et al. |
| 2003/0138481 A1 | 7/2003 | Zadi |
| 2004/0002505 A1 | 1/2004 | Ozawa et al. |
| 2004/0071768 A1 | 4/2004 | Sarris et al. |
| 2007/0110798 A1 | 5/2007 | Drummond et al. |
| 2007/0219268 A1 | 9/2007 | Hausheer |
| 2007/0265324 A1 | 11/2007 | Wernet et al. |
| 2008/0108135 A1 | 5/2008 | Marks et al. |
| 2009/0123419 A1 | 5/2009 | Sherman et al. |
| 2009/0149397 A1 | 6/2009 | Ossovskaya et al. |
| 2010/0056761 A1 | 3/2010 | Schoeberl et al. |
| 2010/0068255 A1 | 3/2010 | Benz et al. |
| 2011/0059076 A1 | 3/2011 | McDonagh et al. |
| 2011/0104256 A1 | 5/2011 | Wang et al. |
| 2011/0123523 A1 | 5/2011 | Schoeberl et al. |
| 2012/0003160 A1 | 1/2012 | Wolf et al. |
| 2012/0034295 A1 | 2/2012 | Spiegel et al. |
| 2012/0045524 A1 | 2/2012 | Wernet et al. |
| 2012/0269812 A1 | 10/2012 | Baum et al. |
| 2012/0282325 A1 | 11/2012 | Tong et al. |
| 2013/0209481 A1 | 8/2013 | Zhou et al. |
| 2013/0236459 A1 | 9/2013 | Baum et al. |
| 2013/0274281 A1 | 10/2013 | Bradley |
| 2014/0065204 A1 | 3/2014 | Hayes et al. |
| 2014/0170075 A1 | 6/2014 | Drummond et al. |
| 2015/0182460 A1 | 7/2015 | Hong et al. |
| 2015/0182521 A1 | 7/2015 | Bayever et al. |
| 2015/0328156 A1 | 11/2015 | Bayever et al. |
| 2015/0374682 A1 | 12/2015 | Bayever et al. |
| 2016/0030341 A1 | 2/2016 | Hong et al. |
| 2016/0030342 A1 | 2/2016 | Hong et al. |
| 2016/0058704 A1 | 3/2016 | Tardi et al. |
| 2016/0074382 A1 | 3/2016 | Bayever et al. |
| 2016/0206615 A1 | 7/2016 | Tangutoori et al. |
| 2016/0303264 A1 | 10/2016 | Hendricks et al. |
| 2016/0346272 A1 | 12/2016 | Bayever et al. |
| 2017/0049767 A1 | 2/2017 | Blanchette et al. |
| 2017/0049775 A1 | 2/2017 | Bayever et al. |
| 2017/0202840 A1 | 7/2017 | Bayever et al. |
| 2017/0333421 A1 | 11/2017 | Adiwijaya et al. |

FOREIGN PATENT DOCUMENTS

| | | |
|---|---|---|
| CN | 101878229 A | 11/2010 |
| CN | 1980637 B | 2/2014 |
| WO | 1997028156 A1 | 8/1997 |
| WO | 2000023052 A1 | 4/2000 |
| WO | 2003013536 A2 | 2/2003 |
| WO | 2003030864 A1 | 4/2003 |
| WO | 2003101474 A1 | 12/2003 |
| WO | 2004017940 A3 | 4/2004 |
| WO | 2004093795 A3 | 11/2004 |
| WO | 2005000900 A1 | 1/2005 |
| WO | 2005107712 A1 | 11/2005 |
| WO | 2006110816 A2 | 10/2006 |
| WO | 2007076117 A2 | 7/2007 |
| WO | 2009040426 A1 | 4/2009 |
| WO | 2009126920 A3 | 3/2010 |
| WO | 2010125462 A2 | 11/2010 |
| WO | 2011066684 A1 | 6/2011 |
| WO | 2011153010 A1 | 12/2011 |
| WO | 2012012454 A1 | 1/2012 |
| WO | 2012031293 A1 | 3/2012 |
| WO | 2012078695 A2 | 6/2012 |
| WO | 2012079582 A1 | 6/2012 |
| WO | 2012146610 A1 | 11/2012 |
| WO | 2013006547 A2 | 1/2013 |
| WO | 2013138371 A1 | 9/2013 |
| WO | 2013158803 A1 | 10/2013 |
| WO | 2013188586 A1 | 12/2013 |
| WO | 2014113167 A1 | 7/2014 |
| WO | 2014157444 A1 | 10/2014 |
| WO | 2016094402 A1 | 6/2016 |
| WO | 2016168451 A1 | 10/2016 |
| WO | 2017031442 A1 | 2/2017 |
| WO | 2017031445 A1 | 2/2017 |
| WO | 2017034957 A1 | 3/2017 |
| WO | 2017066726 A1 | 4/2017 |
| WO | 2017172678 A1 | 10/2017 |
| WO | 2017199093 A1 | 11/2017 |
| WO | 2018083470 A1 | 5/2018 |

OTHER PUBLICATIONS

U.S. Appl. No. 15/375,039: Feb. 16, 2018 Nonfinal Office Action, 11 pages.
U.S. Appl. No. 15/403,441: Dec. 21, 2017 Nonfinal Office Action, 9 pages.
U.S. Appl. No. 15/645,645: Dec. 1, 2017 Nonfinal Office Action, 16 pages.
U.S. Appl. No. 15/652,513: Dec. 20, 2017 Nonfinal Office Action, 13 pages.
U.S. Appl. No. 15/661,868: Dec. 1, 2017 Nonfinal Office Action, 15 pages.
U.S. Appl. No. 15/664,930: Dec. 20, 2017 Nonfinal Office Action, 7 pages.
U.S. Appl. No. 15/664,976: Sep. 11, 2018 Nonfinal Office Action, 23 pages.
U.S. Appl. No. 15/809,815: Mar. 6, 2018 Nonfinal Office Action, 12 pages.
U.S. Appl. No. 15/809,815: Sep. 11, 2018 Final Office Action, 14 pages.
U.S. Appl. No. 15/852,551: Jan. 11, 2019 Nonfinal Office Action, 5 pages.
U.S. Appl. No. 15/967,638: Jan. 14, 2019 Nonfinal Office Action, 14 pages.
American Chemical Society (ACS), http://www.cancer.org/cancer/pancreaticcancer/detailedguide/pancreatic-cancer-what-is-pancreatic-cancer, retrieved Dec. 10, 2017, 7 printed pages.
Chen L, et al., "Effect of Baseline Carbohydrate Antigen 19-9 (CA19-9) Level on Overall Survival (OS) in NAPOLI-1 Trial: a Phase 3 Study of MM-398 (nal-IRI), with or without 5-Fluorouracil and Leucovorin (5-FU/LV), versus 5-FU/LV in Metastatic Pancre-

(56) References Cited

OTHER PUBLICATIONS atic Cancer (mPAC) Previously Treated with Gemcitabine-based Therapy." Poster presented at the Gastrointestinal Cancers Symposium of the ASCO meeting of Jan. 21-23, 2016, San Francisco, California, 16 pages.
Chen L, et al., "Expanded Analyses of NAPOLI-1: Phase 3 Study of MM-398 (nal-IRI), With or Without 5-Fluorouracil and Leucovorin, Versus 5-Fluorouracil and Leucovorin, in Metastatic Pancreatic Cancer (mPAC) Previously Treated with Gemcitabine-Based Therapy." Poster presented at the ASCO meeting of May 29-Jun. 2, 2015, Chicago, Illinois, 7 pages.
Chen L, et al., "Phase I Study of Liposome Encapsulated Irinotecan (PEP02) in Advanced Solid Tumor Patients," Poster presented at the ASCO meeting of May 30-Jun. 3, 2008, Chicago, Illinois, 9 pages.
Conroy T, et al., "FOLFIRINOX versus Gemcitabine for Metastatic Pancreatic Cancer," N Engl J Med. 364(19):1817-25 (2011).
EP2861210: Communication of Notices of Opposition (R. 79(1) EPC), dated Feb. 16, 2018, 1 page.
EP2861210: Notice of Opposition dated Feb. 5, 2018, 6 pages.
EP2861210: Opposition dated Feb. 5, 2018, Annex to Notice of Opposition, Facts and Arguments, 8 pages.
EP2861210: Opposition dated Feb. 5, 2018, D1 (FUSILEV package insert, 2008, 7 pages).
EP2861210: Opposition dated Feb. 5, 2018, D12 (Tsai C, et al., "Nanovector-Based Therapies in Advanced Pancreatic Cancer," J Gastroint Oncol 2(3):185-94 (2011)).
EP2861210: Opposition dated Feb. 5, 2018, D13 (Ko A, et al., "A Multinational Phase II Study of Liposome Irinotecan (PEP02) for Patients with Gemcitabine-Refractory Metastatic Pancreatic Cancer," J Clin Oncol. 29:2011 (Suppl; Abstract 237). 2011 ASCO Annual Meeting (2011), 2 printed pages).
EP2861210: Opposition dated Feb. 5, 2018, D15 (Clinical Trials Identifier NCT01494506: Jan. 25, 2013 version, "A Randomized, Open Label Phase 3 Study of MM-398, With or Without 5-Fluorouracil and Leucovorin, Versus 5 Fluorouracil and Leucovorin in Patients With Metastatic Pancreatic Cancer Who Have Failed Prior Gemcitabine-based Therapy," Retrieved from ClinicalTrials.gov archive, 1 printed page).
EP2861210: Opposition dated Feb. 5, 2018, D2 (Gebbia V, et al., "Irinotecan Plus Bolus/Infusional 5-Fluorouracil and Leucovorin in Patients With Pretreated Advanced Pancreatic Carcinoma: A Multicenter Experience of the Gruppo Oncologico Italia Meridionale," Am J Clin Oncol. 33(5):461-64 (2010)).
EP2861210: Opposition dated Feb. 5, 2018, D3 (Zaniboni A, et al., "FOLFIRI as Second-Line Chemotherapy for Advanced Pancreatic Cancer: A GISCAD Multicenter Phase II Study," Cancer Chemother Pharmacol 69(6):1641-5 (2012)).
EP2861210: Opposition dated Feb. 5, 2018, D4 (Neuzillet C, et al., "FOLFIRI Regimen in Metastatic Pancreatic Adenocarcinoma Resistant to Gemcitabine and Platinum-Salts," World J Gastroenterol. 18(33):4533-41 (2012)).
EP2861210: Opposition dated Feb. 5, 2018, D5 (Yoo C, et al., "A Randomised Phase II Study of Modified FOLFIRI.3 vs Modified FOLFOX as Second-Line Therapy in Patients with Gemcitabine-Refractory Advanced Pancreatic Cancer," Br J Cancer. 101(10):1658-63 (2009)).
EP2861210: Opposition dated Feb. 5, 2018, D6 (Taïeb J., "FOLFIRI. 3, A New Regimen Combining 5-Fluorouracil, Folinic Acid and Irinotecan, for Advanced Pancreatic Cancer: Results of an Association des Gastro-Enterologues Oncologues (Gastroenterologist Oncologist Association) Multicenter Phase II Study," Ann Oncol. 18(3)498-503 (2007), epub Dec. 8, 2006).
EP2861210: Opposition dated Feb. 5, 2018, D7 (Chen L, et al., "Phase I Study of Liposome Encapsulated Irinotecan (PEP02) in Advanced Solid Tumor Patients," J Clin Oncol., 2008 ASCO Annual Meeting Proceedings (Post-Meeting Edition), 26(15S) (May 20 Suppl):2565 (2008), 2 pages).
EP2861210: Opposition dated Feb. 5, 2018, D8 (Infante J, et al., "Phase I and Pharmacokinetic Study of IHL-305 (PEGylated Liposomal Irinotecan) in Patients With Advanced Solid Tumors," Cancer Chemother Pharmacol. 70(5):699-705 (2012)).
EP2861210: Opposition dated Feb. 5, 2018, D9 (Waterhouse D, et al., "Lipid-Based Nanoformulation of Irinotecan: Dual Mechanism of Action Allows for Combination Chemo/Angiogenic Therapy," Nanomedicine 6(9):1645-54 (2011)).
EP2861210: Opposition filed Feb. 5, 2018, D10 (CAMPTOSAR package insert, 2012, 39 pages).
EP2861210: Opposition filed Feb. 5, 2018, D11 (Hoskins J, et al., "UGT1A1*28 Genotype and Irinotecan-Induced Neutropenia: Dose Matters," J Natl Cancer Inst. 99(17):1290-95 (2007)).
EP2861210: Response to EP Opposition Proceedings filed Aug. 24, 2018, 22 pages.
EP2861210: Response to EP Opposition Proceedings filed Aug. 24, 2018, D15a (Clinical Trials Identifier NCT01494506: Dec. 16, 2011 version, "A Randomized, Open Label Phase 3 Study of MM-398 Versus 5-Fluorouracil and Leucovorin in Patients With Metastatic Pancreatic Cancer." Retrieved from ClinicalTrials.gov archive, 3 printed pages).
EP2861210: Response to EP Opposition Proceedings filed Aug. 24, 2018, D17 (European Commission Implementing Decision granting marketing authorisation for Onivyde, Oct. 14, 2016), 39 pages.
EP2861210: Response to EP Opposition Proceedings filed Aug. 24, 2018, D18 (FDA News Release, "FDA Approves New Treatment for Advanced Pancreatic Cancer." Retrieved from http://ww.fda. gov/NewsEvents/Newsroom/PressAnnouncements/ucm468654. htm, Oct. 22, 2015, 3 printed pages).
EP2861210: Response to EP Opposition Proceedings filed Aug. 24, 2018, D19 (Wang-Gillam A, et al., "Nanoliposomal Irinotecan with Flourouracil and Folinic Acid in Metastatic Pancreatic Cancer After Previous Gemcitabine-Based Therapy (NAPOLI-1): A Global, Randomised, Open-Label, Phase 3 Trial," Lancet, 387(10018):545-57 (2016). Epub doi: 10.1016/S0140-6736(15)00986-1, pp. 1-13 (2015)).
EP2861210: Response to EP Opposition Proceedings filed Aug. 24, 2018, D20 (MHRA Public Assessment Report for 5-Fluorouracil, 2006, 60 pages).
FDA News Release, "FDA Approves New Treatment for Advanced Pancreatic Cancer." Retrieved from http://ww.fda.gov/NewsEvents/ Newsroom/PressAnnouncements/ucm468654.htm, Oct. 22, 2015, 3 printed pages.
Ko A, et al., "A Multinational Phase II Study of PEP02 (MM-398), Liposome Irinotecan, for Patients with Gemcitabine-refractory Metastatic Pancreatic Cancer." Poster presented at the American Society of Clinical Oncology meeting, Jun. 3-Jun. 7, 2011, Chicago, Illinois, 9 pages.
Merrimack, "Merrimack Announces Inclusion of ONIVYDE (irinotecan liposome injection) as a Category 1 Treatment Option in the 2016 NCCN Guidelines for Pancreatic Adenocarcinoma," Mar. 24, 2016. Retrieved from http://investors.merrimack.com/news-releases/news-release-details/merrimack-announces-inclusion-onivyder-irinotecan-liposome, 2 printed pages.
Morgan R, et al., "Human Cell Line (COLO 357) of Metastatic Pancreatic Adenocarcinoma," Int J Cancer 25(5):591-8 (1980).
National Comprehensive Cancer Network Clinical Practice Guidelines in Oncology (NCCN Guidelines). "Pancreatic Adenocarcinoma." Version I.2016. Mar. 22, 2016 (PANC-9), 133 pages.
NIH National Cancer Institute, "FDA Approves Irinotecan Liposome to Treat Pancreatic Cancer," Nov. 24, 2015 by NCI Staff, 2 printed pages.
O'Dwyer P, et al., "Uridine Diphosphate Glucuronosyltransferase (UGT) 1A1 and Irinotecan: Practical Pharmacogenomics Arrives in Cancer Therapy," J Clin Oncol. 24(28):4534-8 (2006).
Pliarchopoulou K, et al., "Pancreatic Cancer: Current and Future Treatment Strategies," Cancer Treat Rev. 35(5):431-6 (2009).
U.S. Appl. No. 11/121,294: Aug. 17, 2009 Nonfinal Office Action, 33 pages.
U.S. Appl. No. 11/121,294: Mar. 12, 2010 Final Office Action, 15 pages.
U.S. Appl. No. 11/121,294: May 19, 2010 Advisory Action, 3 pages.
U.S. Appl. No. 11/121,294: Aug. 4, 2010 Nonfinal Office Action, 14 pages.

(56) References Cited

OTHER PUBLICATIONS

U.S. Appl. No. 11/121,294: Dec. 6, 2010 Final Office Action, 17 pages.
U.S. Appl. No. 11/121,294: Apr. 13, 2011 Nonfinal Office Action, 10 pages.
U.S. Appl. No. 11/121,294: Jul. 12, 2011 Examiner Interview Summary, 3 pages.
U.S. Appl. No. 11/121,294: Nov. 23, 2011 Final Office Action, 20 pages.
U.S. Appl. No. 11/601,451: Jan. 11, 2010 Nonfinal Office Action, 14 pages.
U.S. Appl. No. 11/601,451: Aug. 27, 2010 Final Office Action, 17 pages.
U.S. Appl. No. 11/601,451: Jul. 12, 2011 Examiner Interview Summary, 4 pages.
U.S. Appl. No. 13/416,204: May 8, 2012 Pre-Interview Communication, 4 pages.
U.S. Appl. No. 13/416,204: Jun. 29, 2012 Interview Summary and First Action Interview Office Action, 6 pages.
U.S. Appl. No. 13/654,373: Aug. 12, 2013 Nonfinal Office Action and Interview Summary, 10 pages.
Grant S, et al., "Dose-Ranging Evaluation of the Substituted Benzamide Dazopride When Used as an Antiemetic in Patients Receiving Anticancer Chemotherapy," Cancer Chemother Pharmacol. 31(6):442-44 (1993).
Hong K, et al., "Anti-HER2 Immunoliposomes for Targeted Drug Delivery," Ann N Y Acad Sci. 886:293-6 (1999).
Hoskins J, et al., "UGT1A1*28 Genotype and Irinotecan-Induced Neutropenia: Dose Matters," J Natl Cancer Inst. 99(17):1290-95 (2007).
Infante J, et al., "Phase I and Pharmacokinetic Study of IHL-305 (PEGylated Liposomal Irinotecan) in Patients with Advanced Solid Tumors," Cancer Chemother Pharmacol. 70(5):699-705 (2012).
Kambe M, et al., "Phase I Study of Irinotecan by 24-h Intravenous Infusion in Combination with 5-Fluorouracil in Metastatic Colorectal Cancer," Int J Clin Oncol. 17(2):150-4 (2012).
Katsu T, et al., "Ion-Selective Electrode for Transmembrane pH Difference Measurements," Anal. Chem. 73(8):1849-54 (2001).
Kim J, et al., "Sustained Intratumoral Activation of MM-398 Results in Superior Activity over Irinotecan Demonstrated by Using a Systems Pharmacology Approach." Poster presented at the AACR Pancreatic Cancer Symposium, Jun. 18-21, 2012, New York, New York, 8 pages.
Ko A, et al., "A Multinational Phase 2 Study of Nanoliposomal Irinotecan Sucrosofate (PEP02, MM-398) for Patients with Gemcitabine-Refractory Metastatic Pancreatic Cancer," Br J Cancer. 109(4):920-5 (2013).
Ko A, et al., "A Multinational Phase II Study of PEPO2 (Liposome Irinotecan) for Patients with Gemcitabine-Refractory Metastatic Pancreatic Cancer," J Clin Oncol. 29:2011 (Suppl; Abstract 4069). 2011 ASCO Annual Meeting (2011), 2 printed pages.
Köhne C, et al., "Randomized Phase III Study of High-Dose Fluorouracil Given as a Weekly 24-Hour Infusion With or Without Leucovorin Versus Bolus Fluorouracil Plus Leucovorin in Advanced Colorectal Cancer: European Organization of Research and Treatment of Cancer Gastrointestinal Group Study 40952," J Clin Oncol. 21(20):3721-8 (2003).
Kozuch P, et al., "Irinotecan Combined with Gemcitabine, 5-Fluorouracil, Leucovorin, and Cisplatin (G-FLIP) is an Effective and Noncrossresistant Treatment for Chemotherapy Refractory Metastatic Pancreatic Cancer," Oncologist. 6(6):488-95 (2001).
Lee C, et al., "Novel Chondroitin Sulfate-binding Cationic Liposomes Loaded with Cisplatin Efficiently Suppress the Local Growth and Liver Metastasis of Tumor Cells in Vivo," Cancer Res. 62(15):4282-8 (2002).
Maddison J, et al., "Sucralfate," In Small Animal Clinical Pharmacology at p. 474, published by W. B. Saunders (2002).

Makrilia N, et al., "Treatment for Refractory Pancreatic Cancer. Highlights from the '2011 ASCO Gastrointestinal cancers Symposium'. San Francisco, CA, USA, Jan. 20-22, 2011," J Pancreas. 12(2):110-3 (2011).
Miles D, et al., "Combination Versus Sequential Single-Agent Therapy in Metastatic Breast Cancer," Oncologist. 7(suppl 6):13-19 (2002).
Minami H, et al., "Irinotecan Pharmacokinetics/Pharmacodynamics and UGT1A Genetic Polymorphisms in Japanese: Roles of UGT1A1*6 and *28," Pharmacogenet Genomics. 17(7):497-504 (2007).
Münstedt K, et al., "Role of Dexamethasone Dosage in Combination with 5-HT3 Antagonists for Prophylaxis of Acute Chemotherapy-Induced Nausea and Vomiting," Br J Cancer. 79(3-4):637-9 (1999).
Nentwich, F., "Doxorubicin Hydrochloride," In Intravenous Therapy: A Comprehensive Application of Intravenous Therapy and Medication Administration at p. 310. Published by Jones & Bartlett Learning, 1990.
Neuzillet C., et al., "FOLFIRI Regimen as Second-/Third-line Chemotherapy in Patients with Advanced Pancreatic Adenocarcinoma Refradory to Gemcitabine and Platinum Salts: A Retrospective Series of 70 Patients." J Clin Oncol. 29: 2011 (Suppl 4; Abstract 272). 2011 Gastrointestinal Cancers Symposium (2011), 2 printed pages.
ONIVYDE [MM-398] package insert, revision Oct. 22, 2015, retrieved from http://www.accessdata.fda.gov/drugsatfda_docs/label/2015/207793lbl.pdf, 18 pages.
Palomaki G, et al., "Can UGT1A1 Genotyping Reduce Morbidity and Mortality in Patients with Metastatic Colorectal Cancer Treated with Irinotecan? An Evidence-Based Review," Genet Med. 11(1):21-34 (2009).
PCT/US2013/045495: International Preliminary Report on Patentability dated Dec. 16, 2014, 8 pages.
PCT/US2013/045495: International Search Report and Written Opinion dated Aug. 22, 2013, 11 pages.
Rahma O, et al., "Second-Line Treatment in Advanced Pancreatic Cancer: A Comprehensive Analysis of Published Clinical Trials," Ann Oncol. 24(8):1972-9 (2013), epub doi:10.1093/annonc/mdt166, May 12, 2013, pp. 1-8.
Rivory L, et al., "Pharmacokinetic Interrelationships of Irinotecan (CPT-11) and Its Three Major Plasma Metabolites in Patients Enrolled in Phase I/II Trials," Clin Cancer Res. 3(8):1261-6 (1997).
Rothenberg M, et al., "Phase I and Pharmacokinetic Trial of Weekly CPT-11," J Clin Oncol. 11(11):2194-204 (1993).
Sadzuka Y, et al. "Effect of Liposomalization on the Antitumor Activity, Side-Effects and Tissue Distribution of CPT-11," Cancer Lett. 127(1-2): 99-106 (1998).
Saltz L, et al., "Irinotecan Plus Fluorouracil and Leucovorin for Metastatic Colorectal Cancer. Irinotecan Study Group," N Engl J Med. 343(13):905-14 (2000).
Shimada S, et al., "Irinotecan Plus Low-Dose Cisplatin for α-Fetoprotein-Producing Gastric Carcinoma with Multiple Liver Metastases: Report of Two Cases," Surg Today. 32(12):1075-80 (2002).
Taïeb J., "FOLFIRI.3, A New Regimen Combining 5-Fluorouracil, Folinic Acid and Irinotecan, for Advanced Pancreatic Cancer: Results of an Association des Gastro-Enterologues Oncologues (Gastroenterologist Oncologist Association) Multicenter Phase II Study," Ann Oncol. 18(3)498-503 (2007), epub Dec. 8, 2006.
Tsai C, et al., "Nanovector-Based Therapies in Advanced Pancreatic Cancer," J Gastroint Oncol 2(3):185-94 (2011).
Verreault M, et al., "Vascular Normalization in Orthotopic Glioblastoma Following Intravenous Treatment with Lipid-Based Nanoparticulate Formulations of Irinotecan (Irinophore C™), Doxorubicin (Caelyx®) or Vincristine," BMC Cancer. 11:124, pp. 1-18 (2011).
Wang-Gillam A, et al., "Nanoliposomal Irinotecan with Flourouracil and Folinic Acid in Metastatic Pancreatic Cancer After Previous Gemcitabine-Based Therapy (NAPOLI-1): A Global, Randomised, Open-Label, Phase 3 Trial," Lancet, 387(10018):545-57 (2016). Epub doi: 10.1016/S0140-6736(15)00986-1, pp. 1-13 (2015).
Waterhouse D, et al., "Lipid-Based Nanoformulation of Irinotecan: Dual Mechanism of Action Allows for Combination Chemo/Angiogenic Therapy," Nanomedicine 6(9):1645-54 (2011).

(56) References Cited

OTHER PUBLICATIONS

Wilson W, et al., "Targeting Hypoxia in Cancer Therapy," Nat Rev Cancer. 11(6):393-410 (2011).
Yeh B, et al., "Structural Basis for Activation of Fibroblast Growth Factor Signaling by Sucrose Octasulfate," Mol Cell Biol. 22(20):7184-92 (2002).
Yi S, et al, "Irinotecan Monotherapy as Second-Line Treatment in Advanced Pancreatic Cancer," Cancer Chemother Pharmacol. 63(6):1141-5 (2009), Epub Oct. 7, 2008.
Yoo C, et al., "A Randomised Phase II Study of Modified FOLFIRI.3 vs Modified FOLFOX as Second-Line Therapy in Patients with Gemcitabine-Refractory Advanced Pancreatic Cancer," Br J Cancer 101(10):1658-63 (2009).
Zaniboni A, et al., "FOLFIRI as Second-Line Chemotherapy for Advanced Pancreatic Cancer: A GISCAD Multicenter Phase II Study," Cancer Chemother Pharmacol 69(6):1641-5 (2012).
ABRAXANE package insert, revision Dec. 23, 2011, retrieved from https://www.accessdata.fda.gov/drugsatfda_docs/label/2011/021660s025s026s029lbl.pdf, 13 pages.
ABRAXANE package insert, revision Jul. 21, 2015, retrieved from https://www.accessdata.fda.gov/drugsatfda_docs/label/2015/021660s041lbl.pdf, 24 pages.
Ahmad I, et al., "Antibody-Targeted Delivery of Doxorubicin Entrapped in Sterically Stabilized Liposomes Can Eradicate Lung Cancer in Mice," Cancer Res. 53(7):1484-8 (1993).
Author Unknown, "From Antinutrient to Phytonutrient: Phytic Acid Gains Respect" HighBeam Research, Environmental Nutrition, Apr. 1, 2004, 2 printed pages. URL: http://www.highbeam.com/doc/1G1-116341390.html/print (accessed Nov. 4, 2011).
Baker J, et al., "Irinophore C, a Novel Nanoformulation of Irinotecan, Alters Tumor Vascular Function and Enhances the Distribution of 5-Fluorouracil and Doxorubicin," Clin Cancer Res. 14(22):7260-71 (2008).
Brixi-Benmansour H, et al., "Phase II Study of First-line FOLFIRI for Progressive Metastatic Well-differentiated Pancreatic Endocrine Carcinoma," Dig Liver Dis. 43(11):912-6 (2011).
CAMPTOSAR package insert, revision Dec. 19, 2014, retrieved from https://www.accessdata.fda.gov/drugsatfda_docs/label/2014/020571s048lbl.pdf, 40 printed pages.
CAMPTOSAR package insert, revision May 14, 2010, retrieved from https://www.accessdata.fda.gov/drugsatfda_docs/label/2010/020571s031s032s033s036s037lbl.pdf, 37 pages.
CAS Registry Record for 23214-92-8 (doxorubicin), entered STN Nov. 16, 1984, 2 pages.
CAS Registry Record for 97682-44-5 (irinotecan), entered STN Aug. 18, 1985, 1 page.
Chen L, et al., "Phase I Study of Liposome Encapsulated Irinotecan (PEP02) in Advanced Solid Tumor Patients," J Clin Oncol., 2008 ASCO Annual Meeting Proceedings (Post-Meeting Edition), 26(15S) (May 20 Suppl):2565 (2008), 1 page.
Chen L, et al., "Phase I Study of Liposome Irinotecan (PEP02) in Combination with Weekly Infusion of 5-FU/LV in Advanced Solid Tumors," J Clin Oncol., 2010 ASCO Annual Meeting Abstracts, 28(15_suppl) (May 20 Suppl):e13024 (2010), 1 page.
Chou T, et al., "Effect of Composition on the Stability of Liposomal Irinotecan Prepared by a pH Gradient Method," J Biosci Bioeng. 95(4):405-8 (2003).
Clinical Trials Identifier NCT00813163: Mar. 1, 2012 version, "A Phase II Study of PEP02 as a Second Line Therapy for Patients With Metastatic Pancreatic Cancer." Retrieved from ClinicalTrials.gov archive, 3 printed pages.
Clinical Trials Identifier NCT00813163: Jan. 12, 2015 version, "A Phase II Study of PEP02 as a Second Line Therapy for Patients with Metastatic Pancreatic Cancer." Retrieved from ClinicalTrials.gov archive, 3 printed pages.
Clinical Trials Identifier NCT00940758: Jul. 16, 2009 version, "Pharrnacokinetic Study of Biweekly PEP02 (Liposome Irinotecan) in Patients With Metastatic Colorectal Cancer Refractory to First-line Oxaliplatin-based Chemotherapy." Retrieved from ClinicalTrials.gov archive, 3 printed pages.

Clinical Trials Identifier NCT00940758: Feb. 3, 2010 version, "Phase I and Pharmacokinetic Study of Biweekly PEP02 (Liposome Irinotecan) in Patients With Metastatic Colorectal Cancer Refractory to First-line Oxaliplatin-based Chemotherapy." Retrieved from ClinicalTrials.gov archive, 3 printed pages.
Clinical Trials Identifier NCT00940758: Mar. 1, 2012 version, "Phase I and Pharmacokinetic Study of Biweekly PEP02 (Liposome Irinotecan) in Patients With Metastatic Colorectal Cancer Refractory to First-line Oxaliplatin-based Chemotherapy." Retrieved from ClinicalTrials.gov archive, 3 printed pages.
Clinical Trials Identifier NCT01359007: May 23, 2011 version, "A Phase II Study Evaluating the Rate of RO Resection (Microscopically Negative Margins) After Induction Therapy With 5-Fluorouracil, Leucovorin, Oxaliplatin, Irinotecan (FOLFIRINOX) in Patients With Borderline Resectable or Locally Advanced Inoperable Pancreatic Cancer." Retrieved from ClinicalTrials.gov archive, 3 printed pages.
Clinical Trials Identifier NCT01359007: May 28, 2015 version, "A Phase II Study Evaluating the Rate of R0 Resection (Microscopically Negative Margins) After Induction Therapy With 5-Fluorouracil, Leucovorin, Oxaliplatln, Irinotecan (FOLFIRINOX) in Patients With Borderline Resectable or Locally Advanced Inoperable Pancreatic Cancer." Retrieved from ClinicalTrials.gov archive, 3 printed pages.
Clinical Trials Identifier NCT01375816: Jun. 16, 2011 version, "A Randomized Phase II Study of PEP02 or Irinotecan in Combination With Leucovorin and 5-Flourouracil in Second Line Therapy of Metastatic Colorectal Cancer" Retrieved from ClinicalTrials.gov archive, 5 printed pages.
Clinical Trials Identifier NCT01446458: Oct. 4, 2011 version, "Phase I Study of Stereotactic Body Radiation Therapy and 5-Fluorouracil, Oxaliplatin and Irinotecan (FOLFIRINOX) in the Neoadjuvant Therapy of Pancreatic Cancer." Retrieved from ClinicalTrials.gov archive, 5 printed pages.
Clinical Trials Identifier NCT01494506: Dec. 16, 2011 version, "A Randomized, Open Label Phase 3 Study of MM-398 Versus 5-Fluorouracil and Leucovorin in Patients With Metastatic Pancreatic Cancer." Retrieved from ClinicalTrials.gov archive, 3 printed pages.
Clinical Trials Identifier NCT01494506: Aug. 9, 2012 version, "A Randomized, Open Label Phase 3 Study of MM-398, With or Without 5-Fluorouracil and Leucovorin, Versus 5-Fluorouracil and Leucovorin in Patients With Metastatic Pancreatic Cancer Who Have Failed Prior Gemcitabine-based Therapy." Retrieved from ClinicalTrials.gov archive, 3 printed pages.
Clinical Trials Identifier NCT01494506: Aug. 1, 2013 version, "A Randomized, Open Label Phase 3 Study of MM-398, With or Without S~Fluorouracil and Leucovorin, Versus 5 Fluoracil and Leucovorin in Patients with Metastatic Pancreatic Cancer Who Have Failed Prior Gemcitabine-based Therapy." Retrieved from ClinicalTrials.gov archive, 3 printed pages.
Clinical Trials Identifier NCT01494506: Jun. 16, 2016 version, "A Randomized, Open Label Phase 3 Study of MM-398, With or Without 5-Fluorouracil and Leucovorin, Versus 5 Fluoracil and Leucovorin in Patients with Metastatic Pancreatic Cancer Who Have Failed Prior Gemcitabine-based Therapy." Retrieved from ClinicalTrials.gov archive, 5 printed pages.
Clinical Trials Identifier NCT01523457: Jan. 31, 2012 version, "Phase II Study of Modified FOLFIRINOX in Advanced Pancreatic Cancer." Retrieved from ClinicalTrials.gov archive, 4 printed pages.
Clinical Trials Identifier NCT01643499: Jul. 17, 2012 version, "A Genotype-guided Dosing Study of mFOLFIRINOX in Previously Untreated Patients with Advanced Gastrointestinal Malignancies." Retrieved from ClinicalTrials.gov archive, 5 printed pages.
Clinical Trials Identifier NCT01688336: Sep. 18, 2012 version, "Phase II Single Arm Clinical Trial of FOLFIRINOX for Unresectable Locally Advanced and Borderline Resectable Pancreatic Cancer." Retrieved from ClinicalTrials.gov archive, 5 printed pages.
Clinical Trials Identifier NCT01771146: Jan. 17, 2013 version, "A Prospective Evaluation of Neoadjuvant FOLFIRINOX Regimen in Patients with Non-metastatic Pancreas Cancer (Baylor University Medical Center and Texas Oncology Experience)." Retrieved from ClinicalTrials.gov archive, 3 printed pages.

(56) References Cited

OTHER PUBLICATIONS

Clinical Trials Identifier NCT01926197: Aug. 19, 2013 version, "A Randomized Phase III Study Evaluating Modified FOLFIRINOX (mFFX) With or Without Stereotactic Body Radiotherapy (SBRT) in the Treatment of Locally Advanced Pancreatic Cancer." Retrieved from ClinicalTrials.gov archive, 3 printed pages.
Clinical Trials Identifier NCT01992705: Nov. 22, 2013 version, "Neoadjuvant FOLFIRINOX and Stereotactic Body Radiotherapy (SBRT) Followed by Definitive Surgery for Patients with Borderline Resectable Pancreatic Adenocarcinoma: A Single-Arm Pilot Study." Retrieved from ClinicalTrials.gov archive, 5 printed pages.
Clinical Trials Identifier NCT02028806: Jan. 6, 2014 version, "Phase II Trial to Investigate the Efficacy and Safety of mFOLFIRINOX in Patients with Metastatic Pancreatic Cancer in China." Retrieved from ClinicalTrials.gov archive, 4 printed pages.
Clinical Trials Identifier NCT02047474: Jan. 27, 2014 version, "Phase II Study of Peri-Operative Modified Folfirinox in Localized Pancreatic Cancer." Retrieved from ClinicalTrials.gov archive, 5 printed pages.
Clinical Trials Identifier NCT02109341: Apr. 8, 2014 version, "Phase I/II Study to Evaluate Nab-paclitaxel in Substitution of CPT11 or Oxaliplatin in FOLFIRINOX Schedule as First Line Treatment on Metastatic Pancreatic Cancer." Retrieved from ClinicalTrials.gov archive, 5 printed pages.
Clinical Trials Identifier NCT02143219: May 20, 2014 version, "Phase-2 Study Evaluating Overall Response Rate (Efficacy) and Autonomy Daily Living Preservation (Tolerance) of 'FOLFIRINOX' Pharmacogenic Dose Adjusted, in Elderly Patients (70 yo. or Older) With a Metastatic Pancreatic Adenocarcinoma." Retrieved from ClinicalTrials.gov archive, 5 printed pages.
Clinical Trials Identifier NCT02148549: May 27, 2014 version, "The Pilot Study of Neoadjuvant Chemotherapy of FIRINOX for Patients With Borderline Resectable Pancreatic Cancer" Retrieved from ClinicalTrials.gov archive, 4 printed pages.
Clinical Trials Identifier NCT02884128: Aug. 25, 2016 version, "A Study of PEP02 in Combination With 5-fluorouracil (5-FU) and Leucovorin (LV) in Advanced Solid Tumors." Retrieved from ClinicalTrials.gov archive, 3 printed pages.
Clinical Trials Identifier NCT02896803: Sep. 11, 2016 version, "A Phase II Trial of Bolus Fluorouracil and Oxaliplatin (mFLOX) as First-line Regimen for Patients With Unresectable or Metastatic Pancreatic Cancer Not Eligible for Infusional Fluorouracil, Irinotecan and Oxaliplatin." Retrieved from ClinicalTrials.gov archive, 4 printed pages.
Clinical Trials Identifier NCT02896907: Sep. 11, 2016 version, "A Pilot Study of Intravenous Ascorbic Acid and Folfirinox in the Treatment of Advanced Pancreatic Cancer." Retrieved from ClinicalTrials.gov archive, 4 printed pages.
Dawidczyk C, et al., "State-of-the-art in Design Rules for Drug Delivery Platforms: Lessons Learned from FDA-Approved Nanomedicines," J Control Release. 187:133-44 (2014).
Douillard J, et al.,"Irinotecan Combined with Fluorouracil Compared with Fluorouracil Alone as First-line Treatment for Metastatic Colorectal Cancer: A Multicentre Randomised Trial," Lancet. 355(9209):1041-7 (2000).
DOXIL package insert, revision Apr. 16, 2015, retrieved from https://www.accessdata.fda.gov/drugsatfda_docs/label/2015/050718s048lbl.pdf, 28 pages.
DOXIL package insert, revision Jun. 10, 2008, retrieved from https://www.accessdata.fda.gov/drugsatfda_docs/label/2008/050718s033lbl.pdf, 34 pages.
Drummond D, et al., "Development of a Highly Active Nanoliposomal Irinotecan Using a Novel Intraliposomal Stabilization Strategy," Cancer Res. 66(6):3271-77 (2006).
Eisenhauer E, et al., "New Response Evaluation Criteria in Solid Tumours: Revised RECIST Guideline (version 1.1)," Eur J Cancer. 45(2):228-47 (2009).
Fuchs C, et al., "Phase III Comparison of Two Irinotecan Dosing Regimens in Second-Line Therapy of Metastatic Colorectal Cancer," J Clin Oncol. 21(5):807-14 (2003).

Gebbia V, et al., "Irinotecan Plus Bolus/Infusional 5-Fluorouracil and Leucovorin in Patients With Pretreated Advanced Pancreatic Carcinoma: A Multicenter Experience of the Gruppo Oncologico Italia Meridionale," Am J Clin Oncol. 33(5):461-64 (2010).
GEMZAR package insert, revision Feb. 4, 2011, retrieved from https://www.accessdata.fda.gov/drugsatfda_docs/label/2011/020509s069lbl.pdf, 21 pages.
GEMZAR package insert, revision May 8, 2014, retrieved from https://www.accessdata.fda.gov/drugsatfda_docs/label/2014/020509s077lbl.pdf, 18 pages.
U.S. Appl. No. 14/151,632: Apr. 18, 2016 Nonfinal Office Action, 9 pages.
U.S. Appl. No. 14/175,365: Jun. 26, 2014 Nonfinal Office Action, 20 pages.
U.S. Appl. No. 14/406,776: Feb. 26, 2016 Nonfinal Office Action, 9 pages.
U.S. Appl. No. 14/632,422: Jan. 10, 2017 Nonfinal Office Action, 18 pages.
U.S. Appl. No. 14/812,950: Oct. 2, 2015 Pre-Interview Communication, 3 pages.
U.S. Appl. No. 14/844,500: Dec. 16, 2015 Nonfinal Office Action, 25 pages.
U.S. Appl. No. 14/851,111: Feb. 25, 2016 Nonfinal Office Action, 13 pages.
U.S. Appl. No. 14/879,302: Aug. 15, 2016 Nonfinal Office Action, 30 pages.
U.S. Appl. No. 14/879,302: Dec. 15, 2016 Nonfinal Office Action, 14 pages.
U.S. Appl. No. 14/879,358: Dec. 28, 2015 Nonfinal Office Action, 20 pages.
U.S. Appl. No. 14/879,358: Jul. 12, 2016 Nonfinal Office Action, 14 pages.
U.S. Appl. No. 14/964,239: Nov. 4, 2016 Nonfinal Office Action, 21 pages.
U.S. Appl. No. 14/964,239: Apr. 26, 2017 Examiner Interview Summary, 2 pages.
U.S. Appl. No. 14/964,239: Jun. 21, 2017 Nonfinal Office Action, 16 pages.
U.S. Appl. No. 14/964,239: Dec. 11, 2017 Nonfinal Office Action, 15 pages.
U.S. Appl. No. 14/964,571: Feb. 13, 2017 Nonfinal Office Action, 8 pages.
U.S. Appl. No. 14/964,571: Nov. 1, 2017 Final Office Action, 14 pages.
U.S. Appl. No. 14/964,571: Sep. 25, 2018 Nonfinal Office Action, 12 pages.
U.S. Appl. No. 14/965,140: Mar. 10, 2016 Nonfinal Office Action, 24 pages.
U.S. Appl. No. 14/965,140: Jul. 13, 2016 Interview Summary and Nonfinal Office Action, 14 pages.
U.S. Appl. No. 14/965,140: Dec. 19, 2016 Nonfinal Office Action, 9 pages.
U.S. Appl. No. 14/966,458: Dec. 6, 2016 Nonfinal Office Action, 34 pages.
U.S. Appl. No. 14/966,458: Apr. 27, 2017 Examiner Interview Summary, 2 pages.
U.S. Appl. No. 14/979,666: Dec. 9, 2016 Nonfinal Office Action, 20 pages.
U.S. Appl. No. 15/059,640: Dec. 2, 2016 Nonfinal Office Action, 9 pages.
U.S. Appl. No. 15/227,561: Jul. 14, 2017 Nonfinal Office Action, 25 pages.
U.S. Appl. No. 15/227,561: Apr. 26, 2018 Nonfinal Office Action, 13 pages.
U.S. Appl. No. 15/227,561: Dec. 10, 2018 Final Office Action, 18 pages.
U.S. Appl. No. 15/227,631: Jul. 17, 2017 Nonfinal Office Action, 24 pages.
U.S. Appl. No. 15/227,631: Apr. 10, 2018 Nonfinal Office Action, 13 pages.
U.S. Appl. No. 15/227,631: Aug. 31, 2018 Nonfinal Office Action, 15 pages.

(56) References Cited

OTHER PUBLICATIONS

U.S. Appl. No. 15/227,631: Dec. 19, 2018 Final Office Action, 15 pages.
U.S. Appl. No. 15/241,106: Oct. 28, 2016 Pre-Interview Communication, 4 pages.
U.S. Appl. No. 15/241,106: Dec. 29, 2016 Nonfinal Office Action, 15 pages.
U.S. Appl. No. 15/241,106: Jul. 10, 2017 Final Office Action, 16 pages.
U.S. Appl. No. 15/241,128: Nov. 25, 2016 Nonfinal Office Action, 6 pages.
U.S. Appl. No. 15/296,536: Mar. 8, 2017 Nonfinal Office Action, 6 pages.
U.S. Appl. No. 15/331,393: Jan. 19, 2017 Pre-Interview Communication, 4 pages.
U.S. Appl. No. 15/331,393: Mar. 20, 2017: Examiner's Interview Summary and First Action Interview Office Action Summary, 5 pages.
U.S. Appl. No. 15/331,648: Jan. 19, 2017 Pre-Interview Communication, 4 pages.
U.S. Appl. No. 15/331,648: Mar. 17, 2017 Examiner's Interview Summary, 3 pages.
U.S. Appl. No. 15/337,274: Mar. 24, 2017 Nonfinal Office Action, 10 pages.
U.S. Appl. No. 15/341,377: Jan. 30, 2017 Nonfinal Office Action, 12 pages.
U.S. Appl. No. 15/341,377: Apr. 18, 2017 Final Office Action, 13 pages.
U.S. Appl. No. 15/341,619: Apr. 3, 2017 Pre-Interview Communication, 3 pages.
U.S. Appl. No. 15/363,761: Jan. 18, 2017 Nonfinal Office Action, 15 pages.
U.S. Appl. No. 15/363,761: Aug. 1, 2017 Final Office Action, 18 pages.
U.S. Appl. No. 15/363,761: Dec. 14, 2017 Examiner Interview Summary, 3 pages.
U.S. Appl. No. 15/363,923: Feb. 1, 2017 Nonfinal Office Action, 24 pages.
U.S. Appl. No. 15/363,923: Sep. 13, 2017 Final Office Action, 29 pages.
Chuang V and M. Suno, "Levoleucovorin as Replacement for Leucovorin in Cancer Treatment," Ann Pharmacother. 46(10):1349-57 (2012).
EP2861210: Summons to attend oral proceedings including preliminary opinion of the Opposition Division dated Jan. 30, 2019, 12 pages.
EP2861210: Opponent submission in opposition proceedings made following summons to attend oral proceedings, dated May 10, 2019, 20 pages.
EP2861210: Opponent submission in opposition proceedings made following summons to attend oral proceedings, dated May 10, 2019, D1b (Leucovorin calcium injection product label, Nov. 2011, 2 pages).
EP2861210: Opponent submission in opposition proceedings made following summons to attend oral proceedings, dated May 10, 2019, D22 (Chen L, et al., "Phase I Study of Liposome Irinotecan (PEP02) in Combination with Weekly Infusion of 5-FU/LV in Advanced Solid Tumors," J Clin Oncol., 2010 ASCO Annual Meeting Abstracts, 28(15_suppl) (May 20 Suppl):e13024 (2010), 1 page).
EP2861210: Proprietor's Auxiliary Requests in Opposition Proceedings filed Jun. 28, 2019, including cover letter and clean and marked-up AR1, AR2, and AR3, 12 pages.
EP2861210: Minutes of the oral proceedings before the Opposition Division, dated Aug. 28, 2019, 9 pages.
EP2861210: Opposition Division's decision to revoke patent, dated Aug. 28, 2019, 27 pages.
Slatter JG, et al., "Pharmacokinetics, Metabolism, and Excretion of Irinotecan (CPT-11) Following I.V. Infusion of [14C] CPT-11 in Cancer Patients," Drug Metab Dispos, 2000, 28(4):423-33.
U.S. Appl. No. 14/964,571: Jun. 12, 2019 Final Office Action, 15 pages.
U.S. Appl. No. 15/664,976: May 21, 2019 Nonfinal Office Action, 11 pages.
U.S. Appl. No. 15/768,352: Feb. 14, 2019 Non-Final Office Action, 15 pages.
U.S. Appl. No. 15/768,352: Jun. 3, 2019 Examiner Interview Summary, 4 pages.
U.S. Appl. No. 15/768,352: Jun. 12, 2019 Notice of Allowance including Examiner's Reasons for Allowance and Examiner Interview Summary, 21 pages.
U.S. Appl. No. 15/768,352: Aug. 28, 2019 Notice of Allowance including Examiner's Reasons for Allowance and Examiner Interview Summary, 16 pages.
U.S. Appl. No. 15/768,352: Jul. 12, 2019 Examiner Interview Summary, 4 pages.
U.S. Appl. No. 15/809,815: Jul. 8, 2019 Non-Final Office Action, 13 pages.
U.S. Appl. No. 15/896,389: Jul. 18, 2019 Nonfinal Office Action, 24 pages.
U.S. Appl. No. 15/896,436: Jul. 5, 2019 Nonfinal Office Action, 18 pages.
U.S. Appl. No. 16/012,351: Mar. 8, 2019 Non-Final Office Action, 13 pages.
U.S. Appl. No. 16/012,372: Mar. 8, 2019 Non-Final Office Action, 8 pages.
U.S. Appl. No. 16/036,885: Sep. 3, 2019 Non-Final Office Action, 15 pages.
Alberts S, et al. "Gemcitabine and Oxaliptatin for Metastatic Pancreatic Adenocarcinoma: A North Central Cancer Treatment Group Phase II Study," Ann Oncol. 14(4):580-5 (2003).
Assaf E, et al., "5-Fluorouracil/Leucovorin Combined with Irinotecan and Oxaliplatin (FOLFIRINOX) as Second-Line Chemotherapy in Patients with Metastatic Pancreatic Adenocarcinoma," Oncology. 80(5-6):301-6 (2011).
Azrak R, et al., "Therapeutic Synergy Between Irinotecan and 5-Fluorouracil against Human Tumor Xenografts," Clin cancer Res. 10(3):1121-9 (2004).
Boeck S, et al., "Capecitabine Plus Oxaliplatin (CapOx) versus Capecitabine Plus Gemcitabine (CapGem) versus Gemcitabine Plus Oxaliplatin (mGemOx): Final Results of a Multicenter Randomized Phase II Trial in Advanced Pancreatic Cancer," Ann Oncol. 19(2):340-7 (2008), Epub Oct. 24, 2007.
Burris H, et al., "Phase II Trial of Oral Rubitecan in Previously Treated Pancreatic Cancer Patients," Oncologist. 10(3):183-90 (2005).
Cantore M, et al., "Combined Irinotecan and Oxaliplatin in Patients with Advanced Pre-Treated Pancreatic Cancer," Oncology 67(2):93-7 (2004).
Cereda S, et al., "XELIRI or FOLFIRI as Salvage Therapy in Advanced Pancreatic Cancer," Anticancer Res. 30(11):4785-90 (2010).
Chang T, et al., "Phase I Study of Nanoliposomal Irinotecan (PEP02) in Advanced Solid Tumor Patients," Cancer Chemother Pharmacol. 75(3):579-86 (2015).
Chibaudel B, et al., "PEPCOL: A Randomized Non-Comparative Phase II Study to Evaluate the Efficacy and Safety of PEP02 (MM-398) or Irinotecan in Combination with Leucovorin and 5-Fluorouracil as Second-Line Treatment for Patients with Unresectable Metastatic Colorectal Cancer. A GERCOR Study." Poster presented at ASCO 2015, 6 pages.
Chiesa M, et al., "A Pilot Phase II Study of Chemotherapy with Oxaliplatin, Folinic Acid, 5-Fluorouracil and Irinotecan in Metastatic Gastric Cancer," Tumori. 93(3):244-7 (2007).
Conroy T, et al., "Irinotecan Plus Oxaliplatin and Leucovorin-Modulated Fluorouracil in Advanced Pancreatic Cancer—A Groupe Tumeurs Digestives of the Fédération Nationale des Centres de Lutte Contre le Cancer Study," J Clin Oncol. 23(6):1228-36 (2005).
Dean A, et al., "A Phase 2, Open-Label Dose-Exploration Study of Liposomal Irinotecan (nal-IRI) Plus 5-Flurouracil/Leucovorin (5-FU/LV) plus Oxaliplatin (OX) in Patients With Previously Untreated Metastatic Pancreatic Cancer." Poster presented at the American Society of Clinical Oncology Annual Conference, Chicago, IL, Jun. 1-5, 2018, 11 pages.

(56) References Cited

OTHER PUBLICATIONS

Dean A, et al., "A Randomized, Open-label, Phase 2 Study of Nanoliposomal Irinotecan (nal-IRI)-containing Regimens versus nab-Paclitaxel Plus Gemcitabine in Patients with Previously Untreated, Metastatic Pancreatic Adenocarcinoma (mPAC)." Poster presented at the Gastrointestinal Cancers Symposium ASCO 2016, 11 pages.
Dean A, et al., "A Randomized, Open-label, Phase 2 Study of Nanoliposomal Irinotecan (nal-IRI)-containing Regimens versus nab-Paclitaxel Plus Gemcitabine in Patients with Previously Untreated, Metastatic Pancreatic Adenocarcinoma (mPAC)." Poster handout at the Gastrointestinal Cancers Symposium ASCO 2016, 2 pages.
Delord J, et al., "Population Pharmacokinetics of Oxaliplatin," Cancer Chemother Pharmacol. 51(2):127-31 (2003), Epub Dec. 4, 2002.
Ducreux M, et al., "Randomized Phase II Study Evaluating Oxaliplatin Alone, Oxaliplatin Combined with Infusional 5-FU, and Infusional 5-FU Alone in Advanced Pancreatic Carcinoma Patients," Ann Oncol. 15(3): 467-73 (2004).
ELOXATIN package insert, revision Dec. 28, 2011, retrieved from https://www.accessdata.fda.gov/drugsatfda_docs/label/2011/021492s012lbl.pdf, 51 pages.
Extra J, et al., "Phase I Study of Oxaliplatin in Patients with Advanced Cancer," Cancer Chemother Pharmacol. 25(4):299-303 (1990).
Fischel J, et al., "Ternary Combination of Irinotecan, Fluorouracil-Folinic Acid and Oxaliplatin: Results on Human Colon Cancer Cell Lines," Br J Cancer. 84(4):579-85 (2001).
Gaddy D, "Preclinical Anti-tumor Activity of Nanoliposomal Irinotecan (Nal-IRI, MM-398) + 5-FU + Oxaliplatin in Pancreatic Cancer." Abstract presented at AACR 2016, 1 page.
Gaddy D, et al., "Preclinical Anti-tumor Activity of Nanoliposomal Irinotecan (nal-IRI, MM-398) + 5-FU + Oxaliplatin in Pancreatic Cancer." Poster presented at AACR 2016, 5 pages.
GLOBOCAN Cancer Facts Sheets: All Cancers 2012. Available from: http://globocan/arc.fr/old/FactSheets/cancers/all-new.asp, accessed on Oct. 3, 2016, 9 printed pages.
Goldstein D, et al., "nab-Paclitaxel Plus Gemcitabine for Metastatic Pancreatic Cancer: Long-Term Survival From a Phase III Trial," J Natl Cancer Inst. 107(2): dju413, pp. 1-10 (2015).
Guichard S, et al., "Combination of Oxaliplatin and Irinotecan on Human Colon Cancer Cell Lines: Activity In Vitro and In Vivo," Anticancer Drugs. 12(9):741-51 (2001).
Hosein P, et al., "A Retrospective Study of Neoadjuvant FOLFIRINOX in Unresectable or Borderline-Resectable Locally Advanced Adenocarcinoma," BMC Cancer. 12:199, pp. 1-7 (2012).
Jacobs A, et al., "A Randomized Phase III Study of Rubitecan (ORA) vs. Best Choice (BC) in 409 Patients with Refractory Pancreatic Cancer Report from a North-American Multi-Center Study," J Clin Oncol., 2004 ASCO Annual Meeting Proceedings 22(14S):4013 (2004).
Kalra A, et al., "Preclinical Activity of Nanoliposomal Irinotecan Is Governed by Tumor Deposition and Intratumor Pro-Drug Conversion," Cancer Res. Author Manuscript Published OnlineFirst Oct. 1, 2014, 31 pages.
Kalra A, et al., "Preclinical Activity of Nanoliposomal Irinolecan Is Governed by Tumor Deposition and Intratumor Prodrug Conversion," Cancer Res. 74(23):7003-13 (2014), published OnlineFirst, OF1-OF11, Oct. 1, 2014, 12 pages.
Kalra A, et al., "Preclinical Activity of Nanoliposomal Irinotecan Is Governed by Tumor Deposition and Intratumor Prodrug Conversion," Cancer Res. Author queries on manuscript, pp. 1-11 (2014), 13 total pages.
Klinz S, et al., "Identifying Differential Mechanisms of Action for MM-398/PEP02, a Novel Nanotherapeutic Encapsulation of Irinotecan." Poster presented at MCR, Nov. 12-16, 2011, 8 pages.
Ko A, et al., "Excess Toxicity Associated with Docetaxel and Irinotecan in Patients with Metastatic, Gemcitabine-Refractory Pancreatic Cancer: Results of a Phase II Study," Cancer Invest. 26(1):47-52 (2008).

Lee M, et al., "5-Fluorouracil/Leucovorin Combined wtih Irinotecan and Oxaliplatin (FOLFIRINOX) as Second-Line Chemotherapy in Patients with Advanced Pancreatic Cancer Who Have Progressed on Gemcitabine-Based Therapy," Chemotherapy. 59(4):273-9 (2013).
Lordick F, et al., "Phase II Study of Weekly Oxaliplatin Plus Infusional Fluorouracil and Folinic Acid (FUFOX Regiment) as First-Line Treatment in Metastatic Gastric Cancer," Br J Cancer. 93(2):190-4 (2005).
Louvet C, et al., "Gemcitabine in Combination With Oxaliplatin Compared With Gemcitabine Alone in Locally Advanced or Metastatic Pancreatic Cancer: Results of a GERCOR and GISCAD Phase III Trial," J Clin Oncol. 23(15):3509-16 (2005).
Ma W, et al., "Nanoliposomal Irinotecan (nal-IRI, nal-IRI) Population Pharmacokinetics (PK) and Its Association with Efficacy and Safety in Patients with Solid Tumors." Poster presented at 2015 European Cancer Congress, Vienna, Austria, Sep. 25, 2015, 7 pages.
Mahaseth H, et al., "Modified FOLFIRINOX Regimen With Improved Safety and Maintained Efficacy in Pancreatic Adenocarcinoma," Pancreas. 42(8):1311-5 (2013).
Mans D, et al., "Sequence-Dependent Growth Inhibition and DNA Damage Formation by the Irinotecan-5-Fluorouracil Combination in Human Colon Carcinoma Cell Lines," Eur J Cancer. 35(13):1851-61 (1999).
Mathé G, et al., "A Phase I Trial of Trans-1-diamino-cyclohexane Oxalate-platinum (I-OHP)," Biomed Pharmacother, 40(10):372-376 (1986).
Mathé G, et al., "Oxalato-platinum or 1-OHP, a Third-Generation Platinum Complex: An Experimental and Clinical Appraisal and Preliminary Comparison with Cis-platinum and Carboplatinum," Biomed Pharmacother, 43(4):237-50 (1989).
Melis M, et al., "Can We Downstage Regionally Advanced Pancreatic Cancer to Resectable: a Phase I/II Study of Induction Oxaliplatin and 5FU Chemo-Radiation," 52nd Annual Meeting for Society for Surgery of the Alimentary Tract, May 6-10, 2011, http://meetings.ssat.com/abstracts/11ddw/P57.cgi, Abstract P57, 1 printed page.
Mizuno N., "Randomized Phase II Trial of S-1 versus S-1 Plus Irinotecan (IRIS) in Patients with Gemcitabine-Refractory Pancreatic Cancer," J Clin Oncol. 31(Suppl 4):Abstract 263 (2013), 2 printed pages.
Mullany S, et al., "Effect of Adding the Topoisomerase I Poison 7-ethyl-10-hydroxy-camptothecin (SN-38) to 5-Fluorouracil and Folinic Acid in HCT-8 Cells: Elevated dTTP Pools and Enhanced Cytotoxicity," Cancer Chemother Pharmacol. 42(5):391-9 (1998).
Neuzillet C, et al., "FOLFIRI Regimen in Metastatic Pancreatic Adenocarcinoma Resistant to Gemcitabine and Platinum-Salts," World J Gastroenterol. 18(33):4533-41 (2012).
Oettle H, et al., "Second-Line Oxaliplatin, Folinic Acid, and Fluorouracil Versus Folinic Acid and Fluorouracil Alone for Gemcitabine-Refractory Pancreatic Cancer: Outcomes From the CONKO-003 Trial," J Clin Oncol. 32(23):2423-9 (2014).
Oh S, et al., "Pilot Study of Irinotecan/Oxaliplatin (IROX) Combination Chemotherapy for Patients with Gemcitabine- and 5-Fluorouracil-Refractory Pancreatic Cancer," Invest New Drugs. 28(3):343-9 (2010), Epub May 15, 2009.
Ohkawa S, et al., "Randomised Phase II Trial of S-1 Plus Oxaliplatin vs S-1 in Patients with Gemcitabine-Refractory Pancreatic Cancer," Br J Cancer. 112(9):1428-34 (2015).
Okusaka T, et al., "Phase II Study of FOLFIRINOX for Chemotherapy-Naïve Japanese Patients with Metastatic Pancreatic Cancer," Cancer Sci. 105(10):1321-6 (2014).
OXALIPLATIN package insert, revision Nov. 2013, retrieved from https://www.accessdata.fda.gov/drugsatfda_docs/label/2013/022160s009lbl.pdf, 43 pages.
Pavillard V, et al., "Combination of Irinotecan (CPT11) and 5-Fluorouracil with an Analysis of Cellular Determinants of Drug Activity," Biochem Pharmacol. 56(10):1315-22 (1998).
Peddi P, et al., "Multi-Institutional Experience with FOLFIRINOX in Pancreatic Adenocarcinoma," Journal of the Pancreas (JOP). 13(5):497-501 (2012), online access, 11 printed pages.
Pelzer U, et al., "A Randomized Trial in Patients With Gemcitabine Refractory Pancreatic Cancer. Final Results of the CONKO 003

(56) References Cited

OTHER PUBLICATIONS

Study," J Clin Oncol. 2008 ASCO Annual Meeting Proceedings. 26(15S):4508 (2008), 2 printed pages.
Pelzer U, et al., "Second-Line Therapy in Refractory Pancreatic Cancer. Results of a Phase II Study," Onkologie. 32(3):99-102 (2009).
Petrioli R, et al., "Gemcitabine, Oxaliplatin, and Capecitabine (GEMOXEL) Compared with Gemcitabine Alone in Metastatic Pancreatic Cancer: A Randomized Phase II Study," Cancer Chemother Pharmacol. 75(4):683-90 (2015).
Qin B, et al., "In-vitro Schedule-Dependent Interaction Between Oxaliplatin and 5-Fluorouracil in Human Gastric Cancer Cell Lines," Anti-Cancer Drugs. 17(4):445-53 (2006).
Rahib L, et al., "Projecting Cancer Incidence and Deaths to 2030: The Unexpected Burden of Thyroid, Liver, and Pancreas Cancers in the United States," Cancer Res. 74(11):2913-21 (2014).
Reni M, et al., "Salvage Chemotherapy with Mitomycin, Docetaxel, and Irinotecan (MDI Regimen) in Metastatic Pancreatic Adenocarcinoma: A Phase I and II Trial," Cancer Invest. 22(5):688-96 (2004).
Rombouts S, et al., "FOLFIRINOX in Locally Advanced and Metastatic Pancreatic Cancer: A Single Centre Cohort Study," J Cancer 7(13):1861-6 (2016).
Siegel R, et al., "Cancer Statistics, 2015," CA Cancer J Clin. 65(1):5-29 (2015).
Stein S, et al., "Final Analysis of a Phase II Study of Modified FOLFIRINOX in Locally Advanced and Metastatic Pancreatic Cancer," Br J Cancer. 114(7):737-43 (2016).
Takahara N, et al., "Uridine Disphosphate Glucuronosyl Transferase 1 Family Polypeptide Al Gene (UGT1A1) Polymorphisms are Associated with Toxicity and Efficacy in Irinotecan Monotherapy for Refractory Pancreatic Cancer," Cancer Chemother Pharmacol. 71(1):85-92 (2013), Epub Sep. 29, 2012.
Tanaka R, et al., "Synergistic Interaction Between Oxaliplatin and SN-38 in Human Gastric Cancer Cell Lines In Vitro," Oncol Rep. 14(3):683-8 (2005).
Tsubamoto H, et al., "Combination Chemotherapy with Itraconazole for Treating Metastatic Pancreatic Cancer in the Second-line or Additional Setting,". Anticancer Res. 35(7):4191-6 (2015).
Ueno H, et al., "A Phase II Study of Weekly Irinotecan as First-Line Therapy for Patients with Metastatic Pancreatic Cancer," Cancer Chemother Pharmacol. 59(4):447-54 (2007), Epub Jul. 20, 2006.
Ulrich-Pur H, et al., "Irinotecan Plus Raltitrexed vs Raltitrexed Alone in Patients with Gemcitabine-Pretreated Advanced Pancreatic Adenocarcinoma," Br J Cancer. 88(8):1180-4 (2003).
Umemura A, et al., "Modified FOLFIRINOX for Locally Advanced and Metastatic Pancreatic Cancer Patients Resistant to Gemcitabine and S-1 in Japan: A Single Institutional Experience," Hepato-Gastroenterology. 61:00-00 doi10.5754/hge14111, pp. 6-12 (2013).
Van Cutsem E, et al., "A Phase Ib Dose-Escalation Study of Erlotinib, Capecitabine and Oxaliplatin in Metastatic Colorectal Cancer Patients," Ann Oncol. 19(2):332-9 (2008), Epub Nov. 6, 2007.
Wagener D, et al., "Phase II Trial of CPT-11 in Patients with Advanced Pancreatic Cancer: An EORTC Early Clinical Trials Group Study," Ann Oncol. 6(2):129-32 (1995).
Wasserman E, et al., "Combination of Oxaliplatin Plus Irinotecan in Patients With Gastrointestinal Tumors: Results of Two Independent Phase I Studies with Pharmacokinetics," J Clin Oncol. 17(6):1751-9 (1999).
Ychou, M, et al., "An Open Phase I Study Assessing the Feasibility of the Triple Combination: Oxaliplatin Plus Irinotecan Plus Leucovorin/ 5-Fluorouracil Every 2 Weeks in Patients With Advanced Solid Tumors," Ann Oncol. 14(3):481-9 (2003).
Zeghari-Squalli, N et al., "Cellular Pharmacology of the Combination of the DNA Topoisomerase I Inhibitor SN-38 and the Deaminocyclohexane Platinum Derivative Oxaliplatin," Clin Cancer Res. 5(5):1189-96 (1999).
CnicalTrials.gov search results for ONIVYDE, retrieved from clinicaltrials.gov website on Jan. 27, 2021, 27 pages.

Alagoz M, et al., "DNA Repair and Resistance to Topoisomerase I Inhibitors: Mechanisms, Biomarkers and Therapeutic Targets," Curr Med Chem. 19(23):3874-85 (2012).
American Chemical Society (ACS), http://www.cancer.org/cancer/ pancreaticcancer/detailedguide/pancreatic-cancer-what-is-pancreatic-cancer, retrieved Dec. 1, 2016, 4 printed pages.
Amodeo S, et al., "Can we downstage locally advanced pancreatic cancer to resectable? A phase I/II study of induction oxaliplatin and 5-FU chemoradiation," J Gastrointest Oncol. 9(5):922-35 (2018).
CAMPTOSAR package insert, revised May 16, 2002, 37 pages.
Cassileth P, et al., "Antiemetic Efficacy of Dexamethasone Therapy in Patients Receiving Cancer Chemotherapy," Arch Intern Med. 143(7):1347-9 (1983).
Chen L, et al., "Effect of Baseline Carbohydrate Antigen 19-9 (CA19-9) Level on Overall Survival (OS) in NAPOLI-1 Trial: a Phase 3 Study of MM-398 (nal-IRI), with or without 5-Fluorouracil and Leucovorin (5-FU/LV), versus 5-FU/LV in Metastatic Pancreatic Cancer (mPAC) Previously Treated with Gemcitabine-based Therapy." Poster handout at the Gastrointestinal Cancers Symposium of the ASCO meeting of Jan. 21-23, 2016, San Francisco, California, 2 pages.
Chen L, et al., "Expanded Analyses of NAPOLI-1: Phase 3 Study of MM-398 (nal-IRI), with or without 5-Fluorouracil and Leucovorin, versus 5-Fluorouracil and Leucovorin, in Metastatic Pancreatic Cancer (mPAC) Previously Treated with Gemcitabine-based Therapy." Presented Jan. 15, 2015, ASCO GI, 17 pages.
Chen L, et al., "Safety Across Subgroups in NAPOLI-1:A Phase 3 Study of nal-IRI (MM-398) ± 5-Fluorouracil and Leucovorin (5-FU/ LV) Versus 5-FU/LV in Metastatic Pancreatic Cancer (mPAC) Previously Treated with Gemcitabine-Based Therapy." Poster presented at the 18th European Society of Medical Oncology World Congress on Gastrointestinal Cancer; Barcelona, Spain; Jun. 29-Jul. 2, 2016, 10 pages.
Chen L, et al., Abstract PD-023. "Safety Across Subgroups in NAPOLI-1:A Phase 3 Study of nal-IRI (MM-398) ± 5-Fluorouracil and Leucovorin (5-FU/LV) Versus 5-FU/LV in Metastatic Pancreatic Cancer (mPAC) Previously Treated with Gemcitabine-Based Therapy." Annals of Oncology. 27(Suppl 2):ii102-ii117 (2016), 1 page.
Chiang N-J, et al., "A Phase I Dose-Escalation Study of PEP02 (Irinotecan Liposome Injection) in Combination with 5-Fluorouracil and Leucovorin in Advanced Solid Tumors," BMC Cancer. 16(1):907 (2016). doi: 10.1186/s12885-016-2933-6, pp. 1-8.
Clinical Trials Identifier NCT00364143: Jan. 26, 2012 update, first posted Aug. 15, 2006, "A Phase I Study of IHL-305 (Irinotecan Liposome Injection) in Patients With Advanced Solid Tumors." Retrieved from ClinicalTrials.gov archive, 6 printed pages.
Clinical Trials Identifier NCT00813163: Jan. 11, 2011 update, "A Phase II Study of PEP02 as a Second Line Therapy for Patients With Metastatic Pancreatic Cancer." Retrieved from ClinicalTrials.gov archive, 3 printed pages.
Clinical Trials Identifier NCT00813163: Apr. 6, 2017 update, first posted Dec. 22, 2008, "A Phase II Study of PEP02 as a Second Line Therapy for Patients With Metastatic Pancreatic Cancer." Retrieved from ClinicalTrials.gov archive, 6 printed pages.
Clinical Trials Identifier NCT00940758: Apr. 6, 2017 update, first posted Jul. 16, 2009, "Phase I and Pharmacokinetic Study of Biweekly PEP02 (Liposome Irinotecan) in Patients With Metastatic Colorectal Cancer Refractory to First-line Oxaliplatin-based Chemotherapy." Retrieved from ClinicalTrials.gov archive, 5 printed pages.
Clinical Trials Identifier NCT01375816: Jun. 4, 2015 update, first posted Jun. 17, 2011, "A Randomized Phase II Study of PEP02 or Irinotecan in Combination With Leucovorin and 5-Fluorouracil in Second Line Therapy of Metastatic Colorectal Cancer." Retrieved from ClinicalTrials.gov archive, 10 printed pages.
Clinical Trials Identifier NCT02551991: Sep. 30, 2019 update, first posted Sep. 16, 2015, "A Randomized, Open-label, Phase 2 Study of Nanoliposomal Irinotecan (Nal-IRI)-Containing Regimens Versus Nab-Paclitaxel Plus Gemcitabine in Patients With Previously Untreated, Metastatic Pancreatic Adenocarcinoma." Retrieved from ClinicalTrials.gov archive, 5 printed pages.

(56) References Cited

OTHER PUBLICATIONS

Clinical Trials Identifier NCT02884128: Aug. 30, 2016 update, first posted Aug. 30, 2016, "A Multi-Center, Open-Label Phase I Dose-Escalation Study of PEP02 in Combination With 5-fluorouracil (5-FU) and Leucovorin (LV) in Advanced Solid Tumors." Retrieved from ClinicalTrials.gov archive, 5 printed pages.

Dayyani F, et al., Abstract B14. "CA 19-9 levels in patients with metastatic pancreatic adenocarcinoma receiving first-line therapy with liposomal irinotecan plus 5-fluorouracil/leucovorin and oxaliplatin (NAPOX)," In Proceedings of the AACR Special Conference on Pancreatic Cancer Advances in Science and Clinical Care; Sep. 6-9, 2019; Boston, MA; Cancer Res. 2019; 79(24 Suppl): Abstract nr B14, 3 printed pages.

Dean A, et al., "Nanoliposomal Irinotecan (nal-IRI)-Containing Regimens Versus nab-paclitaxel Plus Gemcitabine as First-Line Therapy in Patients With Metastatic Pancreatic Adenocarcinoma (mPAC): A Randomized, Open-Label Phase 2 Study." Poster presented at the 18th European Society of Medical Oncology World Congress on Gastrointestinal Cancer; Barcelona, Spain; Jun. 29-Jul. 2, 2016, 14 pages.

Dean A, et al., Abstract P-287. "Nanoliposomal Irinotecan (nal-IRI)-Containing Regimens Versus nab-paclitaxel Plus Gemcitabine as First-Line Therapy in Patients With Metastatic Pancreatic Adenocarcinoma (mPAC): A Randomized, Open-Label Phase 2 Study." Annals of Oncology. 27(Suppl 2):ii1-i85 (2016), 1 page.

DOXIL package insert, revision Aug. 30, 2013, retrieved from https://www.accessdata.fda.gov/drugsatfda_docs/label/2013/050718s045lbl.pdf, 35 pages.

Drummond D, et al., "Optimizing Liposomes for Delivery of Chemotherapeutic Agents to Solid Tumors," Pharmacol Rev. 51(4):691-743 (1999).

Hsueh C-T, et al., "Nanovectors for Anti-Cancer Drug Delivery in the Treatment of Advanced Pancreatic Adenocarcinoma," World J Gastroenterol. 22(31):7080-90 (2016).

Hubner R, et al., "Effects of nal-IRI (MM-398) ± 5-Fluorouracil on Quality of Life (QoL) in NAPOLI-1: A Phase 3 Study in Patients With Metastatic Pancreatic Ductal Adenocarcinoma (mPDAC) Previously Treated with Gemcitabine-Based Therapy." Poster presented at the 18th European Society of Medical Oncology World Congress on Gastrointestinal Cancer; Barcelona, Spain; Jun. 29-Jul. 2, 2016, 9 pages.

Hubner R, et al., Abstract O-004. "Effects of nal-IRI (MM-398) ± 5-fluorouracil on Quality of Life (QoL) in NAPOLI-1: A Phase 3 Study in Patients with Metastatic Pancreatic Ductal Adenocarcinoma (mPDAC) Previously Treated with Gemcitabine." Annals of Oncology. 27(Suppl 2):ii118-ii128 (2016), 1 page.

Kalra A, et al., Abstract 5696. "Evaluating Determinants for Enhanced Activity of MM-398/PEP02; A Novel Nanotherapeutic Encapsulation of Irinotecan (CPT-11)." In Proceedings of the 103rd Annual Meeting of the American Association for Cancer Research; Mar. 31-Apr. 4, 2012; Chicago, IL. Cancer Res 2012; 72(8 Suppl):Abstract nr 5696. doi:1538-7445.AM2012-5696, 3 printed pages.

Kalra A, et al., "Evaluating Determinants for Enhanced Activity of MM-398/PEP02; A Novel Nanotherapeutic Encapsulation of Irinotecan (CPT-11)." Poster for abstract 5696 presented at American Association for Cancer Research 103rd Annual Meeting 2012, Mar. 31-Apr. 4, 2012, Chicago, IL, 11 pages.

Kalra A, et al., Abstract 5622. "The Tumor Microenvironment Modulates the Delivery and Activation of Liposomal Encapsulated Irinotecan, MM-398." In Proceedings of the 104th Annual Meeting of the American Association of Cancer Research; Apr. 6-10, 2013. Cancer Res 2013;73(8 Suppl):Abstract nr 5622, doi:10.1158/1538-7445. AM2013-5622, 2 printed pages.

Kalra A, et al., "The Tumor Microenvironment Modulates the Delivery and Activation of Liposomal Encapsulated Irinotecan, MM-398," Poster for abstract 5622 presented at the 104th Annual Meeting of the American Association of Cancer Research, Apr. 6-10, 2013, Washington DC, 10 pages.

Kalra A, et al., "Preclinical Activity of Nanoliposomal Irinotecan Is Governed by Tumor Deposition and Intratumor Prodrug Conversion," Cancer Res. 74(23):7003-13 (2014).

Klinz S, et al., "Identifying Differential Mechanisms of Action for MM-398/PEP02, a Novel Nanotherapeutic Encapsulation of Irinotecan," Mol Cancer Ther. 10(11 Suppl):Abstract C207. Molecular Targets and Therapeutics Meeting (2011), 2 printed pages.

Klinz S, et al., "Nanoliposomal Irinotecan (nal-IRI) is an Active Treatment and Reduces Hypoxia as Measured Through Longitudinal Imaging Using [18F]FAZA-PET in an Orthotopic Patient-Derived Tumorgraft Model of Pancreatic Cancer." Poster presented at AACR Pancreatic meeting Orlando, FL, May 12-15, 2016, 10 pages.

Ko A, "Nanomedicine Developments in the Treatment of Metastatic Pancreatic Cancer: Focus on Nanoliposomal Irinotecan," Int J Nanomedicine. 11:1225-35 (2016).

Maxwell F, et al., "CA 19-9 levels in patients with metastatic pancreatic adenocarcinoma receiving first-line therapy with liposomal irinotecan plus 5-fluorouracil/leucovorin and oxaliplatin (NAPOX)," Poster presented at the American Association for Cancer Research (AACR) Special Conference on Pancreatic Cancer: Advances in Science and Clinical Care, Sep. 6-9, 2019, Boston, MA, 7 pages.

Paz N, et al., "MM-398/PEP02, A Novel Liposomal Formulation of Irinotecan Demonstrates Stromal-Modifying Anti-Cancer Properties," Poster for abstract A63 presented at the AACR Special Conference on Pancreatic Cancer: Progress and Challenges; Jun. 18-21, 2012; Lake Tahoe, NV, 9 pages.

Paz N, et al., Abstract A63. "MM-398/PEP02, A Novel Liposomal Formulation of Irinotecan, Demonstrates Stromal-Modifying Anticancer Properties," In Proceedings of the AACR Special Conference on Pancreatic Cancer: Progress and Challenges; Jun. 18-21, 2012; Lake Tahoe, NV. Cancer Res. 2012;72(12 Suppl):Abstract nr A63, 3 printed pages.

Von Hoff D, et al., "NAPOLI 1: Randomized Phase 3 Study of MM-398 (nal-IRI), With or Without 5-Fluorouracil and Leucovorin, Versus 5-Fluorouracil and Leucovorin, in Metastatic Pancreatic Cancer Progressed on or following Gemcitabine-Based Therapy." Poster presented at the ESMO World Congress on Gastrointestinal Cancer 2014, 11 pages.

Wainberg Z, et al., Abstract SO-005: "A Phase 1/2, Open-Label, Dose-Expansion Study of Liposomal Irinotecan (Nal-IRI) Plus 5-Fluorouracil/Leucovorin (5-FU/LV) and Oxaliplatin (OX) in Patients with Previously Untreated Metastatic Pancreatic Cancer," Ann Oncol. 30(Suppl 4): doi:10.1093/annonc/mdz157 | iv123 (Jul. 2019), 1 page.

Wainberg Z, et al., "A phase 1/2, open-label, dose-expansion study of liposomal irinotecan (nal-IRI) plus 5-fluorouracil/leucovorin (5-FU/LV) and oxaliplatin (OX) in patients with previously untreated metastatic pancreatic cancer (mPAC)." Presentation presented at the ESMO 21st World Congress on Gastrointestinal Cancer, Barcelona, Spain, Jul. 3-6, 2019, 13 pages.

Wainberg Z, et al., Abstract LBA-1. "First-line liposomal irinotecan + 5 fluorouracil/leucovorin + oxaliplatin in patients with pancreatic ductal adenocarcinoma: Long-term follow-up results from a phase 1/2 study," Ann Oncol. 31(Suppl 3): S241 doi.org/10.1016/j.annonc. 2020.04.076 (2020).

Wainberg Z, et al., "First-line liposomal irinotecan + 5-fluorouracil/leucovorin + oxaliplatin in patients with pancreatic ductal adenocarcinoma: long-term follow-up results from a phase 1/2 study." Presentation presented at the ESMO World Congress on Gastrointestinal Cancer, Jul. 1-4, 2020, 13 pages.

Ioka T, et al., Abstract 132P. "Liposomal Irinotecan (nal-IRI) Plus 5-Fluorouracil/Levoleucovorin (5-FU/LV) vs 5-FU/LV in Japanese Patients (pts) With Gemcitabine-Refractory Metastatic Pancreatic Cancer (mPAC)," Ann Oncol. 30(Suppl_9):ix47-ix48 doi:10.1093/annonc/mdz422 (2019).

Ioka T, et al., Abstract 274TiP. "A Randomized Phase 2 Study of Nanoliposomal Irinotecan (nal-IRI, BAX2398)-Containing Regimen in Japanese Patients With Metastatic Pancreatic Adenocarcinoma (mPAC)," Ann Oncol. 27(Supp_9):ix84-ix85 doi:10.1093/annonc/mdw582 (2016).

Jameson G, et al., "Adverse Events in Patients with Metastatic Pancreatic Cancer Receiving Liposomal Irinotecan: Understanding

(56) References Cited

OTHER PUBLICATIONS the Occurrence and How Management Affects Patient Outcomes." Poster presented at the Oncology Nursing Society (ONS) Annual Conference, Washington, DC, May 17-20, 2018, 7 pages.

Jameson G, et al., Abstract 1. "Adverse Events in Patients with Metastatic Pancreatic Cancer Receiving Liposomal Irinotecan: Understanding the Occurrence and How Management Affects Patient Outcomes," Oncology Nursing Society (ONS) 43rd Annual Congress, available at ons.confex.com/ons/2018/meetingapp.cgi/Paper/2970, (2018), 2 pages.

Kang S and Saif M, "Optimal Second Line Treatment Options for Gemcitabine Refractory Advanced Pancreatic Cancer Patients. Can We Establish Standard of Care with Available Data?," JOP. J Pancreas (Online) 9(2):83-90 (2008).

Katopodis O, et. al., "Second-Line Chemotherapy With Capecitabine (Xeloda) and Docetaxel (Taxotere) in Previously Treated, Unresectable Adenocarcinoma of Pancreas: The Final Results of a Phase II Trial," Cancer Chemother Pharmacol. 67(2):361-8 (2011). Epub 2010.

Kim G, et al., "Clinical Pathway Implications and Real-World Characteristics and Outcomes for Patients With Metastatic Pancreatic Ductal Adenocarcinoma (mPDAC) Treated With First Line Category 1 National Comprehensive Cancer Network (NCCN) Regimens." Poster presented at the European Society for Medical Oncology (ESMO) Virtual Congress 2020, Sep. 19-21, 2020, 6 pages.

Kim G, et al., "Impact of Treatment Sequence on Overall Survival in Metastatic Pancreatic Cancer Patients Treated with Liposomal Irinotecan in the Real-World Setting." Poster presented at the Hematology Oncology Pharmacy Association (HOPA) Annual Conference, Tampa, FL, Mar. 11-14, 2020, 7 pages.

Kim G, et al., Abstract 1564P. "Clinical Pathway Implications and Real-World Characteristics and Outcomes for Patients With Metastatic Pancreatic Ductal Adenocarcinoma (mPDAC) Treated With First Line Category 1 National Comprehensive Cancer Network (NCCN) Regimens," Ann Oncol. 31(Suppl_4):S881-S897 10.1016/annonc/annonc285 (2020), 2 printed pages.

Kim G, et al., Abstract e16740. "Real-World Use of Liposomal Irinotecan-Based Regimens Among Patients (pts) With Metastatic Pancreatic Adenocarcinoma (mPDAC) in the United States (U.S.)," J Clin Oncol. 38(15_Suppl):e16740 DOI: 10.1200/JCO.2020.38.15_suppl.e16740 (2020), 2 printed pages.

Kim H, et. al., "Phase II Study of Palliative S-1 in Combination With Cisplatin as Second-Line Chemotherapy for Gemcitabine-Refractory Pancreatic Cancer Patients," Oncol Lett. 3(6):1314-8 (2012).

Kim Y, et. al., "Phase II Study of 5-Fluorouracil and Paclitaxel in Patients With Gemcitabine-Refractory Pancreatic Cancer," Cancer Chemother Pharmacol. 63(3):529-33 (2009). Epub 2008.

Kindler H, et. al., "Arsenic Trioxide in Patients With Adenocarcinoma of the Pancreas Refractory to Gemcitabine: A Phase II Trial of the University of Chicago Phase II Consortium," Am J Clin Oncol. 31(6):553-6 (2008).

Kindler H, et. al., "Gemcitabine Plus Bevacizumab Compared With Gemcitabine Plus Placebo in Patients With Advanced Pancreatic Cancer: Phase III Trial of the Cancer and Leukemia Group B (CALGB 80303)," J Clin Oncol. 28(22):3617-22 (2010).

Kipps E, et. al., "Liposomal Irinotecan in Gemcitabine-Refractory Metastatic Pancreatic Cancer: Efficacy, Safety and Place in Therapy," Ther Adv Med Oncol. 9(3):159-70 (2017).

Klapdor R and Fenner C, "Irinotecan(Campto R): Efficacy as Third/Forth Line Therapy in Advanced Pancreatic Cancer," Anticancer Res. 20(6D): 5209-12 (2000).

Klapdor R, et. al., "Reflections on Treatment Strategies for Palliative Chemotherapy of Pancreatic Cancer," Anticancer Res. 27(4A): 1789-94 (2007).

Klinz S, et al., Abstract e16205. "DNA Ddamage With Liposomal Irinotecan (nal-IRI) in Pancreatic Cancer Xenografts: Multimodal Analysis of Deposition Characteristics," J Clin Oncol. 36(15_Suppl):e16205 DOI: 10.1200/JCO.2018.36.15_suppl.e16205 (2018), 2 printed pages.

Ko A, et. al., "A Phase II Study of Bevacizumab Plus Erlotinib for Gemcitabine-Refractory Metastatic Pancreatic Cancer," Cancer Chemother Pharmacol. 66(6):1051-7 (2010).

Koeller J, et al., Abstract e16751. "Trends in Real-World Clinical Outcomes Among Patients (pts) With Metastatic Pancreatic Adenocarcinoma (mPDAC) Treated With Liposomal Irinotecan Based Regimens in the United States (US)," J Clin Oncol. 38(15_Suppl):e16751 DOI: 10.1200/JCO.2020.38.15_suppl.e16751 (2020), 2 printed pages.

Kulke M, et. al., "Capecitabine Plus Erlotinib in Gemcitabine-Refractory Advanced Pancreatic Cancer," J Clin Oncol. 25(30):4787-92 (2007).

Kulke M, et. al., "Randomized Phase II Study of Gemcitabine Administered at a Fixed Dose Rate or in Combination With Cisplatin, Docetaxel, or Irinotecan in Patients With Metastatic Pancreatic Cancer: CALGB 89904," J Clin Oncol. 27(33):5506-12 (2009).

Lakatos G, et al., "Prognostic Value of Baseline Biliary Stents on Outcomes in Patients With Metastatic Pancreatic Ductal Adenocarcinoma (mPDAC) in the NAPOLI-1 Trial." Poster presented at the European Society for Medical Oncology 20th World Congress on Gastrointestinal Cancer, Barcelona, Spain, Jun. 20-23, 2018, 10 pages.

Lakatos G, et al., Abstract P-151. "Prognostic Value of Baseline Biliary Stents on Outcomes in Patients With Metastatic Pancreatic Ductal Adenocarcinoma (mPDAC) in the NAPOLI-1 Trial," Ann Oncol. 29(Suppl_5):v42 doi:10.1093/annonc/mdy151 (2018).

Latimer H, et al., Abstract C5. "Utilization of Hospital Inpatient Services Among Patients With Metastatic Pancreatic Cancer With Commercial and Medicare Insurance Treated With FDA-Approved/NCCN Category 1 Regimens," J Manag Care Spec Pharm. 26(10-a):S20 (2020).

Le A, et. al., "Conceptual Framework for Cutting the Pancreatic Cancer Fuel Supply," Clin Cancer Res. 18(16):4285-90 (2012).

Lee K, et al., Abstract P-153. "Decreased Appetite (DA) at Baseline Impacts Prognosis in the NAPOLI-1 Phase 3 Study in Metastatic Pancreatic Ductal Adenocarcinoma (mPDAC)," Ann Oncol. 29(Suppl_5):v42-v43 doi:10.1093/annonc/mdy151 (2018).

Lee K-H, et al., "Decreased Appetite (DA) at Baseline Impacts Prognosis in the NAPOLI-1 Phase 3 Study in Metastatic Pancreatic Ductal Adenocarcinoma (mPDAC)." Poster presented at the European Society for Medical Oncology 20th World Congress on Gastrointestinal Cancer, Barcelona, Spain, Jun. 20-23, 2018, 9 pages.

Leonard S, et al., "Deposition Characteristics and Resulting DNA Damage Patterns of Liposomal Irinotecan (nal-IRI) in Pancreatic Cancer Xenografts." Poster presented at the American Society of Clinical Oncology Gastrointestinal cancers Symposium (ASCO GI), San Francisco, CA, Jan. 18-20, 2018, 9 pages.

Leonard S, et al., Abstract 335. "Deposition Characteristics and Resulting DNA Damage Patterns of Liposomal Irinotecan (nal-IRI) in Pancreatic Cancer Xenografts," J Clin Oncol. 36(4_Suppl):335 DOI: 10.1200/JCO.2018.36.4_suppl.335 (2018), 2 printed pages.

Li J and Saif M, "Any Progress in the Management of Advanced Pancreatic Cancer? Highlights from the 45th ASCO Annual Meeting." JOP. J Pancreas (Online) 10(4):361-5 (2009).

Li J, et. al., "Any Second-Line Therapy for Advanced Pancreatic Cancer? Highlights from the 2010 ASCO Gastrointestinal Cancers Symposium." JOP. J Pancreas (Online). 11(2):151-3 (2010).

Löhr J, et. al., "Cationic Liposomal Paclitaxel Plus Gemcitabine or Gemcitabine Alone in Patients With Advanced Pancreatic Cancer: A Randomized Controlled Phase II Trial," Ann Oncology. 23(5):1214-22 (2012). Epub 2011.

Ma W, et al., Abstract 2365. "Nanoliposomal Irinotecan (MM-398, nal-IRI) Population Pharmacokinetics (PK) and its 4ssociation With Efficacy and Safety in Patients With Solid Tumors Based on the Phase 3 Study NAPOLI-1 and Five Phase 1 and 2 Studies," Eur J Cancer. 51(3):S458 10.1016/S0959-8049(16)31281-3 (2015).

Macarulla Mercadé T, et al., "NAPOLI-1 Phase 3 Trial Outcomes by Prior Surgery, and Disease Stage, in Patients With Metastatic Pancreatic Ductal Adenocarcinoma (mPDAC)." Poster presented at

(56) References Cited

OTHER PUBLICATIONS the European Society for Medical Oncology Annual Congress, Munich, Germany, Oct. 19-23, 2018, 7 pages.

Macarulla Mercadé T, et al., "Prognostic Effect of Primary Tumour Location in the NAPOLI-1 Phase 3 Study in Metastatic Pancreatic Ductal Adenocarcinoma (mPDAC)." Poster presented at the European Society for Medical Oncology 19th World Congress on Gastrointestinal Cancer, Barcelona, Spain, Jun. 20-23, 2018, 10 pages.

Macarulla Mercadé T, et al., "Selected Subgroup Analyses of Liposomal Irinotecan in Patients With Metastatic Pancreatic Ductal Adenocarcinoma in the Global NAPOLI-1 Phase III Trial." Presentation presented at the European Society for Medical Oncology (ESMO) 20th World Congress on Gastrointestinal Cancer, Barcelona, Spain, Jun. 20-23, 2018, 16 pages.

Macarulla Mercade T, et al., "Subgroup Analysis by Baseline Pain Intensity (BPI) and Baseline Analgesic Use (BAU) in NAPOLI-1, A phase 3 Study of Liposomal Irinotecan (nal IRI)±5-Fluorouracil/Leucovorin (5-FU/LV) in Patients With Metastatic Pancreatic Ductal Adenocarcinoma Previously Treated With Gemcitabine-Based Therapy." Poster presented at the American Society of Clinical Oncology Gastrointestinal Cancers Symposium (ASCO GI), San 7rancisco, CA, Jan. 18-20, 2018, 8 pages.

Macarulla Mercadé T, et al., "Subgroup Analysis by Baseline Weight-Associated Parameters: A phase 3 Study of Liposomal Irinotecan (nal-IRI)±5-Fluorouracil/Leucovorin (5-FU/LV) in Patients With Metastatic Pancreatic Ductal Adenocarcinoma Previously Treated With Gemcitabine-Based Therapy." Poster presented at the American Society of Clinical Oncology Gastrointestinal Cancers Symposium (ASCO GI), San Francisco, CA, Jan. 18-20, 2018, 7 pages.

Macarulla Mercadé T, et al., "The Effect of Best Response to Prior Anticancer Therapy on Efficacy Outcomes in the NAPOLI-1 Trial of Patients With Metastatic Pancreatic Ductal Adenocarcinoma (mPDAC) Previously Treated with Gemcitabine-Based Therapy." Poster presented at the European Society for Medical Oncology 20th World Congress on Gastrointestinal Cancer, Barcelona, Spain, Jun. 20-23, 2018, 10 pages.

Macarulla Mercadé T, et al., Abstract 379. "Subgroup Analysis by Baseline Pain Intensity (BPI) and Analgesic Use (BAU) in NAPOLI-1: A phase III Study of Liposomal Irinotecan (nal IRI)±5-Fluorouracil/ Leucovorin (5-FU/LV) in Patients (pts) With Metastatic Pancreatic Ductal Adenocarcinoma (mPDAC) Previously Treated With Gemcitabine-Based Therapy," J Clin Oncol. 36(4_Suppl):379 DOI: 10.1200/JCO.2018.36.4_suppl.379 (2018), 4 printed pages.

Macarulla Mercadé T, et al., Abstract 410. "Subgroup Analysis by Baseline (BL) Weight-Associated Parameters: A phase III Study of Liposomal Irinotecan (nal-IRI)±5-Fluorouracil/Leucovorin (5-FU/LV) in Patients (pts) With Metastatic Pancreatic Ductal Adenocarcinoma (mPDAC) Previously Treated With Gemcitabine-Based (Gem) Therapy," J Clin Oncol. 36(4_Suppl):410 DOI: 10.1200/JCO.2018.36.4_suppl.410 (2018), 6 printed pages.

Macarulla Mercadé T, et al., Abstract 733P. "NAPOLI-1 Phase III Trial Outcomes by Prior Surgery, and Disease Stage, in Patients With Metastatic Pancreatic Ductal Adenocarcinoma (mPDAC)," Ann Oncol. 29(Supp_8)viii249-viii250 doi:10.1093/annonc/mdy282 (2018).

Macarulla Mercadé T, et al., Abstract O-004. "Selected Subgroup Analyses of Liposomal Irinotecan (nal-IRI) in Patients With Metastatic Pancreatic Ductal Adenocarcinoma (mPDAC) in the Global NAPOLI-1 Phase III Trial," Ann Oncol. 29(Suppl_5)v101 doi:10.1093/annonc/mdy149 (2018).

Macarulla Mercadé T, et al., Abstract P-150. "Prognostic Effect of Primary Tumour Location in the NAPOLI-1 Phase 3 Study in Metastatic Pancreatic Ductal Adenocarcinoma (mPDAC)," Ann Oncol. 29(Suppl_5)v41-v42 doi:10.1093/annonc/mdy151 (2018).

Macarulla Mercadé T, et al., Abstract P-152. "The Effect of Best Response to Prior Anticancer Therapy on Efficacy Outcomes in the NAPOLI-1 Trial of Patients With Metastatic Pancreatic Ductal Adenocarcinoma (mPDAC) Previously Treated with Gemcitabine-Based Therapy," Ann Oncol. 29(Suppl_5):v42 doi:10.1093/annonc/mdy151 (2018).

Macarulla T, et al., "Integrated Population Pharmacokinetic Modelling of Liposomal Irinotecan in Patients With Various Tumour Types, Including Untreated Metastatic Pancreatic Cancer (mPC)." Poster presented at the European Society for Medical Oncology (ESMO) Congress 2019, Barcelona, Spain, Sep. 27-Oct. 1, 2019, 6 pages.

Macarulla T, et al., "Subgroup Analysis by Prior Lines of Metastatic Therapy in NAPOLI-1, A Global, Randomized Phase 3 Study of Liposomal Irinotecan ± 5-Fluorouracil and Leucovorin, vs. 5-Fluorouracil and Leucovorin in Patients With Metastatic Pancreatic Ductal Adenocarcinoma Who Have Progressed Following Gemcitabine-Based Therapy." Poster presented at the American Society of Clinical Oncology (ASCO) Annual Conference, Chicago, IL, Jun. 2-6, 2017, 7 pages.

Macarulla T, et al., Abstract 4127. "Subgroup Analysis by Prior Lines of Metastatic Therapy (mtx) in NAPOLI-1: A Global, Randomized Phase 3 Study of Liposomal Irinotecan (nal-IRI) ± 5-Fluorouracil and Leucovorin (5-FU/LV), vs. 5-FU/LV in Patients (pts) With Metastatic Pancreatic Ductal Adenocarcinoma (mPDAC) Who Have Progressed Following Gemcitabine-Based Therapy," J Clin Oncol. 35(15_Suppl):4127 DOI: 10.1200/JCO.2017.35.15_suppl.4127 (2017), 2 printed pages.

Macarulla T, et al., Abstract 691P. "Integrated Population Pharmacokinetic Modelling of Liposomal Irinotecan in Patients With Various Tumour Types, Including Untreated Metastatic Pancreatic Cancer (mPC)," Ann Oncol. 30(Suppl_5):v263 doi:10.1093/annonc/mdz247 (2019).

Adiwijaya B, et al., "Population Pharmacokinetics of Liposomal Irinotecan in Patients With Cancer," Clin Pharmacol Ther. 102(6):997-1005 (2017).

Alcindor T, et al., "Oxaliplatin: A Review in the Era of Molecularly Targeted Therapy," Curr Oncol. 18(1):18-25 (2011).

Alfert M, et al., "A Selective Staining Method for the Basic Proteins of Cell Nuclei," Proc Natl Acad Sci USA. 39(10):991-9 (1953).

Anders C, et al., "Phase 1 Expansion Study of Irinotecan Liposome Injection (nal-IRI) in Patients with Metastatic Breast Cancer (mBC): Findings from the Cohort with Active Brain Metastasis (BM)." Presentation presented at the Society for Neuro-Oncology Inaugural Conference on Brain Metasteses, Aug. 16-17, 2019, New York, NY, 11 pages.

Anders C, et al., Abstract TRLS-06. "Phase 1 Expansion Study of Irinotecan Liposome Injection (nal-IRI) in Patients with Metastatic Breast Cancer (mBC): Findings from the Cohort with Active Brain Metastasis (BM)," Neuro-Oncology Advances. 1(Suppl 1):i9 doi.org/10.1093/noajnl/vdz014.039 (2019).

Ardizzoni A, et al., "Topotecan, A New Active Drug in the Second-Line Treatment of Small-Cell Lung Cancer: A Phase II Study in Patients with Refractory and Sensitive Disease," J Clin Oncol. 15(5):2090-6 (1997).

Bendell J, et al., "Treatment Patterns and Clinical Outcomes in Patients With Metastatic Colorectal Cancer Initially Treated with FOLFOX-Bevacizumab or FOLFIRI-Bevacizumab: Results From ARIES, a Bevacizumab Observational Cohort Study," Oncologist. 17(12):1486-95 (2012).

Bernards N, et al., "Liposomal Irinotecan Achieves Significant Survival and Tumor Burden Control in a Triple Negative Breast Cancer Model of Spontaneous Metastasis," Mol Pharm. 15(9):4132-8 (2018).

Bernards N, et al., "Liposomal Irinotecan Injection (nal-IRI) Achieves Significant Survival and Tumor Burden Control in a Triple Negative Breast Cancer Model of Spontaneous Metastasis," Poster presented at the World Molecular Imaging Congress Sep. 13-16, 2017, Philadelphia, Pennsylvania, 5 pages.

Butt R, et al., "Postfractionation for Enhanced Proteomic Analyses: Routine Electrophoretic Methods Increase the Resolution of Standard 2D-PAGE," J Proteome Res. 4(3):982-91 (2005).

Chan D, et al., "Evaluating the Pharmacodynamics and Pharmacokinetic Effects of MM-398, a Nanoliposomal Irinotecan (nal-IRI) in Subcutaneous Xenograft Tumor Models of Human Squamous Cell

(56) References Cited

OTHER PUBLICATIONS

Carcinoma and Small Cell Lung Cancers," Cancer Res.74(19 Suppl): Abstract 4626 (2014), 2 printed pages.
Chan D, et al., "Evaluating the Pharmacodynamics and Pharmacokinetic Effects of MM-398, a Nanoliposomal Irinotecan (nal-IRI) in Subcutaneous Xenograft Tumor Models of Human Squamous Cell Carcinoma and Small Cell Lung Cancers," Poster presented at Aacr Annual Meeting Apr. 5-9, 2014, 6 pages.
Chan D, et al., "PEP02 (Liposome Irinotecan) Effectively Inhibits Human Lung Squamous Cell Carcinoma and Small Cell Lung Cancers in Subcutaneous and Orthotopic Xenograft Tumor Models," J Thoracic Oncology. 6(6)(Suppl 2):S420-1 (2011).
Chan D, et al., "PEP02 (Liposome Irinotecan) Effectively Inhibits Human Squamous Cell Carcinoma and Small Cell Lung Cancers in Subcutaneous and Orthotopic Xenograft Tumor Models." Presentation at the 14th World Conference on Lung Cancer, 2011, 11 pages.
Chan D, et al., "PEP02 (Liposome Irinotecan) Effectively Inhibits Human Squamous Cell Carcinoma and Small Cell Lung Cancers in Subcutaneous and Orthotopic Xenograft Tumor Models." Presentation at Santa Monica Lung Cancer Meeting, 2012, 9 pages.
Chen L, et al., "Phase I Study of Biweekly Liposome Irinotecan (PEP02, MM-398) in Metastatic Colorectal Cancer Failed on First-line Oxaliplatin-based Chemotherapy," J Clin Oncol. 30(4_suppl):Abstract 613 (2012), 6 printed pages.
Chen P, et al., "Comparing Routes of Delivery for Nanoliposomal Irinotecan Shows Superior Anti-Tumor Activity of Local Administration in Treating Intracranial Glioblastoma Xenografts," Neuro Oncol. 15(2):189-97 (2013), Epub Dec. 21, 2012.
Chibaudel B, et al., "PEPCOL: a GERCOR Randomized Phase II Study of Nanoliposomal Irinotecan PEP02 (MM-398) or Irinotecan with Leucovorin/5-Fluorouracil as Second-Line Therapy in Metastatic Colorectal Cancer", Cancer Med. 5(4):676-83 (2016).
Chiesa MD, et al., "Sequential Chemotherapy with Dose-Dense Docetaxel, Cisplatin, Folinic Acid and 5-Fluorouracil (TCF-dd) Followed by Combination of Oxaliplatin, Folinic acid, 5-Fluorouracil and Irinotecan (COFFI) in Metastatic Gastric Cancer: Results of a Phase II Trial," Cancer Chemother Pharmacol. 67(1):41-8 (2011), epub 2010.
Clarke J, et al., "A Phase 1 Trial of Intravenous Liposomal Irinotecan in Patients with Recurrent High-Grade Glioma," Cancer Chemother Pharmacol. 79(3):603-10 (2017).
Clinical Trials Identifier NCT00104754: Jul. 20, 2016 update, first posted Mar. 4, 2005, "Phase II Trial of Liposome Encapsulated SN38 (LE-SN38) in the Treatment of Small Cell Lung Cancer." Retrieved from ClinicalTrials.gov archive, 8 printed pages.
Clinical Trials Identifier NCT00311610: Jun. 29, 2016 update, first posted Apr. 6, 2006, "Phase II Trial of LE SN38 in Patients with Metastatic Colorectal Cancer After Progression on Oxaliplatin." Retrieved from ClinicalTrials.gov archive, 8 printed pages.
Clinical Trials Identifier NCT00734682: Jan. 7, 2015 update, first posted Aug. 14, 2008, "A Phase I Trial of Nanoliposomal CPT-11 (NL CPT-11) in Patients With Recurrent High-Grade Gliomas." Retrieved from ClinicalTrials.gov archive, 6 printed pages.
Clinical Trials Identifier NCT00813072: Mar. 2, 2012 update, first posted Dec. 22, 2008, "A Randomized Phase II Study of PEP02, Irinotecan or Docetaxel as a Second Line Therapy in Patients With Locally Advanced or Metastatic Gastric or Gastroesophageal Junction Adenocarcinoma." Retrieved from ClinicalTrials.gov archive, 9 printed pages.
Clinical Trials Identifier NCT01770353: Aug. 9, 2013 update, "A Pilot Study in Patients Treated with MM-398 to Determine Tumor Drug Levels and to Evaluate the Feasibility of Ferumoxytol Magnetic Resonance Imaging to Measure Tumor Associated Macrophages." Retrieved from ClinicalTrials.gov archive, 3 printed pages.
Clinical Trials Identifier NCT01770353: Apr. 26, 2015 update, "A Pilot Study in Patients Treated with MM-398 to Determine Tumor Drug Levels and to Evaluate the Feasibility of Ferumoxytol Magnetic Resonance Imaging to Measure Tumor Associated Macrophages." Retrieved from ClinicalTrials.gov archive, 4 printed pages.
Clinical Trials Identifier NCT01770353: May 6, 2015 update, "A Pilot Study in Patients Treated with MM-398 to Determine Tumor Drug Levels and to Evaluate the Feasibility of Ferumoxytol Magnetic Resonance Imaging to Measure Tumor Associated Macrophages." Retrieved from ClinicalTrials.gov archive, 4 printed pages.
Clinical Trials Identifier NCT01770353: Mar. 22, 2016 update, "A Pilot Study in Patients Treated with MM-398 to Determine Tumor Drug Levels and to Evaluate the Feasibility of Ferumoxytol Magnetic Resonance Imaging to Measure Tumor Associated Macrophages and to Predict Patient Response to Treatment." Retrieved from ClinicalTrials.gov archive, 4 printed pages.
Clinical Trials Identifier NCT01770353: Jul. 7, 2016 update, "A Pilot Study in Patients Treated with MM-398 to Determine Tumor Drug Levels and to Evaluate the Feasibility of Ferumoxytol Magnetic Resonance Imaging to Measure Tumor Associated Macrophages and to Predict Patient Response to Treatment." Retrieved from ClinicalTrials.gov archive, 4 printed pages.
Clinical Trials Identifier NCT02013336: Feb. 6, 2017 update, first posted Dec. 17, 2013, "Phase 1 Dose-escalating Study of MM-398 (Irinotecan Sucrosofate Liposome Injection) Plus Intravenous Cyclophosphamide in Recurrent or Refractory Pediatric Solid Tumors" Retrieved from ClinicalTrials.gov archive, 6 printed pages.
Clinical Trials Identifier NCT02022644: May 8, 2017 update, first posted Dec. 30, 2013, "A Phase I Study of Convection-Enhanced Delivery of Liposomal-Irinotecan Using Real-Time Imaging With Gadolinium in Patients With Recurrent High Grade Glioma." Retrieved from ClinicalTrials.gov archive, 9 printed pages.
Clinical Trials Identifier NCT02631733: Dec. 15, 2015 update, "A Phase I Study of a Combination of MM-398 and Veliparib in Solid Tumors." Retrieved from ClinicalTrials.gov archive, 6 printed pages.
Clinical Trials Identifier NCT02631733: Feb. 16, 2016 update, "A Phase I Study of a Combination of MM-398 and Veliparib in Solid Tumors." Retrieved from ClinicalTrials.gov archive, 6 printed pages.
Clinical Trials Identifier NCT02631733: Jun. 20, 2016 update, "A Phase I Study of a Combination of MM-398 and Veliparib in Solid Tumors." Retrieved from ClinicalTrials.gov archive, 6 printed pages.
Clinical Trials Identifier NCT02631733: Jun. 21, 2016 update, "A Phase I Study of a Combination of MM-398 and Veliparib in Stolid Tumors." Retrieved from ClinicalTrials.gov archive, 6 printed pages.
Clinical Trials Identifier NCT02631733: Jul. 6, 2016 update, "A Phase I Study of a Combination of MM-398 and Veliparib in Solid Tumors." Retrieved from ClinicalTrials.gov archive, 6 printed pages.
Clinical Trials Identifier NCT02631733: Jul. 11, 2016 update, "A Phase I Study of a Combination of MM-398 and Veliparib in Solid Tumors." Retrieved from ClinicalTrials.gov archive, 6 printed pages.
Clinical Trials Identifier NCT02631733: Jul. 19, 2016 update, "A Phase I Study of a Combination of MM-398 and Veliparib in Solid Tumors." Retrieved from ClinicalTrials.gov archive, 6 printed pages.
Clinical Trials Identifier NCT02631733: Aug. 7, 2016 update, "A Phase I Study of a Combination of MM-398 and Veliparib in Solid Tumors." Retrieved from ClinicalTrials.gov archive, 6 printed pages.
Clinical Trials Identifier NCT02631733: Sep. 21, 2016 update, "A Phase I Study of a Combination of MM-398 and Veliparib in Solid Tumors." Retrieved from ClinicalTrials.gov archive, 6 printed pages.
Clinical Trials Identifier NCT02631733: Oct. 4, 2017 update, first posted Dec. 16, 2015, "A Phase I Study of a Combination of MM-398 and Veliparib in Solid Tumors." Retrieved from ClinicalTrials.gov archive, 10 printed pages.
Clinical Trials Identifier NCT03088813: Sep. 30, 2019 update, first posted Mar. 23, 2017, "Study of Irinotecan Liposome Injection (ONIVYDE®) in Patients With Small Cell Lung Cancer." Retrieved from ClinicalTrials.gov archive, 8 printed pages.
Cortés J, et al., Abstract CT154. "Multicenter Open-Label, Phase II Trial, to Evaluate the Efficacy and Safety of Liposomal Irinotecan (nal-IRI) for Progressing Brain Metastases in Patients with HER2-Negative Breast Cancer (The Phenomenal Study)," In Proceedings of the American Association for Cancer Research Annual Meeting 2018; Apr. 14-18, 2018; Chicago, Illinois. Cancer Res. 2018;78(13 Suppl):Abstract nr CT154, 3 printed pages.
Davidson D, et al., "The PARP Inhibitor ABT-888 Synergizes Irinotecan Treatment of Colon Cancer Cell Lines," Invest New Drugs. 31(2);461-8 (2013) DOI: 10.1007/s10637-012-9886-7; Epub Oct. 9, 2012, 8 pages.

(56) References Cited

OTHER PUBLICATIONS

Dickinson P, et al., "Canine Model of Convection-Enhanced Delivery of Liposomes Containing CPT-11 Monitored with Real-Time Magnetic Resonance Imaging," J. Neurosurg. 108(5):989-98 (2008).

Dickinson P, et al., "Canine Spontaneous Glioma: A Translational Model System for Convection-Enhanced Delivery," Neuro Oncol. 12(9):928-40; Epub 10:1093/neuonc/nog046, 1-13 (2010).

Dósa E, et al., "Magnetic Resonance Imaging of Intracranial Tumors: Intra-Patient Comparison of Gadoteridol and Ferumoxytol," Neuro Oncol. 13(2):251-60 (2011) doi: 10.1093/neuonc/noq172. Epub 2010.

Eckardt J, et al., "Phase III Study of Oral Compared With Intravenous Topotecan as Second-Line Therapy in Small-Cell Lung Cancer," J Clin Oncol. 25(15):2086-92 (2007).

English translation of title and abstract for Hasegawa, Y, "Biomarker as Predictive Safety Testing in Oncology", Igaku No Ayumi (Journal of Clinical and Experimental Medicine), 224(13):1171-4 (2008) (original in Japanese).

Fitzgerald J, et al., "Systems Pharmacology Identification of Tumour Nanoparticle Permeability as Predictor of Clinical Anti-Cancer Activity of MM-398, Nanoliposomal Irinotecan, nal-IRI." Poster presented at 15th International Conference on Systems Biology. Sep. 14-18, 2014, 10 pages.

Fleming D. "Importance of sequence in chemotherapy administration," retrieved from http://www.oncologynurseadvisor.com/advisor-forum/importance-of-sequence-in-chemotherapy-administration/article/378072/ (2014).

Gahramanov S, et al., "Pseudoprogression of Glioblastoma After Chemo- and Radiation Therapy: Diagnosis by Using Dynamic Susceptibility-Weighted Contrast-Enhanced Perfusion MR Imaging with Ferumoxytol versus Gadoteridol and Correlation with Survival," Radiology. 266(3):842-52 (2013). doi: 10.1148/radiol. 12111472. Epub Nov. 30, 2012.

Genther Williams S, et al., "Treatment with the PARP Inhibitor, Niraparib, Sensitizes Colorectal Cancer Cell Lines to Irinotecan Regardless of MSI/MSS Status," Cancer Cell Int. 15(1):14, doi: 10.1186/s12935-015-0162-8 (2015), pp. 1-11.

Gilbert D, et al., "Topoisomerase I Inhibition in Colorectal Cancer: Biomarkers and Therapeutic Targets," Br J Cancer. 106(1):18-24 (2012), doi: 10.1038/bjc.2011.498, Epub Nov. 22, 2011.

Hanna N, et al., "Randomized Phase III Trial Comparing Irinotecan/Cisplatin with Etoposide/Cisplatin in Patients with Previously Untreated Extensive-Stage Disease Small-Cell Lung Cancer," J Clin Oncol. 24(13):2038-43 (2006).

Hare J, et al., "Treatment of Colorectal Cancer Using a Combination of Liposomal Irinotecan (Irinophore C(TM)) and 5-Fluorouracil," PLoS One. 8(4):e62349, doi: 10.1371/journal.pone.0062359, 12 pages (2013).

Hayashi H, et al., "Phase II Study of Bi-Weekly Irinotecan for Patients with Previously Treated HER2-Negative Metastatic Breast Cancer: KMBOG0610B," Breast Cancer. 20(2):131-6 (2013); doi: 10.1007/s12282-011-0316-z. Epub Nov. 29, 2011.

Hayes M, et al., "Assembly of Nucleic Acid-Lipid Nanoparticles from Aqueous-Organic Monophases," Biochim Biophys Acta. 1758(4):429-42 (2006).

Honic A, et al., "Brain Metastases in Breast Cancer—an In Vitro Study to Evaluate New Systemic Chemotherapeutic Options," Anticancer Res. 25(3A):1531-7 (2005).

Huber R, et al., "Efficacy of a Toxicity-Adjusted Topotecan Therapy in Recurrent Small Cell Lung Cancer," Eur Respir J. 27(6):1183-9 (2006).

Hycamtin (topotecan hydrochloride) for injection package insert, revision Feb. 28, 2014, retrieved from https://www.accessdata.fda.gov/drugsatfda_docs/label/2014/020671s020lbl.pdf, 23 pages.

HYCAMTIN (topotecan) for injection package insert, revision Jun. 2, 2015, retrieved from https://www.accessdata.fda.gov/drugsatfda_docs/label/2015/020671s021lbl.pdf, 21 pages.

Kalra A, et al., Abstract 2065: "Magnetic Resonance Imaging with an Iron Oxide Nanoparticle Demonstrates Preclinically the Feasibility of Predicting Intratumoral Uptake and Activity of MM-398, a Nanoliposomal Irinotecan (nal-IRI)." Poster presented at American Association for Cancer Research annual meeting 2014, San Diego, CA, 5 pages.

Kalra A., "Magnetic Resonance Imaging (MRI) to Predict Tumor Drug Delivery and Response to Nanoliposomal Therapy." Presentation presented at Tumor Models Boston 2014, 32 pages.

Kang M, et al., "Activity of MM-398, Nanoliposomal Irinotecan (nal-IRI), in Ewing's Family Tumor Xenografts Is Associated with High Exposure of Tumor to Drug and High SLFN11 Expression," Clin Cancer Res. 21(5):1139-50 (2015).

Kim J, et al., "Efficient Prioritization of Potential Diagnostic Biomarkers Using a Systems Pharmacology Approach: Case Study of MM-398 (Irinotecan sucrosofate liposome injection)." Presentation presented at the Pharmacokinetics UK 2013 Meeting, Oct. 31, 2013, Harrogate, North Yorkshire, 34 pages.

Kim J, et al., "Efficient Prioritization of Potential Diagnostic Biomarkers Using a Systems Pharmacology Approach: Case Study of MM-398, an Irinotecan Sucrosofate Liposome Injection)." Abstract for Pharmacokinetics UK 2013 Meeting, Oct. 30-Nov. 1, 2013, Harrogate, North Yorkshire, 2 pages.

Kim J, et al., "Systems Pharmacology Modeling Identifies Unique Parameters That Drive Tumor SN38 Levels for Liposomal Irinotecan (MM-398) Compared to Irinotecan." Abstract presented at 14th International Conference on Systems Biology; Copenhagen, Denmark; Aug. 29-Sep. 4, 2013, 1 page.

Kim J, et al., "Systems Pharmacology Modeling Identifies Unique Parameters That Drive Tumor SN38 Levels for Liposomal Irinotecan (MM-398) Compared to Irinotecan." Poster presented at 14th International Conference on Systems Biology; Copenhagen, Denmark; Aug. 29-Sep. 4, 2013, 11 pages.

Kim J, et al., Abstract A6. "Sustained Intratumoral Activation of MM-398 Results in Superior Activity Over Irinotecan Demonstrated by Using a Systems Pharmacology Approach, " In: Proceedings of the AACR Special Conference on Chemical Systems Biology: Assembling and Interrogating Computational Models of the Cancer Cell by Chemical Perturbations; Jun. 27-30, 2012; Boston, MA. Cancer Res. 2012;72(13 Suppl):Abstract nr A6, 3 printed pages.

Kim J, et. al., "Systems Pharmacology Based Biomarker Potentially Predicts Clinical Anti-Cancer Activity of MM-398, Nanoliposomal Irinotecan, nal-IRI." Poster presented at American Conference on Pharmacometrics, Oct. 12-15, 2014, 10 pages.

Kirpotin D, et al. "Antibody Targeting of Long-Circulating Lipidic Nanoparticles Does Not Increase Tumor Locatlization but Does Increase Internalization in Animal Models," Cancer Res. 66(13):6732-40 (2006).

Klinz S, et al., Abstract C293: "Irinotecan Sucrosofate Liposome Injection, MM-398, Demonstrates Superior Activity and Control of Hypoxia as Measured Through Longitudinal Imaging Using [18F] FAZA PET Compared to Free Irinotecan in a Colon Adenocarcinoma Xenograft Model." Poster presented at AACR-NCI-EORTC International Conference on Molecular Targets and Cancer Therapeutics on Oct. 19, 2013, 7 pages.

Klinz S, et al.,"MM-302 a HER2-targeted Liposomal Doxorubicin, Shows Binding/Uptake and Efficacy in HER2 2+ Cells and Xenograft Models," Cancer Res. 71:Abstract 3637 (2011), 1 printed page.

Korn R, "Advanced Imaging with Ferumoxytol MRI to Predict Drug Delivery." Presentation presented at Pancreatic Cancer 2014, Feb. 22, 2014, 23 pages.

Koshkaryev A, et al., "Differential Tissue Clearance Results in Improved Therapeutic Index for Nanoliposomal Irinotecan (nal-IRI; Onivyde) when Combined with the PARP Inhibitor Veliparib." Poster presented at AACR Meeting an Apr. 16-20, 2016, 5 pages.

Krauze M, et al., "Convection-Enhanced Delivery of Nanoliposomal CPT-11 (Irinotecan) and PEGylated Liposomal Doxorubicin (Doxil) in Rodent Intracranial Brain Tumor Xenografts," Neuro Oncol. 9(4):393-403 (2007).

Kummar S, et al. "Phase I Study of PARP Inhibitor ABT-888 in Combination with Topotecan in Adults with Refractory Solid Tumors and Lymphomas," Cancer Res. 71(17):5626-34 (2011), Epub Jul. 27, 2011.

(56) References Cited

OTHER PUBLICATIONS

Landry R, et al., "Pharmacokinetic Study of Ferumoxytol: A New Iron Repalcement Therapy in Normal Subjects and Hemodialysis Patients," Am J Nephrol. 25(4):400-10 (2005).

Lee H, et al., A Novel 64Cu-Liposome PET Agent (MM-DX-929) Predicts Response to Liposomal Chemotherapeutics in Preclinical Breast Cancer Models, Cancer Res. 72(24 Suppl): Abstract nrP4-02-05 (2012), San Antonio Breast Cancer Symposium, Dec. 4-8, 2012, 2 printed pages.

Lee H, et al., A Novel 64Cu-Liposome PET Agent (MM-DX-929) Predicts Response to Liposomal Chemotherapeutics in Preclinical Breast Cancer Models, Poster presented at San Antonio Breast Cancer Symposium, Dec. 4-8, 2012, 13 pages.

Lee H, et al., "Delivery and Anti-Tumor Activity of Nanoliposomal Irinotecan (Nal-IRI, MM-398) in Metastatic Xenograft Models of Triple Negative Breast Cancer." Poster presented at 39th Annual San Antonio Breast Cancer Symposium, Dec. 6-10, 2016, 8 pages.

Leonard S, et al., "Extended Topoisomerase 1 Inhibition Through Liposomal Irinotecan Results in Improved Efficacy over Topotecan and Irinotecan in Models of Small-Cell Lung Cancer," Anti-Cancer Drugs. 28(10):1086-96 (2017).

Leonard S, et al., "Irinotecan Liposome Injection has Greater Anti-Tumor Activity than Topotecan and Irinotecan in Mouse Models of Small Cell Lung Cancer," Poster presented at AACR 110th Annual World Congress 2017, Washington, DC, Apr. 1-5, 2017, 6 pages.

Leonard S, et al., "Preclinical Support for Evaluation of Irinotecan Liposome Injection (nal-IRI, MM-398) in Small Cell Lung Cancer," Abstracts from the IASLC 17th World Conference on Lung Cancer held Dec. 4-7, 2016, J Thoracic Oncology. 12(1)(Suppl):S699 (2016), 1 page.

Leonard S, et al., "Preclinical Support for Evaluation of Irinotecan Liposome Injection (nal-IRI, MM-398) in Small Cell Lung Cancer," Poster presented at 17th World Conference on Lung Cancer, Vienna, Austria, Dec. 4-7, 2016, 5 pages.

Lorusso P, et al., "Abstract CT325: Combination of the PARP Inhibitor Veliparib (ABT888) with Irinotecan in Patients with Triple Negative Breast Cancer: Preliminary Activity and Signature of Response." Proceedings: AACR 106th Annual Meeting, Apr. 18-22, 2015, Philadelphia, PA (2015), 3 printed pages.

Lorusso P, et al., "Phase I Safety, Pharmacokinetic, and Pharmacodynamic Study of the Poly(ADP-ribose) Polymerase (PARP) Inhibitor Veliparib (ABT-888) in Combination with Irinotecan in Patients with Advanced Solid Tumors," Clin Cancer Res. 22(13):3227-37 (2016), Epub Feb. 3, 2016.

Lorusso P, et al., "Phase I Study of the Safety, Pharmacokinetics (PK), and Pharmacodynamics (PD) of the Poly(ADP-ribose) Polymerase (PARP) Inhibitor Veliparib (ABT-888; V) in Combination with Irinotecan (CPT-11; Ir) in Patients (pts) with Advanced Solid Tumors," Supplement ASCO Meeting Library, Jun. 5, 2011, 1 page.

Lorusso P, et al., "Phase I Study of the Safety, Pharmacokinetics (PK), and Pharmacodynamics (PD) of the Poly(ADP-ribose) Polymerase (PARP) Inhibitor Veliparib (ABT-888; V) in Combination with Irinotecan (CPT-11; Ir) in Patients (pts) with Advanced Solid Tumors," Journal of Clinical Oncology 29.15_suppl: Abstract 3000 (2011), 3 printed pages.

Lorusso P, et al., "Phase I Study of the Safety, Pharmacokinetics, and Pharmacodynamics of the Poly(ADP-ribose) Polymerase (PARP) Inhibitor Veliparib (ABT-888) in Combination with Irinotecan (CPT-11) in Patients with Advanced Solid Tumors," Presentation presented at American Society of Clinical Oncology 2011 Meeting, 37 pages.

LYNPARZA™ (olaparib) capsules package insert, ©AstraZeneca. 2014, Revised: Dec. 2014, 6 pages.

Mamot C, et al., "Epidermal Growth Factor Receptor-Targeted Immunoliposomes Significantly Enhance the Efficacy of Multiple Anticancer Drugs In Vivo," Cancer Res. 65(24):11631-8 (2005).

Mamot C, et al., "Extensive Distribution of Liposomes in Rodent Brains and Brain Tumors Following Convection-Enhanced Delivery," J Neurooncol. 68(1):1-9 (2004).

Masuda N, et al., "CPT-11: A New Derivative of Camptothecin for the Treatment of Refractory or Relapsed Small-Cell Lung Cancer," J Clin Oncol. 10(8):1225-9 (1992).

Merrimack Pharmaceuticals, "Merrimack Pharmaceuticals Initiates Cross-Tumor Study to Investigate Potential Predictive Response Markers for a Developmental Nanotherapeutic Chemotherapy," Dec. 19, 2012. Retrieved from http://investors.merrimack.com/news-releases/news-release-details/merrimack-pharmaceuticals-initiates-cross-tumor-study, 2 printed pages.

Messerer C, et al., "Liposomal Irinotecan: Formulation Development and Therapeutic Assessment in Murine Xenograft Models of Colorectal Cancer," Clin Cancer Res. 10(19):6638-49 (2004).

Miller M, et al. "Predicting Therapeutic Nanomedicine Efficacy Using a Companion Magnetic Resonance Imaging Nanoparticle," Sci Transl Med. 7:314ra183 (2015), pp. 1-12, Editor's Summary (1 page), and Supplementary Materials (24 pages).

Miller M, et al., "Tumour-Associated Macrophages Act as a Slow-Release Reservoir of Nano-Therapeutic Pt(IV) Pro-Drug," Nat. Commun. 6:8692, doi: 10.1038/ncomms9692, 13 pages (2015), Supplementary Figures 1-9 (9 pages), Supplementary Table 1 (1 page), and Supplementary References (1 page).

Mirtsching B, et al., "Irinotecan-induced Immune Thrombocytopenia," Am J Med Sci. 347(2):167-9 (2014).

Pavai S and Yap S, "The Clinical Significance of Elevated Levels of Serum CA19-9," Med J Malaysia. 58(5):667-72 (2003).

Paz-Ares L, et al., "Resilient part 2: An Open-Label, Randomized, Phase 3 Study of Liposomal Irinotecan Injection in Patients With Small-Cell Lung Cancer Who Have Progressed With Platinum-Based First-Line Therapy." Poster presented at the American Society of Clinical Oncology (ASCO) Annual Conference, virtual format, May 29-Jun. 2, 2020, 7 pages.

Paz-Ares L, et al., Abstract TPS9081. "Resilient part II: An Open-Label, Randomized, Phase III Study of Liposomal Irinotecan Injection in Patients With Small-Cell Lung Cancer Who Have Progressed With Platinum-Based First-Line Therapy," J Clin Oncol. 38(15_Suppl):TPS9081 DOI: 10.1200/JCO.2020.38.15_suppl.TPS9081 (2020), 2 printed pages.

Pillai G, "Nanomedicines for Cancer Therapy: An Update of FDA Approved and Those under Various Stages of Development," SOJ Pharm Pharm Sci. 1(2):13 (2014), 13 pages.

Ponce S, et al., "RESILIENT Part 1: Pharmacokinetics of Second-Line (2L) Liposomal Irinotecan in Patients with Small Cell Lung Cancer (SCLC)," Poster presented at the European Society for Medical Oncology (ESMO) Virtual Congress 2020, virtual format, Sep. 19-21, 2020, 8 pages.

Ponce S, et al., Abstract 1793P. "RESILIENT Part 1: Pharmacokinetics of Second-Line (2L) Liposomal Irinotecan in Patients with Small Cell Lung Cancer (SCLC)," Ann Oncol. 31(S4):S1038-S1039 (2020).

Poplin E, et. al.,"Phase III Southwest Oncology Group 9415/Intergroup 0153 Randomized Trial of Fluorouracil, Leucovorin, and Levamisole Versus Fluorouracil Continuous Infusion and Levamisole for Adjuvant Treatment of Stage III and High-Risk Stage II Colon Cancer," J Clin Oncol. 23(9):1819-25 (2005).

Ramsay E, et. al., "Irinophore C: A Liposome Formulation of Irinotecan With Substantially Improved Therapeutic Efficacy Against a Panel of Human Xenograft Tumors," Clin Cancer Res. 14(4):1208-17 (2008).

Rea D, et al., "A Phase I/II and Pharmacokinetic Study of Irinotecan in Combination with Capecitabine as First-Line Therapy for Advanced Colorectal Cancer," Ann Oncol. 16(7):1123-32 (2005).

Reynolds J, et al., "HER2-Targeted Liposomal Doxorubicin Displays Enhanced Anti-Tumorigenic Effects Without Associated Cardiotoxicity," Toxicol Appl Pharmacol. 262(1):1-10 (2012).

Rosenecker J, et al., "Increased Liposome Extravasation in Selected Tissues: Effect of Substance P," Proc Natl Acad Sci U S A. 93(14):7236-41 (1996).

Roth A, et al., "Anti-CD166 Single Chain Antibody-Mediated Intracellular Delivery of Liposomal Drugs to Prostate Cancer Cells," Mol Cancer Ther. 6(10):2737-46 (2007).

Rothenberg M, et. al., "Alternative Dosing Schedules for Irinotecan," Oncology. 12(8 Suppl 6):68-71 (1998). Available at cancernetwork.com/view/alternative-dosing-schedules-irinotecan, 16 printed pages.

(56) References Cited

OTHER PUBLICATIONS

Rubesova E, et al., "Gd-Labeled Liposomes for Monitoring Liposome-Encapsulated Chemotherapy: Quantification of Regional Uptake in Tumor and Effect on Drug Delivery," Acad Radiol. 9(Suppl 2):S525-7 (2002).

Sachdev J, et al., "Phase I Expansion Study of Irinotecan Liposome Injection (nal-IRI) in Patients with Metastatic Breast Cancer (mBC)." Poster presented at the American Association for Cancer Research Annual Meeting 2019; Mar. 29-Apr. 3, 2019; Atlanta, GA, 9 printed pages.

Saif M, et. al., "Pharmacokinetically Guided Dose Adjustment of 5-Fluorouracil: A Rational Approach to Improving Therapeutic Outcomes," J Natl Cancer Inst. 101(22):1543-52 (2009).

Saltz L, "Clincial Use of Irinotecan: Current Status and Future Considerations," Oncologist. 2(6):402-9 (1997).

Saltz LB, et. al., "Phase I Clinical and Pharmacokinetic Study of Irinotecan, Fluorouracil, and Leucovorin in Patients With Advanced Solid Tumors," J Clin Oncol. 14(11):2959-67 (1996).

Satoh T, et. al., "Pharmacokinetic Assessment of Irinotecan, SN-38, and SN-38-Glucuronide: A Substudy of the FIRIS Study," Anticancer Res. 33(9):3845-53 (2013).

Scheithauer W, et. al., "Fluorouracil Plus Racemic Leucovorin Versus Fluorouracil Combined With the Pure I-Isomer of Leucovorin for the Treatment of Advanced Colorectal Cancer: A Randomized Phase III Study," J Clin Oncol. 15(3):908-14 (1997).

Schroen A, et. al., "Challenges to Accrual Predictions to Phase III Cancer Clinical Trials: A Survey of Study Chairs and Lead Statisticians of 248 NCI Sponsored Trials," Clin Trials. 8(5):591-600 (2011), author manuscript version, 14 pages.

Serwer L, et al., "Investigation of Intravenous Delivery of Nanoliposomal Topotecan for Activity Against Orthotopic Glioblastoma Xenografts," Neuro Oncol. 13(12):1288-95 (2011).

Skof E, et. al., "Capecitabine Plus Irinotecan (XELIRI Regimen) Compared to 5-FU/LV Plus Irinotecan (FOLFIRI Regimen) as Neoadjuvant Treatment for Patients With Unresectable Liver-Only Metastases of Metastatic Colorectal Cancer: A Randomised Prospective Phase II Trial," BMC Cancer. 9:120 doi: 101186/1471-2407-9-120 (2009), 9 pages.

Spigel D, et al., "Liposomal Irinotecan in Adults with Small Cell Lung Cancer Who Progressed on Platinum-Based Therapy: Subgroup Analyses by Platinum Sensitivity." Poster presented at the International Association for the Study of Lung Cancer (IASLC) 2020 North America Conference on Lung Cancer (NACLC): virtual meeting, Oct. 16-17, 2020, 9 pages.

Spigel D, et al., "RESILIENT Part 1, An Open-Label, Safety Run-In of Liposomal Irinotecan in Adults With Small Cell Lung Cancer (SCLC) Who Have Progressed With Platinum-Based First-Line Therapy: Subgroup Analyses by Platinum Sensitivity." Poster presented at the American Society of Clinical Oncology (ASCO) Annual Conference, virtual format, May 29-Jun. 2, 2020, 6 pages.

Spigel D, et al., Abstract 9069. "RESILIENT Part I, An Open-Label, Safety Run-In of Liposomal Irinotecan in Adults With Small Cell Lung Cancer (SCLC) Who Have Progressed With Platinum-Based First-Line (1L) Therapy: Subgroup Analyses by Platinum Sensitivity," J Clin Oncol. 38(15_Suppl):9069 DOI: 10.1200/JCO.2020.38.15_suppl.9069 (2020), 2 printed pages.

Spigel D, et al., Abstract MO01.39. "Liposomal Irinotecan in Adults with Small Cell Lung Cancer Who Progressed on Platinum-Based Therapy: Subgroup Analyses by Platinum Sensitivity," IASLC 2020 North America Conference on Lung Cancer Abstracts, p. 80 (2020).

Stathopoulos G and Boulikas T, "Lipoplatin Formulation Review Article," J Drug Deliv. 2012:581363, Article ID 581363, doi:10.1155/2012/581363, Epub 2011, 10 pages.

Stathopoulos G, et. al., "Liposomal Oxaliplatin in the Treatment of Advanced Cancer: A Phase I Study," Anticancer Res. 26(2B):1489-93 (2006).

Stylianopoulos T and Jain R, "Combining Two Strategies to Improve Perfusion and Drug Delivery in Solid Tumors," Proc Natl Acad Sci USA. 110(46):18632-7 (2013).

Takano S, et. al., "Metronomic Treatment of Malignant Glioma Xenografts with Irinotecan (CPT-11) Inhibits Angiogenesis and Tumor Growth," J Neurooncol. 99(2):177-85 (2010).

Tardi P, et. al., "Coencapsulation of Irinotecan and Floxuridine Into Low Cholesterol-Containing Liposomes That Coordinate Drug Release In Vivo," Biochim Biophys Acta. 1768(3):678-87 (2007). Epub 2006.

Toutain P and Bousquet-Melou A, "Plasma terminal half-life," J Vet Pharmacol Ther. 27(6):427-39 (2004).

Tsavaris N, et. al., "Second-Line Treatment With Oxaliplatin, Leucovorin and 5-Fluorouracil in Gemcitabine-Pretreated Advanced Pancreatic Cancer: A Phase II Study," Invest New Drugs. 23(4):369-75 (2005).

Vaage J, et. al., "Therapy of a Xenografted Human Colonic Carcinoma Using Cisplatin or Doxorubicin Encapsulated in Long-Circulating Pegylated Stealth Liposomes," Int J Cancer. 80(1):134-7 (1999).

Veal G, et. al., "A Phase I Study in Paediatric Patients to Evaluate the Safety and Pharmacokinetics of SPI-77, A Liposome Encapsulated Formulation of Cisplatin," Br J Cancer 84(8):1029-35 (2001).

Venook A, "Critical Evaluation of Current Treatments in Metastatic Colorectal Cancer," Oncologist. 10(4):250-61 (2005).

Villalona-Calero M, et. al., "Phase I Study of Low-Dose Suramin as a Chemosensitizer in Patients With Advanced Non-Small Cell Lung Cancer," Clin Cancer Res. 9(9):3303-11 (2003).

Walker S, et. al., "Simulation of Y-Site Compatibility of Irinotecan and Leucovorin at Room Temperature in 5% Dextrose in Water in 3 Different Containers," Can J Hosp Pharm. 58(4):212-22 (2005).

Wang W, et. al., "Weekly 24-Hour Infusion of High-dose 5-Fluorouracil and Leucovorin in Patients with Advanced Colorectal Cancer: Taiwan Experience," Jpn J Clin Oncol. 28(1):16-19 (1998).

Weng K, et al., "Convection-Enhanced Delivery of Targeted Quantum Dot-Immunoliposome Hybrid Nanoparticles to Intracranial Brain Tumor Models," Nanomedicine (Lond). 8(12):1913-25. 2013.

Weng K, et al., "Targeted Tumor Cell Internalization and Imaging of Multifunctional Quantum Dot-Conjugated Immunoliposomes in Vitro and in Vivo," Nano Lett. 8(9):2851-7 (2008).

Willett C, et. al., "Direct Evidence That the VEGF-Specific Antibody Bevacizumab Has Antivascular Effects in Human Rectal Cancer," Nat Med. 10(2):145-7 (2004), author manuscript version, 7 pages.

Wulaningsih W, et. al., "Irinotecan Chemotherapy Combined With Fluoropyrimidines Versus Irinotecan Alone for Overall Survival and Progression-Free Survival in Patients With Advanced and/or Metastatic Colorectal Cancer," Cochrane Database Syst Rev. 2:CD008593 doi: 10.1002/14651858.CD008593.pub3. (2016), 36 pages.

Xeloda (capecitabine) package insert, Roche, revised Nov. 2000, 19 pages.

Yamashita Y, et al., "Convection-Enhanced Delivery of a Topoisomerase I Inhibitor (Nanoliposomal Topotecan) and a Topoisomerase II Inhibitor (Pegylated Liposomal Doxorubicin) in Intracranial Brain Tumor Xenografts," Neuro Oncol. 9(1):20-8 (2007). Epub 2006.

Yamashita Y, et. al., "Convection-Enhanced Delivery of Liposomal Doxorubicin in Intracranial Brain Tumor Xenografts," Targ Oncol. 1:79-85 (2006).

Yang W, et. al. "Development of a Method to Quantify Total and Free Irinotecan and 7-ethyl-10-hydroxycamptothecin (SN-38) for Pharmacokinetic and Bio-Distribution Studies After Administration of Irinotecan Liposomal Formulation," Asian J Pharm Sci. 14(6):687-97 (2019). Epub 2018.

Yang W, et. al., "The Influence of Trapping Agents on the Antitumor Efficacy of Irinotecan Liposomes: Head-to-Head Comparison of Ammonium Sulfate, Sulfobutylether-β-Cyclodextrin and Sucrose Octasulfate," Biomater Sci., 7(1):419-28 (2019).

Yang, et. al., "Oxaliplatin Long-Circulating Liposomes Improved Therapeutic Index of Colorectal Carcinoma," BMC Biotechnology. 11:21 doi: 10.1186/1472-6750-11-21 (2011), 8 pages.

EP2861210: Proprietor's statement of grounds of appeal to opposition decision dated Dec. 30, 2019, 35 pages.

EP2861210: Proprietor's Main and Auxiliary Requests MR, AR1, AR2, and AR3 with Proprietor's Statement of Grounds of Appeal in Opposition Proceedings filed Dec. 30, 2019, 4 pages.

EP2861210: Proprietor's statement of grounds of appeal to opposition decision dated Dec. 30, 2019, D23 (Declaration of Amy

(56) References Cited

OTHER PUBLICATIONS

McKee M.D.) including D23A (Hoos W, et al., "Pancreatic Cancer Clinical Trials and Accrual in the United Sates." J Clin Oncol. 31(27):3432-8 (2013) and accompanying Appendix Table A1, Table A2, and Figure A1) and D23B (BIO Industry Analysis: Clinical Development Success Rates 2006-2015, Jul. 2016), 44 total pages.

FP2861210: Proprietor's statement of grounds of appeal to opposition decision dated Dec. 30, 2019, D24 (Declaration of Bruce Belanger, Ph.D.), 2 pages.

EP2861210: Reply to proprietor's grounds of appeal following opposition and cover letter, dated Jul. 27, 2020, 35 pages.

EP2861210: Reply to proprietor's grounds of appeal to opposition decision dated Jul. 27, 2020, D15c (EU clinical trial database for NAPOLI-1 study from Oct. 12, 2012, corresponds to D15b), 10 pages.

EP2861210: Reply to proprietor's grounds of appeal to opposition decision dated Jul. 27, 2020, D25 (Chen P, et al., "Comparing Routes of Delivery for Nanoliposomal Irinotecan Shows Superior Anti-Tumor Activity of Local Administration in Treating Intracranial Glioblastoma Xenografts," Neuro Oncol. 15(2):189-97 (2013), Epub Dec. 21, 2012).

EP2861210: Reply to proprietor's grounds of appeal to opposition decision dated Jul. 27, 2020, D26 (Drummond D, et al., "Development of a Highly Active Nanoliposomal Irinotecan Using a Novel Intraliposomal Stabilization Strategy," Cancer Res. 66(6):3271-77 (2006)).

EP2861210: Reply to proprietor's grounds of appeal to opposition decision dated Jul. 27, 2020, D27 (Roy A, et al., "A Randomized Phase II Study of PEP02 (MM-398), Irinotecan or Docetaxel as a Second-Line Therapy in Patients With Locally Advanced or Metastatic Gastric or Gastro-Oesophageal Junction Adenocarcinoma," Ann Oncol. 24(6):1567-73 (2013)).

EP2861210: Reply to proprietor's grounds of appeal to opposition decision dated Jul. 27, 2020, D28 (Svenson S, "Clinical Translation of Nanomedicines," Current Opinion in Solid State and Materials Science. 16(6):287-294 (2012), article in press version, 7 pages).

EP2861210: Reply to proprietor's grounds of appeal to opposition decision dated Jul. 27, 2020, D29 (Makrilia N, et al., "Treatment for Refractory Pancreatic Cancer. Highlights from the '2011 ASCO Gastrointestinal Cancers Symposium'. San Francisco, CA, USA, Jan. 20-22, 2011," J Pancreas. 12(2):110-3 (2011)).

EP2861210: Reply to proprietor's grounds of appeal to opposition decision dated Jul. 27, 2020, D30 (Chen L, et al., "Phase I Study of Biweekly Liposome Irinotecan (PEP02, MM-398) in Metastatic Colorectal Cancer Failed on First-line Oxaliplatin-based Chemotherapy," J Clin Oncol. 30(4_suppl):Abstract 613 (2012), 5 printed pages.).

EP2861210: Reply to proprietor's grounds of appeal to opposition decision dated Jul. 27, 2020, D31 (Cunningham D, et al., "Randomized Phase II Study of PEP02, Irinotecan, or Docetaxel as a Second-Line Therapy in Gastric or Gastroesophageal Junction Adenocarcinoma," J Clin Oncol. 29(4_supp):Abstract 6 (2011), 5 printed pages).

EP2861210: Reply to proprietor's grounds of appeal to opposition decision dated Jul. 27, 2020, D32 (Gerber D, "Miscellaneous Agents—Cytotoxics and Hormonal Agents," J Thorac Oncol. 7(12 Suppl 5):S387-9 (2012)).

EP2861210: Reply to proprietor's grounds of appeal to opposition decision dated Jul. 27, 2020, D33 (Noble C, et al., "Novel Nanoliposomal CPT-11 Infused by Convection-Enhanced Delivery in Intracranial Tumors: Pharmacology and Efficacy," Cancer Res. 66(5):2801-6 (2006)).

EP2861210: Reply to proprietor's grounds of appeal to opposition decision dated Jul. 27, 2020, D34 (Krauze M, et al., "Convection-Enhanced Delivery of Nanoliposomal CPT-11 (Irinotecan) and PEGylated Liposomal Doxorubicin (Doxil) in Rodent Intracranial Brain Tumor Xenografts," Neuro Oncol. 9(4):393-403 (2007)).

EP2861210: Reply to proprietor's grounds of appeal to opposition decision dated Jul. 27, 2020, D35 (Mullard A, "How Much Do Phase III Trials Cost?" Nat Rev Drug Discov. 17(11):777 (2018)).

EP2861210: Reply to proprietor's grounds of appeal to opposition decision dated Jul. 27, 2020, D36 (The Medicines or Human Use (Clinical Trials) Regulations, 2004, 86 pages).

Abrams T, et al., "Patterns of Chemotherapy Use in a U.S.-Based Cohort of Patients with Metastatic Pancreatic Cancer," Oncologist. 22(8):925-933 (2017).

Abushahin L, et al., "Multivariable Analysis of Real-World Clinical Outcomes Associated With Dose Reductions (DRs) for Patients (pts) With Metastatic Pancreatic Ductal Adenocarcinoma (mPDAC) Treated with Liposomal Irinotecan." Poster presented at the European Society for Medical Oncology Virtual Congress Sep. 19-21, 2020, 6 pages.

Abushahin L, et al., Abstract 1534P. "Multivariable Analysis of Real-World Clinical Outcomes Associated With Dose Reductions (DRs) for Patients (pts) With Metastatic Pancreatic Ductal Adenocarcinoma (mPDAC) Treated with Liposomal Irinotecan" Ann Oncol. 31(Suppl_4):S881-S897 10.1016/annonc/annonc285 (2020), 2 printed pages.

Abushahin L, et al., Abstract e16780. "Real-World Dosing, Management, and Clinical Outcomes of Patients (pts) With Metastatic Pancreatic Adenocarcinoma (mPDAC) Treated With Liposomal Irinotecan," J Clin Oncol. 38(15_Suppl):e16780 DOI: 10.1200/JCO. 2020.38.15_suppl.e16780 (2020), 2 printed pages.

Ahn D, et al., "Real-World Dosing Patterns of Patients With Metastatic Pancreatic Cancer (mPC) Treated With Liposomal Irinotecan (nal-IRI) in US Oncology Clinics." Poster presented at the European Society for Medical Oncology (ESMO), Munich, Germany, Oct. 19-23, 2018, 8 pages.

Ahn D, et al., Abstract 735P. "Real-World Dosing Patterns of Patients (pts) With Metastatic Pancreatic Cancer (mPC) Treated With Liposomal Irinotecan (nal-IRI) in US Oncology Clinics," Ann Oncol. 29(Suppl_8):viii251 doi:10.1093/annonc/mdy282 (2018).

Amzal B, et al., "Imputing Missing Values to Estimate Health-Related Quality of Life (HR-QoL) in Metastatic Pancreatic Cancer Treated With 5-Fluorouracil and Leucovorin, With and Without Liposomal Irinotecan (nal-IRI)." Poster presented at the International Society for Pharmacoeconomics and Outcomes Research (ISPOR) Annual Meeting, Boston, MA, May 20-24, 2017, 6 pages.

Amzal B, et al., Abstract PCN179. "Imputing Missing Values to Estimate Health-Related Quality of Life (HR-QoL) in Metastatic Pancreatic Cancer (mpc) Treated With 5-Fluorouracil and Leucovorin, With and Without Liposomal Irinotecan (nal-IRI)," Value in Health. 20(5):A119 (2017).

Araneo M, et. al., "Biweekly Low-Dose Sequential Gemcitabine, 5-Fluorouracil, Leucovorin, and Cisplatin (GFP): A Highly Active Novel Therapy for Metastatic Adenocarcinoma of the Exocrine Pancreas," Cancer Invest. 21(4):489-96 (2003).

Atkins K, et al., "A Phase I Study of Nanoliposomal Irinotecan and 5-Fluorouracil/Folinic Acid in Combination With Interleukin-1-alpha Antagonist for Advanced Pancreatic Cancer Patients With Cachexia (OnFX)." Poster presented at the American Society of Clinical Oncology Gastrointestinal Cancers Symposium (ASCO GI), San Francisco, CA, Jan. 23-25, 2020, 1 page.

Atkins K, et al., Abstract TPS780. "A Phase I Study of Nanoliposomal Irinotecan and 5-Fluorouracil/Folinic Acid in Combination With Interleukin-1-alpha Antagonist for Advanced Pancreatic Cancer Patients With Cachexia (OnFX)," J Clin Oncol. 38(4_Suppl):TPS780 DOI: 10.1200/JCO.2020.38.4_suppl.TPS780 (2020), 2 printed pages.

Barbier S, et al., Abstract e16724. "Differentiation of Liposomal Irinotecan From Dose-Dense Non-Liposomal Irinotecan in Patient-Derived Pancreatic Cancer Xenograft Tumor Models," J Clin Oncol. 38(15_Suppl):e16724 DOI: 10.1200/JCO.2020.38.15_suppl. e16724 (2020), 5 printed pages.

Barzi A, et al., Abstract e16229. "Real World Outcomes of Metastatic Pancreatic Cancer (mPC) Patients (pts) Treated With Liposomal Irinotecan (nal-IRI) in the US," J Clin Oncol. 36(15_Suppl):e16229 DOI: 10.1200/JCO.2018.36.15_suppl.e16229 (2018), 2 printed pages.

Becker C, et al., "Multivariate Analysis of Health-Related Quality of Life (HR-QoL) in Metastatic Pancreatic Cancer Treated with 5-Fluorouracil and Leucovorin (5-FU/LV), With and Without Liposomal Irinotecan (nal-IRI)." Poster presented at the International Society

(56) References Cited

OTHER PUBLICATIONS for Pharmacoeconomics and Outcomes Research (ISPOR) Annual Meeting, Boston, MA, May 20-24, 2017, 7 pages.
Becker C, et al., Abstract PCN182. "Multivariate Analysis of Health-Related Quality of Life (HR-QoL) in Metastatic Pancreatic Cancer (mPC) Treated with 5-Fluorouracil and Leucovorin, With and Without Liposomal Irinotecan (nal-IRI)," Value in Health. 20(5):A120 (2017).
Becker C, et al., Abstract PCN58. "Budget Impact Analysis of Nanoliposomal Irinotecan for Treatment of Pancreatic Cancer Following Progression on Gemcitabine—A US Payer Perspective," Value in Health. 19(7):A718-A719 (2016).
Blanc J, et al., "Subgroup Analysis by Prior Non-Liposomal Irinotecan Therapy in NAPOLI-1: A Phase 3 Study of nal-IRI ± 5-Fluorouracil/Leucovorin in Patients With Metastatic Pancreatic Ductal Adenocarcinoma Previously Treated with Gemcitabine-Based Therapy." Poster presented at the European Society for Medical Oncology Asia 2017 Congress, Singapore, Nov. 17-19, 2017, 8 pages.
Blanc J, et al., Abstract 228P. "Subgroup Analysis by Prior Non-Liposomal Irinotecan Therapy in NAPOLI-1: A Phase 3 Study of nal-IRI ± 5-Fluorouracil/Leucovorin in Patients With Metastatic Pancreatic Ductal Adenocarcinoma Previously Treated with Gemcitabine-Based Therapy," Ann Oncol. 28(Suppl_10):x67-x68 doi:10.1093/annonc/mdx660 (2017).
Blanc J, et al., Abstract PD-18. "Subgroup Analysis by Prior Non-Liposomal Irinotecan Therapy in NAPOLI-1: A Phase 3 Study of nal-IRI ± 5-Fluorouracil/Leucovorin in Patients With Metastatic Pancreatic Ductal Adenocarcinoma Previously Treated With Gemcitabine-Based Therapy," Ann Oncol. 28(Suppl_3):7 doi:10.1093/annonc/mdx263 (2017).
BlueCross Blue Shield of North Carolina Corporate Medical Policy, Bevacizumab in Advanced Adenocarcinoma of the Pancreas, File Name: bevacizumab_in_advanced_adenocarcinoma_of_the_pancreas, Origination: Mar. 2010, Last review: Feb. 2019, 5 pages.
Boeck S and Heinemann V, "Second-Line Therapy in Gemcitabine-Pretreated Patients With Advanced Pancreatic Cancer," J Clin Oncol. 26(7):1178-9 (2008).
Brus C and Saif M, "Second Line Therapy for Advanced Pancreatic Adenocarcinoma: Where Are We and Where Are We Going?," J Pancreas (Online) 11(4):321-3 (2010).
Burris H and Rocha-Lima C, "New Therapeutic Directions for Advanced Pancreatic Cancer: Targeting the Epidermal Growth Factor and Vascular Endothelial Growth Factor Pathways," Oncologist. 13(3):289-98 (2008).
Cascinu S, et al., "Pancreatic Cancer: ESMO Clinical Practice Guidelines for Diagnosis, Treatment and Follow-up," Ann Oncol. 21(Suppl 5):v55-v58 (2010).
Cerenzia W, et al., Abstract e16233. "Identifying Continuing Educational Needs Among Oncologists in Managing Patients With Pancreatic Cancer," J Clin Oncol. 36(15_Suppl):e16233 DOI: 10.1200/JCO.2018.36.15_suppl.e16233 (2018), 2 printed pages.
Chen L-T, et al., "CA19-9 Decrease and Overall Survival (OS) in the NAPOLI-1 Trial of Liposomal Irinotecan (nal-IRI) ± 5-Fluorouracil and Leucovorin (5-FU/LV) in Metastatic Pancreatic Ductal Adenocarcinoma (mPDAC) Previously Treated With Gemcitabine-Based Therapy." Poster presented at the European Society for Medical Oncology (ESMO) World Congress on Gastrointestinal Cancer, Barcelona, Spain, Jun. 28-Jul. 1, 2017, 5 pages.
Chen L-T, et al., "CA19-9 Decrease and Overall Survival in the NAPOLI-1 Trial of Liposomal Irinotecan (nal-IRI) ± 5-Fluorouracil and Leucovorin (5-FU/LV) in Metastatic Pancreatic Ductal Adenocarcinoma Previously Treated With Gemcitabine-Based Therapy." Poster presented at the European Society for Medical Oncology Asia 2017 Congress, Singapore, Nov. 17-19, 2017, 8 pages.
Chen L-T, et al., "Early Dose Reduction/Delay and the Efficacy of Liposomal Irinotecan With Fluorouracil and Leucovorin in Metastatic Pancreatic Ductal Adenocarcinoma (mPDAC): A Post Hoc Analysis of NAPOLI-1," Pancreatology. 21(1):192-9 (2021). Epub 2020.

Chen L-T, et al., "Efficacy and Safety of Liposomal Irinotecan (nal-IRI) + 5-Fluorouracil and Leucovorin in Patients With Metastatic Pancreatic Ductal Adenocarcinoma Who Previously Received Gemcitabine-Based Therapy: Post Hoc Analysis of the NAPOLI-1 Trial." Poster presented at the American Society of Clinical Oncology Gastrointestinal Cancers Symposium (ASCO GI), San Francisco, CA, Jan. 19-21, 2017, 9 pages.
Chen L-T, et al., "Final Results of NAPOLI-1: A Phase 3 Study of nal-IRI (MM-398) ± 5-Fluorouracil and Leucovorin (5-FU/LV) vs 5-FU/LV in Metastatic Pancreatic Ductal Adenocarcinoma (mPDAC) Previously Treated With Gemcitabine-Based Therapy." Poster presented at the European Society for Medical Oncology (ESMO) Annual Congress, Copenhagen, Denmark, Oct. 7-11, 2016, 8 pages.
Chen L-T, et al., "Impact of Dose Reduction or Dose Delay on the Efficacy of Liposomal Irinotecan (nal-IRI)+5-Fluorouracil/Leucovorin (5-FU/LV): Survival Analysis From NAPOLI-1." Poster presented at the European Society for Medical Oncology (ESMO) Annual Congress, Munich, Germany, Oct. 19-23, 2018, 9 pages.
Chen L-T, et al., "The Prognostic Value of the Modified Glasgow Prognostic Score (mGPS) in Predicting Overall Survival (OS) in Patients With Metastatic Pancreatic Ductal Adenocarcinoma (mPDAC) Receiving Liposomal Irinotecan (nal-IRI)+5-Fluorouracil and Leucovorin (5-FU/LV)." Poster presented at the European Society for Medical Oncology (ESMO) Annual Congress, Munich, Germany, Oct. 19-23, 2018, 9 pages.
Chen L-T, et al., Abstract 221PD. "Efficacy and Safety of Nanoliposomal Irinotecan (nal-IRI, MM-398, PEP02, BAX-2398) in Patients With Metastatic Pancreatic Cancer in Asia: A Subgroup Analysis of the Phase 3 NAPOLI-1 Study," Ann Oncol. 27(Supp_9):ix69-ix70 doi:10.1093/annonc/mdw582 (2016).
Chen L-T, et al., Abstract 227P. "CA19-9 Decrease and Overall Survival (OS) in the NAPOLI-1 Trial of Liposomal Irinotecan (nal-IRI) ± 5-Fluorouracil and Leucovorin (5-FU/LV) in Metastatic Pancreatic Ductal Adenocarcinoma (mPDAC) Previously Treated With Gemcitabine-Based Therapy," Ann Oncol. 28(Suppl_10):x66-x67 doi:10.1093/annonc/mdx660 (2017).
Chen L-T, et al., Abstract 303. "Efficacy and Safety of Liposomal Irinotecan (nal-IRI) + 5-Fluorouracil and Leucovorin (5-FU/LV) in Patients (pts) With Metastatic Pancreatic Ductal Adenocarcinoma (mPDAC) Who Previously Received Gemcitabine (Gem)-Based Therapy: Post Hoc Analysis of the NAPOLI-1 Trial," J Clin Oncol. 35(4_Suppl):303 DOI: 10.1200/JCO.2017.35.4_suppl.303 (2017), 2 printed pages.
Chen L-T, et al., Abstract 3707. "Final Results of NAPOLI-1: A Phase 3 Study of nal-IRI (MM-398) ± 5-Fluorouracil and Leucovorin (5-FU/LV) vs 5-FU/LV in Metastatic Pancreatic Cancer (mPAC) Previously Treated With Gemcitabine-Based Therapy," Ann Oncol. 27(6):207-242 10.1093/annonc/mdw371 (2016), 4 printed pages.
Chen L-T, et al., Abstract 734P. "Impact of Dose Reduction or Dose Delay on the Efficacy of Liposomal Irinotecan (nal-IRI)+5-Fluorouracil/Leucovorin (5-FU/LV): Survival Analysis From NAPOLI-1," Ann Oncol. 29(Suppl_8):viii250-viii251 doi:10.1093/annonc/mdy282 (2018).
Chen L-T, et al., Abstract 749P. "The Prognostic Value of the Modified Glasgow Prognostic Score (mGPS) in Predicting Overall Survival (OS) in Patients With Metastatic Pancreatic Ductal Adenocarcinoma (mPDAC) Receiving Liposomal Irinotecan (nal-IRI)+5-Fluorouracil and Leucovorin (5-FU/LV)," Ann Oncol. 29(Suppl_8):viii255-viii256 doi:10.1093/annonc/mdy282 (2018).
Chen L-T, et al., Abstract PD-017. "CA19-9 Decrease and Overall Survival (OS) in the NAPOLI-1 Trial of Liposomal Irinotecan (nal-IRI) ± 5-Fluorouracil and Leucovorin (5-FU/LV) in Metastatic Pancreatic Ductal Adenocarcinoma (mPDAC) Previously Treated With Gemcitabine-Based Therapy," Ann Oncol. 28(Supp_3):6-7 doi:10.1093/annonc/mdx263 (2017).
Chin V, et. al., "Chemotherapy and Radiotherapy for Advanced Pancreatic Cancer (Review)," Cochrane Database Syst Rev. 3(3):CD011044 doi: 10.1002/14651858.CD011044.pub2 (2018), 143 pages.
Choi C, et al., "Effects of 5-Fluorouracil and Leucovorin in the Treatment of Pancreatic-Biliary Tract Adenocarcinomas," Am J Clin Oncol. CCT 23(4): 425-8 (2000), 7 printed pages.
Clinical Trials Identifier NCT00426127: Dec. 29, 2017 update, first posted Jan. 24, 2007, "Docetaxel and Liposomal Doxorubicin

(56) References Cited

OTHER PUBLICATIONS

Chemotherapy With Enoxaparin in Patients With Advanced Pancreatic Cancer," Retrieved from ClinicalTrials.gov archive, 8 printed pages.
Cockrum P, et al., "Impact of Dose Reductions on Clinical Outcomes Among Patients With Metastatic Pancreatic Cancer Treated With Liposomal Irinotecan in Oncology Clinics in the US." Poster presented at the American Society of Clinical Oncology Gastrointestinal Cancers Symposium (ASCO GI), San Francisco, CA, Jan. 23-25, 2020, 8 pages.
Cockrum P, et al., Abstract 665. "Impact of Dose Reductions on Clinical Outcomes Among Patients (pts) With Vletastatic Pancreatic Cancer (mPC) Treated With Liposomal Irinotecan (nal-IRI) in Oncology Clinics in the United States," J Clin Oncol. 38(4_Suppl):665 DOI: 10.1200/JCO.2020.38.4_suppl.665 (2020), 2 printed pages.
Cockrum P, et al., Abstract e16739. "National Comprehensive Cancer Network (NCCN) Category I/FDA-Approved Metastatic Pancreatic Adenocarcinoma (mPDAC) Treatments in Commercially Insured Patients: An Analysis of Inpatient (IP) and Emergency Room (ER) Admissions," J Clin Oncol. 38(15_Suppl):e16739 DOI: 10.1200/JCO.2020.38.15_suppl.e16739 (2020), 2 printed pages.
Cockrum P, et al., Abstract PCN134. "An Examination of Quality Metrics: Inpatient and Emergency Department Burden of Commercially Insured Treated Metastatic Pancreatic Cancer (mPC) Patients in the United States (US)," Value in Health. 23(Suppl 1):S46 (2020).
Cockrum P, et al., Abstract PCN167. "An Integrated Delivery Network Focus on Cost Drivers in Chemotherapy: The Economic Burden of Neutropenia and Inpatient Admissions Among Commercially Insured Metastatic Pancreatic Cancer Patients (mPC)," Value in Health. 23(Suppl 1):S52 (2020).
Colucci G, et. al., "Randomized Phase III Trial of Gemcitabine Plus Cisplatin Compared With Single-Agent Gemcitabine as First-Line Treatment of Patients With Advanced Pancreatic Cancer: The GIP-1 Study," J Clin Oncol. 28(10):1645-51 (2010).
Conroy T et al., Abstract 4010. "Randomized Phase III Trial Comparing FOLFIRINOX (F: 5FU/Leucovorin [LV], Irinotecan [I}, and Oxaliplatin [O]) Versus Gemcitibine (G) as First-Line Treatment for Metastatic Pancreatic Adenocarcinoma (MPA): Preplanned Interim Analysis Results of the PRODIGE 4/ACCORD 11 Trial" J Clin Oncol. 28(15_Suppl):4010 (2010), 3 printed pages.
Custodio A, et. al., "Second-Line Therapy for Advanced Pancreatic Cancer: A Review of the Literature and Future Directions," Cancer Treat Rev. 35(8):676-84 (2009).
Abra R, et. al., "The Next Generation of Liposome Delivery Systems: Recent Experience With Tumor-Targeted, Sterically-Stabilized Immunoliposomes and Active-Loading Gradients," J Liposome Res. 12(1-2):1-3 (2002).
Alese O, et al., "A Phase I/II Study of Trifluridine/Tipiracil (TAS-102) in Combination With Nanoliposomal Irinotecan (NAL-IRI) in Advanced GI Cancers." Poster presented at Chan E, et al., "A Phase 1/2 Study Combining MM-151 + nal-IRI + 5-FU + Leucovorin in RAS/RAF Wild-Type Metastatic Colorectal Cancer." Poster presented at the American Society of Clinical Oncology (ASCO) Annual Meeting, Chicago, Illinois, Jun. 1-5, 2018, 1 page.
Alese O, et al., Abstract TPS4155. "A Phase I/II Study of Trifluridine/Tipiracil (TAS-102) in Combination With Nanoliposomal Irinotecan (NAL-IRI) in Advanced GI Cancers," J Clin Oncol. 36(15_Suppl):TPS4155 DOI: 10.1200/JCO.2018.36.15_suppl.TPS4155 (2018), 5 printed pages.
Allegrini G, et. al., "A Pharmacokinetic and Pharmacodynamic Study on Metronomic Irinotecan in Metastatic Colorectal Cancer Patients," Br J Cancer. 98(8):1312-19 (2008).
Alves Da Silva A, et. al., "Standardization of the Infusion Sequence of Antineoplastic Drugs Used in the Treatment of Breast and Colorectal Cancers," Einstein (São Paulo). 16(2):eRW4074 doi: 10.1590/S1679-45082018RW4074 (2018), 9 pages.
Anders C, et al., Abstract e12003. "Pharmacokinetic (PK) Characterization of Irinotecan Liposome Injection in Patients (pts) With Metastatic Breast Cancer (mBC)," J Clin Oncol. 37(15_Suppl):e12003 DOI: 10.1200/JCO.2019.37.15_suppl.e12003 (2019), 2 printed pages.
Andre T, et. al., "Phase III Study Comparing a Semimonthly With a Monthly Regimen of Fluorouracil and Leucovorin as Adjuvant Treatment for Stage II and III Colon Cancer Patients: Final Results of GERCOR C96.1," Clin Oncol. 25(24):3732-8 (2007).
Aranda E, et. al., "Randomized Study of Weekly Irinotecan Plus High-Dose 5-Fluorouracil (FUIRI) Versus Biweekly Irinotecan Plus 5-Fluorouracil/Leucovorin (FOLFIRI) as First-Line Chemotherapy for Patients With Metastatic Colorectal Cancer: A Spanish Cooperative Group for the Treatmentof Digestive Tumors Study," Ann Oncol. 20(2):251-7 (2009).
Awasthi N, et al., "Antitumor Efficacy of a Liposomal Formulation of Irinotecan in Preclinical Gastric Cancer Models: Augmenting Its Response by Antiangiogenic Agents." Poster presented at the Annual Meeting of the American Association for Cancer Research 2020, Philadelphia, PA, Apr. 27-28, 2020 and Jun. 22-24, 2020, 6 pages.
Awasthi N, et al., Abstract 553. "Antitumor Efficacy of a Liposomal Formulation of Irinotecan in Preclinical Gastric Cancer Models: Augmenting Its Response by Antiangiogenic Agents," In Proceedings of the Annual Meeting of the American Association for Cancer Research 2020; Apr. 27-28, 2020 and Jun. 22-24, 2020. Cancer Res. 2020;80(16 Suppl):Abstract nr 553, DOI: 10.1158/1538-7445.AM2020-553, 2 printed pages.
Barenholz Y, "Development of Liposomal Drugs and Nano-Drugs: From Academic Research via Incubators and Startups to FDA and EMA Approved Products. Part I: Science and Technology," Presentation presented at Barcelona NanoMed, Mar. 4-5, 2014, 89 pages.
Barenholz Y, "Doxil®—The First FDA-Approved Nano-Drug: Lessons Learned," J Control Release. 160(2):117-34 (2012).
Barone C, et. al., "Schedule-Dependent Activity of 5-Fluorouracil and Irinotecan Combination in the Treatment of Human Colorectal Cancer: In Vitro Evidence and a Phase I Dose-Escalating Clinical Trial," Br J Cancer. 96(1):21-8 (2007). Epub 2006.
Basu S, et. al., "Development and Validation of an UPLC-MS/MS Method for the Quantification of Irinotecan, SN 38 and SN-38 Glucuronide in Plasma, Urine, Feces, Liver and Kidney: Application to a Pharmacokinetic Study of Irinotecan in Rats," J Chromatogr B Analyt Technol Biomed Life Sci. 1015-1016: 34-41 (2016).
Batist G, et al., Abstract 2014. "Phase 1 Study of CPX-1, A Fixed Ratio Formulation of Irinotecan (IRI) and Floxuridine (FLOX), in Patients With Advanced Solid Tumors," J Clin Oncol. 24(18_suppl):2014 (2006), 2 printed pages.
Batist G, et al., Abstract 2549. "Ratiometric Dosing of Irinotecan (IRI) and Floxuridine (FLOX) in a Phase I Trial: A New Approach for Enhancing the Activity of Combination Chemotherapy," J Clin Oncol. 25(18_suppl):2549 (2007), 5 printed ppages.
Borner M, et. al., "A Randomized Phase II Trial of Capecitabine and Two Different Schedules of Irinotecan in First-Line Treatment of Metastatic Colorectal Cancer: Efficacy, Quality-of-Life and Toxicity," Ann Oncol. 16(2): 282-8 (2005).
Boulikas T, "Clinical Overview on Lipoplatin: A Successful Liposomal Formulation of Cisplatin," Expert Opin Investig Drugs. 18(8):1197-218 (2009), author manuscript version, 22 pages.
Bozzuto G and Molinari A, "Liposomes as Nanomedical Devices," Int J Nanomedicine. 10:975-99 (2015).
Bulbake U, et al., "Liposomal Formulations in Clinical Use: An Updated Review," Pharmaceutics. 9(2):12 doi: 10.3390/pharmaceutics9020012 (2017), 33 pages.
Butowski N, et al., "A Phase I Study of CED of Nanoliposomal-Irinotecan Using Real-Time Imaging With Gadolinium in Patients With Recurrent High Grade Glioma." Poster presented at the American Society of Clinical Oncology (ASCO) Annual Conference, Chicago, IL, May 29-Jun. 2, 2015, 4 pages.
Butowski N, et al., Abstract TPS2081. "A Phase I Study of Convection-Enhanced Delivery of Nanoliposomal Irinotecan Using Real-Time Imaging in Patients With Recurrent High Grade Glioma," J Clin Oncol. 33(15_Suppl):2081 DOI: 10.1200/jco.2015.33.15_suppl.tps2081 (2015), 2 printed pages.
Caelyx (doxorubicin), MedBroadcast, accessed Jan. 26, 2021 from medbroadcast.com/drug/getdrug/caelyx, 11 printed pages.

(56) References Cited

OTHER PUBLICATIONS

Cao S, et. al., "Synergistic Antitumor Activity of Capecitabine in Combination with Irinotecan," Clin Colorectal Cancer. 4(5):336-43 (2005).

Cao Y, et al., "A Gold Nanoparticle Bouquet Held on Plasma Membrane: An Ultrasensitive Dark-Field Imaging Approach for Cancer Cell Analysis," Nanotheranostics. 4(4):201-209 (2020).

Carter K, et. al., "Sphingomyelin Liposomes Containing Porphyrin-Phospholipid for Irinotecan Chemophototherapy," Theranostics. 6(13):2329-36 (2016).

Chabot G, "Clinical Pharmacokinetics of Irinotecan," Clin. Pharmacokinet. 33(4):245-59 (1997).

Chan E, et al., "A Phase 1/2 Study Combining MM-151 + nal-IRI + 5-FU + Leucovorin in RAS/RAF Wild-Type Metastatic Colorectal Cancer." Poster presented at the American Society of Clinical Oncology (ASCO) Annual Meeting, Chicago, Illinois, Jun. 3-7, 2016, 7 pages.

Chan E, et al., Abstract TPS3633. "A Phase 1b/2 Study Combining MM-151 + nal-IRI + 5-FU + Leucovorin in RAS-Wildtype Metastatic Colorectal Cancer (mCRC)," J Clin Oncol. 34(15_Suppl):TPS3633 10.1200/JCO.2016.34.15_suppl.TPS3633 (2016), 4 printed pages.

Chauhan V, et. al., "Normalization of Tumour Blood Vessels Improves the Delivery of Nanomedicines in a Size-Dependent Manner," Nat Nanotechnol. 7(6):383-8 (2012), author manuscript version, 15 pages.

Chen J, et al., "Improved Pharmacokinetics and Reduced Toxicity of Brucine After Encapsulation into Stealth Liposomes: Role of Phosphatidylcholine," Int J Nanomedicine. 7:3567-77 (2012).

Chu C-J, et al., "Efficiency of Cytoplasmic Delivery by pH-Sensitive Liposomes to Cells in Culture," Pharm Res. 7(8):824-34 (1990).

Clarke J, et al., "A Phase I Trial of Intravenous Liposomal Irinotecan in Patients With Recurrent High-Grade Gliomas." Poster presented at the American Society of Clinical Oncology (ASCO) Annual Conference, Chicago, IL, May 29-Jun. 2, 2015, 7 pages.

Clarke J, et al., Abstract 2029. "A Phase I Trial of Intravenous Liposomal Irinotecan in Patients With Recurrent High-Grade Gliomas," J Clin Oncol. 33(15_Suppl):2029 DOI: 10.1200/jco.2015.33.15_suppl.2029 (2015), 2 printed pages.

Comella P, et. al., "Irinotecan Plus Leucovorin-Modulated 5-Fluorouracil I.V. Bolus Every Other Week May Be a Suitable Therapeutic Option Also for Elderly Patients With Metastatic Colorectal Carcinoma," Br J Cancer. 89(6):992-6 (2003).

Daleke D, et al., "Endocytosis of Liposomes by Macrophages: Binding, Acidification and Leakage of Liposomes Monitored by a New Fluorescence Assay," Biochim Biophys Acta. 1024(2):352-66 (1990).

DaunoXome (daunorubicin citrate liposome injection) package insert, rev. Dec. 2011, 11 pages.

Delord J, et. al., "A Phase I Clinical and Pharmacokinetic Study of Capecitabine (Xeloda®) and Irinotecan Combination Therapy (XELIRI) in Patients With Metastatic Gastrointestinal Tumours," Br J Cancer 92(5):820-6 (2005).

Derksen J, et. al., "Interaction of Immunoglobulin-Coupled Liposomes with Rat Liver Macrophages In Vitro," Exp Cell Res. 168(1):105-15 (1987).

Dewhirst M, et al., "Microvascular Studies on the Origins of Perfusion-Limited Hypoxia," Br J Cancer Suppl. 27:S247-51 (1996).

Dos Santos N, et al., "Improved Retention of Idarubicin After Intravenous Injection Obtained for Cholesterol-Free Liposomes," Biochim Biophys Acta. 1561(2):188-201 (2002).

Drummond D, et al., "Clinical Development of Histone Deacetylase Inhibitors as Anticancer Agents," Annu Rev Pharmacol Toxicol. 45:495-528 and C1-C2 (2005).

Drummond D, et al., "Development of a Highly Stable and Targetable Nanoliposomal Formulation of Topotecan," J Control Release. 141(1):13-21 (2010). Epub 2009.

Drummond D, et al., "Improved Pharmacokinetics and Efficacy of a Highly Stable Nanoliposomal Vinorelbine," J Pharmacol Exp Ther. 328(1):321-30 (2009). Epub 2008.

Drummond D, et al., "Liposome Targeting to Tumors using Vitamin and Growth Factor Receptors," Vitam Horm. 60:285-332 (2000).

Drummond D, et al., Chapter 8, "Intraliposomal Trapping Agents for Improving In Vivo Liposomal Drug Formulation Stability," In Liposome Technology, Third Edition, vol. 2, Ed. G. Gregoriadis, pp. 149-168 (2006).

Drummond D, et al., Chapter 9, "Liposomal Drug Delivery Systems for Cancer Therapy," In Drug Discovery System in Cancer Therapy, Ed. D Brown, Humana Press, Totowa, NJ, pp. 191-213 (2004).

Duffour J, et al., "Efficacy of Prophylactic Anti-Diarrhoeal Treatment in Patients Receiving Campto for Advanced Colorectal Cancer," Anticancer Res. 22(6B): 3727-31 (2002).

Elinzano H, et al., "Nanoliposomal Irinotecan and Metronomic Temozolomide for Patients With Recurrent Glioblastoma BrUOG329, A Phase I Brown University Oncology Research Group Trial," Am J Clin Oncol. 44(2):49-52 (2021). Epub 2020 version, pp. 1-4.

Elinzano H, et al., Abstract e14548. "Nanoliposomal Irinotecan and Metronomic Temozolomide for Patients With Recurrent Glioblastoma: BrUOG329, A Phase IIB/IIA Brown University Oncology Research Group (BrUOG) Trial," J Clin Oncol. 38(15_Suppl):e14548 DOI: 10.1200/JCO.2020.38.15_suppl.e14548 (2020), 2 printed pages.

De Jong F, et al., Abstract. "Effects of nal-IRI (MM-398; a Liposomal Formulation of Irinotecan) ± 5-Fluorouracil (5-FU) on Quality of Life (QoL) in NAPOLI-1: A Phase 3 Study in Patients With Metastatic Pancreatic Ductal Adenocarcinoma (mPDAC) Previously Treated With Gemcitabine," Australian Gastro-Intestinal Trials Group, 18th Annual Scientific Meeting, Melbourne, Australia, Sep. 14-16, 2016, 2 pages.

De Jong F, et al., "Effects of nal-IRI (MM-398; a Liposomal Formulation of Irinotecan) ± 5-Fluorouracil (5-FU) on Quality of Life (QoL) in NAPOLI-1: A Phase 3 Study in Patients With Metastatic Pancreatic Ductal Adenocarcinoma Previously Treated With Gemcitabine," Poster presented at the Australian Gastro-Intestinal Trials Group, 18th Annual Scientific Meeting, Melbourne, Australia, Sep. 14-16, 2016, 10 pages.

Dean A, et al., "First-Line (1L) Liposomal Irinotecan + 5-Fluorouracil/Leucovorin (5-FU/LV) + Oxaliplatin (OX) in Patients With Locally Advanced or Metastatic Pancreatic Ductal Adenocarcinoma: Exploratory Subgroup Analyses of Survival by Changes in CA 19-9 Levels." Poster presented at the European Society for Medical Oncology (ESMO) Virtual Congress 2020, Sep. 19-21, 2020, 7 pages.

Dean A, et al., "First-Line Liposomal Irinotecan + 5-Fluorouracil/Leucovorin + Oxaliplatin in Patients With Pancreatic Ductal Adenocarcinoma: Results From a Phase 1/2 Study." Presentation presented at the Clinical Oncology Society of Australia (COSA): Virtual meeting, Nov. 11-13, 2020, 10 pages.

Dean A, et al., "NAPOLI-3: An Open-Label, Randomized, Phase III Study of First-Line Liposomal Irinotecan + 5-Fluorouracil/Leucovorin + Oxaliplatin Versus nab-Paclitaxel + Gemcitabine in Patients With Metastatic Pancreatic Ductal Adenocarcinoma." Presentation presented at the Clinical Oncology Society of Australia (COSA): Virtual meeting, Nov. 11-13, 2020, 10 pages.

Dean A, et al., Abstract 1529P. "First-Line (10 Liposomal Irinotecan + 5-Fluorouracil/Leucovorin (5-FU/LV) + Oxaliplatin (OX) in Patients With Locally Advanced or Metastatic Pancreatic Ductal Adenocarcinoma (mPDAC): Exploratory Subgroup Analyses of Survival by Changes in CA 19-9 Levels," Ann Oncol. 31(Suppl_4):S881-S897 10.1016/annonc/annonc285 (2020), 3 printed pages.

Dean A, et al., Abstract 222. "First-Line Liposomal Irinotecan + 5-Fluorouracil/Leucovorin + Oxaliplatin in Patients With Pancreatic Ductal Adenocarcinoma: Results From a Phase 1/2 Study," Asia-Pac J Clin Oncol. 16(Suppl. 8):118-119 (2020).

Dean A, et al., Abstract 407. "NAPOLI-3: An Open-Label, Randomized, Phase III Study of First-Line Liposomal Irinotecan + 5-Fluorouracil/Leucovorin + Oxaliplatin Versus nab-Paclitaxel + Gemcitabine in Patients With Metastatic Pancreatic Ductal Adenocarcinoma," Asia-Pac J Clin Oncol. 16(Suppl. 8):202-3 (2020).

Dean A, et al., Abstract 4111. "A Phase 1/2, Open-Label Dose-Escalation Study of Liposomal Irinotecan (nal-IRI) Plus 5-Fluorouracil/

(56) References Cited

OTHER PUBLICATIONS

Leucovorin (5-FU/LV) and Oxaliplatin (OX) in Patients with Previously Untreated Metastatic Pancreatic cancer (mPAC)," J Clin Oncol. 36(15_Suppl):4111 10.1200/JCO.2018.36.15_suppl.4111 (2018), 1 page.

Dean A, et al., Abstract. "Expanded Analyses of NAPOLI-1: Phase 3 Study of MM-398 (nal-IRI), With or Without 5-Fluorouracil and Leucovorin (5-FU/LV), Versus 5-FU/LV, in Metastatic Pancreatic Cancer (mPAC) Previously Treated With Gemcitabine-Based Therapy," 18th Annual Scientific Meeting of the Australasian Gastro-Intestinal Trials Group (AGITG), Melbourne, Australia, Sep. 14-16, 2016, 2 pages.

Dean A, et al., Abstract. "Liposomal Irinotecan (nal-IRI, MM-398)-Containing Regimens Versus nab-Paclitaxel Plus Gemcitabine as First-Line Therapy in Patients With Metastatic Pancreatic Adenocarcinoma (mPAC): A Randomized, Open-Label Phase 2 Study," 18th Annual Scientific Meeting of the Australasian Gastro-Intestinal Trials Group (AGITG), Melbourne, Australia, Sep. 14-16, 2016, 2 pages.

Dieguez G, et al., "Real-World Rates of Hematologic Laboratory Abnormalities and Associated Cost Among Metastatic Pancreatic Cancer Therapeutic Regimens," Poster presented at the American Society of Clinical Oncology Gastrointestinal Cancers Symposium (ASCO GI), San Francisco, CA, Jan. 23-25, 2020, 6 pages.

Dieguez G, et al., Abstract 670. "Real-World Rates of Hematology Lab Abnormalities and Associated Cost Among Metastatic Pancreatic Cancer (mPC) Therapeutic Regimens," J Clin Oncol. 38(4_Suppl):670 DOI: 10.1200/JCO.2020.38.4_suppl.670 (2020), 2 printed pages.

Doris J, et al., Abstract CT12. "The Cost of Adverse Events for FDA-Approved/NCCN Category 1 Treatments for Medicare Fee-For-Service (FFS) Patients With Metastatic Pancreatic Cancer: Focus on Liposomal Irinotecan-Based Regimens," Hematology Oncology Pharmacy Association (HOPA) Annual Conference, Mar. 11-14, 2020, available at eventscribe.com/2020/posters/HOPAahead/SplitViewer.asp?PID=Njg0NzA2NjU1NjE, (2020), 2 pages.

Figer A, et. al., "A Comparison of Two Dose Regimens in Pancreatic Cancer," J Chemother. 12(5):442-5 (2000).

Gaddy D, et al., "A Systematic Literature Review to Identify and Compare Clinical Trials Evaluating Novel Therapeutic Agents in Post-Gemcitabine Advanced Pancreatic Cancer Patients." Poster presented at the International Society for Pharmacoeconomics and Outcomes Research (ISPOR) 18th Annual European Congress, Milan, Italy, Nov. 7-11, 2015, 6 pages.

Gaddy D, et al., "Preclinical Anti-tumor Activity of Nanoliposomal Irinotecan (Nal-IRI, MM-398) Supports Utilization as a Foundation of Front-Line Pancreatic Cancer Regimens." Poster presented at the American Society of Clinical Oncology Gastrointestinal Cancers Symposium (ASCO GI), San Francisco, CA, Jan. 19-21, 2017, 5 pages.

Gaddy D, et al., Abstract 336. "Preclinical Antitumor Activity of Nanoliposomal Irinotecan (Nal-IRI, MM-398) and Utilization as a Foundation of Front-Line Pancreatic Cancer Regimens," J Clin Oncol. 35(4_Suppl):336 DOI: 10.1200/JCO.2017.35.4_suppl.336 (2017), 2 printed pages.

Gaddy D, et al., Abstract PCN29. "A Systematic Literature Review to Identify and Compare Clinical Trials Evaluating Novel Therapeutic Agents in Post-Gemcitabine Advanced Pancreatic Cancer," Value in Health. 18(7):A434 (2015).

Gebbia V, et al., "Second-Line Chemotherapy in Advanced Pancreatic Carcinoma: A Multicenter Survey of the Gruppo Oncologico Italia Meridionale on the Activity and Safety of the FOLFOX4 Regimen in Clinical Practice," Ann Oncol. 18(Suppl 6):vi124-7 (2007).

Gill S, et al., "PANCREOX: A Randomized Phase III Study of Fluorouracil/Leucovorin With or Without Oxaliplatin for Second-Line Advanced Pancreatic Cancer in Patients Who Have Received Gemcitabine-Based Chemotherapy," J Clin Oncol. 34(32):3914-20 and Appendix (2016).

Glassman D, et al., "Nanoliposomal Irinotecan With Flurouracil for the Treatment of Advanced Pancreatic Cancer." Poster presented at the American Society of Clinical Oncology Gastrointestinal Cancers Symposium (ASCO GI), San Francisco, CA, Jan. 18-20, 2018, 7 pages.

Glassman D, et al., Abstract 471. "Nano-Liposomal Irinotecan and 5-FU/LV (N+F) for the Treatment of Advanced PDAC: Memorial Sloan Kettering (MSK) Single Cancer Center Evaluation," J Clin Oncol. 36(4_Suppl):471 DOI: 10.1200/JCO.2018.36.4_suppl.471 (2018), 2 printed pages.

Gounaris I, et. al., "Options for the Treatment of Gemcitabine-Resistant Advanced Pancreatic Cancer," JOP. J Pancreas (Online) 11(2):113-23 (2010).

Gourzoulidis G, et al., "The Cost-Effectiveness of Nanoliposomal Irinotecan and 5-Fluorouracil (5-FU)/ Leucovorin (LV) for the Treatment of Patients With Metastatic Adenocarcinoma of Pancreas Who Have Progressed Following the Use of Gemcitabine-Related Therapies in Greece." Poster presented at the Virtual International Society for Pharmacoeconomics and Outcomes Research (ISPOR) European Congress, Milan, Italy, Nov. 16-19, 2020, 9 pages.

Gourzoulidis G, et al., Abstract PCN57. "The Cost-Effectiveness of Nanoliposomal Irinotecan and 5-Fluorouracil (5-FU)/ Leucovorin (LV) for the Treatment of Patients With Metastatic Adenocarcinoma of Pancreas Who Have Progressed Following the Use of Gemcitabine-Related Therapies in Greece," Virtual International Society for Pharmacoeconomics and Outcomes Research (ISPOR) European Congress, Milan, Italy, Nov. 16-19, 2020, available at ispor.org/heor-resources/presentations-database/presentation/euro2020-3282/105175, 2 printed pages.

Haller D, "Chemotherapy for Advanced Pancreatic Cancer," Int J Radiat Oncol Biol Phys. 56(4 Suppl):16-23 (2003).

Hann B, et. al., Abstract 5648. "Lipidic Nanoparticle CPT-11 in a Bioluminescent Orthotopic Pancreas Cancer Model," Cancer Res. 67(9 Suppl):5648 (2007), 4 printed pages.

Heinemann V, et. al., "Randomized Phase III Trial of Gemcitabine Plus Cisplatin Compared With Gemcitabine Alone in Advanced Pancreatic Cancer," J Clin Oncol. 24(24):3946-52 (2006).

Herrera-Restrepo O, et al., "Budget Impact in the USA of Liposomal Irinotecan as a Post-Gemcitabine Treatment Option for Patients With Metastatic Pancreatic Adenocarcinoma (mPC)." Poster presented at the International Society for Pharmacoeconomics and Outcomes Research (ISPOR) Annual Meeting, New Orleans, LA, May 18-22, 2019, 12 pages.

Herrera-Restrepo O, et al., Abstract PCN80. "Budget Impact in the USA of Liposomal Irinotecan as a Post-Gemcitabine Treatment Option for Patients With Metastatic Pancreatic Adenocarcinoma (mPC)," Value in Health. 22(Suppl 2):S70 (2019).

Hidalgo M, "Pancreatic Cancer," N Engl J Med. 362(17):1605-17 (2010).

Hirsch J, et al., "Comparing Total Cost of Care for Medicare Fee-For-Service Patients With Pancreatic Cancer, by Chemotherapy Regimen." Poster presented at the American Society of Clinical Oncology Gastrointestinal Cancers Symposium (ASCO GI), San Francisco, CA, Jan. 23-25, 2020, 5 pages.

Hirsch J, et al., "Comparing Total Costs of Care for Medicare Fee-For-Service (FFS) Patients With Metastatic Pancreatic Cancer by Chemotherapy Regimen," Poster presented at the Academy of Managed Care Pharmacy, Nexus (AMCP, Nexus): virtual meeting, week of Oct. 19, 2020, 8 pages.

Hirsch J, et al., "The Cost of Adverse Events for FDA-Approved/NCCN Category 1 Treatments for Medicare Fee-For-Service (FFS) Patients With Metastatic Pancreatic Cancer." Poster presented at the Hematology Oncology Pharmacy Association (HOPA) Annual Conference, Tampa, FL, Mar. 11-14, 2020, 6 pages.

Hirsch J, et al., "The Cost of Adverse Events for FDA-Approved/NCCN Category 1 Treatments for Medicare Fee-For-Service Patients With Metastatic Pancreatic Cancer." Poster presented at the American Society of Health-System Pharmacists (ASHP) Midyear 2019 Clinical Meeting and Exhibition, Las Vegas, NV, Dec. 8-12, 2019, 6 pages.

Hirsch J, et al., Abstract 4-138. "The Cost of Adverse Events for FDA-Approved/NCCN Category 1 Treatments for Medicare Fee-For-Service Patients With Metastatic Pancreatic Cancer," American

(56) References Cited

OTHER PUBLICATIONS

Society of Health-System Pharmacists (ASHP) Midyear Clinical Meeting Professional Poster Abstracts, (2019), 2 pages.

Hirsch J, et al., Abstract 721. "Comparing Total Cost of Care for Medicare FFS Patients With Pancreatic Cancer by Chemotherapy Regimen," J Clin Oncol. 38(4_Suppl):721 DOI: 10.1200/JCO.2020. 38.4_suppl.721 (2020), 2 printed pages.

Hirsch J, et al., Abstract e19394. "Comparing Total Cost of Care for Medicare FFS Patients With Pancreatic Cancer by Chemotherapy Regimen," J Clin Oncol. 38(15_Suppl):e19394 DOI: 10.1200/JCO. 2020.38.15_suppl.e19394 (2020), 2 printed pages.

Hubner R, et al., "Effects of nal-IRI (MM-398) ± 5-Fluorouracil on Quality of Life (QoL) in NAPOLI-1: A Phase 3 Study in Patients With Metastatic Pancreatic Ductal Adenocarcinoma (mPDAC) Previously Treated With Gemcitabine," Presentation presented at the European Society for Medical Oncology (ESMO) World Congress on Gastrointestinal Cancer, Barcelona, Spain, Jun. 29-Jul. 2, 2016, 13 pages.

Hubner R, et al., "Prognostic Value of Baseline Neutrophil-to-Lymphocyte Ratio (NLR) for Predicting Clinical Outcome in Metastatic Pancreatic Ductal Adenocarcinoma (mPDAC) Patients Treated With Liposomal Irinotecan (nal-IRI) + 5-Fluorouracil and Leucovorin (5-FU/LV) vs 5-FU/LV Alone." Poster presented at the European Society for Medical Oncology (ESMO) Annual Congress, Madrid, Spain, Sep. 8-12, 2017, 5 pages.

Hubner R, et al., "Time Course of Selected Treatment-Emergent Adverse Events in NAPOLI-1: A Phase 3 Study of Liposomal Irinotecan (nal-IRI; MM-398) ± 5-Fluorouracil and Leucovorin (5-FU/LV) vs 5-FU/LV in Metastatic Pancreatic Cancer Previously Treated With Gemcitabine-Based Therapy." Poster presented at the European Society for Medical Oncology (ESMO) Annual Congress, Copenhagen, Denmark, Oct. 7-11, 2016, 8 pages.

Hubner R, et al., Abstract 242P. "Effects of nal-IRI (MM-398) ± 5-Fluorouracil on Quality of Life (QoL) of Patients With Metastatic Pancreatic Ductal Adenocarcinoma (mPDAC) Previously Treated With Gemcitabine Based Therapy: Results From NAPOLI-1 ," Ann Oncol. 27(Supp_9):ix76 doi:10.1093lannonc/mdw582 (2016).

Hubner R, et al., Abstract 3832. "Time Course of Selected Treatment Emergent Adverse Events (TEAES) in NAPOLI-1: A Phase 3 Study of nal-IRI (MM-398) ± 5-Fluorouracil and Leucovorin (5-FU/LV) vs 5-FU/LV in Metastatic Pancreatic Cancer (mPAC) Previously Treated With Gemcitabine-Based Therapy," Ann Oncol. 27(6):207-242 10.1093/annonc/mdw371 (2016), 4 printed pages.

Hubner R, et al., Abstract 741P. "Prognostic Value of Baseline Neutrophil-to-Lymphocyte Ratio (NLR) for Predicting Clinical Outcome in Metastatic Pancreatic Ductal Adenocarcinoma (mPDAC) Patients Treated With Liposomal Irinotecan (nal-IRI) + 5-Fluorouracil and Leucovorin (5-FU/LV) vs 5-FU/LV Alone," Ann Oncol. 28(Suppl_5):253 doi:10.1093/annonc/mdx369 (2017).

Hubner R, et al., Abstract. "Expanded Analyses of NAPOLI-1: Phase 3 Study of nal-IRI (MM-398), With or Without 5-Fluorouracil (5FU) and Leucovorin (LV), Versus 5-Fluorouracil and Leucovorin (5FU/LV), in Metastatic Pancreatic Cancer (mPAC) Previously Treated With Gemcitabine-Based Therapy," 2015 National Cancer Research Institute (NCRI) Cancer Conference, Nov. 1-4, 2015, 2 printed pages.

Hwang J, et al., Abstract 4618. "A Randomized Phase II Study of FOLFOX or FOLFIRI.3 as Second-Line Therapy in Patients With Advanced Pancreatic Cancer Previously Treated With Gemcitabine-Based Chemotherapy," J Clin Oncol. 27(15_Suppl):4618 (2009), 2 printed pages.

Ignatius R, et al., "Presentation of Proteins Encapsulated in Sterically Stabilized Liposomes by Dendritic Cells Initiates CD8+ T-cell Responses in Vivo," Blood. 96(10):3505-13 (2000).

Ilson D, "Nanlipoosomal Irinotecan Effective for Pancreatic Cancer," NEJM journal Watch, available at jwatch.org/na39795/2015/12/08/nanoliposomal-irinotecan-effective-pancreatic-cancer, (2015), 7 printed pages.

Ioka T, et al., "Liposomal Irinotecan (nal-IRI) Plus 5-Fluorouracil/Levoleucovorin (5-FU/LV) vs 5-FU/LV in Japanese Patients (pts) With Gemcitabine-Refractory Metastatic Pancreatic Cancer (mPAC)." Poster presented at the European Society for Medical Oncology (ESMO) Asia 2019 Congress, Singapore, Nov. 22-24, 2019, 9 pages.

Sachdev J, et al., "Characterization of Metastatic Breast Cancer Lesions with Ferumoxytol MRI and Treatment Response to MM-398, Nanoliposomal Irinotecan (nal-IRI)," Cancer Res.75(9 Suppl): Abstract P5-01-06 (2015), 3 printed pages.

Sachdev J, et al., Abstract C1048. "Phase I Expansion Study of Irinotecan Liposome Injection (nal-IRI) in Patients with Metastatic Breast Cancer (mBC)," Cancer Res. In Proceedings of the American Association for Cancer Research Annual Meeting 2019; Mar. 29-Apr. 3, 2019; Atlanta, GA. Cancer Res. 2019; 79(13 Suppl):Abstract nr CT048, 4 printed pages.

Saito R, et al., "Distribution of Liposomes into Brain and Rat Brain Tumor Models by Convection-Enhanced Delivery Monitored with Magnetic Resonance Imaging," Cancer Res. 64(7):2572-9 (2004).

Saito R, et al., "Gadolinium-loaded Liposomes Allow for Real-Time Magnetic Resonance Imaging of Convection-Enhanced Delivery in the Primate Brain," Exp Neurol. 196(2):381-9 (2005).

Saito R, et al., "Tissue Affinity of the Infusate Affects the Distribution Volume During Convection-Enhanced Delivery Into Rodent Brains: Implications for Local Drug Delivery," J Neurosci Methods. 154(1-2):225-32 (2006).

Tahara M, et al., "The Use of Olaparib (AZD2281) Potentiates SN-38 Cytotoxicity in Colon Cancer Cells by Indirect Inhibition of Rad51-Mediated Repair of DNA Double-Strand Breaks," Mol Cancer Ther. 13(5):1170-80 (2014).

Tardi P, et al., "Drug Ratio-Dependent Antitumor Activity of Irinotecan and Cisplatin Combinations In Vitro and In Vivo," Mol Cancer Ther. 8(8):2266-75 (2009).

Tentori L, et al., "Influence of MLH1 on Colon Cancer Sensitivity to Poly(ADP-ribose) Polymerase Inhibitor Combined with Irinotecan," Int J Oncol. 43(1):210-8 (2013).

U.S. Appl. No. 15/664,976: Nov. 4, 2019 Nonfinal Office Action, 9 pages.

U.S. Appl. No. 15/664,976: May 18, 2020 Final Office Action, 11 pages.

U.S. Appl. No. 15/664,976: Oct. 13, 2020 Notice of Allowance including Examiner's Reasons for Allowance, 13 pages.

U.S. Appl. No. 15/809,815: Feb. 27, 2020 Final Office Action, 16 pages.

U.S. Appl. No. 15/896,389: Jan. 31, 2020 Final Office Action, 28 pages.

U.S. Appl. No. 15/896,389: Mar. 26, 2020 Examiner Interview Summary and Applicant slides, 22 pages.

U.S. Appl. No. 15/896,389: Apr. 9, 2020 Advisory Action, 3 pages.

U.S. Appl. No. 15/896,389: Jun. 5, 2020 Notice of Allowance including Examiner's Reasons for Allowance and Examiner Interview Summary, 13 pages.

U.S. Appl. No. 16/012,351: Jan. 7, 2020 Final Office Action, 9 pages.

U.S. Appl. No. 16/012,372: Jan. 7, 2020 Final Office Action, 9 pages.

U.S. Appl. No. 16/012,372: Jul. 27, 2020 Non-Final Office Action, 8 pages.

U.S. Appl. No. 16/302,050: Jan. 17, 2020 Non-Final Office Action, 17 pages.

U.S. Appl. No. 16/510,394: Mar. 6, 2020 Non-Final Office Action, 15 pages.

U.S. Appl. No. 16/567,902: Apr. 27, 2020 Non-Final Office Action, 20 pages.

U.S. Appl. No. 16/567,902: Aug. 10, 2020 Final Office Action, 21 pages.

U.S. Appl. No. 16/586,609: Oct. 5, 2020 Non-Final Office Action, 5 pages.

Ventura M, et al., "Ferumoxytol as an MR Imaging Surrogate Marker of Liposomal Drug Deposition and Longitudinal Efficacy in a Preclinical Model of Breast Cancer." Poster presented at World Molecular Imaging Congress, Sep. 13-16, 2017, Philadelphia, Pennsylvania, 6 pages.

Ventura M, et al., "Imaging-Based Assessment of the Treatment Efficacy of Nanoliposomal Irinotecan (nal-IRI) in a Triple Negative

(56) References Cited

OTHER PUBLICATIONS

Breast Cancer Model of Spontaneous Metastasis." Poster presented at Annual World Molecular Imaging Congress, Sep. 7-10, 2016, 8 pages.
Von Pawel J, et aL, "Randomized Phase III Trial of Amrubicin Versus Topotecan as Second-Line Treatment for Patients with Small-Cell Lung Cancer," J Clin Oncol. 32(35):4012-9 and appendix (1 page) (2014).
Von Pawel J, et al., "Topotecan Versus Cyclophosphamide, Doxorubicin, and Vincristine for the Treatment of Recurrent Small-Cell Lung Cancer," J Clin Oncol. 17(2):658-67 (1999).
Wåhlby C, et al., "Sequential Immunofluorescence Staining and Image Analysis for Detection of Large Numbers of Antigens in Individual Cell Nuclei," Cytometry. 47(1):32-41 (2002).
Zander S, et al., "EZN-2208 (PEG-SN38) Overcomes ABCG2-Mediated Topotecan Resistance in BRCA1-Deficient Mouse Mammary Tumors," PLoS One. 7(9):345248 (2012), pp. 1-9.
Zhang Y, et al. "Poly(ADP-ribose) Polymerase and XPF-ERCC1 Participate in Distinct Pathways for the Repair of Topoisomerase I-Induced DNA Damage in Mammalian Cells," Nucleic Acids Res. 39(9):3607-20 (2011).
Zhao M, et al., "Clinical Observation of Irinotecan or Topotecan as Second-Line Chemotherapy on Treating 43 Patients with Small-Cell Lung Cancer," Chin Oncol. 21(2):156-8 (2011), text in Chinese with Tables 1-3 and Figure 1 in English.
Zheng J, et al., "[18F]FAZA-PET Detection of Hypoxia Changes following Anti-cancer Therapy." Poster presented at Annual World Molecular Imaging Congress, Sep. 18-21, 2013, 7 pages.
Zheng J, et al., "Longitudinal Tumor Hypoxia Imaging with [18F[FAZA-PET Provides Early Prediction of Nanoliposomal Innotecan (nal-IRI) Treatment Activity," EJNMMI Res 5(1):57, 10 pages (2015).
Zhou X, et al., "Clinical Analysis of Bevacizumab Plus FOLFIRI Regimen as Front-Line Therapy for Chinese Patients with Advanced Colorectal Cancer," J Cancer Ther 2(4):470-4 (2011).
Znojek P. et al., "Preferential Potentiation of Topoisomerase I Poison Cytotoxicity by PARP Inhibition in S Phase," Br J Cancer. 111(7):1319-26 (2014).
Markham C, et al., "A Phase II Irinotecan-Cisplatin Combination in Advanced Pancreatic Cancer," Br J Cancer. 89(10):1860-4 (2003).
Matrisian , et. al., "The Past, Present, and Future of Pancreatic Cancer Clinical Trials," American Society of Clinical Oncology Educational Book. 35:e205-15 (2016).
Melisi D, et al., Abstract B04. "Effects of Nanoliposomal Irinotecan (nal-IRI; MM-398) ± 5-Fluorouracil and Leucovarin (5-FU/LV) on Quality of Life (QoL) in Patients (pts) With Metastatic Pancreatic Adenocarcinoma (mPAC) Previously Treated With Gemcitabine-Based Therapy: Results From the Phase 3 NAPOLI-1 Study," Ann Oncol. 27(Supp_4):iv18 doi:10.1093/annonc/mdw333.4 (2016).
Moore M, et. al., "Erlotinib Plus Gemcitabine Compared With Gemcitabine Alone in Patients With Advanced Pancreatic Cancer: A Phase III Trial of the National Cancer Institute of Canada Clinical Trials Group," J Clin Oncol. 25(15):1960-6 (2007).
Muldoon L, et al., "Comparing Service Utilization and Costs for Medicare FFS Patients With Metastatic Pancreatic Cancer by Chemotherapy Regimen and Line of Therapy." Poster presented at the International Society for Pharmacoeconomics and Outcomes Research (ISPOR) Annual Meeting, New Orleans, LA, May 18-22, 2019, 6 pages.
Muldoon L, et al., Abstract e18357. "Treatment Patterns, Survival Rate, and Parts A and B Costs by Line of Therapy or FDA-Approved/NCCNCategory 1 Treatments for Patients With Metastatic Pancreatic Cancer," J Clin Oncol. 37(15_Suppl):e18357 DOI: 10.1200/JCO.2019.37.15_suppl.e18357 (2019), 2 printed pages.
Muldoon L, et al., Abstract PCN302. "Comparing Service Utilization and Costs for Medicare FFS Patients With Metastatic Pancreatic Cancer by Chemotherapy Regimen and Line of Therapy," Value in Health. 22(Suppl 2):S113-S114 (2019).
Nakai Y, et. al., "Inhibition of Renin—Angiotensin System Affects Prognosis of Advanced Pancreatic Cancer Receiving Gemcitabine," Br J Cancer 103(11):1644-8 (2010).

Neesse A, et al., "Stromal Biology and Therapy in Pancreatic Cancer," Gut. 60(6):861-8 (2011). Epub 2010.
Nelson R, "Lipsomal Irinotecan Boosts Survival in Pancreatic Cancer," Medscape, available at medscape.com/viewarticle/838501, 2015, 2 printed pages.
Nieto J, et. al., "Metastatic Pancreatic Cancer 2008: Is the Glass Less Empty?," Oncologist. 13(5):562-76 (2008) and erratum found at Oncologist 13(6):738 (2008).
Novarino A, et. al., "Oxaliplatin, 5-Fluorouracil, and Leucovorin as Second-Line Treatment for Advanced Pancreatic Cancer," Am J Clin Oncol. 32(1):44-8 (2009).
Oberstein P and Olive K, "Pancreatic Cancer: Why Is It So Hard to Treat?" Ther Adv Gastroenterol. 6(4):321-7 (2013).
Oettle H and Lehmann T, "Gemcitabine-Resistant Pancreatic Cancer: A Second-Line Option," Lancet. 387(10018):507-8 (2016). Epub 2015.
Olszewski A, et. al., "Phase I Study of Oxaliplatin in Combination with Gemcitabine, Irinotecan, and 5-Fluorouracil/Leucovorin(G-FLIE) in Patients with Metastatic Solid Tumors Including Adenocarcinoma of the Pancreas," J Gastrointest Cancer. 44(2):182-9 (2013).
O'Reilly E, et al., "Impact of Prior Irinotecan Exposure on Outcomes of Metastatic Pancreatic Cancer Patients." Poster presented at the American Society of Clinical Oncology Gastrointestinal Cancers Symposium (ASCO GI), San Francisco, CA, Jan. 23-25, 2020, 6 pages.
O'Reilly E, et al., "Real-World Patterns of Care Among Patients With Metastatic Pancreatic Cancer." Poster presented at the American Society of Clinical Oncology Gastrointestinal Cancers Symposium (ASCO GI), San Francisco, CA, Jan. 23-25, 2020, 6 pages.
O'Reilly E, et al., Abstract 666. "Real-World Patterns of Care Among Patients With Metastatic Pancreatic Cancer (mPC)," J Clin Oncol. 38(4_Suppl):666 DOI: 10.1200/JCO.2020.38.4_suppl.666 (2020), 2 printed pages.
O'Reilly E, et al., Abstract 667. "Impact of Prior Irinotecan Exposure on Outcomes of Metastatic Pancreatic Cancer (mPC) Patients," J Clin Oncol. 38(4_Suppl):667 DOI: 10.1200/JCO.2020_38.4_suppl.667 (2020), 2 printed pages.
O'Reilly E, et. al., "A Cancer and Leukemia Group B Phase II Study of Sunitinib Malate in Patients with Previously Treated Metastatic Pancreatic Adenocarcinoma (CALGB 80603)," Oncologist. 15(12):1310-9 (2010).
Pan-Canadian Oncology Drug Review (pCODR) Expert Review Committee (pERC) Final Recommendation for Irinotecan Liposome (Onivyde) for Metastaic Pancreatic Cancer, pERC Meeting: Oct. 19, 2017, pERC Reconsideration Meeting: Dec. 17, 2017, pp. 1-14.
Papadatos-Pastos D, et.al., "FOLFIRINOX—A New Paradigm in the Treatment of Pancreatic Cancer," Expert Rev Anticancer Ther. 14(10):1115-25 (2014).
Parekh H, et al., "A Phase II, Open-Label Pilot Study Evaluating the Safety and Activity of Nal-IRI in Combination With 5-FU and Oxaliplatin in Preoperative Treatment of Pancreatic Adenocarcinoma (NEO-Nal-IRI Study)." Poster presented at the American Society of Clinical Oncology Gastrointestinal Cancers Symposium (ASCO GI), San Francisco, CA, Jan. 23-25, 2020, 3 pages.
Parekh H, et al., Abstract TPS790. "A Phase II, Open-Label Pilot Study Evaluating the Safety and Activity of Nal-IRI in Combination With 5-FU and Oxaliplatin in Preoperative Treatment of Pancreatic Adenocarcinoma (NEO-Nal-IRI Study) (NCT03483038)," J Clin Oncol. 38(4_Suppl):TPS790 (2020), 2 printed pages.
Park J, English abstract and Table 1 and Figure 1 of "Second Line Chemotherapy for Pancreatic Cancer," Korean J Gastroenterol. 57(4):207-12 (2011).
Pellino A, et al., "Observational Retrospective Evaluation of Treatment With Liposomal Irinotecan Plus Fluorouracil/Leucovorin for Metastatic Pancreatic Cancer Patients: An Italian Large Real-World Analysis." Poster presented at the American Society of Clinical Oncology Gastrointestinal Cancers Symposium (ASCO GI), San Francisco, CA, Jan. 23-25, 2020, 5 pages.
Pellino A, et al., Abstract 660. "Observational Retrospective Evaluation of Treatment With Liposomal Irinotecan Plus Fluorouracil/Leucovorin for Metastatic Pancreatic Cancer Patients: An Italian

(56) References Cited

OTHER PUBLICATIONS

Large Real-World Analysis," J Clin Oncol. 38(4_Suppl):660 DOI: 10.1200/JCO.2020.38.4_suppl.660 (2020), 2 printed pages.

Pelzer U, et al., "A Randomized Trial in Patients With Gemcitabine Refractory Pancreatic Cancer. Final Results of the CONKO-003 Study." Presentation presented at the American Society of Clinical Oncology (ASCO) Annual Meeting, Chicago, Illinois, May 30-Jun. 3, 2008, 18 pages.

Pelzer U, et al., "Best Supportive Care (BSC) Versus Oxaliplatin, Folinic Acid and 5-Fluorouracil (OFF) Plus BSC in Patients for Second-Line Advanced Pancreatic Cancer: A Phase III-Study from the German CONKO-Study Group," Eur J Cancer. 47(11):1676-81 (2011).

Pelzer U, et al., Abstract P865. "Quality-Adjusted Time Without Symptoms or Toxicity (Q-TWiST) of Nanoliposomal Irinotecan (nal-IRI;MM-398) Plus 5-Fluorouracil and Leucovorin (5-FU/LV) vs 5-FU/LV alone in patients (pts) With Metastatic Pancreatic Adenocarcinoma (mPAC) Previously Treated With Gemcitabine-Based Therapy," Oncol Res Treat. 39(Suppl 3):260 (2016).

Petrelli F, et al., "What Else in Gemcitabine-Pretreated Advanced Pancreatic Cancer? An Update of Second Line Therapies," Rev Recent Clin Trials. 5(1):43-56 (2010).

Philip P, et al., "Consensus Report of the National Cancer Institute Clinical Trials Planning Meeting on Pancreas Cancer Treatment," J Clin Oncol. 27(33):5660-9 (2009).

Picozzi V, et al., "An Assessment of the Total Cost of Pancreatic Cancer Using Real-World Evidence." Poster presented at the American Society of Clinical Oncology Gastrointestinal Cancers Symposium (ASCO GI), San Francisco, CA, Jan. 23-25, 2020, 6 pages.

Picozzi V, et al., Abstract 773. "An Assessment of the Total Cost of Pancreatic Cancer Using Real-World Evidence," J Clin Oncol. 38(4_Suppl):773 DOI: 10.1200/JCO.2020.38.4_suppl.773 (2020), 2 printed pages.

Pino M, et. al., "Capecitabine and Celecoxib as Second-Line Treatment of Advanced Pancreatic and Biliary Tract Cancers," Oncology. 76(4):254-61 (2009).

Poplin E, et. al., "Phase III, Randomized Study of Gemcitabine and Oxaliplatin Versus Gemcitabine (Fixed-Dose Rate Infusion) Compared With Gemcitabine (30-Minute Infusion) in Patients With Pancreatic Carcinoma E6201: A Trial of the Eastern Cooperative Oncology Group," J Clin Oncol. 27(23):3778-85 (2009).

Rahib L, et. al., "Evaluation of Pancreatic Cancer Clinical Trials and Benchmarks for Clinically Meaningful Future Trials: A Systematic Review," JAMA Oncol. 2(9):1209-16 (2016).

Ramnani K, et al., Abstract CT13. "Impact of Treatment Sequence on Overall Survival in Metastatic Pancreatic Cancer Patients Treated with Liposomal Irinotecan in the Real-World Selling," Hematology Oncology Pharmacy Association (HOPA) Annual Conference, Mar. 11-14, 2020, available at eventscribe.com/2020/posters/HOPAahead/SplitViewer.asp?PID=Njg0NzMyODlyNzY, (2020), 2 pages.

Reni M, et. al., "Raltitrexed-Eloxatin Salvage Chemotherapy in Gemcitabine-Resistant Metastatic Pancreatic Cancer," Br J Cancer. 94(6):785-91 (2006).

Renouf D, et. al., "A Phase II Study of Erlotinib in Gemcitabine Refractory Advanced Pancreatic Cancer," Eur J Cancer. 50(11):1909-15 (2014).

Rocha Lima C, et al., "Irinotecan Plus Gemcitabine Results in No Survival Advantage Compared With Gemcitabine Monotherapy in Patients With Locally Advanced or Metastatic Pancreatic Cancer Despite Increased Tumor Response Rate," J Clin Oncol. 22(18):3776-83 (2004).

Sancho A, et. al., Abstract 15625. "Oxaliplatin and Capecitabine After Gemcitabine Failure in Patients With Advanced Pancreatic, Biliary, and Gallbladder Adenocarcinoma (APBC)," J Clin Oncol. 26(15_suppl):15625 (2008), 5 printed pages.

Shi S, et al., "Combinatational Therapy: New Hope for Pancreatic Cancer?" Cancer Lett. 317(2):127-35 (2012). Epub 2011.

Siveke J, et al., "Subgroup Analysis by Measurable Metastatic Lesion (ML) Number and Selected Lesion Locations (LL) at Baseline (BL) in NAPOLI-1: A Phase 3 Study of Liposomal Irinotecan (nal-IRI)±5-Fluorouracil/Leucovorin (5-FU/LV) in Patients With Metastatic Pancreatic Ductal Adenocarcinoma Previously Treated With Gemcitabine-Based Therapy." Poster presented at the American Society of Clinical Oncology Gastrointestinal Cancers Symposium (ASCO GI), San Francisco, CA, Jan. 18-20, 2018, 8 pages.

Siveke J, et al., Abstract 460. "Subgroup Analysis by Measurable Metastatic Lesion (ML) Number and Selected Lesion Locations (LL) at Baseline (BL) in NAPOLI-1: A Phase III Study of Liposomal Irinotecan (nal-IRI) ±5-Fluorouracil/Leucovorin (5-FU/LV) in Patients (pts) With Metastatic Pancreatic Ductal Adenocarcinoma (mPDAC) Previously Treated With Gemcitabine-Based Therapy," J Clin Oncol. 36(4_Suppl):460 DOI: 10.1200/JCO.2018.36.4_suppl.460 (2018), 2 printed pages.

Siveke J, et al., Abstract ID0596. "Expanded Analyses of NAPOLI-1: Phase 3 Study of nal-IRI (MM-398), With or Without 5-Fluorouracil (5FU) and Leucovorin (LV), Versus 5-Fluorouracil and Leucovorin (5FU/LV), in Metastatic Pancreatic Cancer (mPAC) Previously Treated With Gemcitabine-Based Therapy," Oncol Res Treat. 39(Suppl 1):170 (2016).

Siveke J, et al., Abstract P863. "Effects of Nanoliposomal Irinotecan (nal-IRI;MM-398) ± 5-Fluorouracil und Leucavorin (5-FU/LV) on Quality of Life (QoL) in NAPOLI-1: A Phase 3 Study in Patients (pts) With Metastatic Pancreatic Adenocarcinoma (mPAC) Previously Treated With Gemcitabine-Based Therapy," Oncol Res Threat. 39(Suppl 3):259 (2016).

Soares H, et. al., "A Phase II Study of Capecitabine Plus Docetaxel in Gemcitabine-Pretreated Metastatic Pancreatic Cancer Patients: CapTere," Cancer Chemother Pharmacol. 73(4):839-45 (2014).

Sohal D et. al., "Metastatic Pancreatic Cancer: ASCO Clinical Practice Guideline Update," J Clin Oncol. 36(24):2545-2556 and appendix (2018).

Sohal D, et. al., "Metastatic Pancreatic Cancer: American Society of Clinical Oncology Clinical Practice Guideline," J Clin Oncol. 34(23):2784-96 and Appendix (2016).

Mohammad A, et al., "Liposomal Irinotecan Accumulates in Metastatic Lesions, Crosses the Blood-Tumor Barrier (BTB), and Prolongs Survival in an Experimental Model of Brain Metastases of Triple Negative Breast Cancer," Pharm Res. 35(2):31; doi.org/10.1007/s11095-017-2278-0 (2018), 10 pages.

Mukhtar R, et al., "Elevated PCNA+ Tumor-Associated Macrophages in Breast Cancer are Associated with Early Recurrence and Non-Caucasian Ethnicity," Breast Cancer Res Treat. 130(2):635-44 (2011).

Murai J, et al., "Identification of Novel PARP Inhibitors Using a Cell-Based TDP1 Inhibitory Assay in a Quantitative High-Throughput Screening Platform," Author manuscript; Published in final edited form as: DNA Repair (Arnst). 21:177-82 (2014), 13 pages.

Murai J, et al., "Rationale for Poly(ADP-ribose) Ploymerase (PARP) Inhibitors in Combination Therapy with Campothecins or Temozolomide Based on PARP Trapping versus Catalytic Inhibition," J Pharmacol Exp Ther. 349(3):408-16 (2014).

No authors listed. "5HT3-receptor Antagonists as Antiemetics in Cancer," Drug Ther Bull. 43(8):57-62 (2005).

Noble C, et al., "Novel Nanoliposomal CPT-11 Infused by Convection-Enhanced Delivery in Intracranial Tumors: Pharmacology and Efficacy," Cancer Res. 66(5):2801-6 (2006).

Noble C, et al. "Pharmacokinetics, Tumor Accumulation and Antitumor Activity of Nanoliposomal Irinotecan Following Systemic Treatment of Intracranial Tumors," Nanomedicine. 9(14):2099-108 (2014).

O'Brien M, et al., "Phase III Trial Comparing Supportive Care Alone With Supportive Care With Oral Topotecan in Patients With Relapsed Small-Cell Lung Cancer," J Clin Oncol. 24(34):5441-7 (2006).

Owonikoko T, et al., "A Systematic Analysis of Efficacy of Second-Line Chemotherapy in Sensitive and Refractory Small-Cell Lung Cancer," J Thorac Oncol. 7(5):866-72 (2012).

Pallis A, et al., "A Multicenter Randomized Phase II Study of the Irinotecan/Gemcitabine Doublet Versus Irinotecan Monotherapy in Previously Treated Patients with Extensive Stage Small-Cell Lung Cancer," Lung Cancer. 65(2):187-91 (2009), Epub Dec. 18, 2008.

(56) References Cited

OTHER PUBLICATIONS

Park J, et al., "Anti-HER2 Immunoliposomes: Enhanced Efficacy Attributable to Targeted Delivery," Clin Cancer Res. 8(4):1172-81 (2002).
Patton W, "Detection Technologies in Proteome Analysis," J Chromatogr B. 771(1-2):3-31 (2002).
Paz-Ares L, et al., "Efficacy and Safety of Irinotecan Liposome Injection (nal-IRI) in Patients with Small Cell Lung Cancer (SCLC)," Presentation presented at 2019 World Conference on Lung Cancer; Sep. 7-10, 2019; Barcelona, Spain; 9 pages.
Paz-Ares L, et al., "Liposomal Irinotecan vs Topotecan in Patients with Small Cell Lung Cancer Who Have Progressed On/After Platinum-Based Therapy." Poster presented Sep. 23-26, 2018 at 19th World Conference on Lung Cancer meeting, 9 pages.
Paz-Ares L, et al., "RESILIENT: Study of Irinotecan Liposome Injection (nal-IRI) in Patients with Small Cell Lung Cancer—Preliminary Findings from Part 1 Dose-Defining Phase," Poster presented at ASCO in Chicago, IL May 31-Jun. 4, 2019, 6 pages.
Paz-Ares L, et al., "RESILIENT: Study of Irinotecan Liposome Injection (nal-IRI) in Patients with Small Cell Lung Cancer—Preliminary Findings from Part 1 Dose-Defining Phase," Abstract No. 8562, J Clin Oncol. 37(15)(Suppl):8562 (2019), 3 pages.
Paz-Ares Rodriguez L, et al., Abstract OA03.03. "Initial Efficacy and Safety Results of Irinotecan Liposome Injection (Nal-IRI) in Patients With Small Cell Lung Cancer," 2019 World Conference on Lung Cancer Abstracts; Sep. 7-10, 2019; Barcelona, Spain; pp. 220-221.
PCT/GB2017/053293: PCT International Preliminary Report on Patentability dated May 7, 2019, 7 pages.
PCT/GB2017/053293: PCT International Search Report and Written Opinion dated Feb. 2, 2018, 12 pages.
PCT/IB2017/000681: PCT International Preliminary Report on Patentability dated Nov. 20, 2018, 6 pages.
PCT/IB2017/000681: PCT International Search Report and Written Opinion dated Aug. 25, 2017, 8 pages.
PCT/US2005/015349: PCT International Search Report and Written Opinion dated Aug. 18, 2005, 14 pages.
PCT/US2013/046914: PCT International Preliminary Report on Patentability dated Dec. 23, 2014, 7 pages.
PCT/US2013/046914: PCT International Search Report dated Sep. 2, 2013, 3 pages.
PCT/US2013/075513: PCT International Preliminary Report on Patentability dated Jun. 16, 2015, 7 pages.
PCT/US2013/075513: PCT International Search Report dated Jun. 6, 2014, 2 pages.
PCT/US2014/062007: PCT International Preliminary Report on Patentability dated Apr. 26, 2016, 10 pages.
PCT/US2014/062007: PCT International Search Report dated Jan. 9, 2015, 3 pages.
PCT/US2015/064491: PCT International Preliminary Report on Patentability dated Jun. 13, 2017, 7 pages.
PCT/US2015/064491: PCT International Search Report dated Feb. 19, 2016, 4 pages.
PCT/US2016/027515: PCT International Preliminary Report on Patentability dated Oct. 17, 2017, 8 pages.
PCT/US2016/027515: PCT International Search Report dated Jun. 27, 2016, 4 pages.
PCT/US2016/047727: PCT International Preliminary Report on Patentability dated Feb. 27, 2018, 6 pages.
PCT/US2016/047727: PCT International Search Report and Written Opinion dated Nov. 16, 2016, 8 pages.
PCT/US2016/047814: PCT International Preliminary Report on Patentability dated Feb. 20, 2018, 6 pages.
PCT/US2016/047814: PCT International Search Report dated Nov. 17, 2016, 3 pages.
PCT/US2016/047827: PCT International Preliminary Report on Patentability dated Feb. 20, 2018, 6 pages.
PCT/US2016/047827: PCT International Search Report dated Nov. 17, 2016, 3 pages.
PCT/US2016/057247: PCT International Preliminary Report on Patentability dated Apr. 17, 2018, 8 pages.
PCT/US2016/057247: PCT International Search Report dated on Dec. 23, 2016, 4 pages.
Peinert S, et al., "Safety and Efficacy of Weekly 5-Fluorouracil/Folinic Acid/Oxaliplatin/Irinotecan in the First-Line Treatment of Gastrointestinal Cancer," Ther Adv Med Oncol. 2(3):161-74 (2010).
Pfizer Background Document on the UGT1A1 Polymorphisms and Irinotecan Toxicity: ACPS Nov. 3, 2004 Advisory Committee Meeting, 19 pages.
Ramanathan R, et al., "Correlation between Ferumoxytol Uptake in Tumor Lesions by MRI and Response to Nanoliposomal Irinotecan in Patients with Advanced Solid Tumors: A Pilot Study," Clin Cancer Res. 23(14):3638-48 (2017).
Ramanathan R, et al., "Lesion Characterization with Ferumoxytol MRI in Patients with Advanced Solid Tumors and Correlation with Treatment Response to MM-398, Nanoliposomal Irinotecan (nal-IRI)." Poster presented at EORTC-NICI-AACR International Conference on Molecular Targets and Cancer Therapeutics on Nov. 20, 2014, 7 pages.
Ramanathan R, et al., "Lesion Characterization with Ferumoxytol MRI in Patients with Advanced Solid Tumors and Correlation with Treatment Response to MM-398, Nanoliposomal Irinotecan (nal-IRI)," Abstract No. 261. Eur. J. Cancer, 50:87 (2014).
Ramanathan R, et al., "Pilot Study in Patients with Advanced Solid Tumors to Evaluate Feasibility of Ferumoxytol (FMX) as a Tumor Imaging Agent Prior to MM-398, a Nanoliposomal Irinotecan (nal-IRI)." Poster presented at AACR Annual Meeting 2014, San Diego, CA, 9 pages.
Raymond E, et al., "Multicentre Phase II Study and Pharmacokinetic Analysis of Irinotecan in Chemotherapy-Naive Patients with Glioblastoma," Ann Oncol. 14(4):603-14 (2003).
Roy A, et al., "A Randomized Phase Ii Study of PEP02 (MM-398), Irinotecan or Docetaxel as a Second-Line Therapy in Patients With Locally Advanced or Metastatic Gastric or Gastro-Oesophageal Junction Adenocarcinoma," Ann Oncol. 24(6):1567-73 (2013).
Sachdev J, et al., "A Phase 1 Study in Patients with Metastatic Breast Cancer to Evaluate the Feasibility of Magnetic Resonance Imaging with Ferumoxytol as a Potential Biomarker for Response to Treatment with Irinotecan Liposome Injection (nal-IRI, MM-398)." Poster presented at 38th Annual San Antonio Breast Cancer Symposium on Dec. 8, 2015, 10 pages.
Sachdev J, et al., "Characterization of Metastatic Breast Cancer Lesions with Ferumoxytol MRI and Clinical Response to MM-398, Nanoliposomal Irinotecan (nal-IRI), in 3 Subjects." Poster presented at San Antonio Breast Cancer Symposium 2014, 8 pages.
Yoo C, et al., "Multicenter Randomized Phase II Trial of 5-Fluorouracil/Leucovorin (5-FU/LV) With or Without Liposomal Irinotecan (nal-IRI) in Metastatic Biliary Tract Cancer (BTC) as Second-Line Therapy After Progression on Gemcitabine Plus Cisplatin (GemCis): NIFTY Trial." Poster presented at the European Society for Medical Oncology (ESMO) 2019 Congress, Barcelona, Spain, Sep. 27-Oct. 1, 2019, 6 pages.
Yoo C, et al., Abstract 829TiP. "Multicenter Randomized Phase II Trial of 5-Fluorouracil/Leucovorin (5-FU/LV) With or Without Liposomal Irinotecan (nal-IRI) in Metastatic Biliary Tract Cancer (BTC) as Second-Line Therapy After Progression on Gemcitabine Plus Cisplatin (GemCis): NIFTY Trial," Ann Oncol. 30(Supp_5):v318 /doi.org/10.1093/annonc/mdz247.155 (2019).
Younis I, et. al., "Enterohepatic Recirculation Model of Irinotecan (CPT-11) and Metabolite Pharmacokinetics in Patients With Glioma," Cancer Chemother Pharmacol. 63(3):517-24 (2009), author manuscript version, 16 pages.
Zamboni W, et. al., "Phase I and Pharmacokinetic Study of Pegylated Liposomal CKD-602 in Patients with Advanced Malignancies," Clin Cancer Res. 15(4):1466-72 (2009) and correction found at Clin Cancer Res. 15(8):2949-50 (2009).
Zhang K, et al., "Comprehensive Optimization of a Single-Chain Variable Domain Antibody Fragment as a Targeting Ligand for a Cytotoxic Nanoparticle," MAbs. 7(1):42-52 (2015).
Sohal D, et. al., "Reply to A. Wang-Gillam et al," J Clin Oncol. 35(6):690-1 (2017). Epub 2016.

(56) References Cited

OTHER PUBLICATIONS

Son J, et al., "Glutamine Supports Pancreatic Cancer Growth Through a Kras-Regulated Metabolic Pathway," Nature. 496(7443):101-5 (2013), author manuscript version, 16 pages.
Sousa C and Kimmelman A, "The Complex Landscape of Pancreatic Cancer Metabolism," Carcinogenesis. 35(7):1441-50 (2014).
Starling N, et. al., "A Dose Escalation Study of Gemcitabine Plus Oxaliplatin in Combination With Imatinib for Gemcitabine-Refractory Advanced Pancreatic Adenocarcinoma," Ann Oncol. 23(4):942-7 (2012). Epub 2011.
Stathis A and Moore M, "Advanced Pancreatic Carcinoma: Current Treatment and Future Challenges," Nat Rev Clin Oncol. 7(3):163-72 (2010).
Stathopoulos G, et. al., "A Multicenter Phase III Trial Comparing Irinotecan-Gemcitabine (IG) With Gemcitabine (G) Monotherapy as First-Line Treatment in Patients With Locally Advanced or Metastatic Pancreatic Cancer," Br J Cancer. 95(5):587-92 (2006).
Stathopoulos G, et. al., "Lipsomal Cisplatin Combined With Gemcitabine in Pretreated Advanced Pancreatic Cancer Patients: A phase I-II Study," Oncol Rep. 15(5):1201-4 (2006).
Takada T et. al., "Comparison of 5-Fluorouracil, Doxorubicin and Mitomycin C with 5-Fluorouracil Alone in the Treatment of Pancreatic-Biliary Carcinomas," Oncology. 51(5):396-400 (1994).
Takahara N, et. al., "A Retrospective Study of S-1 and Oxaliplatin Combination Chemotherapy in Patients With Refractory Pancreatic Cancer," Cancer Chemother Pharmacol. 72(5):985-90 (2013).
Tempero M, et. al., "NCCN Clinical Practice Guidelines in Oncology: Pancreatic Adenocarcinoma," Version 1.2012. National Comprehensive Cancer Network, Inc. (2011), 79 pages.
Tempero M, et. al., "NCCN Clinical Practice Guidelines in Oncology: Pancreatic Adenocarcinoma," Version 2.2012. National Comprehensive Cancer Network, Inc. (2011), 94 pages.
Tempero M, et. al., "NCCN Clinical Practice Guidelines in Oncology: Pancreatic Adenocarcinoma," Version 2.2014. National Comprehensive Cancer Network, Inc. (2014), 122 pages.
Tempero M, et. al., "Pancreatic Adenocarcinoma: Clinical Practice Guidelines in Oncology," J Natl Compr Canc Netw. 8(9):972-1017 (2010).
Thota R, et. al., "Treatment of Metastatic Pancreatic Adenocarcinoma: A Review," Oncology. 28(1):70-4 (2014). Available at cancernetwork. com/view/treatment-metastatic-pancreatic-adenocarcinoma-review, 6 printed pages.
Todaka A, et. al., "S-1 Monotherapy as Second-line Treatment for Advanced Pancreatic Cancer after Gemcitabine Failure," Jpn J Clin Oncol. 40(6):567-72 (2010).
Togawa A, et. al., "Treatment With an Oral Fluoropyrimidine, S-1, Plus Cisplatin in Patients Who Failed Postoperative Gemcitabine Treatment for Pancreatic Cancer: A Pilot Study," Int J Clin Oncol. 12(4):268-73 (2007).
Tomicki S, et al., "Utilization of Hospital Inpatient Services Among Patients With Metastatic Pancreatic Cancer With Commercial and Medicare Insurance Treated With FDA-Approved/NCCN Category 1 Regimens." Poster presented at the Academy of Managed Care Pharmacy, Nexus (AMCP, Nexus): virtual meeting, week of Oct. 19, 2020, 6 pages.
Van Cutsem E et. al., "Phase III Trial of Bevacizumab in Combination With Gemcitabine and Erlotinib in Patients With Metastatic Pancreatic Cancer," J Clin Oncol. 27(13):2231-7 (2009).
Van Rijswijk R, et. al., "Weekly High-Dose 5-Fluorouracil and Folinic Acid in Metastatic Pancreatic Carcinoma: A Phase II Study of the EORTC Gastrointestinal Tract Cancer Cooperative Group," Eur J Cancer. 40(14):2077-81 (2004).
Ventura M, et al., "Efficacy of nal-IRI and Hypoxia Modulation in Orthotopic Patient-Derived Pancreatic Tumor Models of High (OCIP51) and Low (OCIP19) Hypoxia," Presentation presented at the World Molecular Imaging Congress 2017, Philadelphia, Pennsylvania, Sep. 13-16, 2017, 15 pages.
Ventura M, et al., Abstract. "Efficacy of nal-IRI and Hypoxia Modulation in Orthotopic Patient-Derived Pancreatic Tumor Models of High (OCIP51) and Low (OCIP19) Hypoxia," The World Molecular Imaging Congress 2017, Philadelphia, Pennsylvania, Sep. 13-16, 2017, 1 page.
Vickers M, et. al., "Comorbidity, Age and Overall Survival in Patients With Advanced Pancreatic Cancer—Results from NCIC CTG PA.3: A Phase III Trial of Gemcitabine Plus Erlotinib or Placebo," Eur J Cancer. 48(10):1434-42 (2012). Epub 2011.
Von Hoff D, et. al., "Gemcitabine Plus nab-Paclitaxel Is an Active Regimen in Patients With Advanced Pancreatic Cancer: A PhaseI/II Trial," J Clin Oncol. 29(34):4548-54 (2011).
Von Hoff D, et. al., "Increased Survival in Pancreatic Cancer with nab-Paclitaxel plus Gemcitabine," N Engl J Med. 369(18):1691-703 (2013).
Wainberg Z, et al., "First-Line Liposomal Irinotecan + 5-Fluorouracil/Leucovorin + Oxaliplatin in Patients With Pancreatic Ductal Adenocarcinoma: Long-Term Follow-Up Results From a Phase 1/2 Study." Poster presented at the European Society for Medical Oncology (ESMO) World Congress on Gastrointestinal Cancer, virtual format, Jul. 1-4, 2020, 7 pages.
Wainberg Z, et al., "NAPOLI-3: An Open-Label, Randomized, Phase 3 Study of First-Line Liposomal Irinotecan + 5 Fluorouracil/Leucovorin + Oxaliplatin Versus Nab-Paclitaxel + Gemcitabine in Patients With Metastatic Pancreatic Ductal Adenocarcinoma." Poster presented at the American Society of Clinical Oncology (ASCO) Annual Conference, virtual format, May 29-Jun. 2, 2020, 6 pages.
Wainberg Z, et al., Abstract TPS4661. "NAPOLI-3: An Open-Label, Randomized, Phase III Study of First-Line Liposomal Irinotecan + 5 Fluorouracil/Leucovorin + Oxaliplatin Versus Nab-Paclitaxel + Gemcitabine in Patients With Metastatic Pancreatic Ductal Adenocarcinoma," J Clin Oncol. 38(15_Suppl):TPS4661 DOI: 10.1200/JCO.2020.38.15_suppl.TPS4661 (2020), 2 printed pages.
Walker E and Ko A, "Beyond First-Line Chemotherapy for Advanced Pancreatic Cancer: An Expanding Array of Therapeutic Options?" World J Gastroenterol. 20(9):2224-36 (2014).
Wang-Gillam A, et al., "Characteristics of Long-Term Survivors in a Randomized Phase 3 Trial (NAPOLI-1) of Patients With Metastatic Pancreatic Ductal Adenocarcinoma (mDPAC) Treated With Liposomal Irinotecan (nal-IRI; MM-398) + 5-FU/LV." Poster presented at the American Society of Clinical Oncology Gastrointestinal Cancers Symposium (ASCO GI), San Francisco, CA, Jan. 19-21, 2017, 9 pages.
Wang-Gillam A, et al., "Dose Modifications of Liposomal Irinotecan (nal-IRI) + 5-Fluorouracil/Leucovorin (5-FU/LV) in NAPOLI-1: Impact on Efficacy." Poster presented at the American Society of Clinical Oncology Gastrointestinal Cancers Symposium (ASCO GI), San Francisco, CA, Jan. 18-20, 2018, 8 pages.
Wang-Gillam A, et al., "Nomogram for Predicting Overall Survival in Patients Treated With Liposomal Irinotecan (nal-IRI) ± 5-Fluorouracil/Leucovorin (5-FU/LV) in Metastatic Pancreatic Ductal Adenocarcinoma (mPDAC) Previously Treated With Gemcitabine-Based Therapy in NAPOLI-1." Poster presented at the American Society of Clinical Oncology Gastrointestinal Cancers Symposium (ASCO GI), San Francisco, CA, Jan. 18-20, 2018, 9 pages.
Wang-Gillam A, et al., "Updated Overall Survival Analysis of NAPOLI-1: Phase 3 Study of Nanoliposomal Irinotecan (nal-IRI, MM-398), With or Without 5-Fluorouracil and Leucovorin (5-FU/LV), Versus 5-FU/LV in Metastatic Pancreatic Cancer (mPAC) Previously Treated With Gemcitabine-Based Therapy." Poster presented at the American Society of Clinical Oncology Gastrointestinal Cancers Symposium (ASCO GI), San Francisco, CA, Jan. 21-23, 2016, 11 pages.
Wang-Gillam A, et al., "Updated Overall Survival Analysis of NAPOLI-1: Phase 3 Study of Nanoliposomal Irinotecan (nal-IRI, MM-398), With or Without 5-Fluorouracil and Leucovorin, vs 5-Fluorouracil and Leucovorin in Metastatic Pancreatic Ductal Adenocarcinoma Previously Treated With Gemcitabine." Poster presented at the American Society of Clinical Oncology (ASCO) Annual Meeting, Chicago, Illinois, Jun. 3-7, 2016, 8 pages.
Wang-Gillam A, et al., Abstract 293. "Characteristics of Long-Term Survivors in a Randomized Phase III Trial (NAPOLI-1) of Patients With Metastatic Pancreatic Ductal Adenocarcinoma (mPDAC) Treated

(56) References Cited

OTHER PUBLICATIONS

With Liposomal Irinotecan (nal-IRI; MM-398) + 5-FU/LV," J Clin Oncol. 35(4_Suppl):293 DOI: 10.1200/JCO.2017.35.4_suppl.293 (2017), 2 printed pages.
Wang-Gillam A, et al., Abstract 388. "Dose Modifications of Liposomal Irinotecan (nal-IRI) + 5-Fluorouracil/Leucovorin (5-FU/LV) in NAPOLI-1: Impact on Efficacy," J Clin Oncol. 36(4_Suppl):388 DOI: 10.1200/JCO.2018.36.4_suppl.388 (2018), 2 printed pages.
Wang-Gillam A, et al., Abstract 4126. "Updated Overall Survival (OS) Analysis of NAPOLI-1: Phase 3 Study of Nanoliposomal Irinotecan (nal-IRI, MM-398), With or Without 5-Fluorouracil and Leucovorin (5-FU/LV), vs 5-FU/LV in Metastatic Pancreatic Cancer (mPAC) Previously Treated With Gemcitabine (Gem)-Based Therapy," J Clin Oncol. 34(15_Suppl):4126 DOI: 10.1200/JCO.2016.34.15_suppl.4126 (2016), 5 printed pages.
Wang-Gillam A, et al., Abstract 417. "Updated Overall Survival Analysis of NAPOLI-1: Phase III Study of Nanoliposomal Irinotecan (nal-IRI, MM-398), With or Without 5-Fluorouracil and Leucovorin (5-FU/LV), Versus 5-FU/LV in Metastatic Pancreatic Cancer (mPAC) Previously Rreated With Gemcitabine-Based Therapy," J Clin Oncol. 34(4_Suppl):417 DOI: 10.1200/jco.2016.34.4_suppl.417 (2016), 2 printed pages.
Wang-Gillam A, et al., Abstract 459. "Nomogram for Predicting Overall Survival (OS) in Patients (pts) Treated With Liposomal Irinotecan (nal-IRI) ± 5-Fluorouracil/Leucovorin (5-FU/LV) in Metastatic Pancreatic Ductal Adenocarcinoma (mPDAC) Previously Treated With Gemcitabine-Based Therapy in NAPOLI-1," J Clin Oncol. 36(4_Suppl):459 DOI: 10.1200/JCO.2018.36.4_suppl.459 (2018), 2 printed pages.
Wang-Gillam A, et al., Abstract e15795. "The Prognostic Value of Baseline Neutrophil-to-Lymphocyte Ratio (NLR) and Platelet-to-Lymphocyte ratio (PLR) for Predicting Clinical Outcome in Patients with Metastatic Pancreatic Ductal Adenocarcinoma (mPDAC) Treated With Liposomal Irinotecan (nalIRI; MM398) + 5-Fluorouracil and Leucovorin (5-FU/LV) vs 5-FU/LV," J Clin Oncol. 35(15_Suppl):e15795 DOI: 10.1200/JCO.2017.35.15_suppl.e15795 (2017), 3 printed pages.
Wang-Gillam A, et al., Abstract e16204. "A Survival Prediction Nomogram for Liposomal Irinotecan (nal-IRI)+5-Fluorouracil/Leucovorin (5-FU/LV) in Patients (pts) With Metastatic Pancreatic Ductal Adenocarcinoma (mPDAC) Previously Treated With Gemcitabine-Based Therapy," J Clin Oncol. 36(15_Suppl):e16204 DOI: 10.1200/JCO.2018.36.15_suppl.e16204 (2018), 2 printed pages.
Wang-Gillam A, et. al., letter to editor, "Nanoliposomal Irinotecan in the Clinical Practice Guideline for Metastatic Pancreatic Cancer: Applicability to Clinical Situations," J Clin Oncol. 35(6):689-90 (2017). Epub 2016.
Xiong H, et. al., "Phase 2 Trial of Oxaliplatin Plus Capecitabine (XELOX) as Second-line Therapy for Patients With Advanced Pancreatic Cancer," Cancer. 113(8):2046-52 (2008).
Yu K, et al., "Hospitalizations and Real-World Clinical Outcomes of Liposomal Irinotecan in a NAPOLI1-Based Regimen Among Patients With Metastatic Pancreatic Ductal Adenocarcinoma (mPDAC): A Multi-Center Chart Review," Poster presented at the Academy of Managed Care Pharmacy, Nexus (AMCP, Nexus): virtual meeting, week of Oct. 19, 2020, 9 pages.
Yu K, et al., Abstract C3. "Hospitalizations and Real-World Clinical Outcomes of Liposomal Irinotecan in a NAPOLI1-Based Regimen Among Patients With Metastatic Pancreatic Ductal Adenocarcinoma (mPDAC): A Multi-Center Chart Review," J Manag Care Spec Pharm. 26(10-a):S19 (2020).
Yu K, et al., "A US Multicenter Chart Review Study of Patients With Metastatic Pancreatic Ductal Adenocarcinoma Receiving Liposomal Irinotecan after Gemcitabine-Based Therapy." Poster presented at the International Conference on Pharmacoepidemiology & Therapeutic Risk Management (ICPE) All Access, Sep. 16-17, 2020, 8 pages.
Yu K, et al., "Real-World Treatment Patterns and Effectiveness of Liposomal Irinotecan in a NAPOLI1-Based Regimen Among Patients With Metastatic Pancreatic Ductal Adenocarcinoma (mPDAC): A Multi-Academic Center Chart Review." Poster presented at the European Society for Medical Oncology (ESMO) Virtual Congress 2020, Sep. 19-21, 2020, 9 pages.
Yu K, et al., Abstract 1555P. "Real-World Treatment Patterns and Effectiveness of Liposomal Irinotecan in a NAPOLI1-Based Regimen Among Patients With Metastatic Pancreatic Ductal Adenocarcinoma (mPDAC): A Multi-Academic Center Chart Review," Ann Oncol. 31(Suppl_4):S950-S951 doi.org/10.1016/j.annonc.2020.08.2038 (2020), 2 printed pages.
Yu K, et al., Abstract e16733. "A Multicenter Chart Review Study of Patients with Metastatic Pancreatic Ductal Adenocarcinoma Receiving Liposomal Irinotecan after Gemcitabine-Based Therapy," J Clin Oncol. 38(15_Suppl):e16733 DOI: 10.1200/JCO.2020.38.15_suppl.e16733 (2020), 4 printed pages.
Yu K, et al., Abstract PO-3727. "A US Multicenter Chart Review Study of Patients With Metastatic Pancreatic Ductal Adenocarcinoma Receiving Liposomal Irinotecan after Gemcitabine-Based Therapy," International Conference on Pharmacoepidemiology & Therapeutic Risk Management (ICPE), Sep. 14, 2020, available at eventscribe.com/2020/ICPEAllAccess/PosterTitles.asp?pfp=PosterTitles, 1 page.
Yu X, et. al., "Targeted Drug Delivery in Pancreatic Cancer," Biochim Biophys Acta. 21805(1):97-104 (2010). Epub 2009, author manuscript version, 16 pages.
Kraut E, et. al., Abstract 2017. "Final Results of a Phase I Study of Liposome Encapsulated SN-38 (LE-SN38): Safety, Pharmacogenomics, Pharmacokinetics, and Tumor Response," J Clin Oncol. 23(16_Suppl):2017 (2005), 3 printed pages.
Kulke M, et. al., "A Phase II Trial of Irinotecan and Cisplatin in Patients with Metastatic Neuroendocrine Tumors," Dig Dis Sci. 51(6):1033-8 (2006).
Lamichhane N, et. al., "Liposomes: Clinical Applications and Potential for Image-Guided Drug Delivery," Molecules. 23(2):288 doi: 10.3390/molecules2302028 (2018), 17 pages.
Larsen A, et al., "Influence of Liposomal Irinotecan (nal-IRI) and Non-Liposomal Irinotecan, Alone and in Combination, on Tumor Growth and Angiogenesis in Colorectal Cancer (CRC) Models." Poster presented at the American Society of Clinical Oncology Gastrointestinal Cancers Symposium (ASCO GI), San Francisco, CA, Jan. 18-20, 2018, 9 pages.
Larsen A, et al., Abstract 771. "Influence of Liposomal Irinotecan (nal-IRI) and Non-Liposomal Irinotecan, Alone and in Combination, on Tumor Growth and Angiogenesis in Colorectal Cancer (CRC) Models," J Clin Oncol. 36(4_Suppl):711 DOI: 10.1200/JCO.2018.36.4_suppl.711 (2018), 2 printed pages.
Lecovorin Calcium package insert, Teva, revised Oct. 2009, 6 pages.
Lee H, et al., "(64)Cu-MM-302 Positron Emission Tomography Quantifies Variability of Enhanced Permeability and Retention of Nanoparticles in Relation to Treatment Response in Patients with Metastatic Breast Cancer," Clin Cancer Res. 23(15):4190-4202 (2017).
Lee H, et al., "A Gradient-Loadable (64)Cu-Chelator for Quantifying Tumor Deposition Kinetics of Nanoliposomal Therapeutics by Positron Emission Tomography," Nanomedicine. 11(1):155-65 (2015). Epub 2014.
Liu B, et al., "Mapping Tumor Epitope Space by Direct Selection of Single-Chain Fv Antibody Libraries on Prostate Cancer Cells," Cancer Res. 64(2):704-10 (2004).
Liu B, et al., "Recombinant Full-Length Human IgG1s Targeting Hormone-Refractory Prostate Cancer," J Mol Med (Berl). 85(10):1113-23 (2007).
Liu J-J, et al., "Simple and Efficient Liposomal Encapsulation of Topotecan by Ammonium Sulfate Gradient: Stability, Pharmacokinetic and Therapeutic Evaluation," Anticancer Drugs. 13(7):709-17 (2002).
Lundberg B, et al., "Conjugation of Apolipoprotein B with Liposomes and Targeting to Cells in Culture," Biochim Biophys Acta. 1149(2):305-12 (1993).
Ma W, et al., Abstract e13588. "Population Pharmacokinetics and Exposure-Safety Relationship of Nanoliposomal Irinotecan (MM-398, nal-IRI) in Patients With Solid Tumors," J Clin Oncol. 33(15_Suppl):e13588 DOI: 10.1200/ico.2015.33.15_suppl.e13588 (2015), 2 printed pages.

(56) References Cited

OTHER PUBLICATIONS

Mabro M, et. al., "A Phase II Study of FOLFIRI-3 (Double Infusion of Irinotecan Combined With LV5FU) After FOLFOX in Advanced Colorectal Cancer Patients," Br J Cancer. 94(9):1287-92 (2006).
Mabro M, et. al., "Bimonthly Leucovorin, Infusion 5-Fluorouracil, Hydroxyurea, and Irinotecan (FOLFIRI-2) for Pretreated Metastatic Colorectal Cancer," Am J Clin Oncol. 26(3):254-8 (2003).
Mackenzie M, et. al., "A Phase I Study of OSI-211 and Cisplatin as Intravenous Infusions Given on Days 1, 2 and 3 Every 3 Weeks in Patients With Solid Cancers," Ann Oncol. 15(4):665-70 (2004).
Malet-Martino M and Martino R, "Clinical Studies of Three Oral Prodrugs of 5-Fluorouracil (Capecitabine, UFT, S-1): A Review," Oncologist. 7(4):288-323 (2002).
Mamot C, et al., "Epidermal Growth Factor Receptor (EGFR)-Targeted Immunoliposomes Mediate Specific and Efficient Drug Delivery to EGFR- and EGFRvIII-Overexpressing Tumor Cells," Cancer Res. 63(12):3154-61 (2003).
Mamot C, et al., "Liposome-Based Approaches to Overcome Anticancer Drug Resistance," Drug Resist Updat. 6(5):271-9 (2003).
Mancini R and Modlin J, "Chemotherapy Administration Sequence: A Review of the Literature and Creation of a Sequencing Chart," J Hematol Oncol Pharm. 1(1):17-25 (2011).
Martin L, et. al., "VEGF Remains an Interesting Target in Advanced Cancreas Cancer (APCA): Results of a Multi-Institutional Phase II Study of Bevacizumab, Gemcitabine, and Infusional 5-Fluorouracil in Patients With APCA," Ann Oncol. 23(11):2812-20 (2012).
Mathijssen R, et. al., "Clinical Pharmacokinetics and Metabolism of Irinotecan (CPT-11)," Clin Cancer Res. 7(8):2182-94 (2001).
Matsusaka S, et. al., "Differential Effects of Two Fluorouracil Administration Regimens for Colorectal Cancer," Oncol Rep. 10(1):109-13 (2003).
Mayer L, et. al.,"Ratiometric Dosing of Anticancer Drug Combinations: Controlling Drug Ratios After Systemic Administration Regulates Therapeutic Activity in Tumor-Bearing Mice," Mol Cancer Ther. 5(7):1854-63 (2006).
McNamara M, et al., "NET-02: A Multi-Centre, Randomized, Phase II Trial of Liposomal Irinotecan (nal-IRI) and 5-Fluorouracil (5-FU)/Folinic Acid or Docetaxel as Second-Line Therapy in Patients (pts) With Progressive Poorly Differentiated Extra-Pulmonary Neuroendocrine Carcinoma (PD-EP-NEC)." Poster presented at the 17th Annual European Neuroendocrine Tumor Society (ENETS) Conference for the Diagnosis and Treatment of Neuroendocrine Tumor Disease, Virtual Conference, Mar. 11-13, 2020, 4 pages.
McNamara M, et al., Abstract P04. "NET-02: A Phase II Trial of Liposomal Irinotecan (nal-IRI) and 5-Fluorouracil (5-FU)/Folinic Acid or Docetaxel as Second-Line Therapy in Patients (pts) With Progressive Poorly Differentiated Extra-Pulmonary Neuroendocrine Carcinoma (PD-EP-NEC)," In Abstracts of the 17th Annual European Neuroendocrine Tumor Society (ENETS) Conference for the Diagnosis and Treatment of Neuroendocrine Tumor Disease, Virtual Conference, Mar. 11-13, 2020, p. 374.
Meerum Terwogt J, et. al., "Phase I and Pharmacokinetic Study of SPI-77, a Liposomal Encapsulated Dosage Form of Cisplatin," Cancer Chemother Pharmacol. 49(3):201-10 (2002).
Messerer C, et. al., "Liposomal Encapsulation of Irinotecan and Potential for the Use of Liposomal Drug in the Treatment of Liver Metastases Associated with Advanced Colorectal Cancer," MS Thesis, University of British Columbia, 2000, 90 pages.
Munzone E, "Adverse Side Effects Associated to Metronomic Chemotherapy," Presentation presented at Aiom Cancer Metronomic Therapy, Feb. 26, 2016, Milan, 32 pages.
Myocet liposomal, Summary of product characteristics and labelling and package leaflet, European Medicines Agency, available at ema.europa.eu/en/documents/product-information/myocet-liposomal-previously-myocet-epar-product-information_en.pdf, Date of first authorisation: Jul. 13, 2000, Date of latest renewal: Jul. 2, 2010, 37 pages.
Nakajima T, et. al., "Synergistic Antitumor Activity of the Novel SN-38-Incorporating Polymeric Micelles, NK012, Combined With 5-Fluorouracil in a Mouse Model of Colorectal Cancer, as Compared With That of Irinotecan Plus 5-Fluorouracil," Int J Cancer. 122(9):2148-53 (2008).
Nardi M, et. al., Abstract 14520. "Metronomic Irinotecan and Standard FOLFIRI Regimen as First-Line Chemotherapy in Metastatic Colorectal Cancer (MCRC). Final Results of Phase II Study," J Clin Oncol. 25(18_suppl):14520 (2007), 1 printed page.
National Cancer Institute, "Irinotecan Hydrochloride Liposome,"Posted: Oct. 27, 2015, Updated:Mar. 28, 2019, available at cancer.gov/about-cancer/treatment/drugs/irinotecan-hydrochloride-liposome, 2 pages.
Noble C, et al, "Development of Ligand-Targeted Liposomes for Cancer Therapy," Expert Opin Ther Targets. 8(4):335-53 (2004).
Noordhuis P, et. al., "5-Fluorouracil Incorporation into RNA and DNA in Relation to Thymidylate Synthase Inhibition of Human Colorectal Cancers," Ann Oncol. 15(7):1025-32 (2004).
Ogata Y, et. al., "Dosage Escalation Study of S-1 and Irinotecan in Metronomic Chemotherapy against Advanced Colorectal Cancer," Kurume Med J. 56(1-2):1-7 (2009).
Oncology NEWS International, "Experts Debate Bolus vs Continuous Infusion 5-FU." Feb. 1, 2003, vol. 12, Issue 2, 3 printed pages.
O'Reilly S, "Topotecan: What Dose, What Schedule, What Route?" Clin Cancer Res. 5(1):3-5 (1999).
Pal A, et. al., "Preclinical Safety, Pharmacokinetics and Antitumor Efficacy Profile of Liposome-Entrapped SN-38 Formulation," Anticancer Res. 25(1A):331-41 (2005).
Papahadjopoulos D, et al., "Targeting of Drugs to Solid Tumors Using Anti-HER2 Immunoliposomes," J Liposome Res. 8(4):425-42 (1998).
Papahadjopoulos D, et. al., "Sterically Stabilized Liposomes: Improvements in Pharmacokinetics and Antitumor Therapeutic Efficacy," Proc Natl Acad Sci USA. 88(24):11460-4 (1991).
Papi M, et. al., "Clinically Approved PEGylated Nanoparticles Are Covered by a Protein Corona That Boosts the Uptake by Cancer Cells," Nanoscale. 9(29):10327-34 (2017).
Park J, et al., "Anti-HER2 Immunoliposomes for Targeted Therapy of Human Tumors," Cancer Lett. 118(2):153-60 (1997).
Park J, et al., "Development of Anti-p185HER2 Immunoliposomes for Cancer Therapy," Proc Natl Acad Sci U S A. 92(5):1327-31 (1995).
Park J, et al., "Immunoliposomes for Cancer Treatment," Adv Pharmacol. 40:399-435 (1997).
Park J, et al., "Sterically Stabilized Immunoliposomes: Formulations for Delivery of Drugs and Genes to Tumor Cells In Vivo," In Targeting of Drugs 6: Strategies for Stealth Therapeutic Systems, Gregoriadis G, et al., eds., Plenum Press, New York, pp. 41-47 (1998).
Park J, et al., "Tumor Targeting Using Anti-HER2 Immunoliposomes," J Control Release. 74(1-3):95-113 (2001).
Park J, el al., "Anti-HER2 Immunoliposomes for Targeted Drug Delivery," Med Chem Res. 8(7/8):383-91 (1998).
Patankar N, et. al., "Topophore C: A Liposomal Nanoparticle Formulation of Topotecan for Treatment of Ovarian Cancer," Invest New Drugs. 31(1):46-58 (2013). Epub 2012.
Patel M, et. al., "Effects of Oxaliplatin and CPT-11 on Cytotoxicity and Nucleic Acid Incorporation of the Fluoropyrimidines," J Cancer Res Clin Oncol. 130(8):453-9 (2004).
Ettrich T, et al., Abstract TPS4145. "Liposomal Irinotecan (nal-IRI) Plus 5-Fluorouracil (5-FU) and Leucovorin (LV) or Gemcitabine Plus Cisplatin in Advanced Cholangiocarcinoma: The AIO-NIFE-Trial, an Open Label, Randomized, Multicenter Phase II Trial," J Clin Oncol. 36(15_Suppl):TPS4145 DOI: 10.1200/JCO.2018.36.15_suppl.TPS4145 (2018), 2 printed pages.
Ettrich T, et al., "Liposomal Irinotecan (nal-IRI) Plus 5-Fluorouracil (5-FU) and Leucovorin (LV) or Gemcitabine Plus Cisplatin in Advanced Cholangiocarcinoma: The AIO-NIFE-Trial, an Open Label, Randomized, Multicenter Phase II Trial," Poster presented at the American Society of Clinical Oncology (ASCO) Annual Meeting, Chicago, Illinois, Jun. 1-5, 2018, 5 pages.
Falcone A, et al., "Sequence Effect of Irinotecan and Fluorouracil Treatment on Pharmacokinetics and Toxicity in Chemotherapy-Naive Metastatic Colorectal Cancer Patients," J Clin Oncol. 19(15):3456-62 (2001).

(56) References Cited

OTHER PUBLICATIONS

Fannon M, et al., "Sucrose Octasulfate Regulates Fibroblast Growth Factor-2 Binding, Transport, and Activity: Potential for Regulation of Tumor Growth," J Cell Physiol. 215(2):434-41 (2008), NIH public access author manuscript version, 19 pages.

Farncombe M, "Management of Bleeding in a Patient with Colorectal Cancer: A Case Study," Support Care Cancer. 1(3):159-160 (1993).

FDA, "Draft Guidance on Daunorubicin Citrate," Jul. 2014, 6 pages.

FDA, "Draft Guidance on Doxorubicin Hydrochloride," Recommended Feb. 2010, Revised Nov. 2013, Dec. 2014, 6 pages.

Fioravanti A, et. al., "Metronomic 5-Fluorouracil, Oxaliplatin and Irinotecan in Colorectal Cancer," Eur J Pharmacol. 619(1-3): 8-14 (2009).

Fleming G, et. al., "Phase I and Pharmacokinetic Study of 24-Hour Infusion 5-Fluorouracil and Leucovorin in Patients With Organ Dysfunction," Ann Oncol. 14(7):1142-7 (2003).

Freise C, et al., "Characterization of a Cyclosporine-Containing Liposome," Transplant Proc. 23(1 Pt 1):473-4 (1991).

Freise C, et al., "Increased Efficacy of Cyclosporin Liposomes in a Rat Orthotopic Liver Transplant Model," Surgical Forum. 43:395-7 (1992).

Freise C, et al., "The Increased Efficacy and Decreased Nephrotoxicity of a Cyclosporine Liposome," Transplantation. 57(6):928-932 (1994).

Gaber M, et al., "Thermosensitive Liposomes: Extravasation and Release of Contents in Tumor Microvascular Networks," Int J Radiat Oncol Biol Phys. 36(5):1177-87 (1996).

Gaber M, et al., "Thermosensitive Sterically Stabilized Liposomes: Formulation and in Vitro Studies on the Mechanism of Doxorubicin Release by Bovine Serum and Human Plasma," Pharm Res. 12(10):1407-16 (1995).

Garcia-Alfonso P, et. al., "Capecitabine in Combination with Irinotecan (XELIRI), Administered as a 2-Weekly Schedule, as First-Line Chemotherapy for Patients With Metastatic Colorectal Cancer: A Phase II Study of the Spanish GOTI Group," Br J Cancer. 101(7):1039-43 (2009).

Garcia-Carbonero R and Supko J, "Current Perspectives on the Clinical Experience, Pharmacology, and Continued Development of the Camptothecins," Clin Cancer Res. 8(3):641-61 (2002).

Garufi C, et. al., "A Phase II Study of Irinotecan Plus Chronomodulated Oxaliplatin, 5-Fluorouracil and Folinic Acid in Advanced Colorectal Cancer Patients," Br J Cancer. 89(10):1870-5 (2003).

Geddie M, et al., "Improving the Developability of an Anti-EphA2 Single-Chain Variable Fragment for Nanoparticle Targeting," MAbs. 9(1):58-67 (2017). Epub 2016.

Gelmon K, et. al., "A Phase 1 Study of OSI-211 Given as an Intravenous Infusion Days 1, 2, and 3 Every Three Weeks in Patients With Solid Cancers," Invest New Drugs. 22(3):263-75 (2004).

GEMZAR (gemcitabine HCl) package insert, revision Apr. 1998, 24 pages.

Giles F, et. al., "Phase I and Pharmacokinetic Study of a Low-Clearance, Unilamellar Liposomal Formulation of Lurtotecan, a Topoisomerase 1 Inhibitor, in Patients with Advanced Leukemia," Cancer. 100(7):1149-58 (2004).

Glimelius B, et. al., "A Randomized Phase III Multicenter Trial Comparing Irinotecan in Combination With the Nordic Bolus 5-FU and Folinic Acid Schedule or the Bolus/Infused de Gramont Schedule (Lv5FU2) in Patients With Metastatic Colorectal Cancer," Ann Oncol. 19(5):909-14 (2008).

Glimelius B, et. al., "Prediction of Irinotecan and 5-Fluorouracil Toxicity and Response in Patients With Advanced Colorectal Cancer," Pharmacogenomics J. 11(1):61-71 (2011). Epub 2010.

Goldberg R, et. al., "A Randomized Controlled Trial of Fluorouracil Plus Leucovorin, Irinotecan, and Oxaliplatin Combinations in Patients With Previously Untreated Metastatic Colorectal Cancer," J Clin Oncol. 22(1):23-30 (2004). Epub 2003.

Greiner P, et. al., "Pharmacokinetics of (-)-Folinic Acid After Oral and Intravenous Administration of the Racemate," Br J Clin Pharmacol. 28(3):289-95 (1989).

Guichard S, et. al., "Cellular Interactions of 5-Fluorouracil and the Camptothecin Analogue CPT-11 (Irinotecan) in a Human Colorectal Carcinoma Cell Line," Biochem Pharmacol. 55(5):667-76 (1998).

Guichard S, et. al., "Sequence-Dependent Activity of the Irinotecan-5FU Combination in Human Colon-Cancer Model HT-29 In Vitro and In Vivo," Int J Cancer. 73(5):729-34 (1997).

Han S, et al., Abstract ACTR-33. "A Phase I Study of Convection-Enhanced Delivery of Liposomal-Irinotecan Using Real-Time Imaging With Gadolinium in Patients With Recurrent High Grade Glioma," Neuro-Oncology. 18(Suppl_6):vi9 doi.org/10.1093/neuonc/now212.031 (2016).

Hare J, "Utilization of Liposomes in Combination Cancer Chemotherapy," PhD thesis, University of Alberta, Department of Pharmacology, 2011, 367 pages.

Harker-Murray P, et al., Abstract CT146. "Plasma Pharmacokinetics of Liposomal Irinotecan (nal-iri) in Pediatric Oncology Patients with Recurrent or Refractory Solid Tumors: South Plains Oncology Consortium Study 2012-001," In Proceedings of the American Association for Cancer Research Annual Meeting 2017; Apr. 1-5, 2017. Washington, DC. Cancer Res. 2017;77(13 Suppl):Abstract nr CT146, doi:10.1158/1538-7445.AM2017-CT146, 2 printed pages.

Hashimoto S, et al., "Depletion of Alveolar Macrophages Decreases Neutrophil Chemotaxis to Pseudomonas Airspace Infections," Am J Physiol. 270(5 Pt 1):L819-28 (1996).

Hay M, et. al., "Clinical Development Success Rates for Investigational Drugs," Nature Biotechnol. 32(1):40-51 (2014).

Hayes M, et al., "Genospheres: Self-Assembling Nucleic Acid-Lipid Nanoparticles Suitable for Targeted Gene Delivery," Gene Ther. 13(7):646-51 (2006).

Hayes M, et al., "Increased Target Specificity of Anti-HER2 Genospheres by Modification of Surface Charge and Degree of PEGylation," Mol Pharm. 3(6):726-36 (2006).

Hsu M and Juliano R, "Interactions of Liposomes With the Reticuloendothelial System. II: Nonspecific and Receptor-Mediated Uptake of Liposomes by Mouse Peritoneal Macrophages," Biochim Biophys Acta. 720(4):411-419 (1982).

Huang S, et al., "Liposomes and Hyperthermia in Mice: Increased Tumor Uptake and Therapeutic Efficacy of Doxorubicin in Sterically Stabilized Liposomes," Cancer Res. 54(8):2186-91 (1994).

Huang S, et al., "Microscopic Localization of Sterically Stabilized Liposomes in Colon-Carcinoma Bearing Mice," Cancer Res. 52(19):5135-43 (1992).

Huang S, et. al., "Pharmacokinetics and Therapeutics of Sterically Stabilized Liposomes in Mice Bearing C-26 Colon Carcinoma," Cancer Res. 52(24):6774-81 (1992).

Huang S, et al., "Light Microscopic Localization of Silver Enhanced Liposome-Entrapped Colloidal Gold in Mouse Tissues," Biochim Biophys Acta. 1069(1):117-21 (1991).

Hwang J, et. al., "Improving the Toxicity of Irinotecan/5-FU/Leucovorin: A 21-Day Schedule," Oncology. 17(9):37-43 (2003). Available at cancernetwork.com/view/improving-toxicity-irinotecan5-fu-leucovorin-21-day-schedule, 13 printed pages.

Ignatiadis M, et. al., "A Multicenter Phase II Study of Docetaxel in Combination with Gefitinib in Gemcitabine-Pretreated Patients with Advanced/Metastatic Pancreatic Cancer," Oncology. 71(3-4):159-63 (2006).

Immordino M, et al., "Stealth Liposomes: Review of the Basic Science, Rationale, and Clinical Applications, Existing and Potential," Int J Nanomedicine. 1(3):297-315 (2006).

Jones S, et. al., Abstract 2547. "Phase I and Pharmacokinetic (PK) Study of IHL-305 (Pegylated Liposomal Irinotecan) in Patients With Advanced Solid Tumors," J Clin Oncol. 27(15_suppl):2547 and Table 1 (2009), 6 printed pages.

Kalra A, et al., Abstract 2065. "Magnetic Resonance Imaging with an Iron Oxide Nanoparticle Demonstrates the Preclinical Feasibility of Predicting Intratumoral Uptake and Activity of MM-398, a Nanoliposomal Irinotecan (nal-IRI)." In Proceedings of the 105th Annual Meeting of the American Association for Cancer Research; Apr. 5-9, 2014. Cancer Res 2014;74(19 Suppl):Abstract nr 2065, doi:10.1158/1538-7445.AM2014-2065, 1 printed page.

(56) References Cited

OTHER PUBLICATIONS

KHAPZORY (levoleucovrin) package insert, revised Oct. 2018, accessed from accessdata.fda.gov/drugsatfda_docs/label/2018/211226s000lbl.pdf, 9 pages.
Kirpotin D, et al., "Building and Characterizing Antibody-Targeted Lipidic Nanotherapeutics," Methods Enzymol. 502:139-66 (2012).
Kirpotin D, et al., "Targeting of Liposomes to Solid Tumors: The Case of Sterically Stabilized Anti-HER2 Immunoliposomes," J Liposome Res. 7:391-417 (1997).
Kirpotin D, et al., Chapter 4.7, "Targeting of Sterically Stabilized Liposomes to Cancers Overexpressing HER2/neu Proto-Oncogene," In Medical Applications of Liposomes, Lasic D and Papahadjopoulos D, eds., pp. 325-345 (1998).
Kline C, et. al., "Preliminary Observations Indicate Variable Patterns of Plasma 5-Fluorouracil (5-FU) Levels During Dose Optimization of Infusional 5-FU in Colorectal Cancer Patients," Cancer Biol Ther. 12(7):557-68 (2011).
Krauss W, et al., "Emerging Antibody-Based HER2 (ErbB2/neu) Therapeutics," Breast Dis. 11:113-24 (2000).
Batist G, et al., "Safety Pharmacokinetics, and Efficacy of CPX-1 Liposome Injection in Patients with Advanced Solid Tumors," Clin Cancer Res. 15(2):692-700 (2009).
Boman N, et al., "Optimization of the Retention Properties of Vincristine in Liposomal Systems," Biochim Biophys Acta. 1152(2):253-58 (1993).
Bouché O, et al. "Randomized Multicenter Phase II Trial of a Biweekly Regimen of Fluorouracil and Leucovorin LV5FU2), LV5FU2 Plus Cisplatin, or LV5FU2 Plus Irinotecan in Patients With Previously Untreated Metastatic Gastric Cancer: A Federation Francophone De Cancerologie Digestive Group Study—FFCD 9803," J Clin Oncol. 22 (21):14319-28 (2004).
Chiang, N-J, et al., "Development of Nanoliposomal Irinotecan (nal-IRI, MM-398, PEP02) in the Management of Metastatic Pancreatic Cancer," Expert Opin Pharmacother. 17(10):1413-20 (2016).
Colbern G, et al., "Encapsulation of the Topoisomerase I Inhibitor GL147211C in Pegylated (STEALTH) Liposomes: Pharmacokinetics and Antitumor Activity in HT29 Colon Tumor Xenografts," Clin Cancer Res. 4(12):3077-82 (1998).
Dicko A, et al., "Intra and Inter-Molecular Interactions Dictate the Aggregation State of Irinotecan Co-Encapsulated with Floxuridine Inside Liposomes," Pharm Res. 25(7):1702-13 (2008).
Drummond D, et al., "Pharmacokinetics and In Vivo Drug Release Rates in Liposomal Nanocarrier Development," J Pharm Sci. 97(11):4696-740 (2008).
Emerson D, et al., "Antitumor Efficacy, Pharmacokinetics, and Biodistribution of NX 211: A Low-Clearance Liposomal Formulation of Lurtotecan," Clin Cancer Res 6(7):2903-12 (2000).
EP Patent Application No. 05745505.7: European Search Report dated Sep. 1, 2010, 6 pages.
European Medicines Agency Assessment Report for Onivyde, Committee for Medicinal Products for Human Use (CHMP), Jul. 21, 2016, 107 pages.
Fugit K, et al., "The Role of pH and Ring-opening Hydrolysis Kinetics on Liposomal Release of Topotecan," J Control Release. 174:88-97 (2014), Epub Nov. 12, 2013, Author manuscript, pp. 1-27.
Hattori Y, et al., "Novel Irinotecan-Loaded Liposome Using Phytic Acid with High Therapeutic Efficacy for Colon Tumors," J Control Release. 136(1):30-7 (2009).
Koizumi W, at al. "Phase I/II Study of Bi-weekly Irinotecan plus Cisplatin in the Treatment of Advanced Gastric Dancer," Anticancer Res. 25(2B):1257-62 (2005).
Morise M, et al., "Low-dose Irinotecan as a Second-line Chemotherapy for Recurrent Small Cell Lung Cancer," Jpn J Clin Oncol. 44(9):846-51 (2014).
Pavillard V, et al., "Determinants of the Cytotoxicity of Irinotecan in Two Human Colorectal Tumor Cell Lines," Cancer Chemother Pharmacol. 49(4):329-35 (2002).

Peikov V, et al., "pH-Dependent Association of SN-38 with Lipid Bilayers of a Novel Liposomal Formulation," Int J Pharm 299(1-2):92-9 (2005).
Pharmaengine, www.phamnaengine.com/pep02.html Webpage titled "PEP02". Aug. 4, 2011, 4 printed pages.
Riviere K, et al., "Anti-Tumor Activity of Liposome Encapsulated Fluoroorotic Acid as a Single Agent and in Combination with Liposome Irinotecan," J Control Release. 153(3):288-96 (2011), Author manuscript, pp. 1-19.
Sadzuka Y, et al., "Effective Irinotecan (CPT-11)-containing Liposomes: Intraliposomal Conversion to the Active Metabolite SN-38." Jpn J Cancer Res. 90(2):226-32 (1999).
Tardi P, et al., "Liposomal Encapsulation of Topotecan Enhances Anticancer Efficacy in Murine and Human Xenograft Models," Cancer Res. 60(13):3389-93 (2000).
Wainberg Z, et al., "First-line Liposomal Irinotecan With Oxaliplatin, 5-Fluorouracil and Leucovorin (NALIRIFOX) in Pancreatic Ductal Adenocarcinoma: A Phase I/II Study," Eur J Cancer. 151:14-24 (2021).
Wei H, et al., "Active Loading Liposomal Irinotecan Hydrochloride: Preparation, In Vitro and In Vivo Evaluation," Asian J Pharm Sci. 8(5):303-11 (2013).
Zhang L, et al., PEG-Coated Irinitecan Cationic Liposomes Improve the Therapeutic Efficacy of Breast Cancer in Animals, Eur Rev Med Pharmacol Sci. 17(24):3347-61 (2013).
EP2861210: Proprietor's response to opponent's reply to proprietor's grounds of appeal following opposition, dated Jun. 30, 2021, 23 pages.
EP2861210: Proprietor's response to opponent's reply to proprietor's grounds of appeal following opposition, dated Jun. 30, 2021, D37 (Declaration of Carla Schoonderbeek) including D37A (Directive 2001/20/EC of the European Parliament and of the Counsel of Apr. 4, 2001 ("the Clinical Trials Directive" or CTD)), 26 total pages.
EP2861210: Proprietor's response to opponent's reply to proprietor's grounds of appeal following opposition, dated Jun. 30, 2021, D38 (Declaration of Grant H. Castle, Ph D.) including D38A (European Commission: "Communication Yom the Commission - Detailed guidance on the request to the competent authorities for authorisation of a clinical trial on a medicinal product for human use, the notification of substantial amendments and the declaration of the end of the Yial (CT-1)"), 23 total pages.
EP3337478: EPO Notice of Sandoz AG Opposition dated May 6, 2021, 5 pages.
EP3337478: Sandoz AG Opposition dated May 6, 2021, 22 pages.
EP3337478: Sandoz AG Opposition dated May 6, 2021, D1 (History of Changes for Study NCT02551991, retrieved Yom ClinicalTrials.gov archive on May 3, 2021, 4 pages).
EP3337478: Sandoz AG Opposition dated May 6, 2021, D2 (Abstract O-0003. Von Hoff D, et al., "NAPOL11 Randomized Phase 3 Study of MM-398 (nal-lRI), With or Without 5-Fluorouracil and Leucovorin, Versus 5-Fluorouracil and Leucovorin, in Metastatic Pancreatic Cancer Progressed on or Following Gemcitabine-Based Therapy." Ann Oncol. 25(Suppl 2):ii105 (2014)).
EP3337478: Sandoz AG Opposition dated May 6, 2021, D3 (Marsh R, et al., "Pancreatic Cancer and Folfirinox A New Era and New Questions," Cancer Med. 4(6):853-63 (2015)).
EP3337478: Sandoz AG Opposition dated May 6, 2021, D4 (Onivyde [MM-398] package insert, revision Oct. 22, 2015, 18 pages).
EP3337478: Sandoz AG Opposition dated May 6, 2021, D5 (Carnevale J and Ko A, "MM-398 (Nanoliposomal Yinotecan): Emergence of a Novel Therapy for the Treatment of Advanced Pancreatic Cancer," Future Oncol. 12 (4);453-64 (2016). Epub 2015).
EP3337478: Sandoz AG Opposition dated May 6, 2021, D6 (Dean A, et al., Abstract TPS482. "A Randomized, Open-abel Phase II Study of Nanoliposomal Irinotecan (nal-IRI)-Containing Regimens Versus nab-Paclitaxel Plus Gemcitabine in Patients With Previously Untreated Metastatic Pancreatic Adenocarcinoma (mPAC)," J Clin Oncol. 34 4_Suppl):tps482 (2016), DOI: 10.1200/jco.2016.34.4_suppLtps482, 5 printed pages).
EP3337478: Sandoz AG Opposition dated May 6, 2021, D7 (Zhang H, "Onivyde for the Therapy of Multiple Solid Fumors," Onco Targets Ther. 9:3001-3007 (2016)).

(56) References Cited

OTHER PUBLICATIONS

EP3337478: Sandoz AG Opposition dated May 6, 2021, D8 (Gaddy D, et al., "Abstract 4830: Preclinical Anti-tumor Activity of Nanoliposomal Irinotecan (Nal-IRI, MM-398) + 5-FU + Oxaliplatin in Pancreatic Cancer." In: Proceedings of the 107th Annual Meeting of the American Association for Cancer Research; Apr. 16-20, 2016; New Orleans, LA. Dancer Res. 76(14 Suppl):Abstract nr 4830 (2016), 4 printed pages).
ZP3337478: Sandoz AG Opposition dated May 6, 2021, D9 (Parhi P, et al., "Nanotechnology-Based Combinational Drug Delivery: An Emerging Approach for Cancer Therapy," Drug Discov Today. 17(17-18):1044-52 (2012)).
EP3337478: Epo Notice of Generics [UK] Limited Opposition dated May 12, 2021, 5 pages.
EP3337478: Generics [UK] Limited Opposition dated May 12, 2021, 9 pages.
EP3337478: Generics [UK] Limited Opposition dated May 12, 2021, D10 (Conroy T, et al., "FOLFIRINOX versus Gemcitabine for Metastatic Pancreatic Cancer," N Engl J Med. 364(19): 1817-25 (2011)).
EP3337478: Generics [UK] Limited Opposition dated May 12, 2021, D11 (Gourgou-Bourgade S, et al., "Impact of FOLFIRINOX Compared With Gemcitabine on Quality of Life With Metastatic Pancreatic Cancer: Results From the Prodige 4/ACCORD 11 Randomized Trial," J Clin Oncol. 31 (1 ):23-9 (2013). Epub 2012.).
EP3337478: Generics [UK] Limited Opposition dated May 12, 2021, D12 (Ko A, et al., "A Multinational Phase 2 Study of Nanoliposomal Irinotecan Sucrosofate (PEP02, MM-398) for Patients with Gemcitabine-Refractory Metastatic Pancreatic Cancer," Br J Cancer. 109(4):920-5 (2013)).
EP3337478: Generics [UK] Limited Opposition dated May 12, 2021, D13 (Hann B, et al., Abstract 5648. "Lipidic Nanoparticle CPT-11 in a Bioluminescent Orthotopic Pancreas Cancer Model," Cancer Res. 67(9 Suppl):5648 (2007), 4 printed pages).
EP3337478: Generics [UK] Limited Opposition dated May 12, 2021, D14 (Chang T, et al., "Phase I Study of Nanoliposomal Irinotecan (PEP02) in Advanced Solid Tumor Patients," Cancer Chemother Pharmacol. 75(3):579-86 12015)).
FP3337478: Generics [UK] Limited Opposition dated May 12, 2021, D15 (Chen L, et al., "Phase I Study of Liposome Yinotecan (PEP02) in Combination with Weekly Infusion of 5-FU/LV in Advanced Solid Tumors," J Clin Oncol., 2010 ASCO Annual Meeting Abstracts, 28(15_suppl) (May 20 Suppl):e13024 (2010), 4 printed pages).
EP3337478: Generics [UK] Limited Opposition dated May 12, 2021, D16 (Pubmed abstract retrieved on May 6, 2021 for Mahaseih H, et al., "Modified FOLFIRINOX Regimen With Improved Safety and Maintained Efficacy in Pancreatic Adenocarcinoma," Pancreas. 42(8):1311-5 (2013), 2 printed pages).
EP3337478: Generics [UK] Limited Opposition dated May 12, 2021, D17 (Drummond D, et al., "Development of a Highly Active Nanoliposomal Irinotecan Using a Novel Intraliposomal Stabilization Strategy," Cancer Res. 66 (6):3271-77 (2006)).
EP2861210: Communication of the Board of Appeals, Preliminary Opinion, dated Aug. 9, 2021, 21 pages.
Brendel K, et al., "Population Pharmacokinetics of Liposomal Irinotecan in Patients With Cancer and Exposure-Safety Analyses in Patients With Metastatic Pancreatic Cancer," CPT Pharmacometrics Syst Pharmacol. 10 (12);1550-63, doi: 10.1002/psp4.12725 (2021).
Gebauer F, et al., "Study Protocol of an Open-Label, Single Arm Phase II Trial Investigating the Efficacy, Safety and Duality of Life of Neoadjuvant Chemotherapy With Liposomal Irinotecan Combined With Oxaliplatin and 5-Fluorouracil/-olinic Acid Followed by Curative Surgical Resection in Patients With Hepatic Oligometastatic Adenocarcinoma of the Pancreas (Holipanc)," BMC Cancer. 21(1):1239, doi: 10.1186/s12885-021-08966-3, pp. 1-11 (2021).
George B, et al., "The Association of Real-World CA 19-9 Level Monitoring Patterns and Clinical Outcomes Among Patients With Metastatic Pancreatic Ductal Adenocarcinoma," Front Oncol. 11:754687, doi: 10.3389/onc.2021.754687, pp. 1-8 (2021).

Az-Ares L, et al., "RESILIENT Part 1: A Phase 2 Dose-Exploration and Dose-Expansion Study of Second-Line Jposomal Irinotecan in Adults With Small Cell Lung Cancer," Cancer, doi: 10.1002/cncr. 34123, online ahead of print, bages 1-11 (2022).
Sachdev J, et al., "Phase I Study of Liposomal Irinotecan in Patients With Metastatic Breast Cancer: Findings from he Expansion Phase," Breast Cancer Res Treat 185(3):759-71 (2021), Epub 2020.
Tomicki S, et al., "Real-World Cost of Care for Commercially Insured Versus Medicare Patients With Metastatic Pancreatic Cancer Who Received Guideline-Recommended Therapies," Am Health Drug Benefits 14(2):70-78 (2021).
Yoo C, et al., "Liposomal Irinotecan Plus Fluorouracil and Leucovorin Versus Fluorouracil and Leucovorin for Metastatic Biliary Tract Cancer After Progression on Gemcitabine Plus Cisplatin (Nifty): A Multicentre, Open-Label, Randomized, Phase 2b Study," Lancet Oncol. 22(11):1560-1572, doi: 10.1016/S1470-2045(21)00486-1, pp. 1-13 (2021).
Yu K, et al., "Clinical Outcomes Among Patients With Metastatic Pancreatic Ductal Adenocarcinoma Treated With Jposomal Irinotecan," Front Oncol. 11:678070. doi: 10.3389/fonc.2021.678070, pp. 1-9 (2021).
Yu K, et al., "Real-World Prognostic Factors for Survival Among Treated Patients With Metastatic Pancreatic Ductal Adenocarcinoma," Cancer Med. 10(24):8934-43 (2021).
EP3337478: Proprietor's Submission in Response to Oppositions, dated Dec. 7, 2021, including main request and auxiliary requests 1-3, 62 pages.
EP3337478: Proprietor's Submission in Response to Oppositions, dated Dec. 7, 2021, D18 (Wain Berg Z, et al., "First-line Liposomal Irinotecan With Oxaliplatin, 5-Fluorouracil and Leucovorin (NALIRIFOX) in Pancreatic Ductal Adenocarcinoma: A Phase I/II Study," Eur J Cancer. 151:14-24 (2021)).
EP3337478: Proprietor's Submission in Response to Oppositions, dated Dec. 7, 2021, D19 (Declaration of Dr. Bin Zhang, including Annex A and Annex B, 15 pages).
EP3337478: Proprietor's Submission in Response to Oppositions, dated Dec. 7, 2021, D20 (Eisenhauer E, et al., "New Response Evaluation Criteria in Solid Tumours: Revised RECIST Guideline (version 1.1)," Eur J Cancer. 45 (2):228-47 (2009)).
EP3337478: Proprietor's Submission in Response to Oppositions, dated Dec. 7, 2021, D21 (Jang G, et al., "Comparison of RECIST Version 1.0 and 1.1 in Assessment of Tumor Response by Computed Tomography in Advanced Gastric Cancer," Chin J Cancer Res. 25(6):689-694 (2013)).
EP3337478: Proprietor's Submission in Response to Oppositions, dated Dec. 7, 2021, D22 (Kim J, et al., "Comparison of RECIST 1.0 and RECIST 1.1 in Patients with Metastatic Cancer: A Pooled Analysis," J Cancer. 6 (4);387-393 (2015)).
EP3337478: Proprietor's Submission in Response to Oppositions, dated Dec. 7, 2021, D23 (Trial Protocol for Conroy T, et al., "FOLFIRINOX versus Gemcitabine for Metastatic Pancreatic Cancer," N Engl J Med. 364 (19);1817-25 (2011), 88 pages).
EP3337478: Proprietor's Submission in Response to Oppositions, dated Dec. 7, 2021, D24 (Package leaflet for Campto 20 mg/mL concentration for solution for infusion irinotecan hydrochloride, trihydrate, last revised May 2021, 11 pages).
EP3337478: Sandoz AG Response to Proprietor's Reply to the Notice of Opposition dated Feb. 1, 2022, 17 pages.
EP3337478: Sandoz AG Response to Proprietor's Reply to the Notice of Opposition dated Feb. 1, 2022, D25 TSAI C, et al., "Nanovector-Based Therapies in Advanced Pancreatic Cancer," J Gastroint Oncol 2(3):185-94 (2011)).
EP3337478: Sandoz AG Response to Proprietor's Reply to the Notice of Opposition dated Feb. 1, 2022, D26 (Yoo C, et al., "A Randomised Phase II Study of Modified FOLFIRL3 vs Modified FOLFOX as Second-Line Therapy in Patients with Gemcitabine-Refractory Advanced Pancreatic Cancer," Br J Cancer. 101(10):1658-63 (2009)).
EP3337478: Sandoz AG Response to Proprietor's Reply to the Notice of Opposition dated Feb. 1, 2022, D27 (Kalra A, et al., "Preclinical Activity of Nanoliposomal Irinotecan Is Governed by Tumor Deposition and Intratumor Prodrug Conversion," Cancer Res. 74(23):7003-13 (2014)).

(56) References Cited

OTHER PUBLICATIONS

EP3337478: Proprietor's Response to Sandoz AG's Submission of Feb. 1, 2022, dated Feb. 28, 2022, 17 pages.
EP3337467: Sandoz AG Opposition dated Sep. 9, 2021, 24 pages.
EP3337467: Sandoz AG Opposition dated Sep. 9, 2021, D1 (Lorusso P, et al., "Phase I Study of the Safety, Pharmacokinetics (PK), and Pharmacodynamics (PD) of the Poly(ADP-ribose) Polymerase (PARP) Inhibitor Veliparib ABT-888; V) in Combination with Irinotecan (CPT-11; Ir) in Patients (pts) with Advanced Solid Tumors," J Clin Oncol 29(15) Suppl:3000 (2011), 2 pages).
EP3337467: Sandoz AG Opposition dated Sep. 9, 2021, D1a (Lorusso P, et al., "Phase I Study of the Safety, Pharmacokinetics, and Pharmacodynamics of the Poly(ADP-ribose) Polymerase (PARP) Inhibitor Veliparib (ABT-888) n Combination with Irinotecan (CPT-11) in Patients with Advanced Solid Tumors," Presentation presented at American Society of Clinical Oncology 2011 Meeting, 37 pages).
EP3337467: Sandoz AG Opposition dated Sep. 9, 2021, D2 (Berlin J, et al., "A Phase 1 Dose-Escalation Study of Veliparib with Bimonthly FOLFIRI in Patients with Advanced Solid Tumors," J Clin Oncol. 32(15) Suppl:2574 (2014), 4 pages).
EP3337467: Sandoz AG Opposition dated Sep. 9, 2021, D3 (Tahara M, et al., "The Use of Olaparib (AZD2281) Potentiates SN-38 Cytotoxicity in Colon Cancer Cells by Indirect Inhibition of Rad51-Mediated Repair of DNA Double-Strand Breaks," Mol Cancer Ther. 13(5):1170-80 (2014)).
EP3337467: Sandoz AG Opposition dated Sep. 9, 2021, D4 (Neijzen R, et al., "Irinophore C™, a Lipid Nanoparticle Formulation of Irinotecan, Improves Vascular Function, Increases the Delivery of Sequentially Administered 5-FU in HT-29 Tumors, and Controls Tumor Growth in Patient Derived Xenografts of Colon Cancer," J Control Release. 199:72-83 (2015), Epub 2014).
EP3337467: Sandoz AG Opposition dated Sep. 9, 2021, D5 (Clinical Trials Identifier NCT01770353: May 5, 2015 update submitted, "A Pilot Study in Patients Treated with MM-398 to Determine Tumor Drug Levels and to Evaluate he Feasibility of Ferumoxytol Magnetic Resonance Imaging to Measure Tumor Associated Macrophages." 5 pages).
EP3337467: Sandoz AG Opposition dated Sep. 9, 2021, D6 (Shah M, et al., "The Relevance of Drug Sequence n Combination Chemotherapy," Drug Resist Updat. 3(6):335-356 (2000)).
EP3337467: Sandoz AG Opposition dated Sep. 9, 2021, D7 (O'sullivan C, et al., "Beyond Breast and Dvarian Cancers: PARP Inhibitors for BRCA Mutation-Associated and BRCA-Like Solid Tumors," Front Oncol. 4:42 doi: 10.3389/fonc.2014.00042 (2014), 13 pages).
EP3337467: Sandoz AG Opposition dated Sep. 9, 2021, D8 (Onivyde package insert, revision Oct. 22, 2015, 18 pages).
EP3337467: Sandoz AG Opposition dated Sep. 9, 2021, D9 (Carnevale J and Ko A, "MM-398 'Nanoliposomal Irinotecan): Emergence of a Novel Therapy for the Treatment of Advanced Pancreatic Cancer," Future Oncol. 12(4):453-64 (2016). Epub 2015).
EP3337467: Sandoz AG Opposition dated Sep. 9, 2021, D10 (Clinical Trials Identifier NCT02631733 Dec. 15, 2015 submitted, "A Phase I Study of a Combination of MM-398 and Veliparib in Solid Tumors." 7 pages).
EP3337467: Sandoz AG Opposition dated Sep. 9, 2021, D11 (Koshkaryev A, et al., "Differential Tissue Clearance Results in Improved Therapeutic Index for Irinotecan Liposome Injection (ONIVYDE) When Combined with the PARP Inhibitor Veliparib in Preclinical Cervical Tumors," In: Proceedings of the 107th Annual Meeting of the American Association for Cancer Research; Apr. 16-20, 2016; Cancer Res. 76(14 Suppl):Abstract nr 2075 (2016), 2 pages).
EP3337467: Sandoz AG Opposition dated Sep. 9, 2021, D12 (Livraghi L, et al., "PARP Inhibitors in the Management of Breast Cancer: Current Data and Future Prospects," BMC Med. 13:188; doi: 10.1186/512916-015-0425-1 (2015), 16 pages)).
EP3337467: Proprietor's Submission in Response to Oppositions, dated Feb. 3, 2022, including main request and auxiliary requests 1-23, 140 pages.
EP3337467: Proprietor's Submission in Response to Oppositions, dated Feb. 3, 2022, D13 (Written transcript of he presentation associated with D1a: Lorusso P, et al., "Phase I Study of the Safety, Pharmacokinetics, and Pharmacodynamics of the Poly(ADP-ribose) Polymerase (PARP) Inhibitor Veliparib (ABT-888) in Combination with Yinotecan (CPT-11) in Patients with Advanced Solid Tumors," American Society of Clinical Oncology 2011 Meeting), 7 pages).
EP3337467: Proprietor's Submission in Response to Oppositions, dated Feb. 3, 2022, D14 (Shah M, et al., "A Phase I Clinical Trial of the Sequential Combination of Irinotecan Followed by Flavopiridol," Clin Cancer Res. 11 (10):3836-45 (2005)).
EP3337467: Proprietor's Submission in Response to Oppositions, dated Feb. 3, 2022, D15 (Sadetzki S, et al., Childhood Exposure to External Ionising Radiation and Solid Cancer Risk, Br J Cancer. 100(7):1021-25 (2009)).
EP3337467: Proprietor's Submission in Response to Oppositions, dated Feb. 3, 2022, D16 (Practical Medical Dncology Textbook, Eds Russio A, et al., Springer Nature Switzerland AG, Table of Contents, pp. I-XI (2021)).
EP3337467: Proprietor's Submission in Response to Oppositions, dated Feb. 3, 2022, D17 (Camptosar jackage insert, 2014, 39 pages).
Alese O, et al., "A Phase 1 Trial of Trifluridine/Tipiracil in Combination With Nanoliposomal Irinotecan in Advanced GI Dancers," Abstract PD-4, doi org/10 1016/j annonc2021.05.022, Annals Oncol. 32(S3):S200 (2021).
Bai L, et al., "A Phase 2 Study of Liposomal Irinotecan With 5-Fluorouracil and Leucovorin in Squamous Cell Carcinoma of Head and Neck or Esophagus After Prior Platinum-Based Chemotherapy or Chemoradiotherapy," J Clin Oncol. 39(15_suppl):6025-6025, DOI: 10.1200/JC0.2021.39.15_suppl.6025 (2021), 4 printed pages.
Choi G, et al., "Safety and Effectiveness of Prospective Observational Postmarketing Surveillance Study for Pancreatic Adenocarcinoma Treated by Liposomal Irinotecan Plus 5-Flurouracil/Leucovorin in Korea," Abstract P196, 2nd American Association for Cancer Research - Korean Cancer Association Joint Conference on Precision Medicine n Solid Tumors, Nov. 10-11, 2021 (EST), 1 page.
Chotzagiannoglou V, et al., Abstract PCN154. "Budget Impact Analysis of Liposomal Irinotecan for Treatment of Metastatic Adenocarcinoma of Pancreas Following Progression on Gemcitabine-Based Therapies from Greek Payer's Perspective," Value in Health. 23(S2):S450 (2020).
Dieguez G et al., "Risk Adjustment and Total Cost of Care Per Month of Overall Survival Among Medicare Fee-for-Service (FFS) Patients Receiving NCCN Category-1 Treatments for Metastatic Pancreatic Cancer," Abstract, doi. org/10.1093/ajhp/zxab362. Found at American Journal of Health-System Pharmacy, 78(20):1831-1918 (2021), 2 printed pages.
Dieguez G, et al., "Trends in Treatment Patterns Among Medicare Fee-For-Service (FFS) Patients Receiving Treatment for Metastatic Pancreatic Cancer," Abstract 1478P, doi.org/10.1016/j.annonc.2021. 08.805, Annals Oncol. 32(S5):S1091-S1092 (2021).
Dieguez G, et al., "Trends in Use of One, Two, and Three-Line NCCN Category 1 Regimens Among Medicare Fee-For-Service (FFS) Patients Receiving Treatment for Metastatic Pancreatic Cancer," J Clin Oncol. 39 K28_suppl):297-297, DOI:10.1200/JC0.2020. 39.28_suppl.297 (2021), 4 printed pages.
Elias R, et al., "Comparison of First-Line (1L) Treatment (Tx) Patterns and Overall Survival by Age at Diagnosis Among Patients With Metastatic Pancreatic Ductal Adenocarcinoma (mPDAC)," J Clin Oncol. 39(3 suppl):388-388, DOI: 10.1200/JC0.2021.39.3_suppl.388, (2021), 5 printed pages.
George B, et al., "Real-World Impact of Prior Surgery on Outcomes of Patients With Metastatic Ductal Adenocarcinoma (mPDAC) Treated With Liposomal Irinotecan-Based Regimens," Abstract PCN17, Value in Health. 24(Suppl 1):S21 (2021).
George B, et al., "Real-World Serum CA19-9 Level Monitoring Patterns and Its Association With Clinical Outcomes Among Patients With Metastatic Pancreatic Ductal Adenocarcinoma (mPDAC)," https://doi.Org/10.1158/1538-7445. AM2021-765, Cancer Res. 81(13_Suppl):765 (2021).
George B, et al., "The Association Between Real-World CA19-9 Level Monitoring Patterns and With Clinical Outcomes Among

(56) References Cited

OTHER PUBLICATIONS

Patients With Metastatic Pancreatic Ductal Adenocarcinoma (mPDAC) in the Second- and Third-Line of Therapy," J Clin Oncol. 39(15_suppl):e16251, DOI: 10.1200/JC0.2021.39.15_suppl.e16251 (2021), 4 printed pages.
Gourzoulidis G, et al., Abstract PCN108. "The Cost-Effectiveness of Liposomal Irinotecan and 5-Fluorouracil (5-FU)/ Leucovorin (LV) for the Treatment of Patients With Metastatic Adenocarcinoma of Pancreas Who Have Progressed Following the Use of Gemcitabine-Related Therapies in Greece," Value in Health. 23(S2):S442 (2020).
Kim G, et al., "Real-World Characteristics and Outcomes of Patients With Metastatic Ductal Adenocarcinoma (mPDAC) Treated With Liposomal Irinotecan-Based Regimens by Race," Abstract PCN27, Value in Health. 24(Suppl 1):S23 [2021].
Kim G, et al., "Real-World One-Year Overall Survival Among Patients With Metastatic Pancreatic Ductal Adenocarcinoma (mPDAC) Treated With Liposomal Irinotecan in the NAPOLI-1 Based Regimen," J Clin Oncol. 39 [3_suppl):392-392, DOI: 10.1200/JC0.2021.39.3_suppl.392, (2021), 4 printed pages.
Kim G, et al., "Real-World Progression Outcomes Among Patients (pts) With Metastatic Pancreatic Ductal Adenocarcinoma (mPDAC) Treated With Liposomal Irinotecan-Based Regimens in the United States," Abstract 1480P, doi.org/10.1016/j.annonc.2021.08.807, Annals Oncol. 32(S5):S1092-S1093 (2021).
Kim G, et al., "Real-World Safety and Medication Use of Second-Line (2L) 5-Fluorouracil (5-FU)-Based Regimens Among Patients (pts) With Metastatic Pancreatic Ductal Adenocarcinoma (mPDAC)," J Clin Oncol. 39(15 suppl) F16248, Doi: 10.1200/JC0.2021.39.15_suppLe16248 (2021), 5 printed pages.
Kim G, et al., "Real-World Safety Data and Differentiation of Second-Line (2L) 5-Fluorouracil (5-FU) Based Regimens Among Patients With Metastatic Pancreatic Ductal Adenocarcinoma (mPDAC)," J Clin Oncol. 39(3 suppl):390-390, DOI: 10.1200/JC0.2021.39.3_suppl.390, (2021), 5 printed pages.
Kim G, et al., "Real-World Treatment Discontinuation Patterns Among Patients (pts) With Metastatic Pancreatic Ductal Adenocarcinoma (mPDAC) Treated With Liposomal Irinotecan-Based Regimens in the United States," Abstract 1513P, doi.org/10.1016/j.annonc.2021.08.842, Annals Oncol. 32(S5):S1107-S1108 (2021).
Kokhreidze J, et al., "Psychometric Properties of Patient Reported Outcome (PRO) Instruments in Patients With Small Cell Lung Cancer (SCLC) in RESILIENT Part 1," J Clin Oncol. 39(15_suppl):e24027, DOI: 10.1200/JC0.2021.39.15_suppLe24027, (2021), 4 printed pages.
Latimer H, et al., "Dispersion in Total Cost of Care for Medicare Fee-For-Service (FFS) Patients With Metastatic Pancreatic Cancer Receiving FDA-Approved/NCCN Category 1 Regimens at 340B Versus Non-340B Institutions," J Clin Oncol. 39(15_suppl):e18843, DOI: 10.1200/JC0.2021.39.15_suppLe18843 (2021), 4 printed pages.
Latimer H, et al., "Dispersion in Total Cost of Care for Medicare Fee-For-Service (FFS) Patients With Metastatic Pancreatic Cancer Receiving FDA-Approved/NCCN Category 1 Regimens at Teaching Versus Non-Teaching nstitutions," J Clin Oncol. 39(15 suppl):e16244, Doi: 10.1200/JC0.2021.39.15 suppl.e16244 (2021), 4 printed pages.
Latimer H, et al., "Total Cost of Care and Utilization Among Medicare Fee-For-Service (FFS) Patients With Metastatic Pancreatic Cancer Treated With FDA-Approved/NCCN® Category 1 Regimens at Teaching vs. NonTeaching Hospitals," Abstract PDB2, Value in Health. 24(Suppl 1):S78 (2021).
Laursen A, et al., "Real-World Patterns of Pain Medication Use Among Patients With Metastatic Pancreatic Ductal Adenocarcinoma (mPDAC)," J Clin Oncol. 39(28_suppl):302-302, DOL 10.1200/JC0.2020.39.28_suppl.302 (2021), 4 printed pages.
O'reilly E, et al., "Real-World Overall Survival of Patients Diagnosed With Recurrent Versus de novo Metastatic Pancreatic Ductal Adenocarcinoma (Pdac)," J Clin Oncol. 39(15_suppl):e16250, DOL 10.1200/JC0.2021.39.15_suppLe1625 (2021), 4 printed pages.
Paluri R, et al., "Impact of the COVID-19 Pandemic on Care Delivery and Outcomes for Patients With Metastatic Pancreatic Ductal Adenocarcinoma (mPDAC)," J Clin Oncol. 39(15_suppl):4137-4137, DOI: 10.1200/JCO.2021.39.15_suppl.4137 (2021), 4 printed pages.
Paz-Ares L, et al., "RESILIENT Part 1: Safety and Efficacy of Second-Line Liposomal Irinotecan in Patients With Small Cell Lung Cancer," Abstract FP10.04, J Thoracic Oncol. 16(3S):S216 (2021).
Oaz-Ares L, et al., "RESILIENT Part 2: A Phase 3 Study of Liposomal Irinotecan in Patients With Small-Cell Lung Cancer in the Second-Line Setting," Abstract P48 14, J Thoracic Oncol 16(3S):S505 (2021).
Perkhofer L, et al., "Nal-IRI With 5-Fluorouracil (5-FU) and Leucovorin or Gemcitabine Plus Cisplatin in Advanced 3iliary Tract Cancer: Final Results of the NIFE-trial (Aio-Ymo HEP-0315), A Randomized Phase II Study of the AIO Biliary Tract Cancer Group," Abstract LBA10, doi.org/10.1016/j.annonc.2021.08.2082, Annals Oncol 32(S5):S1282 [2021].
Rogers S, et al., "A Phase II, Open-Label Pilot Study Evaluating the Safety and Activity of Liposomal Irinotecan Nal-IRI) in Combination With 5-FU and Oxaliplatin (NALIRIFOX) in Preoperative Treatment of Pancreatic Adenocarcinoma (NEO-Nal-IRI study) (NCT03483038)," J Clin Oncol. 39(15 suppl):TPS4170, DOI: 10.1200/JC0.2021.39.3_suppLTPS446 (2021), 4 printed pages.
Faieb J, et al., "Real-World Study of Treatment Patterns and Outcomes Among Patients With Metastatic Pancreatic Ductal Adenocarcinoma (PDAC) in Europe," J Clin Oncol. 39(3_suppl):391-391, DOL 10.1200/JCO.2021.39.3_suppl.391 (2021), 4 printed pages.
Faieb J, et al., "Treatment Sequences and Prognostic Factors in Metastatic Pancreatic Ductal Adenocarcinoma Univariate and Multivariate Analyses of a Real-World Study in Europe," Abstract SO-3, doi.org/10.1016/j. annonc.2021.05.027, Annals Oncol. 32(S3):S203 (2021).
Fomicki S, et al., "Total Cost of Care and Utilization Among Medicare Fee-For-Service (FFS) Patients With Metastatic Pancreatic Cancer Treated With FDA-Approved/NCCN® Category 1 Regimens at 340B vs. Non-340B Hospitals," Abstract PDB17, Value in Health. 24(Suppl 1):S80-S81 (2021).
Yoo C, et al., "Liposomal Irinotecan (nal-IRI) in Combination With Fluorouracil (5-FU) and Leucovorin (LV) for Patients Nith Metastatic Biliary Tract Cancer (BTC) After Progression on Gemcitabine Plus Cisplatin (GemCis): Multicenter Comparative Randomized Phase 2b Study (Nifty)," J Clin Oncol. 39(15 suppl):4006-4006, DOL 10.1200/JCO.2021.39.15_suppl.4006 (2021), 4 printed pages.
Yu K, et al., "Population-Based, Real-World Prognostic Factors Related to Survival Among Patients With Metastatic Pancreatic Ductal Adenocarcinoma (mPDAC)," J Clin Oncol. 39(3_suppl):389-389, DOI: 10.1200/JCO.2021.39.3_suppl.389, (2021), 4 printed pages.
Zhu Z, et al., "Assessing Real-World Survival Outcomes of Patients (pts) With Metastatic Pancreatic Ductal Adenocarcinoma (mPDAC) Treated With First-Line FOLFIRINOX Compared to Patients From a Phase 1/2 Trial Treated With Nalirifox," J Clin Oncol. 39(15_suppl):e16252, DOI: 10.1200/JC0.2021.39.15_suppl.e1625 (2021), 4 printed pages.
Chang E, et al. "The Role of Tumor Size in the Radiosurgical Management of Patients with Ambiguous Brain Metastases," Neurosurgery 53(2):272-280; discussion at 280-281 (2003).
De Forni M, et al., "Phase I and Pharmacokinetic Study of the Camptothecin Derivative Irinotecan, Administered on a Weekly Schedule in Cancer Patients," Cancer Res. 54(16):4347-4354 (1994).
Marsh R, et al., "Pancreatic Cancer and Folfirinox: A New Era and New Questions," Cancer Med. 4(6):853-63 [2015].
Bai L, et al., "A Phase 2 Study of Liposomal Irinotecan With 5-Fluorouracil and Leucovorin in Squamous Cell Carcinoma of Head and Neck or Esophagus After Prior Platinum-Based Chemotherapy or Chemoradiotherapy," Poster presented at American Society of Clinical Oncology 2021 Meeting, Jun. 4-8, 2021, 6 pages.
Dieguez G et al., "Risk Adjustment and Total Cost of Care Per Month of Overall Survival Among Medicare Fee-for-Service (FFS) Beneficiaries Receiving Treatment for Metastatic Pancreatic Cancer," Poster presented at American Society of Health-System Pharmacists (ASHP) Midyear Clinical Meeting & Exhibition, Dec. 6-7, 2021, 6 pages.

(56) References Cited

OTHER PUBLICATIONS

Dieguez G, et al., "Trends in Treatment Patterns Among Medicare Fee-For-Service (FFS) Patients Receiving Treatment for Metastatic Pancreatic Cancer," Poster presented at European Society for Medical Oncology (ESMO) Congress 2021, Sep. 16-21, 2021, 5 pages.
Dieguez G, et al., "Trends in Use of One, Two, and Three-Line NCCN Category 1 Regimens Among Medicare Fee-For-Service (FFS) Patients Receiving Treatment for Metastatic Pancreatic Cancer," Poster presented at ASCO Quality Dare Symposium 2021, Sep. 24-25, 2021, 5 pages.
Elias R, et al., "Comparison of First-Line (1L) Treatment (Tx) Patterns and Overall Survival by Age at Diagnosis Among Patients With Metastatic Pancreatic Ductal Adenocarcinoma (mPDAC)," Poster Presented at the American Society of Clinical Oncology Gastrointestinal Cancer Symposium (ASCO Gl) 2021, Jan. 15-17, 2021, Virtual Congress, 6 pages.
George B, et al., "Real-World Impact of Prior Surgery on Outcomes of Patients With Metastatic Ductal Adenocarcinoma (mPDAC) Treated With Liposomal Irinotecan-Based Regimens," Presented at International Society tor Pharmacoeconomics and Outcomes, May 17-19, 2021, Virtual poster, 10 pages.
George B, et al., "Real-World Serum CA19-9 Level Monitoring Patterns and Its Association With Clinical Outcomes Among Patients With Metastatic Pancreatic Ductal Adenocarcinoma (mPDAC)," Poster presented at the American Association for Cancer Research (AACR) 2021 Virtual Congress, Apr. 10-15, 2021, 8 pages.
Kim G, et al., "Real-World Characteristics and Outcomes of Patients With Metastatic Ductal Adenocarcinoma (mPDAC) Treated With Liposomal Irinotecan-Based Regimens by Race," Presented at International Society for Pharmacoeconomics and Outcomes, May 17-19, 2021, Virtual poster, 9 pages.
Kim G, et al., "Real-World One-Year Overall Survival Among Patients With Metastatic Pancreatic Ductal Adenocarcinoma (mPDAC) Treated With Liposomal Irinotecan in the NAPOLI-1 Based Regimen," Poster presented at the American Society of Clinical Oncology Gastrointestinal Cancer Symposium (ASCO Gl) 2021, Jan. 15-17, 2021, Virtual Congress, 6 printed pages.
Kim G, et al., "Real-World Progression Outcomes Among Patients (pts) With Metastatic Pancreatic Ductal Adenocarcinoma (mPDAC) Treated With Liposomal Irinotecan-Based Regimens in the United States," Poster presented at European Society for Medical Oncology (ESMO) Congress,, Virtual Congress, Sep. 16 -21, 2021, 5 pages.
Kim G, et al., "Real-World Safety Data and Differentiation of Second-Line (2L) 5-Fluorouracil (5-FU) Based Regimens Among Patients With Metastatic Pancreatic Ductal Adenocarcinoma (mPDAC)," Poster presented at the American Society of Clinical Oncology Gastrointestinal Cancer Symposium (ASCO Gl) 2021, Jan. 15-17, 2021, Virtual Congress, 7 pages.
Kim G, et al., "Real-World Treatment Discontinuation Patterns Among Patients (pts) With Metastatic Pancreatic Ductal Adenocarcinoma (mPDAC) Treated With Liposomal Irinotecan-Based Regimens in the United States," Presented at European Society for Medical Oncology (ESMO) Congress, Virtual Congress, Sep. 16-21, 2021, 5 pages.
Latimer H, et al., "Total Cost of Care and Utilization Among Medicare Fee-For-Service (FFS) Patients With Metastatic Pancreatic Cancer Treated With FDA-Approved/NCCN® Category 1 Regimens at Teaching vs. Non-Teaching Hospitals," Presented at International Society for Pharmacoeconomics and Outcomes, May 17-19, 2021, Virtual poster, 11 pages.
Laursen A, et al., "Real World Patterns of Pain Medication Use Among Patients With Metastatic Pancreatic Ductal Adenocarcinoma (mPDAC)," Poster presented at ASCO Quality Care Symposium 2021. Boston, MA, Online, Sep. 24 -25, 2021,4 pages.
Paluri R, et al., "Impact of the COVID-19 Pandemic on Metastatic Pancreatic Ductal Adenocarcinoma (mPDAC) Dare Delivery," Presented at the American Society for Clinical Oncology (ASCO) Annual Meeting: Jun. 4 - 8, 2021 Virtual, 6 pages.
Paz-Ares L, et al., "RESILIENT Part 1: A Phase II Dose-Exploration and Dose-Expansion Study of Second-Line Liposomal Irinotecan Monotherapy in Adults With Small Cell Lung Cancer," Presented at World Conference on Lung Dancer, Jan. 28-31, 2021, Virtual event, 12 pages.
Paz-Ares L, et al., "RESILIENT Part 2: A Phase III Study of Liposomal Irinotecan in Patients With Small-Cell Lung Dancer in the Second-Line Setting," Presented at World Conference on Lung Cancer, Jan. 28-31, 2021, Virtual event, 9 pages.
Perkhofer L, et al., "Nal-IRI With 5-FU and Leucovorin or Gemcitabine Plus Cisplatin in Advanced Biliary Tract Dancer: Final Results of the Randomized Phase 2 NIFE Trial (Aio-Ymo HEP-0315)," Presentation at the European Society for Medical Oncology (ESMO) Congress, Virtual Congress Sep. 16-21, 2021, 9 pages.
Ramnaraign B, et al., "A Phase II, Open-Label Pilot Study Evaluating the Safety and Activity of Nal-IRI in Combination With 5-FU and Oxaliplatin (NALIRIFOX) in Preoperative Treatment of Pancreatic Adenocarcinoma (NEO-Nal-IRI study)," Poster presented at the American Society of Clinical Oncology Gastrointestinal Cancer Symposium ASCO Gl) 2021, Jan. 15-17, 2021, Virtual Congress, 4 pages.
Taieb J, et al., "Real-World Study of Treatment Patterns and Outcomes Among Patients With Metastatic Pancreatic Ductal Adenocarcinoma (PDAC) in Europe," Poster presented at the American Society of Clinical Oncology Gastrointestinal Cancer Symposium (ASCO Gl) 2021, Jan. 15-17, 2021, Virtual Congress, 6 pages.
Tomicki S, et al., "Total Cost of Care and Utilization Among Medicare Fee-For-Service (FFS) Patients With Metastatic Pancreatic Cancer Treated With FDA-Approved/NCCN® Category 1 Regimens at 340B vs. Non-340B Hospitals," Presented at International Society for Pharmacoeconomics and Outcomes, May 17-19, 2021, Virtual poster, 11 pages.
Yoo C, et al., "Liposomal Irinotecan (nal-IRI) in Combination With Fluorouracil (5-FU) and Leucovorin (LV) for Patients pts) With Metastatic Biliary Tract Cancer (BTC) After Progression on Gemcitabine Plus Cisplatin (GemCis) Multicenter Comparative Randomized Phase 2B Study (Nih Iy)," Presented at the American Society of Clinical Dncology 2021 Meeting, Jun. 4-8, 2021, 18 pages.
Yu K, et al., "Population-Based, Real-World Prognostic Factors Related to Survival Among Patients With Metastatic Pancreatic Ductal Adenocarcinoma (mPDAC)," Poster presented at the American Society of Clinical Oncology Gastrointestinal Cancer Symposium (ASCO Gl) 2021, Jan. 15-17, 2021, Virtual Congress, 7 pages.
EP2861210: Proprietor Response to the Board of Appeals' Preliminary Opinion, dated Dec. 21, 2021, 12 pages.
EP3266456: Epo Notice of Sandoz AG Opposition dated Feb. 1, 2022, 6 pages.
EP3266456: Sandoz AG Opposition dated Feb. 1, 2022, 23 pages.
EP3266456: Epo Notice of Teva Pharmaceuticals Industries Ltd. Opposition dated Feb. 2, 2022, 6 pages.
EP3266456: Teva Pharmaceutical Industries Ltd. Opposition dated Feb. 2, 2022, 12 pages.
EP3266456: Epo Notice of Generics [UK] Limited Opposition dated Feb. 4, 2022, 5 pages.
EP3266456: Generics [UK] Ltd. Opposition dated Feb. 4, 2022, 13 pages.
EP3266456: Epo Opposition Consolidated List of Citations, Feb. 4, 2022, 2 pages.
EP3266456: Consolidated Opposition dated Feb. 2022, D1 (Chen L, et al., "Phase I Study of Liposome Yinotecan (PEP02) in Combination with Weekly Infusion of 5-FU/LV in Advanced Solid Tumors," J Clin Oncol. 28 15_suppl):abstract e13024 (2010), 2 pages).
EP3266456: Consolidated Opposition dated Feb. 2022, D2 (Chen L, et al., "Phase I Study of Biweekly Liposome Yinotecan (PEP02, MM-398) in Metastatic Colorectal Cancer Failed on First-line Oxaliplatin-based Chemotherapy," J Clin Oncol. 30(4_suppl):Abstract 613 (2012), 2 pages).
EP3266456: Consolidated Opposition dated Feb. 2022, D3 (Ko A, et al., "A Multinational Phase II Study of Liposome Irinotecan (PEP02) for Patients with Gemcitabine-Refractory Metastatic Pancreatic Cancer," J Clin Oncol. 29 4_suppl):Abstract 237 (2011), 2 pages).
EP3266456: Consolidated Opposition dated Feb. 2022, D4 (Chen L, et al., "Phase I Study of Liposome Encapsulated Irinotecan (PEP02)

(56) References Cited

OTHER PUBLICATIONS in Advanced Solid Tumor Patients," J Clin Oncol., 26(15_suppl):abstract 2565 2008), 2 pages).
EP3266456: Consolidated Opposition dated Feb. 2022, D5 ((Clinical Trials Identifier NCT01494506: 2012-05-29 version submitted, "A Randomized, Open Label Phase 3 Study of MM-398 Versus 5-Fluorouracil and Leucovorin in Patients With Metastatic Pancreatic Cancer." 6 pages).
EP3266456: Consolidated Opposition dated Feb. 2022, D5a ((Clinical Trials Identifier NCT01494506:2012-08-08 submitted, "A Randomized, Open Label Phase 3 Study of MM-398, With or Without 5-Fluorouracil and Leucovorin, Versus 5-Fluorouracil and Leucovorin in Patients with Metastatic Pancreatic Cancer Who Have Failed Prior Gemcitabine-based Therapy." 7 pages).
EP3266456: Consolidated Opposition dated Feb. 2022, D6 ((Clinical Trials Identifier NCT01375816: 2011-06-16 version submitted, "A Randomized Phase II Study of PEP02 or Irinotecan in Combination with Leucovorin and 5-Fluorouracil in Second Line Therapy of Metastatic Colorectal Cancer." 6 pages).
EP3266456: Consolidated Opposition dated Feb. 2022, D7 (Tsai C, et al., "Nanovector-Based Therapies in Advanced Pancreatic Cancer," J Gastroint Oncol 2(3): 185-94 (2011)).
EP3266456: Consolidated Opposition dated Feb. 2022, D8 (Camptosar package insert, 2009, 37 pages).
EP3266456: Consolidated Opposition dated Feb. 2022, D9 (Fusilev package insert, 2008, 7 pages).
EP3266456: Consolidated Opposition dated Feb. 2022, D10 (Yoo C, et al., "A Randomised Phase II Study of Modified FOLFIRI.3 vs Modified FOLFOX as Second-Line Therapy in Patients with Gemcitabine-Refractory Advanced Pancreatic Cancer," Br J Cancer. 101 (10): 1658-63 (2009)).
EP3266456: Consolidated Opposition dated Feb. 2022, D11 (Drummond D, et al., "Development of a Highly Active Nanoliposomal Irinotecan Using a Novel Intraliposomal Stabilization Strategy," Cancer Res. 66(6):3271-77 (2006)).
EP3266456: Consolidated Opposition dated Feb. 2022, D12 (Baker J, et al., "Irinophore C, a Novel Nanoformulation of Irinotecan, Alters Tumor Vascular Function and Enhances the Distribution of 5-Fluorouracil and Doxorubicin," Clin Cancer Res. 14(22)7260-71 (2008)).
EP3266456: Consolidated Opposition dated Feb. 2022, D13 (Venditto V, et al., "Cancer Therapies Utilizing the Camptothecins: A Review of the in Vivo Literature," Mol Pharm. 7(2):307-349 (2010)).
EP3266456: Consolidated Opposition dated Feb. 2022, D14 (Tardi P, et al., "Coencapsulation of Irinotecan anti Floxuridine Into Low Cholesterol-Containing Liposomes That Coordinate Drug Release In Vivo," Biochim Biophys Acta 1768(3):678-87 (2007). Epub 2006).
EP3266456: Consolidated Opposition dated Feb. 2022, D15 (Opposition Division's decision to revoke EP2861210, dated Aug. 28, 2019,24 pages).
EP3266456: Consolidated Opposition dated Feb. 2022, D16 (EP2861210: Communication of the Board of Appeals, Preliminary Opinion, dated Aug. 9, 2021,21 pages).
EP3266456: Consolidated Opposition dated Feb. 2022, D17 (Clinical Trials Identifier NCT01494506: 2011-12-16 version, "A Randomized, Open Label Phase 3 Study of MM-398 Versus 5-Fluorouracil and Leucovorin in Patients With Metastatic Pancreatic Cancer." 2 pages).
EP3266456: Consolidated Opposition dated Feb. 2022, D18 (Hoskins J, et al., "UGT1A1'28 Genotype and Yinotecan-Induced Neutropenia: Dose Matters," J Natl Cancer Inst. 99(17):1290-95 (2007)).
EP3266456: Consolidated Opposition dated Feb. 2022, D19 (Brixi-Benmansour H, et al., "Phase II Study of First-line FOLFIRI for Progressive Metastatic Well-differentiated Pancreatic Endocrine Carcinoma," Dig Liver Dis. 43 [11):912-6 (2011)).
EP3266456: Consolidated Opposition dated Feb. 2022, D20 (Infante J, et al., "Phase I and Pharmacokinetic Study of IHL-305 (PEGylated Liposomal Irinotecan) in Patients with Advanced Solid Tumors," Cancer Chemother Pharmacol. 70(5):699-705 (2012)).
EP3266456: Consolidated Opposition dated Feb. 2022, D23 (European Commission Implementing Decision granting marketing authorisation for Onivyde, Oct. 14, 2016, 39 pages).
EP3266456: Consolidated Opposition dated Feb. 2022, D24 (Wang-Gillam A, et al., "Nanoliposomal Irinotecan with Flourouracil and Folinic Acid in Metastatic Pancreatic Cancer After Previous Gemcitabine-Based Therapy [NAPOLI-1): A Global, Randomised, Open-Label, Phase 3 Trial," Lancet, 387(10018):545-57 (2016). Epub doi 10.1016/S0140-6736(15)00986-1, pp. 1-13 (2015)).
EP3266456: Consolidated Opposition dated Feb. 2022, D25 (Fda News Release, "FDA Approves New Treatment for Advanced Pancreatic Cancer." http://ww.fda.gov/NewsEvents/Newsroom/PressAnnouncements/ucm468654.htm, Oct. 22, 2015, 3 pages).
EP3266456: Consolidated Opposition dated Feb. 2022, D26 (Mhra Public Assessment Report for 5-Fluorouracil 2006, 60 pages).
EP3266456: Consolidated Opposition dated Feb. 2022, D27 (Gebbia V, et al., "Irinotecan Plus Bolus/lnfusional 5-Fluorouracil and Leucovorin in Patients With Pretreated Advanced Pancreatic Carcinoma: A Multicenter Experience of the Gruppo Oncologico Italia Meridionale," Am J Clin Oncol. 33(5):461-64 (2010)).
EP3266456: Consolidated Opposition dated Feb. 2022, D28 (Chen P, et al., "Comparing Routes of Delivery for Nanoliposomal Irinotecan Shows Superior Anti-Tumor Activity of Local Administration in Treating Intracranial Glioblastoma Xenografts," Neuro Oncol. 15(2):189-97 (2013), Epub Dec. 21, 2012).
U.S. Appl. No. 15/664,976: Apr. 21, 2021 Notice of Allowance including Examiner's Reasons for Allowance, 14 pages.
U.S. Appl. No. 15/809,815: Aug. 26, 2021 Non-Final Office Action, 14 pages.
U.S. Appl. No. 16/012,351: Mar. 8, 2021 Notice of Allowance including Examiner's Reasons for Allowance, 9 pages.
U.S. Appl. No. 16/012,372: Feb. 11, 2021 Notice of Allowance including Examiner's Reasons for Allowance, 9 pages.
U.S. Appl. No. 16/302,050: Aug. 11, 2021 Non-Final Office Action, 17 pages.
U.S. Appl. No. 16/567,902: Mar. 8, 2021 Notice of Allowance including Examiner's Reasons for Allowance and Examiner Interview Summary, 20 pages.
U.S. Appl. No. 16/711,072: Dec. 10, 2021 Non-Final Office Action, 19 pages.
U.S. Appl. No. 16/906,601: Jan. 7, 2022 Non-Final Office Action, 21 pages.

Activity of MM-398 (Ls-CPT11) in an Orthotopic
Pancreas Tumor Model Expressing Luciferase (L3.6pl).

Accumulation of SN-38 in Tumors Following Treatment
with Free Irinotecan or Nanoliposomal Irinotecan (MM-398).

MM-398 PK in q3w (irinotecan, liposomes + free drug)

| Dose (mg/m²) & Study | PEP0203 | | | | PEP0201 | | PEP0206 | | Campto® Package insert | |
|---|---|---|---|---|---|---|---|---|---|---|
| | 60 | 80 | 100 | 120 | 120 | 180 | 120 | 300 | 125 | 340 |
| | (n=3) | (n=6) | (n=4) | (n=2) | (n=6) | (n=4) | (n=37) | Campto® (n=27) | mg/m² (N=64) | mg/m² (N=6) |
| Parameters | | | | | | | | | | |
| $C_{max}$ (µg/mL) | 28.93 (±15.75) | 29.16 (±5.24) | 44.06 (±7.65) | 47.94 (±16.24) | 79.4 (±13.9) | 102 (±17.6) | 60.8 (±36.6) | 4.3 (±1.2) | 1.66 (±0.797) | 3.392 (±0.874) |
| $t_{1/2}$ (h) | 24.02 (±16.76) | 32.09 (±18.21) | 48.11 (±17.41) | 30.65 (±5.32) | 29.5 (±17.2) | 22.2 (±11.5) | 21.2 (±18.3) | 7.7 (±4.4) | 5.8 (±0.7) | 11.7 (±1.0) |
| $AUC_{0-T}$ (µg·h/mL) | 1,047 (±1,156) | 1,116 (±810) | 2,193 (±1,017) | 1,117 (±308) | 2,835 (±1,817) | 1,945 (±1,029) | 1,651.5 (±1,412.0) | 24.2 (±7.7) | 10.2 (±3.27) | 20.604 (±6.027) |
| $AUC_{0-\infty}$ (µg·h/mL) | 1,114 (±1,270) | 1,211 (±924) | 2,472 (±1261) | 1,261 (±500) | 2,963 (±1,947) | 1,963 (±1,035) | 1,812.2 (±1,601.9) | 26.2 (±9.0) | — | — |
| Cl (L/h/m²) | 0.1249 (±0.1058) | 0.1164 (±0.0949) | 0.0547 (±0.0358) | 0.1033 (±0.0409) | 0.0591 (±0.0367) | 0.119 (±0.0703) | 0.191 (±0.260) | 12.9 (±4.7) | 13.3 (±6.01) | 13.9 (±4.0) |
| $V_{ss}$ (L/m²) | 2.6 (±1.44) | 2.93 (±0.60) | 2.63 (±0.49) | 3.16 (±0.38) | 1.8 (±0.771) | 1.97 (±0.342) | 2.23 (±0.69) | 98.5 (±29.0) | 110 (±48.5) | 234 (±69.6) |

Note: AUC 0-T is defined as T = 24 hours for Camptosar package insert, T = 49.5 hours for Camptosar in the PEP0206 study and T = 169.5 hours for MM-398.

FIG. 5

Note: AUC 0-T is defined as T = 24 hours for Camptosar package insert, T = 49.5 hours for Camptosar in the PEP0206 study and T = 169.5 hours for MM-398.

MM-398 PK in q3w (SN-38)

| Dose (mg/m²) & Study | PEP0203 | | | | PEP0201 | | PEP0206 | | Campto® Package insert | |
|---|---|---|---|---|---|---|---|---|---|---|
| | 60 | 80 | 100 | 120 | 120 | 180 | PEP02 120 | Campto® 300 | 125 mg/m² | 340 mg/m² |
| | (n=3) | (n=6) | (n=4) | (n=2) | (n=6) | (n=4) | (n=37) | (n=27) | (N=64) | (N=6) |
| Parameters | | | | | | | | | | |
| $C_{max}$ (ng/mL) | 7.02 (±5.64) | 7.98 (±4.39) | 7.39 (±1.68) | 16.64 (±9.36) | 9.2 (±3.5) | 14.3 (±6.16) | 8.79 (±8.68) | 44.1 (±28.2) | 26.3 (±11.9) | 56.0 (±28.2) |
| $t_{1/2}$ (h) | 183.81 (±172.3) | 53.75 (±15.6) | 73.41 (±18.3) | 26.23 (±6.53) | 75.4 (±43.8) | 58.0 (±32.8) | 88.8 (±114.6) | 22.8 (±10.9) | 10.4 (±3.1) | 21.0 (±4.3) |
| $AUC_{0-T}$ (ng·h/mL) | 367.40 (±227) | 354.77 (±145) | 551.40 (±381.8) | 367.60 (±155.7) | 710 (±395) | 1,160 (±969) | 467 (±310) | 361 (±125) | 229 (±108) | 474 (±245) |
| $AUC_{0-\infty}$ (ng·h/mL) | 1,373.3 (±1,119) | 502.15 (±153) | 844.28 (±444) | 474.00 (±209) | 997 (±680) | 1,420 (±1,134) | 879 (±1,426) | 440 (±162) | : | : |

FIG. 6

| | MM-398 + 5-FU/LV (N=117) | 5-FU/LV (N=119) | MM-398 (N=151) | 5-FU/LV (N=149) |
|---|---|---|---|---|
| Age | Median years (min, max) | 63 (41, 81) | 62 (34, 80) | 65 (31, 87) | 63 (34, 83) |
| Sex | Male, % | 59 | 56 | 58 | 54 |
| | Female, % | 41 | 44 | 42 | 46 |
| KPS | 90-100, % | 56 | 56 | 56 | 56 |
| | 70-80, % | 44 | 44 | 44 | 44 |
| Race | Caucasian, % | 64 | 63 | 60 | 60 |
| | East Asian, % | 29 | 30 | 35 | 34 |
| | Other, % | 7 | 7 | 5 | 6 |
| Pancreatic primary location | Head, % | 64 | 58 | 65 | 54 |
| | Other, % | 36 | 42 | 35 | 46 |
| CA19-9* | > 30 U/mL, % | 84 | 81 | 86 | 81 |

\* CA19-9 at baseline was unknown in 3% of patients

FIG. 10

| Parameter | PP (N=66) | Non-PP (N=51) | PP (N=71) | Non-PP (N=48) |
|---|---|---|---|---|
| KPS 90 and 100, % | 62 | 49 | 61 | 50 |
| Albumin ≥ 4.0 g/dL, % | 48 | 41 | 48 | 42 |
| Race, (%) | | | | |
| Caucasian | 71 | 55 | 63 | 63 |
| East Asian | 21 | 39 | 31 | 29 |
| CA 19-9 ≥ 40, %* | 82 | 79 | 76 | 86 |
| Pancreatic head tumor, % | 61 | 71 | 68** | 44** |
| Liver Metastasis, % | 64 | 65 | 75 | 65 |
| Line of Treatment, % | | | | |
| First line | 14 | 12 | 13 | 13 |
| Second line | 53 | 53 | 59 | 52 |
| Post-second line | 33 | 35 | 28 | 35 |
| Time since last therapy, months*** | 1.4 (0.9, 2.1) | 1.4 (1.0, 2.8) | 1.2 (1.0, 2.3) | 1.2 (1.0, 2.1) |
| Time since diagnosis, months*** | 10.3 (5.2, 15.8) | 10.8 (6.6, 19.1) | 10.3 (6.5, 15.1) | 10.5 (5.6, 16.2) |
| Stage 4 at diagnosis, % | 53 | 51 | 51 | 54 |

FIG. 15

|  | Safety Population | | PP | |
|---|---|---|---|---|
|  | MM-398 + 5-FU/LV (N=117) | 5-FU/LV (N=134) | MM-398 + 5-FU/LV (N=66) | 5-FU/LV (N=71) |
| Number of patients with Treatment Emergent Adverse Events resulting in, n (%) | | | | |
| Dose Reduction | 39 (33) | 5 (4) | 22 (33) | 2 (3) |
| Dose Delays | 72 (62) | 43 (32) | 40 (61) | 15 (21) |
| Treatment Discontinuation | 13 (11) | 10 (8) | 3 (5) | 2 (3) |
| Average relative dose intensity (%) | | | | |
| MM-398 | 83.2 | - | 85.4 | - |
| 5-FU | 83.9 | 95.6 | 86.4 | 97.9 |
| Average duration of exposure (weeks)* | 15 | 10 | 21 | 13 |

FIG. 16

|  | Safety Population[1] | | PP | |
|---|---|---|---|---|
|  | MM-398 + 5-FU/LV (N=117) | 5-FU/LV (N=134) | MM-398 + 5-FU/LV (N=66) | 5-FU/LV (N=71) |
| Grade ≥ 3 nonhematologic AEs in > 5% patients, %[2] | | | | |
| Fatigue | 14 | 4 | 14 | 6 |
| Diarrhea | 13 | 5 | 12 | 7 |
| Vomiting | 11 | 3 | 8 | 3 |
| Nausea | 8 | 3 | 9 | 1 |
| Asthenia | 8 | 7 | 5 | 6 |
| Abdominal pain | 7 | 6 | 5 | 3 |
| Grade ≥ 3 hematologic AEs based on laboratory values, %[2,3] | | | | |
| Neutrophil count decreased | 20 | 2 | 15 | 3 |
| Hemoglobin decreased | 6 | 5 | 6 | 4 |
| Platelet count decreased | 2 | 0 | 2 | 0 |
| Patients with at least 1 AE leading to death (all causes), % | 2 | 7 | 0 | 6 |

[1] Patients receiving at least one dose of study drug; [2] Per CTCAE Version 4; [3] Includes only patients who had at least one post-baseline assessment

FIG. 17 nal-IRI, nanoliposomal irinotecan.

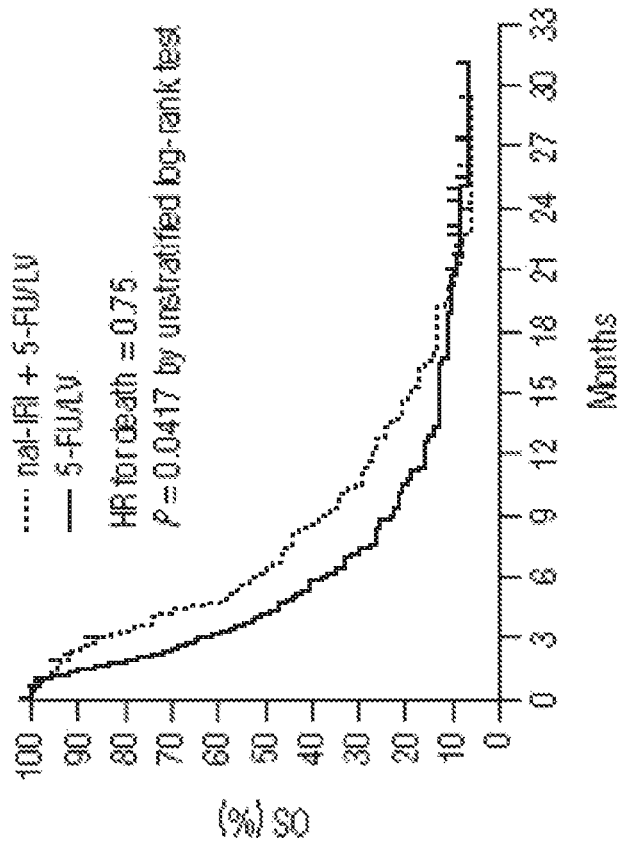
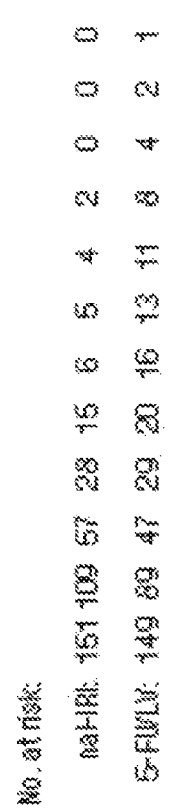
FIG. 21A nal-IRI + 5-FU/LV versus 5-FU/LV
FIG. 21B nal-IRI versus 5-FU/LV

Demographics and Baseline Characteristics (PRO Population)

| Parameter | nal-IRI + 5-FU/LV<br>n = 71 | 5-FU/LV<br>n = 57 |
|---|---|---|
| Sex, n (%) | | |
| Male | 43 (60.6) | 31 (54.4) |
| Female | 28 (39.4) | 26 (45.6) |
| Age, median (range), years | 63.0 (41-81) | 63.0 (41-80) |
| Ethnicity, n (%) | | |
| White | 42 (59.2) | 39 (68.4) |
| East Asian | 22 (31.0) | 16 (28.1) |
| Other | 7 (9.9) | 2 (3.5) |
| KPS score, n (%) | | |
| 100 | 12 (16.9) | 8 (14.0) |
| 90 | 31 (43.7) | 23 (40.4) |
| 80 | 24 (33.8) | 22 (38.6) |
| 70 | 3 (4.2) | 4 (7.0) |
| 60 | 1 (1.4) | 0 |

FIG. 25

Treatment-Emergent Adverse Events From the Primary Analysis of the NAPOLI-1 Trial

| | nal-IRI + 5-FU/LV n = 117 | | 5-FU/LV n = 134 | |
|---|---|---|---|---|
| | Any Grade | Grades 3/4 | Any Grade | Grades 3/4 |
| Diarrhea | 69 (59) | 15 (13) | 35 (26) | 6 (4) |
| Vomiting | 61 (52) | 13 (11) | 35 (26) | 4 (3) |
| Nausea | 60 (51) | 9 (8) | 46 (34) | 4 (3) |
| Decreased appetite | 52 (44) | 5 (4) | 43 (32) | 3 (2) |
| Fatigue | 47 (40) | 16 (14) | 37 (28) | 5 (4) |
| Neutropenia[a] | 46 (39) | 32 (27) | 7 (5) | 2 (1) |
| Anemia | 44 (38) | 11 (9) | 31 (23) | 9 (7) |

FIG. 30

Demographics and Baseline Characteristics (Safety Population)

| Parameter | nal-IRI + 5-FU/LV<br>n = 117 | 5-FU/LV<br>n = 134 |
|---|---|---|
| Sex, n (%) | | |
| Male | 67 (57.3) | 73 (54.5) |
| Female | 50 (42.7) | 61 (45.5) |
| Age, median (range), years | 63 (41-81) | 63 (30-83) |
| Ethnicity, n (%) | | |
| White | 73 (62.4) | 85 (63.4) |
| East Asian | 33 (28.2) | 44 (32.8) |
| Other | 11 (9.4) | 5 (3.7) |
| KPS score, n (%) | | |
| 100 | 19 (16.2) | 16 (11.9) |
| 90 | 50 (42.7) | 50 (37.3) |
| 80 | 39 (33.3) | 57 (42.5) |
| 70 | 7 (6.0) | 11 (8.2) |
| 60 | 2 (1.7) | 0 |
| Previous lines of metastatic therapy, n (%) | | |
| 0 | 15 (12.8) | 18 (13.4) |
| 1 | 63 (53.8) | 79 (59.0) |
| ≥2 | 39 (33.3) | 37 (27.6) |
| Previous anticancer therapy,[b] n (%) | | |
| Gemcitabine alone | 54 (46.2) | 61 (45.5) |
| Gemcitabine combination | 63 (53.8) | 73 (54.5) |
| Fluorouracil | 50 (42.7) | 53 (39.6) |
| Irinotecan | 12 (10.3) | 14 (10.4) |
| Platinum | 37 (31.6) | 38 (28.4) |

FIG. 31

TEAEs by Age

| | nal-IRI + 5-FU/LV | | | | | 5-FU/LV | | | |
|---|---|---|---|---|---|---|---|---|---|
| | <65 Years n = 63 | | ≥65 Years n = 54 | | | <65 Years n = 78 | | ≥65 Years n = 56 | |
| | Any Grade | Grade ≥3 | Any Grade | Grade ≥3 | | Any Grade | Grade ≥3 | Any Grade | Grade ≥3 |
| Any TEAE | 63 (100) | | 53 (98.1) | | | 77 (98.7) | | 55 (98.2) | |
| Any TEAE, grade ≥3 | 53 (84.1) | | 37 (68.5) | | | 44 (56.4) | | 31 (55.4) | |
| Any TEAE resulting in dose modification[a] | 46 (73.0) | | 37 (68.5) | | | 25 (32.1) | | 23 (41.1) | |
| TEAEs (reported in ≥30% of patients in any arm) | | | | | | | | | |
| Vomiting | 41 (65.1) | 9 (14.3) | 20 (37.0) | 4 (7.4) | | 22 (28.2) | 2 (2.6) | 13 (23.2) | 2 (3.6) |
| Diarrhea | 39 (61.9) | 9 (14.3) | 30 (55.6) | 6 (11.1) | | 22 (28.2) | 5 (6.4) | 13 (23.2) | 1 (1.8) |
| Nausea | 38 (60.3) | 3 (4.8) | 22 (40.7) | 6 (11.1) | | 29 (37.2) | 1 (1.3) | 17 (30.4) | 3 (5.4) |
| Decreased appetite | 30 (47.6) | 2 (3.2) | 22 (40.7) | 3 (5.6) | | 22 (28.2) | 3 (3.8) | 21 (37.5) | 0 |
| Neutropenia[b] | 24 (38.1) | 17 (27.0) | 22 (40.7) | 15 (27.8) | | 4 (5.1) | 2 (2.6) | 3 (5.4) | 0 |
| Fatigue | 23 (36.5) | 8 (12.7) | 24 (44.4) | 8 (14.8) | | 21 (26.9) | 3 (3.8) | 16 (28.6) | 2 (3.6) |
| Anemia | 19 (30.2) | 5 (7.9) | 25 (46.3) | 6 (11.1) | | 13 (16.7) | 5 (6.4) | 18 (32.1) | 4 (7.1) |
| Abdominal pain | 17 (27.0) | 5 (7.9) | 10 (18.5) | 3 (5.6) | | 23 (29.5) | 6 (7.7) | 19 (33.9) | 2 (3.6) |

FIG. 32

TEAEs by Ethnicity

| | nal-IRI + 5-FU/LV | | | | 5-FU/LV | | | |
|---|---|---|---|---|---|---|---|---|
| | White n = 73 | | East Asian n = 33 | | White n = 85 | | East Asian n = 44 | |
| | Any Grade | Grade ≥3 | Any Grade | Grade ≥3 | Any Grade | Grade ≥3 | Any Grade | Grade ≥3 |
| Any TEAE | 72 (98.6) | | 33 (100) | | 84 (98.8) | | 43 (97.7) | |
| Any TEAE, grade ≥3 | 51 (69.9) | | 29 (87.9) | | 48 (56.5) | | 24 (54.5) | |
| Any TEAE resulting in dose modification[a] | 48 (65.8) | | 28 (84.8) | | 33 (38.8) | | 13 (29.5) | |
| TEAEs (reported in ≥30% of patients in any arm) | | | | | | | | |
| Diarrhea | 45 (61.6) | 14 (19.2) | 16 (48.5) | 1 (3.0) | 24 (28.2) | 4 (4.7) | 11 (25.0) | 2 (4.5) |
| Nausea | 37 (50.7) | 6 (8.2) | 18 (54.5) | 2 (6.1) | 28 (32.9) | 3 (3.5) | 16 (36.4) | 1 (2.3) |
| Fatigue | 35 (47.9) | 14 (19.2) | 8 (24.2) | 0 | 25 (29.4) | 3 (3.5) | 10 (22.7) | 2 (4.5) |
| Vomiting | 34 (46.6) | 10 (13.7) | 22 (66.7) | 2 (6.1) | 23 (27.1) | 4 (4.7) | 12 (27.3) | 0 |
| Anemia | 29 (39.7) | 4 (5.5) | 13 (39.4) | 7 (21.2) | 16 (18.8) | 3 (3.5) | 15 (34.1) | 6 (13.6) |
| Decreased appetite | 24 (32.9) | 2 (2.7) | 22 (66.7) | 2 (6.1) | 24 (28.2) | 1 (1.2) | 18 (40.9) | 2 (4.5) |
| Neutropenia[a] | 21 (28.8) | 13 (17.8) | 22 (66.7) | 18 (54.5) | 4 (4.7) | 0 | 2 (4.5) | 1 (2.3) |
| Abdominal pain | 20 (27.4) | 6 (8.2) | 6 (18.2) | 2 (6.1) | 30 (35.3) | 7 (8.2) | 11 (25.0) | 1 (2.3) |
| White blood cell count decreased | 4 (5.5) | 2 (2.7) | 12 (36.4) | 7 (21.2) | 1 (1.2) | 0 | 0 | 0 |

FIG. 33

**TEAEs by UGT1A1*28 Allele (TA7/TA7 Genotype)**

| | nal-IRI + 5-FU/LV | | | | 5-FU/LV | | | |
|---|---|---|---|---|---|---|---|---|
| | TA7/TA7 Genotype n = 7 | | No TA7/TA7 Genotype n = 110 | | TA7/TA7 Genotype n = 13 | | No TA7/TA7 Genotype n = 121 | |
| | Any Grade | Grade ≥3 | Any Grade | Grade ≥3 | Any Grade | Grade ≥3 | Any Grade | Grade ≥3 |
| Any TEAE | 7 (100) | | 109 (99.1) | | 13 (100) | | 110 (90.3) | |
| Any TEAE grade ≥3 | 5 (71.4) | | 85 (77.3) | | 8 (61.5) | | 67 (55.4) | |
| Any TEAE resulting in dose modification[a] | 4 (57.1) | | 79 (71.8) | | 5 (38.5) | | 43 (35.5) | |
| TEAEs (reported in ≥30% of patients in any arm) | | | | | | | | |
| Anemia | 5 (71.4) | 0 | 39 (35.5) | 11 (10.0) | 1 (7.7) | 0 | 30 (24.8) | 9 (7.4) |
| Nausea | 3 (42.9) | 0 | 57 (51.8) | 9 (8.2) | 8 (61.5) | 1 (7.7) | 38 (31.4) | 3 (2.5) |
| Vomiting | 3 (42.9) | 1 (14.3) | 58 (52.7) | 12 (10.9) | 7 (53.8) | 1 (7.7) | 28 (23.1) | 3 (2.5) |
| Abdominal pain | 2 (28.6) | 0 | 25 (22.7) | 8 (7.3) | 6 (46.2) | 1 (7.7) | 36 (29.8) | 7 (5.8) |
| Decreased appetite | 2 (28.6) | 0 | 50 (45.5) | 5 (4.5) | 7 (53.8) | 0 | 36 (29.8) | 3 (2.5) |
| Diarrhea | 2 (28.6) | 1 (14.3) | 67 (60.9) | 14 (12.7) | 4 (30.8) | 1 (7.7) | 31 (25.6) | 5 (4.1) |
| Neutropenia[a] | 2 (28.6) | 2 (28.6) | 44 (40.0) | 30 (27.3) | 0 | 0 | 7 (5.8) | 2 (1.7) |
| Constipation | 1 (14.3) | 0 | 25 (22.7) | 0 | 4 (30.8) | 1 (7.7) | 28 (23.1) | 1 (0.8) |
| Fatigue | 1 (14.3) | 0 | 46 (41.8) | 16 (14.5) | 4 (30.8) | 1 (7.7) | 33 (27.3) | 4 (3.3) |

FIG. 34

TEAEs by Albumin Level

| | nal-IRI + 5-FU/LV | | | | 5-FU/LV | | | |
|---|---|---|---|---|---|---|---|---|
| | Albumin ≥4.0 g/dL n = 68 | | Albumin <4.0 g/dL n = 47 | | Albumin ≥4.0 g/dL n = 70 | | Albumin <4.0 g/dL n = 62 | |
| | Any Grade | Grade ≥3 | Any Grade | Grade ≥3 | Any Grade | Grade ≥3 | Any Grade | Grade ≥3 |
| Any TEAE | 68 (100) | | 46 (97.9) | | 70 (100) | | 60 (96.8) | |
| Any TEAE, grade ≥3 | 55 (80.9) | | 33 (70.2) | | 32 (45.7) | | 42 (67.7) | |
| Any TEAE resulting in dose modification[a] | 48 (70.6) | | 33 (70.2) | | 21 (30.0) | | 26 (41.9) | |
| TEAEs (reported in ≥30% of patients in any arm) | | | | | | | | |
| Diarrhea | 41 (60.3) | 12 (17.6) | 27 (57.4) | 3 (6.4) | 12 (17.1) | 1 (1.4) | 23 (37.1) | 5 (8.1) |
| Nausea | 38 (55.9) | 4 (5.9) | 20 (42.6) | 4 (8.5) | 24 (34.3) | 3 (4.3) | 21 (33.9) | 1 (1.6) |
| Vomiting | 38 (55.9) | 8 (11.8) | 23 (48.9) | 5 (10.6) | 17 (24.3) | 2 (2.9) | 17 (27.4) | 2 (3.2) |
| Decreased appetite | 33 (48.5) | 2 (2.9) | 19 (40.4) | 3 (6.4) | 22 (31.4) | 1 (1.4) | 20 (32.3) | 2 (3.2) |
| Fatigue | 31 (45.6) | 11 (16.2) | 16 (34.0) | 5 (10.6) | 21 (30.0) | 3 (4.3) | 15 (24.2) | 2 (3.2) |
| Neutropenia[a] | 29 (42.6) | 20 (29.4) | 17 (36.2) | 12 (25.5) | 4 (5.7) | 1 (1.4) | 3 (4.8) | 1 (1.6) |
| Anemia | 24 (35.3) | 6 (8.8) | 20 (42.6) | 5 (10.6) | 14 (20.0) | 4 (5.7) | 16 (25.8) | 5 (8.1) |
| Abdominal pain | 19 (27.9) | 6 (8.8) | 7 (14.9) | 2 (4.3) | 24 (34.3) | 4 (5.7) | 17 (27.4) | 4 (6.5) |
| Constipation | 16 (23.5) | 0 | 9 (19.1) | 0 | 22 (31.4) | 2 (2.9) | 10 (16.1) | 0 |

FIG. 35

TEAEs by KPS Score

| | nal-IRI + 5-FU/LV | | | | | | | | 5-FU/LV | | | |
|---|---|---|---|---|---|---|---|---|---|---|---|---|
| | KPS Score ≥90 n = 69 | | | KPS Score <90 n = 48 | | | KPS Score ≥90 n = 66 | | | KPS Score <90 n = 68 | | |
| | Any Grade | Grade ≥3 | | Any Grade | Grade ≥3 | | Any Grade | Grade ≥3 | | Any Grade | Grade ≥3 | |
| Any TEAE | 69 (100) | | | 47 (97.9) | | | 65 (98.5) | | | 67 (98.5) | | |
| Any TEAE, grade ≥3 | 52 (75.4) | | | 38 (79.2) | | | 27 (40.9) | | | 48 (70.6) | | |
| Any TEAE resulting in dose modification[a] | 48 (69.6) | | | 35 (72.9) | | | 19 (28.8) | | | 29 (42.6) | | |
| TEAEs (reported in ≥30% of patients in any arm) | | | | | | | | | | | | |
| Diarrhea | 40 (58.0) | 8 (11.6) | | 29 (60.4) | 7 (14.6) | | 22 (33.3) | 3 (4.5) | | 13 (19.1) | 3 (4.4) | |
| Nausea | 37 (53.6) | 4 (5.8) | | 23 (47.9) | 5 (10.4) | | 19 (28.8) | 1 (1.5) | | 27 (39.7) | 3 (4.4) | |
| Vomiting | 36 (52.2) | 8 (11.6) | | 25 (52.1) | 5 (10.4) | | 16 (24.2) | 2 (3.0) | | 19 (27.9) | 2 (2.9) | |
| Fatigue | 29 (42.0) | 8 (11.6) | | 18 (37.5) | 8 (16.7) | | 18 (27.3) | 1 (1.5) | | 19 (27.9) | 4 (5.9) | |
| Neutropenia[a] | 29 (42.0) | 20 (29.0) | | 17 (35.4) | 12 (25.0) | | 4 (6.1) | 1 (1.5) | | 3 (4.4) | 1 (1.5) | |
| Decreased appetite | 28 (40.6) | 1 (1.4) | | 24 (50.0) | 4 (8.3) | | 21 (31.8) | 0 | | 22 (32.4) | 3 (4.4) | |
| Anemia | 25 (36.2) | 6 (8.7) | | 19 (39.6) | 5 (10.4) | | 18 (27.3) | 4 (6.1) | | 13 (19.1) | 5 (7.4) | |
| Abdominal pain | 16 (23.2) | 3 (4.3) | | 11 (22.9) | 5 (10.4) | | 18 (27.3) | 2 (3.0) | | 24 (35.3) | 6 (8.8) | |
| Constipation | 11 (15.9) | 0 | | 15 (31.3) | 0 | | 12 (18.2) | 0 | | 20 (29.4) | 2 (2.9) | |

FIG. 36

METHODS FOR TREATING PANCREATIC CANCER USING COMBINATION THERAPIES

CROSS-REFERENCE TO RELATED APPLICATIONS

This application is a continuation of U.S. patent application Ser. No. 15/664,930 (filed Jul. 31, 2017), which is a continuation of U.S. patent application Ser. No. 15/241,128 (filed Aug. 19, 2016) now U.S. Pat. No. 9,717,724, issued Aug. 1, 2017, which is a continuation-in-part of U.S. patent application Ser. No. 14/406,776 (filed Dec. 10, 2014), now U.S. Pat. No. 9,452,162, issued Sep. 27, 2016, which are incorporated by reference herein in their entirety, and which in turn is a 371 of international application number PCT/US2013/045495 which claims the benefit of priority of U.S. Provisional Application No. 61/659,211 (filed Jun. 13, 2012) and U.S. Provisional Application No. 61/784,382 (filed Mar. 14, 2013), all of which are incorporated herein by reference.

BACKGROUND

Despite improvements in cancer treatments, there remains a critical need to further improve therapies so as to prolong patients' lives while maintaining quality of life, particularly in the case of advanced cancers such as pancreatic cancers that often are, or become, resistant to current therapeutic modalities.

Incidence of pancreatic cancer has markedly increased during the past several decades. It now ranks as the fourth leading cause of cancer death in the United States. Pancreatic cancer's high mortality rate is due to a dearth of effective therapies and a complete absence of reliably durable therapies. Because of the location of the pancreas, pancreatic cancer is typically not diagnosed until a tumor has become large enough to produce systemic symptoms. This, coupled with the absence of good screening tools and a limited understanding of risk factors, results in patients usually having advanced disease, often advanced metastatic disease, at the time of diagnosis. Metastatic pancreatic cancer has a dismal prognosis and is almost uniformly fatal, with an overall survival rate of less than 4% at 5 years.

Chemotherapy with one or more of 5-fluorouracil (5-FU) and gemcitabine has been shown to prolong survival in pancreatic cancer. Combination therapies including folinic acid (leucovorin or levoleucovorin (LV)), 5-fluorouracil, and irinotecan (FOLFIRI), folinic acid, 5-fluorouracil, irinotecan and oxaliplatin (FOLFIRINOX), or, less commonly, a combination of folinic acid, 5-fluorouracil, and oxaliplatin (FOLFOX) are also used to treat some pancreatic cancers. Irinotecan is 7-ethyl-10-[4-(1-piperidino)-1-piperidino] carbonyloxycampothecin, IUPAC name (S)-4,11-diethyl-3,4,12,14-tetrahydro-4-hydroxy-3,14-dioxo1H-pyrano[3',4':6,7]-indolizino[1,2-b]quinolin-9-yl-[1,4'bipiperidine]-1'-carboxylate. Irinotecan is a member of the topoisomerase I inhibitor class of drugs and is a semi-synthetic and water soluble analog of the naturally-occurring alkaloid, camptothecin. Also known as CPT-11, irinotecan is currently marketed formulated as an aqueous solution as Camptosar® (irinotecan hydrochloride injection). Topoisomerase I inhibitors such as irinotecan work to arrest uncontrolled cell growth by inhibiting the unwinding of DNA and thereby preventing DNA replication.

The pharmacology of irinotecan is complex, with extensive metabolic conversions involved in the activation, inactivation, and elimination of the drug. Irinotecan is a prodrug that is converted by nonspecific carboxylesterases into a 100-1000 fold more active metabolite, SN-38. SN-38 is not recognized by P-glycoprotein, a drug transporter that plays an important role in acquired drug resistance by pumping certain drugs out of cells, so irinotecan is likely to be active in tumors resistant to other standard chemotherapies. In the body, SN-38 is cleared via glucuronidation, for which major pharmacogenetic variability has been described, and biliary excretion. These drug properties contribute to the marked heterogeneities in efficacy and toxicity observed clinically with irinotecan. Irinotecan hydrochloride injection is approved in the United States for treatment of metastatic colon or renal cancer and is also used to treat colorectal, gastric, lung, uterine cervical and ovarian cancers.

There are few approved treatment options for advanced or metastatic pancreatic cancers, particularly for those of exocrine origin. Single-agent gemcitabine is the current standard of care in first-line treatment of advanced and metastatic pancreatic adenocarcinoma. In clinical trials, single-agent gemcitabine has consistently demonstrated a median prolongation of survival of 5 to 6 months and a 1-year survival rate of about 20%. Single agent gemcitabine was also approved as second line treatment for patients previously treated with but no longer responsive to 5-fluorouracil, with a median overall prolongation of survival of 3.9 months.

Based upon what is known of the biology of pancreatic cancer, a variety of targeted agents have been evaluated, but only erlotinib, a protein tyrosine kinase inhibitor targeted to EGFR, has been approved for first-line use in advanced pancreatic cancer, and the approval is only for use in combination with gemcitabine. The co-administration of erlotinib with gemcitabine resulted in a statistically significant benefit in survival, and improvements in median survival (6.4 months vs. 5.9 months), and 1-year survival rate (24% vs. 17%) compared to gemcitabine alone. Clinical trials evaluating other targeted agents, including studies testing the antibodies bevacizumab and cetuximab, have been disappointingly negative. Thus, there is an urgent need for improvements in, and effective alternatives to, current therapies for pancreatic cancer. The disclosed invention addresses this need and provides other benefits.

SUMMARY

Provided are methods for treating pancreatic cancer in a patient (i.e., a human patient) comprising administering to the patient liposomal irinotecan (e.g., irinotecan sucrose octasulfate salt liposome injection, also referred to as MM-398) alone or in combination with 5-fluorouracil (5-FU) and leucovorin (together, 5-FU/LV), according to a particular clinical dosage regimen. Compositions adapted for use in such methods are also provided.

Preferably, the liposomal irinotecan is irinotecan sucrose octasulfate salt liposome injection. MM-398 irinotecan liposome injection contains the topoisomerase 1 inhibitor irinotecan encapsulated with sucrose octasulfate in a lipid bilayer vesicle or liposome and formulated for intravenous administration. MM-398 is indicated in combination with 5-fluorouracil and leucovorin for the treatment of patients with metastatic adenocarcinoma of the pancreas whose disease has progressed following gemcitabine-based therapy.

In one aspect, a method for treatment (e.g., effective treatment) of pancreatic cancer in a patient is provided, the method comprising: administering to the patient, and affective amount of liposomal irinotecan, wherein the method comprises at least one cycle, wherein the cycle is a period of 3 weeks, and wherein for each cycle the liposomal irinotecan is administered on day 1 of the cycle at a dose of 120 mg/m$^2$, except if the patient is homozygous for the UGT1A1*28 allele, wherein liposomal irinotecan is administered on day 1 of cycle 1 at a dose of 80 mg/m$^2$. In one embodiment, the dose of liposomal irinotecan administered to the patient homozygous for the UGT1A1*28 allele is increased after one cycle in increments of 20 mg/m$^2$, up to a maximum of 120 mg/m$^2$.

In another aspect, a method for treatment of pancreatic cancer in a patient is provided, the method comprising co-administering to the patient an effective amount each of liposomal irinotecan, 5-fluorouracil (5-FU), and leucovorin, wherein the method comprises at least one cycle of administration, wherein the cycle is a period of 2 weeks, and wherein for each cycle:

(a) liposomal irinotecan is administered to patients not homozygous for the UGT1A1*28 allele on day 1 of each cycle at a dose of 80 mg/m$^2$, and to patients homozygous for the UGT1A1*28 allele on day 1 of cycle 1 at a dose of 60 mg/m$^2$ and on day 1 of each subsequent cycle at a dose of ranging from 60 mg/m$^2$ to 80 mg/m$^2$ (e.g., 60 mg/m$^2$ or 70 mg/m$^2$ or 80 mg/m$^2$);

(b) 5-FU is administered at a dose of 2400 mg/m$^2$; and (c) leucovorin is administered at a dose of 200 mg/m$^2$ (l form, or levoleucovorin) or 400 mg/m$^2$ (l+d racemic form).

In one embodiment, the dose of liposomal irinotecan administered to the patient homozygous for the UGT1A1*28 allele is increased after one cycle to 80 mg/m$^2$. In one embodiment, in each cycle, the liposomal irinotecan is administered prior to the leucovorin and the leucovorin is administered prior to the 5-FU.

In another embodiment, the liposomal irinotecan is administered intravenously over 90 minutes.

In another embodiment, the 5-FU is administered intravenously over 46 hours.

In another embodiment, leucovorin is administered intravenously over 30 minutes.

In another embodiment, prior to each administration of liposomal irinotecan, the patient is pre-medicated with dexamethasone and/or a 5-HT3 antagonist or another antiemetic.

In another embodiment, the pancreatic cancer is an exocrine pancreatic cancer selected from the group consisting of acinar cell carcinoma, adenocarcinoma, adenosquamous carcinoma, giant cell tumor, intraductal papillary-mucinous neoplasm (IPMN), mucinous cystadenocarcinoma, pancreatoblastoma, serous cystadenocarcinoma, and solid and pseudopapillary tumors. Metastatic Pancreatic Cancer (mPAC) represents a significant unmet need, with approximately 80% of patients with mPAC succumbing to disease within 12 months.

In one embodiment, treating the patient results in a positive outcome, wherein the positive outcome is pathologic complete response (pCR), complete response (CR), partial response (PR) or stable disease (SD). In another embodiment, the combination therapy with liposomal irinotecan, 5-FU and leucovorin results in therapeutic synergy. In another embodiment, the liposomal irinotecan is formulated as irinotecan sucrose octasulfate salt liposome injection (MM-398). Irinotecan sucrose octasulfate salt liposome injection may also be referred to as irinotecan HCl liposome injection because irinotecan HCl is the active pharmaceutical ingredient that is used to load irinotecan into liposomes containing triethylammonium sucrose octasulfate to prepare MM-398 liposomes. This nomenclature may be used even though the hydrochloride ion of the irinotecan HCl reacts with the triethylammonium ion of the triethylammonium sucrose octasulfate to yield triethylammonium chloride (triethylamine hydrochloride), leaving irinotecan sucrose octasulfate salt as the entrapped pharmaceutical agent within the MM-398 liposomes. In another aspect, kits for treating pancreatic cancer in a patient are provided, the kit comprising a dose of liposomal irinotecan and instructions for using liposomal irinotecan as described herein.

In another aspect, kits for treating pancreatic cancer in a patient are provided, the kit comprising a dose of each liposomal irinotecan, 5-fluorouracil (5-FU), and leucovorin, and instructions for using liposomal irinotecan, 5-FU, and leucovorin as described herein.

In one embodiment, the kit encompasses treating an exocrine pancreatic cancer selected from the group consisting of acinar cell carcinoma, adenocarcinoma, adenosquamous carcinoma, giant cell tumor, intraductal papillary-mucinous neoplasm (IPMN), mucinous cystadenocarcinoma, pancreatoblastoma, serous cystadenocarcinoma, and solid and pseudopapillary tumors.

In one embodiment, the liposomal irinotecan is liposomal irinotecan sucrose octasulfate salt injection (MM-398).

In another aspect, a formulation of liposomal irinotecan for co-administration with 5-fluorouracil (5-FU) and leucovorin in at least one cycle is provided, wherein the cycle is a period of 2 weeks, the formulation of irinotecan is a liposomal formulation of irinotecan, and wherein:

(a) liposomal irinotecan is administered to patients not homozygous for the UGT1A1*28 allele on day 1 of each cycle at a dose of 80 mg/m$^2$ and to patients homozygous for the UGT1A1*28 allele on day 1 of cycle 1 at a dose of 60 mg/m$^2$ and on day 1 of each subsequent cycle at a dose of 60 mg/m$^2$ or 80 mg/m$^2$;

(b) 5-FU is administered at a dose of 2400 mg/m$^2$; and (c) leucovorin is administered at a dose of 200 mg/m$^2$ (l form, or levoleucovorin) or 400 mg/m$^2$ (l+d racemic form).

In one embodiment, after cycle 1 the dose of liposomal irinotecan administered to the patient homozygous for the UGT1A1*28 allele is increased to 80 mg/m$^2$. In another embodiment, the liposomal irinotecan is administered intravenously over 90 minutes.

In another embodiment, the 5-FU is administered intravenously over 46 hours.

In another embodiment, leucovorin is administered intravenously over 30 minutes.

In another embodiment, prior to each administration of liposomal irinotecan, the patient is pre-medicated with dexamethasone and/or a 5-HT3 antagonist or another antiemetic.

In another embodiment, the pancreatic cancer is an exocrine pancreatic cancer selected from the group consisting of acinar cell carcinoma, adenocarcinoma, adenosquamous carcinoma, giant cell tumor, intraductal papillary-mucinous neoplasm (IPMN), mucinous cystadenocarcinoma, pancreatoblastoma, serous cystadenocarcinoma, and solid and pseudopapillary tumors.

In another embodiment, the liposomal formulation of irinotecan is irinotecan sucrose octasulfate salt liposome injection.

In another aspect is provided a method of improving chemotherapy outcomes by increasing tumor vascularity, the method comprising administering to a patient having a tumor an amount of irinotecan sucrose octasulfate salt liposome injection effective to increase tumor vascularity and concomitantly administering an effective amount of a chemotherapy agent other than irinotecan to the patient.

In another aspect is provided irinotecan sucrose octasulfate salt liposome injection for concomitant administration to a patient having a tumor of 1) an amount of irinotecan sucrose octasulfate salt liposome injection effective to increase tumor vascularity and 2) an effective amount of a chemotherapy agent other than irinotecan.

The therapy can be safely and effectively administered to patients diagnosed with metastatic adenocarcinoma of the pancreas after disease progression following gemcitabine-based therapy. The amount of leucovorin administered can be selected to provide a desired effect of the 5-fluorouracil (e.g., an amount of leucovorin comprising 200 mg/m$^2$ of levo-leucovorin, such as 400 mg/m$^2$ of the (l+d) racemic form of leucovorin). For example, the patient can be treated with an antineoplastic therapy (referred to herein as "MM-398+5-FU/LV (MM-398 80 mg/m$^2$ q2w regimen)") comprising: 80 mg/m$^2$ of irinotecan encapsulated in a MM-398 irinotecan liposome (e.g., as a 90 minute intravenous infusion) followed by 400 mg/m$^2$ of the antineoplastic agent (l+d) racemic leucovorin (e.g., as a 30 minute intravenous infusion) followed by 2,400 mg/m$^2$ of the antineoplastic agent 5-fluorouracil (e.g., as an intravenous infusion over 46 hours), without administering any other antineoplastic agents for the treatment of the pancreatic cancer (e.g., without administering gemcitabine).

Unless otherwise indicated, recitation of the amount of the irinotecan in liposomal irinotecan is expressed herein as the amount of irinotecan hydrochloride trihydrate (molecular weight of about 677 g/mol) providing a given amount of irinotecan free base: for example, 80 mg/m$^2$ of irinotecan hydrochloride trihydrate (e.g., as approved under the non-liposomal irinotecan product CAMPTOSAR®) contains about the equivalent amount of irinotecan free base as a dose of 70 mg/m$^2$ of irinotecan in the MM-398 liposome formulation.

BRIEF DESCRIPTION OF THE DRAWINGS

FIG. 5 summarizes the pharmacokinetics of MM-398 in q3w (irinotecan, liposome+free drug).

FIG. 6 summarizes the pharmacokinetics of MM-398 in q3w.

FIG. 10 is a table providing the baseline characteristics of the Intent to Treat (ITT) (all randomized patients) population. In the table, CA19-9 at baseline was unknown in 3% of the patients.

FIG. 13 represents the PP population and FIG. 14 represents the Non-PP population.

FIG. 15 is a table providing the demographic characteristics for the Per Protocol (PP) patient population vs. the Non-Per Protocol (Non-PP) patient population. CA19-9 includes only patients who had a measured CA19-9 prior to treatment. "" denotes results that showed a statistically significant difference (p value ≤0.01). "*" denotes the median (1st quartile, 3rd quartile).

FIG. 16 is a table providing the dose modifications and treatment exposure. Duration of exposure is the time from (the date of the last administration of the study drug+the projected days to the next dose of the study drug administration–the date of the first study drug administration).

FIG. 17 is a table providing the safety data (adverse events) for the study. In the table, (1) the safety population refers to those patients receiving at least one dose of the study drug; (2) percentages of the populations having adverse events (AE's) were provided per CTCAE Version 4; and (3) hematologic adverse events include only those patients who had at least one post-baseline assessment.

FIG. 21A is a graphical representation of the Overall Survival Rate (OS) corresponding to treatment with MM-398+5-FU/LV vs. 5-FU/LV alone.

FIG. 21B is a graphical representation of the Overall Survival Rate (OS) corresponding to treatment with MM-398 vs. 5-FU/LV alone.

FIG. 25 is a table providing demographics and baseline characteristics (PRO Population).

FIG. 30 is a table providing Treatment-Emergent Adverse Events From the Primary Analysis of the NAPOLI-1 Trial. 5-FU is 5-flourouracil; LC is leucovorin; nal-IRI is liposomal irinotecan. Data are number of patients (%). The table shows grade 3 and 4 adverse events reported in ≥5% of patients with ≥2% incidence versus 5-FU/LV. [a]Includes agranulocytosis, febrile neutropenia, granulocytopenia, neutropenia, neutropenic sepsis, decreased neutrophil count, and pancytopenia.

FIG. 31 is a table providing Demographics and Baseline Characteristics (Safety Population). 5-FU is 5-fluorouracil; KPS is Karnofsky performance status, LV is leucovorin; nal-IRI is liposomal irinotecan. [a]Patients received neoadjuvant, adjuvant, or locally advanced treatment, but no previous therapy for metastatic disease. [b]Columns add to >100% because some patients received more than 1 line of therapy, and regimens may include multiple drug classes.

FIG. 32 is a table providing TEAEs by Age. 5-FU is 5-fluorouracil; LV is leucovorin; nal-IRI is nanoliposomal irinotecan; TEAE is treatment-emergent adverse event. [a]Dose modification included dose reduction, dose delay, and dose discontinuation. [b]Includes agranulocytosis, febrile neutropenia, granulocytopenia, neutropenia, neutrophil sepsis, neutrophil count decreased, and pancytopenia.

FIG. 33 is a table providing TEAEs by Ethnicity. 5-FU is 5-fluorouracil; LV is leucovorin; nal-IRI is nanoliposomal irinotecan; TEAE is treatment-emergent adverse event. [a]Dose modification included dose reduction, dose delay, and dose discontinuation. [b]Includes agranulocytosis, febrile neutropenia, granulocytopenia, neutropenia, neutrophil sepsis, neutrophil count decreased, and pancytopenia.

FIG. 34 is a table providing TEAEs by UGT1A1*28 Allele (TA7/TA7 Genotype). 5-FU is 5-fluorouracil; LV is leucovorin; nal-IRI is nanoliposomal irinotecan; TEAE is treatment-emergent adverse event. [a]Dose modification included dose reduction, dose delay, and dose discontinuation. [b]Includes agranulocytosis, febrile neutropenia, granulocytopenia, neutropenia, neutrophil sepsis, neutrophil count decreased, and pancytopenia.

FIG. 35 is a table providing TEAEs by Albumin Level. 5-FU is 5-fluorouracil; LV is leucovorin; nal-IRI is nanoliposomal irinotecan; TEAE is treatment-emergent adverse event. [a]Dose modification included dose reduction, dose delay, and dose discontinuation. [b]Includes agranulocytosis, febrile neutropenia, granulocytopenia, neutropenia, neutrophil sepsis, neutrophil count decreased, and pancytopenia.

FIG. 36 is a table providing TEAEs by KPS Score. 5-FU is 5-fluorouracil; KPS is Karnofsky performance status; LV is leucovorin; nal-IRI is nanoliposomal irinotecan; TEAE is treatment-emergent adverse event. [a]Dose modification included dose reduction, dose delay, and dose discontinuation. [b]Includes agranulocytosis, febrile neutropenia, granulocytopenia, neutropenia, neutrophil sepsis, neutrophil count decreased, and pancytopenia.

DETAILED DESCRIPTION

I. Definitions

Figure 1:
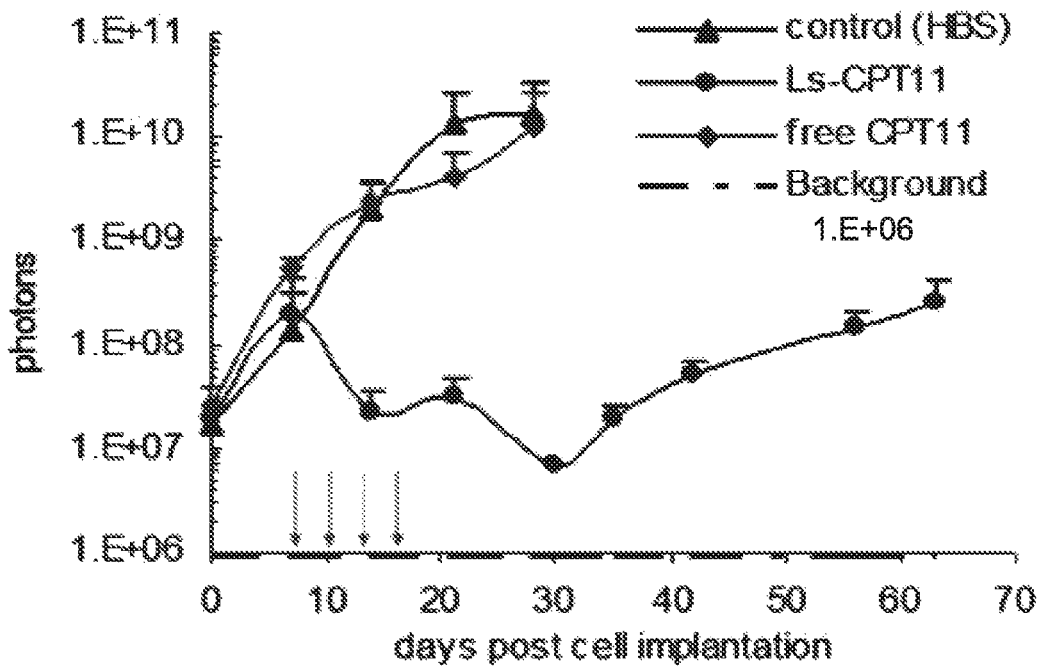
FIG. 1 is a graph showing the anti-tumor activity of MM-398 in an orthotopic pancreatic tumor model expressing luciferase (L3.6pl).

As used herein, the term "subject" or "patient" is a human cancer patient.

As used herein, "effective treatment" refers to treatment producing a beneficial effect, e.g., amelioration of at least one symptom of a disease or disorder. A beneficial effect can take the form of an improvement over baseline, i.e., an improvement over a measurement or observation made prior to initiation of therapy according to the method. A beneficial effect can also take the form of arresting, slowing, retarding, or stabilizing of a deleterious progression of a marker of a cancer. Effective treatment may refer to alleviation of at least one symptom of a cancer. Such effective treatment may, e.g., reduce patient pain, reduce the size and/or number of lesions, may reduce or prevent metastasis of a cancer tumor, and/or may slow growth of a cancer tumor.

The term "effective amount" refers to an amount of an agent that provides the desired biological, therapeutic, and/or prophylactic result. That result can be reduction, amelioration, palliation, lessening, delaying, and/or alleviation of one or more of the signs, symptoms, or causes of a disease, or any other desired alteration of a biological system. In reference to cancers, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay tumor development. In some embodiments, an effective amount is an amount sufficient to prevent or delay tumor recurrence. An effective amount can be administered in one or more administrations. The effective amount of the drug or composition may: (i) reduce the number of cancer cells; (ii) reduce tumor size; (iii) inhibit, retard, slow to some extent and may stop cancer cell infiltration into peripheral organs; (iv) inhibit (i.e., slow to some extent and may stop) tumor metastasis; (v) inhibit tumor growth; (vi) prevent or delay occurrence and/or recurrence of tumor; and/or (vii) relieve to some extent one or more of the symptoms associated with the cancer.

The terms "combination therapy," "co-administration," "co-administered" or "concurrent administration" (or minor variations of these terms) include simultaneous administration of at least two therapeutic agents to a patient or their sequential administration within a time period during which the first administered therapeutic agent is still present in the patient when the second administered therapeutic agent is administered.

The term "monotherapy" refers to administering a single drug to treat a disease or disorder in the absence of co-administration of any other therapeutic agent that is being administered to treat the same disease or disorder.

"Dosage" refers to parameters for administering a drug in defined quantities per unit time (e.g., per hour, per day, per week, per month, etc.) to a patient. Such parameters include, e.g., the size of each dose. Such parameters also include the configuration of each dose, which may be administered as one or more units, e.g., taken at a single administration, e.g., orally (e.g., as one, two, three or more pills, capsules, etc.) or injected (e.g., as a bolus). Dosage sizes may also relate to doses that are administered continuously (e.g., as an intravenous infusion over a period of minutes or hours). Such parameters further include frequency of administration of separate doses, which frequency may change over time.

"Dose" refers to an amount of a drug given in a single administration.

As used herein, "cancer" refers to a condition characterized by abnormal, unregulated, malignant cell growth. In one embodiment, the cancer is an exocrine pancreatic cancer. In another embodiment, the exocrine pancreatic cancer selected from the group consisting of acinar cell carcinoma, adenocarcinoma, adenosquamous carcinoma, giant cell tumor, intraductal papillary-mucinous neoplasm (IPMN), mucinous cystadenocarcinoma, pancreatoblastoma, serous cystadenocarcinoma, and solid and pseudopapillary tumors.

The terms "resistant" and "refractory" refer to tumor cells that survive treatment with a therapeutic agent. Such cells may have responded to a therapeutic agent initially, but subsequently exhibited a reduction of responsiveness during treatment, or did not exhibit an adequate response to the therapeutic agent in that the cells continued to proliferate in the course of treatment with the agent.

II. Irinotecan Nanoparticle Formulations

As provided herein, irinotecan is administered in a composition of irinotecan nanoparticles with a diameter of about 80-140 nm formulated to provide an irinotecan terminal elimination half-life in the human patient of at least about 2-fold higher than that of 125 mg/m² free irinotecan as CPT-11 irinotecan hydrochloride injection, and preferably also include a $C_{max}$ and AUC within the ranges specified in Table 4. Preferably, the irinotecan is contained within a lipid matrix, for example as described in PCT publication WO2005/107712 (see, e.g., Example 11 describing CPT-11 liposome formulations prepared with TEA-Pn and TEA-SOS, incorporated herein by reference). The lipid matrix composition can comprise entrapped irinotecan in a pharmaceutically acceptable salt form, in 1,2-Distearoyl-SN-phosphatidylcholine (DSPC) (Mol. wt. 790) 3 molar parts (59.8 mol. %); Cholesterol (Chol) (Mol. weight 387) 2 molar parts (39.9 mol. %); and N-(omega-methoxy-poly(ethylene glycol)-oxycarbonyl)-1,2-distearoylphosphatidyl ethanolamine (Mol. weight 2787) (PEG-DSPE) 0.015 molar parts (approx. 0.3 mol. %).

Figure 18:
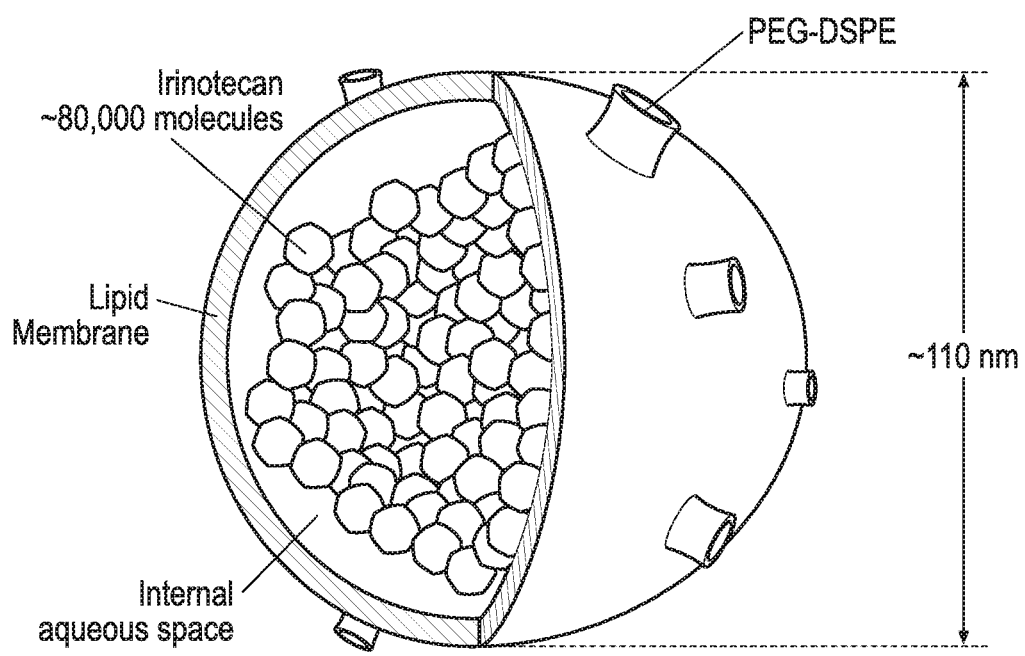
FIG. 18 is a pictorial representation of nanoliposomal irinotecan (MM-398).
Figure 19:
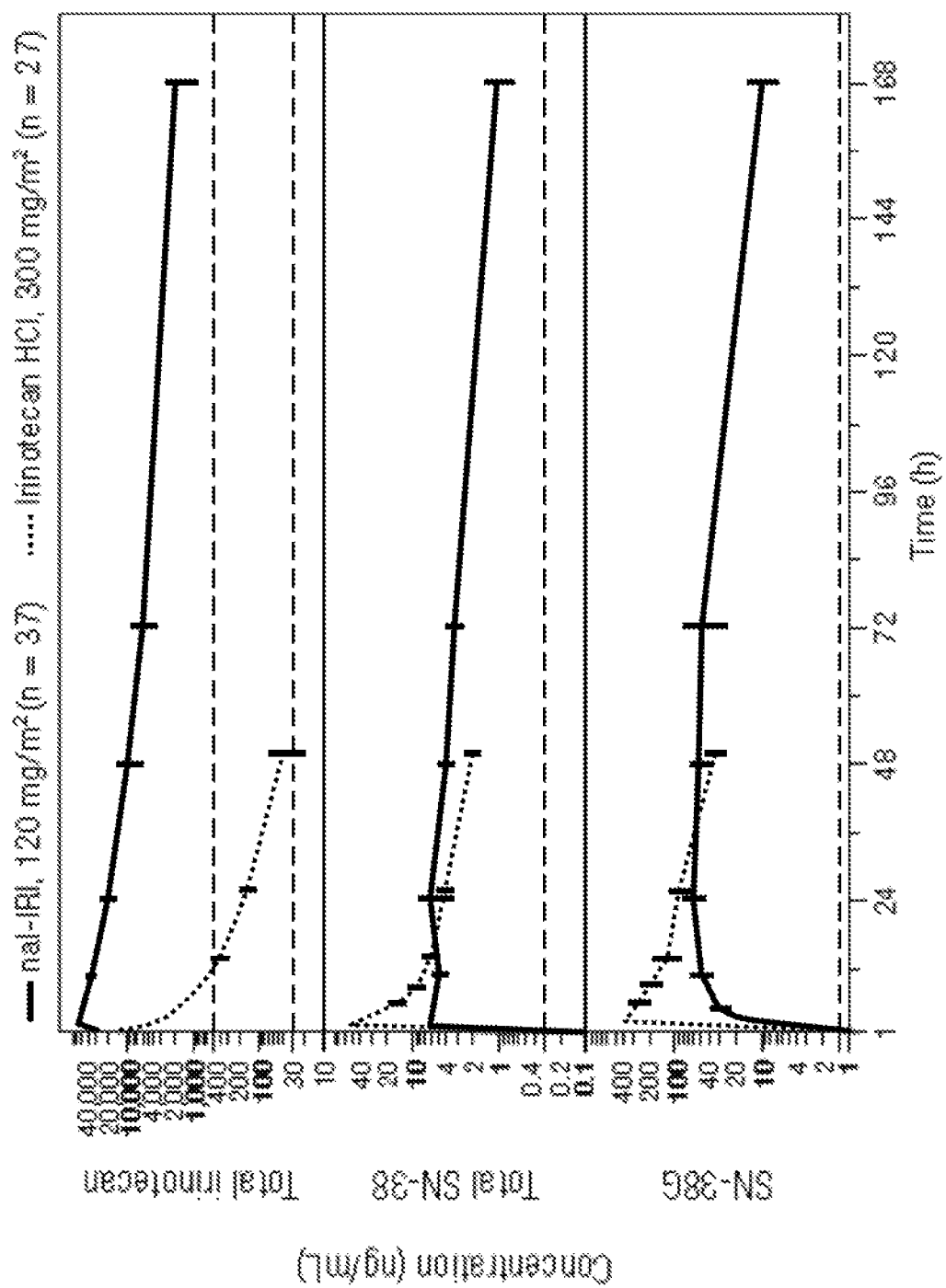
FIG. 19 provides a pharmacokinetic analysis of the extended circulation of irinotecan and the SN38 metabolite after administration of irinotecan within the liposome vs. irinotecan HCl, in patients with gastric cancer. Nal-IRI is nanoliposomal Irinotecan; AUC is area under the curve; $C_{max}$ is maximal concentration. Comparing nal-IRI with irinotecan HCl, total irinotecan AUC was 46 times greater and total irinotecan $C_{max}$ was 13.4 times greater, SN-38 AUC was 1.4 times greater, and SN-38 $C_{max}$ was 0.19 times greater. The peak of SN-38 metabolite was lower with nal-IRI versus irinotecan HCl, without an increase in SN-38 plasma AUC.
Figure 20:
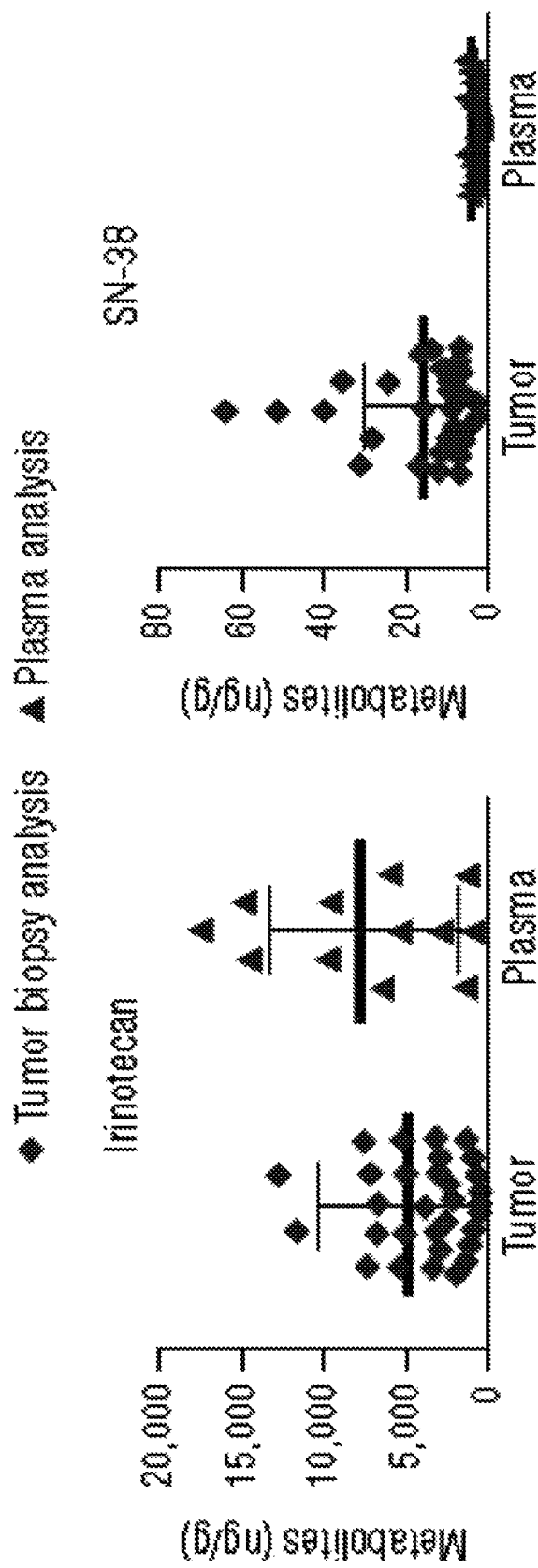
FIG. 20 provides irinotecan and SN38 levels in tumor tissue and plasma 72 hours after treatment with MM-398. Nal-IRI is nanoliposomal irinotecan; LLoQ is the lower limit of quantitation. Drug metabolite quantitation in tumor biopsies and plasma from patients in a study of patients (N=14) with advanced solid tumors. Tumor biopsy material averaged 10.5 mg (range, 3.3-21.9 mg); metabolite detection was in an LC/MS/MS TSQ Vantage instrument, with LLoQ of 50 pg/mL for irinotecan and 100 pg/mL for SN-38. Plasma analysis was performed at QPS according to validated procedures, with LLoQ of 140 ng/mL for irinotecan and 600 pg/mL for SN-38.

In some embodiments, the irinotecan is administered in a lipid matrix as a liposomal formulation encapsulating irinotecan sucrose sulfate liposome. The liposome can have the structure shown in FIG. 18. For example, the irinotecan nanoparticle can be an "irinotecan sucrose octasulfate salt liposome injection" or "irinotecan sucrosofate liposome injection" product, including the formulation referred to herein as "MM-398" (also known as PEP02 or nanoliposomal irinotecan or liposomal irinotecan or "nal-IRI").

For example, an MM-398 liposome is a unilamellar lipid bilayer vesicle of approximately 80-140 nm in diameter that encapsulates an aqueous space which contains irinotecan complexed in a gelated or precipitated state as a salt with sucrose octasulfate. The lipid membrane of the liposome is composed of phosphatidylcholine, cholesterol, and a polyethyleneglycol-derivatized phosphatidyl-ethanolamine in the amount of approximately one polyethyleneglycol (PEG) molecule for 200 phospholipid molecules.

This stable liposomal formulation of irinotecan has several attributes that may provide an improved therapeutic index. The controlled and sustained release improves activity of this schedule-dependent drug by increasing duration of exposure of tumor tissue to drug, an attribute that allows it to be present in a higher proportion of cells during the S-phase of the cell cycle, when DNA unwinding is required as a preliminary step in the DNA replication process. The long circulating pharmacokinetics and high intravascular drug retention in the liposomes can promote an enhanced permeability and retention (EPR) effect. EPR allows for deposition of the liposomes at sites, such as malignant tumors, where the normal integrity of the vasculature (capillaries in particular) is compromised resulting in leakage out of the capillary lumen of particulates such as liposomes. EPR may thus promote site-specific drug delivery of liposomes to solid tumors. EPR of MM-398 may result in a subsequent depot effect, where liposomes accumulate in tumor associated macrophages (TAMs), which metabolize irinotecan, converting it locally to the substantially more cytotoxic SN-38. This local bioactivation is believed to result in reduced drug exposure at potential sites of toxicity and increased exposure at cancer cells within the tumor.

The chemical name of irinotecan hydrochloride trihydrate is (S) 4,11-diethyl-3,4,12,14-tetrahydro-4-hydroxy-3,14-dioxo1H-pyrano[3',4':6,7]-indolizino[1,2 b]quinolin-9-yl-[1,4'bipiperidine]-1'-carboxylate, monohydrochloride, trihydrate. The empirical formula is $C_{33}H_{38}N_4O_6 \cdot HCl \cdot 3H_2O$ and the molecular weight is 677.19 g/mole. The molecular structure is:

Structural formula

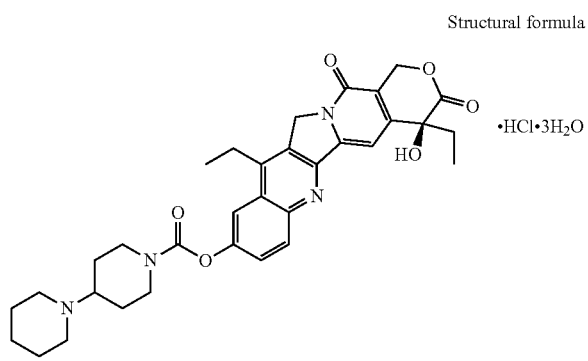 [SMILES: CCc1c2c(nc3ccc(OC(=O)N4CCC(N5CCCCC5)CC4)cc13)-c1cc3c(c(=O)n1C2)COC(=O)[C@]3(O)CC]

The chemical name of irinotecan is (S) 4,11-diethyl-3,4,12,14-tetrahydro-4-hydroxy-3,14-dioxo1H-pyrano[3',4':6,7]-indolizino[1,2 b]quinolin-9-yl-[1,4'bipiperidine]-1'-carboxylate. The empirical formula is $C_{33}H_{38}N_4O_6$ and the molecular weight is 586.68 g/mole. The molecular structure of irinotecan free base is:

Structural formula

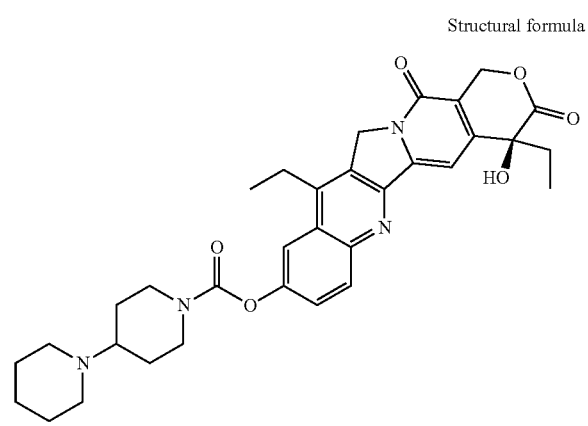 [SMILES: CCc1c2c(nc3ccc(OC(=O)N4CCC(N5CCCCC5)CC4)cc13)-c1cc3c(c(=O)n1C2)COC(=O)[C@]3(O)CC]

MM-398 is a topoisomerase I inhibitor indicated for the treatment of metastatic adenocarcinoma of the pancreas after disease progression following gemcitabine-based therapy. MM-398 (irinotecan liposome injection), in combination with 5-fluorouracil and leucovorin, is indicated for the treatment of patients with metastatic adenocarcinoma of the pancreas whose disease has progressed following gemcitabine-based therapy. Administer MM-398 prior to leucovorin and 5-fluorouracil. MM-398 is not indicated as a single agent for the treatment of metastatic adenocarcinoma of the pancreas. MM-398 is not substituted for other drugs containing non-liposome formulations of irinotecan hydrochloride or irinotecan hydrochloride trihydrate.

Converting a dose based on irinotecan hydrochloride trihydrate to a dose based on irinotecan free base is accomplished by multiplying the dose based on irinotecan hydrochloride trihydrate with the ratio of the molecular weight of irinotecan free base (586.68 g/mol) and the molecular weight of irinotecan hydrochloride trihydrate (677.19 g/mol). This ratio is 0.87 which can be used as a conversion factor. For example, an 80 mg/m² dose based on irinotecan hydrochloride trihydrate is equivalent to a 69.60 mg/m² dose based on irinotecan free base (80×0.87). In the clinic this is rounded to 70 mg/m².

Alternatively, the dose of irinotecan liposome can be expressed as the amount of irinotecan free base encapsulated in the irinotecan liposome where indicated ("free base dose"). Unless otherwise indicated, the irinotecan liposome dose free base dose recited in MM-398 is expressed in terms of the amount of irinotecan hydrochloride trihydrate salt (herein referred to as a "(salt)" dose) containing the same amount of irinotecan free base. Examples of equivalent MM-398 doses are provided in table 1 below based on both free base dose and salt based dose.

TABLE 1

| Irinotecan liposome free base dose in MM-398 (mg/m²) ("free base") | Corresponding MM-398 irinotecan liposome hydrochloride trihydrate salt dose (mg/m²) ("salt") |
|---|---|
| 100 | 120 |
| 70 | 80 |
| 60 | 70 |
| 50 | 60 |
| 43 | 50 |
| 35 | 40 |

The recommended dose of MM-398 is 80 mg/m² (salt) (70 mg/m² free base) intravenous infusion over 90 minutes (i.e., 70 mg irinotecan free base in the irinotecan liposome per m² patient body surface area, containing about the same amount of irinotecan that would be in 80 mg/m² of irinotecan hydrochloride trihydrate). Preferably, the recommended dose of MM-398 is 80 mg/m² administered by intravenous infusion over 90 minutes every 2 weeks. A corticosteroid and an anti-emetic is preferably administered to the patient 30 minutes prior to MM-398.

Pharmacogenetics of Irinotecan Glucuronidation

The enzyme produced by the UGT1A1 gene, UDP-glucuronosyltransferase 1, is responsible for bilirubin metabolism and also mediates SN-38 glucuronidation, which is the initial step in the predominant metabolic clearance pathway of this active metabolite of irinotecan. Besides its anti-tumor activity, SN-38 is also responsible for the severe toxicity sometimes associated with irinotecan therapy. Therefore, the glucuronidation of SN-38 to the inactive form, SN-38 glucuronide, is an important step in the modulation of irinotecan toxicity.

Mutational polymorphisms in the promoter of the UGT1A1 gene have been described in which there is a variable number of thymine adenine (ta) repeats. Promoters containing seven thymine adenine (ta) repeats (found in the UGT1A1*28 allele) have been found to be less active than the wild-type six repeats, resulting in reduced expression of UDP-glucuronosyltransferase 1. Patients who carry two deficient alleles of UGT1A1 exhibit reduced glucuronidation of SN-38. Some case reports have suggested that individuals who are homozygous for UGT1A1*28 alleles (referred to as having the UGT1A1 7/7 genotype, because both alleles are UGT1A1*28 alleles that contain 7 ta repeats, as opposed to the wild-type UGT1A1 6/6 genotype in which both alleles contain 6 ta repeats) and who have fluctuating elevation in serum bilirubin, (e.g., Gilbert's Syndrome patients), may be at greater risk of toxicity upon receiving standard doses of irinotecan. This suggests that there is a link between homozygosity of the UGT1A1*28 allele, bilirubin levels and irinotecan toxicity.

The metabolic transformation of MM-398 to SN-38 (e.g., in plasma) includes two critical steps: (1) the release of irinotecan from the liposome and (2) the conversion of free irinotecan to SN-38. While not intending to be limited by theory, it is believed that once irinotecan leaves the liposomes, it is catabolized by the same metabolic pathways as conventional (free) irinotecan. Therefore the genetic polymorphisms in humans predictive for the toxicity and efficacy of irinotecan and those of MM-398 can be considered similar. Nonetheless, due to the smaller tissue distribution, lower clearance, higher systemic exposure and longer elimination half-life of SN-38 of the MM-398 formulation compared to free irinotecan, the deficient genetic polymorphisms may show more association with severe adverse events and/or efficacy.

Patients with Reduced UGT1A1 Activity

Individuals who are homozygous for the UGT1A1*28 allele (UGT1A1 7/7 genotype) have been shown to be at increased risk for neutropenia following initiation of irinotecan treatment. According to the prescribing information for irinotecan (Camptosar®), in a study of 66 patients who received single-agent irinotecan (350 mg/m² once every-3-weeks), the incidence of grade 4 neutropenia in patients homozygous for the UGT1A1*28 allele was as high as 50%, and in patients heterozygous for this allele (UGT1A1 6/7 genotype) the incidence was 12.5%. Importantly, no grade 4 neutropenia was observed in patients homozygous for the wild-type allele (UGT1A1 6/6 genotype). In other studies, a lower prevalence of life threatening neutropenia is described. For this reason, patients who are enrolled in the phase 3 study described in the Examples herein and are homozygous for the UGT1A1*28 allele (UGT1A1 7/7 genotype) will have MM-398 treatment initiated at a lower dose than patients with one (e.g., UGT1A1 6/7) or two (UGT1A1 6/6) wild-type alleles.

The recommended starting dose of MM-398 in patients known to be homozygous for the UGT1A1*28 allele is 60 mg/m² (salt) (equivalent to a dose of 50 mg/m² (base)) administered by intravenous infusion over 90 minutes. Increase the dose of MM-398 to 80 mg/m² (salt) as tolerated in subsequent cycles.

In some embodiments, methods of administering MM-398 to patients having one or more characteristics can include reducing or otherwise modifying the dose of MM-398 administered according to the embodiments herein. In some embodiments, the dose of MM-398 is modified according to Table 2.

TABLE 2

Recommended Dose Modifications for MM-398 (salt)

| Toxicity NCI CTCAE v4.0 | Occurrence | MM-398 adjustment in patients receiving 80 mg/m²‡ (salt) | Patients homozygous for UGT1A1*28 without previous increase to 80 mg/m² (salt) |
|---|---|---|---|
| Grade 3 or 4 adverse reactions | | Withhold MM-398. Initiate loperamide for late onset diarrhea of any severity. Administer intravenous or subcutaneous atropine 0.25 to 1 mg (unless clinically contraindicated) for early onset diarrhea of any severity. Upon recovery to ≤ Grade 1 or baseline grade resume MM-398 at: | |
| | First | 60 mg/m² | 50 mg/m² |
| | Second | 50 mg/m² | 40 mg/m² |
| | Third | Discontinue MM-398 | Discontinue MM-398 |
| Interstitial Lung Disease | First | Discontinue MM-398 | Discontinue MM-398 |
| Anaphylactic Reaction | First | Discontinue MM-398 | Discontinue MM-398 |

Additional Genotypic Modifiers of Irinotecan Metabolism

Although the UGT1A1*28 allele is relatively common in Caucasians (estimates 10%), the prevalence is varied in other ethnic groups. Furthermore, additional UGT1A1 genotypes are found with higher prevalence for example in Asian populations and these could be important for the metabolism of irinotecan in these populations. For example, the UGT1A1*6 allele is more prevalent in Asians. This allele is not associated with a to repeat, but with a Gly71Arg mutation that reduces enzyme activity. In previous and ongoing studies of MM-398, pharmacogenetic information has been collected on patients being enrolled. In a study referred to as the PEP0203 study, the relationship of genetic polymorphism of UGT1A family and of DPYD (dihydropyrimidine dehydrogenase, an enzyme associated with catabolism of 5-FU) with pharmacokinetic parameters of MM-398 and toxicity did not provide a clear correlation with the small sample size of subjects evaluated. However, it was observed that patients with UGT1A1*6/*28 combined polymorphism had higher dose-normalized AUCs of SN-38 and experienced DLT.

III. 5-Fluorouracil (5-FU) and Leucovorin

5-Fluorouracil is a pyrimidine antagonist that interferes with nucleic acid biosynthesis. The deoxyribonucleotide of the drug inhibits thymidylate synthetase, thus inhibiting the formation of thymidylic acid from deoxyuridylic acid, thus interfering in the synthesis of DNA. It also interferes with RNA synthesis.

Leucovorin (also called folinic acid) acts as a biochemical cofactor for 1-carbon transfer reactions in the synthesis of purines and pyrimidines. Leucovorin does not require the enzyme dihydrofolate reductase (DHFR) for conversion to tetrahydrofolic acid. The effects of methotrexate and other DHFR-antagonists are inhibited by leucovorin. Leucovorin can potentiate the cytotoxic effects of fluorinated pyrimidines (i.e., 5-fluorouracil and floxuridine). After 5-FU is activated within the cell, it is accompanied by a folate cofactor, and inhibits the enzyme thymidylate synthetase, thus inhibiting pyrimidine synthesis. Leucovorin increases the folate pool, thereby increasing the binding of folate cofactor and active 5-FU with thymidylate synthetase.

Leucovorin has dextro- and levo-isomers, only the latter one being pharmacologically useful. As such, the bioactive levo-isomer ("levoleucovorin") has also been approved by the FDA for treatment of cancer. The dosage of levoleucovorin is typically half that of the racemic mixture containing both dextro (d) and levo (l) isomers. Unless otherwise indicated, doses requiring 200 mg/m² leucovorin are to be understood to require 200 mg/m² of the (l) enantiomer of leucovorin, and doses requiring 400 mg/m² leucovorin are to be understood to require 400 mg/m² of the (l+d) racemate of leucovorin. Unless otherwise indicated, a dose having 200 mg/m² of the (l) enantiomer of leucovorin, and a dose having 400 mg/m² of the (l+d) racemate of leucovorin contain equivalent amounts of the pharmaceutically active (l) form of leucovorin.

FU and leucovorin will be stored and handled according to the country specific package inserts.

IV. Administration

Liposomal irinotecan is administered intravenously, either alone or in combination with 5-fluorouracil (5-FU) and/or leucovorin. In one embodiment, liposomal irinotecan is administered prior to 5-FU and leucovorin. In another embodiment, leucovorin is administered prior to 5-FU. In another embodiment, liposomal irinotecan is administered intravenously over 90 minutes. In another embodiment, 5-FU is administered intravenously over 46 hours. In another embodiment, leucovorin is administered intravenously over 30 minutes. In various embodiments the liposomal irinotecan is MM-398.

V. Patient Populations

In one embodiment, a patient treated using the methods and compositions disclosed herein exhibits evidence of recurrent or persistent pancreatic cancer following primary chemotherapy.

In another embodiment, the patient has had and failed at least one prior platinum based chemotherapy regimen for management of primary or recurrent disease, e.g., a chemotherapy regimen comprising carboplatin, cisplatin, or another organoplatinum compound.

In an additional embodiment, the patient has failed prior treatment with gemcitabine or become resistant to gemcitabine.

In one embodiment a resistant or refractory tumor is one where the treatment-free interval following completion of a course of therapy for a patient having the tumor is less than 6 months (e.g., owing to recurrence of the cancer) or where there is tumor progression during the course of therapy.

In another embodiment, the pancreatic cancer of the patient undergoing treatment is advanced pancreatic cancer, which is a pancreatic tumor that exhibits either or both of distant metastasis or peripancreatic extension of the tumor.

The compositions and methods disclosed herein are useful for the treatment of all pancreatic cancers, including pancreatic cancers that are refractory or resistant to other anti-cancer treatments.

VI. Combination Therapy

In one embodiment, liposomal irinotecan is co-administered to patients having pancreatic cancer in combination with 5-fluorouracil (5-FU) and leucovorin, according to a particular clinical dosage regimen, such as those described herein. In one embodiment, the liposomal irinotecan is MM-398.

As used herein, adjunctive or combined administration (coadministration) includes simultaneous administration of the compounds in the same or different dosage form, or separate administration of the compounds (e.g., sequential administration). For example, liposomal irinotecan can be simultaneously administered with 5-FU and leucovorin. Alternatively, liposomal irinotecan can be administered in combination with 5-FU and leucovorin, wherein liposomal irinotecan, 5-FU and leucovorin are formulated for separate administration and are administered concurrently or sequentially. For example, liposomal irinotecan can be administered first followed by (e.g., immediately followed by) the administration of the 5-FU and leucovorin. Such concurrent or sequential administration preferably results in liposomal irinotecan, 5-FU, and leucovorin being simultaneously present in treated patients. In a particular embodiment, liposomal irinotecan is administered prior to 5-FU and leucovorin. In another particular embodiment, leucovorin is administered prior to 5-FU.

In another embodiment, liposomal irinotecan, 5-FU, and leucovorin are formulated for intravenous administration. In a particular embodiment, the patient is administered an effective amount each of liposomal irinotecan, 5-fluorouracil (5-FU), and leucovorin, wherein the treatment comprises at least one cycle, wherein the cycle is a period of 2 weeks, and wherein for each cycle: (a) liposomal irinotecan is administered on day 1 of the cycle at a dose of 80 mg/m$^2$, except if the patient is homozygous for the UGT1A1*28 allele, wherein liposomal irinotecan is administered on day 1 of cycle 1 at a dose of 60 mg/m$^2$; (b) 5-FU is administered at a dose of 2400 mg/m$^2$; and (c) leucovorin is administered at a dose of 200 mg/m$^2$ (l form) or 400 mg/m$^2$ (l+d racemic form) In a particular embodiment, the dose of liposomal irinotecan administered to the patient homozygous for the UGT1A1*28 allele is increased after one cycle to 80 mg/m$^2$.

In one embodiment, liposomal irinotecan may be initially administered at a high dose and may be lowered over time. In another embodiment, liposomal irinotecan is initially administered at a low dose and increased over time. In one embodiment, liposomal irinotecan is administered as a monotherapy.

In another embodiment, the dose of 5-FU is varied over time. For example, 5-FU may be initially administered at a high dose and may be lowered over time. In another embodiment, 5-FU is initially administered at a low dose and increased over time.

In another embodiment, the dose of leucovorin is varied over time. For example, leucovorin may be initially administered at a high dose and may be lowered over time. In another embodiment, leucovorin is initially administered at a low dose and increased over time.

VII. Treatment Protocols

Other treatment protocols include, for example, those wherein the patient is administered an effective amount of liposomal irinotecan, wherein the treatment comprises at least one cycle, wherein the cycle is a period of 3 weeks, and wherein for each cycle the liposomal irinotecan is administered on day 1 of the cycle at a dose of 120 mg/m$^2$, except if the patient is homozygous for the UGT1A1*28 allele, wherein liposomal irinotecan is administered on day 1 of cycle 1 at a dose of 80 mg/m$^2$. In one embodiment, the dose of liposomal irinotecan administered to the patient homozygous for the UGT1A1*28 allele is increased after one cycle in increments of 20 mg/m$^2$, up to a maximum of 120 mg/m$^2$.

In another embodiment, the treatment protocol includes administering to the patient an effective amount each of liposomal irinotecan, 5-fluorouracil (5-FU), and leucovorin, wherein the treatment comprises at least one cycle, wherein the cycle is a period of 2 weeks, and wherein for each cycle: (a) liposomal irinotecan is administered on day 1 of the cycle at a dose of 80 mg/m$^2$, except if the patient is homozygous for the UGT1A1*28 allele, wherein liposomal irinotecan is administered on day 1 of cycle 1 at a dose of 60 mg/m$^2$; (b) 5-FU is administered at a dose of 2400 mg/m$^2$; and (c) leucovorin is administered at a dose of 200 mg/m$^2$ (l form) or 400 mg/m$^2$ (l+d racemic form). In a particular embodiment, the dose of liposomal irinotecan administered to the patient homozygous for the UGT1A1*28 allele is increased after one cycle to 80 mg/m$^2$.

VIII. Outcomes

Provided herein are methods for treating pancreatic cancer in a patient comprising administering to the patient liposomal irinotecan (MM-398), alone or in combination with 5-fluorouracil (5-FU) and leucovorin, according to a particular clinical dosage regimen. Preferably, the combination therapy with liposomal irinotecan with 5-FU and leucovorin exhibits therapeutic synergy.

"Therapeutic synergy" refers to a phenomenon where treatment of patients with a combination of therapeutic agents manifests a therapeutically superior outcome to the outcome achieved by each individual constituent of the combination used at its optimum dose (T. H. Corbett et al., 1982, Cancer Treatment Reports, 66, 1187). In this context a therapeutically superior outcome is one in which the patients either a) exhibit fewer incidences of adverse events while receiving a therapeutic benefit that is equal to or greater than that where individual constituents of the combination are each administered as monotherapy at the same dose as in the combination, or b) do not exhibit dose-limiting toxicities while receiving a therapeutic benefit that is greater than that of treatment with each individual constituent of the combination when each constituent is administered in at the same doses in the combination(s) as is administered as individual components. In xenograft models, a combination, used at its maximum tolerated dose, in which each of the constituents will be present at a dose generally not exceeding its individual maximum tolerated dose, manifests therapeutic synergy when decrease in tumor growth achieved by administration of the combination is greater than the value of the decrease in tumor growth of the best constituent when the constituent is administered alone.

Thus, in combination, the components of such combinations have an additive or superadditive effect on suppressing pancreatic tumor growth, as compared to monotherapy with liposome-encapsulated irinotecan alone or treatment with the chemotherapeutic(s) in the absence of liposomal irinotecan therapy. By "additive" is meant a result that is greater in extent (e.g., in the degree of reduction of tumor mitotic index or of tumor growth or in the degree of tumor shrinkage or the frequency and/or duration of symptom-free or symptom-reduced periods) than the best separate result achieved by monotherapy with each individual component, while "superadditive" is used to indicate a result that exceeds in extent the sum of such separate results. In one embodiment, the additive effect is measured as slowing or stopping of pancreatic tumor growth. The additive effect can also be measured as, e.g., reduction in size of a pancreatic tumor, reduction of tumor mitotic index, reduction in number of metastatic lesions over time, increase in overall response rate, or increase in median or overall survival.

One non-limiting example of a measure by which effectiveness of a therapeutic treatment can be quantified is by calculating the log 10 cell kill, which is determined according to the following equation:

$$\log 10 \text{ cell kill} = T\ C(\text{days})/3.32 \times Td$$

in which T C represents the delay in growth of the cells, which is the average time, in days, for the tumors of the treated group (T) and the tumors of the control group (C) to have reached a predetermined value (1 g, or 10 mL, for example), and Td represents the time, in days necessary for the volume of the tumor to double in the control animals. When applying this measure, a product is considered to be active if log 10 cell kill is greater than or equal to 0.7 and a product is considered to be very active if log 10 cell kill is greater than 2.8. Using this measure, a combination, used at its own maximum tolerated dose, in which each of the constituents is present at a dose generally less than or equal to its maximum tolerated dose, exhibits therapeutic synergy when the log 10 cell kill is greater than the value of the log 10 cell kill of the best constituent when it is administered alone. In an exemplary case, the log 10 cell kill of the combination exceeds the value of the log 10 cell kill of the best constituent of the combination by at least 0.1 log cell kill, at least 0.5 log cell kill, or at least 1.0 log cell kill.

Responses to therapy may include:

Pathologic complete response (pCR): absence of invasive cancer in the breast and lymph nodes following primary systemic treatment.

Complete Response (CR): Disappearance of all target lesions. Any pathological lymph nodes (whether target or non-target) which has reduction in short axis to <10 mm;

Partial Response (PR): At least a 30% decrease in the sum of dimensions of target lesions, taking as reference the baseline sum diameters;

Stable Disease (SD): Neither sufficient shrinkage to qualify for partial response, nor sufficient increase to qualify for progressive disease, taking as reference the smallest sum diameters while on study; or Meanwhile, non-CR/Non-PD denotes a persistence of one or more non-target lesion(s) and/or maintenance of tumor marker level above the normal limits.

Progressive Disease (PD) denotes at least a 20% increase in the sum of dimensions of target lesions, taking as reference the smallest sum on study (this includes the baseline sum if that is the smallest on study). In addition to the relative increase of 20%, the sum must also demonstrate an absolute increase of 5 mm. The appearance of one or more new lesions is also considered progression.

In exemplary outcomes, patients treated according to the methods disclosed herein may experience improvement in at least one sign of pancreatic cancer.

In one embodiment the patient so treated exhibits pCR, CR, PR, or SD.

In another embodiment, the patient so treated experiences tumor shrinkage and/or decrease in growth rate, i.e., suppression of tumor growth. In another embodiment, unwanted cell proliferation is reduced or inhibited. In yet another embodiment, one or more of the following can occur: the number of cancer cells can be reduced; tumor size can be reduced; cancer cell infiltration into peripheral organs can be inhibited, retarded, slowed, or stopped; tumor metastasis can be slowed or inhibited; tumor growth can be inhibited; recurrence of tumor can be prevented or delayed; one or more of the symptoms associated with cancer can be relieved to some extent.

In other embodiments, such improvement is measured by a reduction in the quantity and/or size of measurable tumor lesions. Measurable lesions are defined as those that can be accurately measured in at least one dimension (longest diameter is to be recorded) as ≥10 mm by CT scan (CT scan slice thickness no greater than 5 mm), 10 mm caliper measurement by clinical exam or >20 mm by chest X-ray. The size of non-target lesions, e.g., pathological lymph nodes can also be measured for improvement. In one embodiment, lesions can be measured on chest x-rays or CT or MRI films.

In other embodiments, cytology or histology can be used to evaluate responsiveness to a therapy. The cytological confirmation of the neoplastic origin of any effusion that appears or worsens during treatment when the measurable tumor has met criteria for response or stable disease can be considered to differentiate between response or stable disease (an effusion may be a side effect of the treatment) and progressive disease.

In some embodiments, administration of effective amounts of liposomal irinotecan, 5-FU and leucovorin according to any of the methods provided herein produce at least one therapeutic effect selected from the group consisting of reduction in size of a breast tumor, reduction in number of metastatic lesions appearing over time, complete remission, partial remission, stable disease, increase in overall response rate, or a pathologic complete response. In some embodiments, the provided methods of treatment produce a comparable clinical benefit rate (CBR=CR+PR+SD≥6 months) better than that achieved by the same combinations of anti-cancer agents administered without concomitant MM-398 administration. In other embodiments, the improvement of clinical benefit rate is about 20%, 30%, 40%, 50%, 60%, 70%, 80% or more compared to the same combinations of anti-cancer agents administered without concomitant MM-398 administration.

The following examples are illustrative and should not be construed as limiting the scope of this disclosure in any way; many variations and equivalents will become apparent to those skilled in the art upon reading the present disclosure.

EXAMPLES

Example 1: Activity of MM-398 in an Orthotopic Pancreas Tumor Model Expressing Luciferase (L3.6pl)

The anti-tumor activity of MM-398 was assessed in an orthotopic pancreatic cancer model (L3.6pl), a highly hypoxic preclinical tumor model. Approximately $2.5 \times 10^{-5}$ L3.6pl pancreatic tumor cells were implanted by direct injection into the pancreas. The bioluminescence images (BLI) were followed over time for tumor burden detection/quantitation. MM-398 and free irinotecan were dosed at a dose of 20 mg/kg/dose weekly for three weeks. As shown in FIG. 1, MM-398 (liposomal CPT11) had significant anti-tumor activity, as compared to a control (HBS) and free CPT11.

Example 2: Accumulation of SN-38 in Tumors Following Treatment with Free Irinotecan or Liposomal Irinotecan (MM-398)

It was hypothesized that the anti-tumor activity observed in the orthotopic pancreatic cancer model is due to the effect of macrophages in converting irinotecan to the more active SN-38 locally. To test this hypothesis, human colon cancer cells (HT-29) were injected subcutaneously into SCID mice, 40 mg/kg of free irinotecan or MM-398 was injected intravenously when the tumors reached 1000 mm$^3$ in size. Tumor-bearing mice were sacrificed at different time points, tumors from both groups were extracted and the concentrations of SN-38 were measured.

Figure 2:
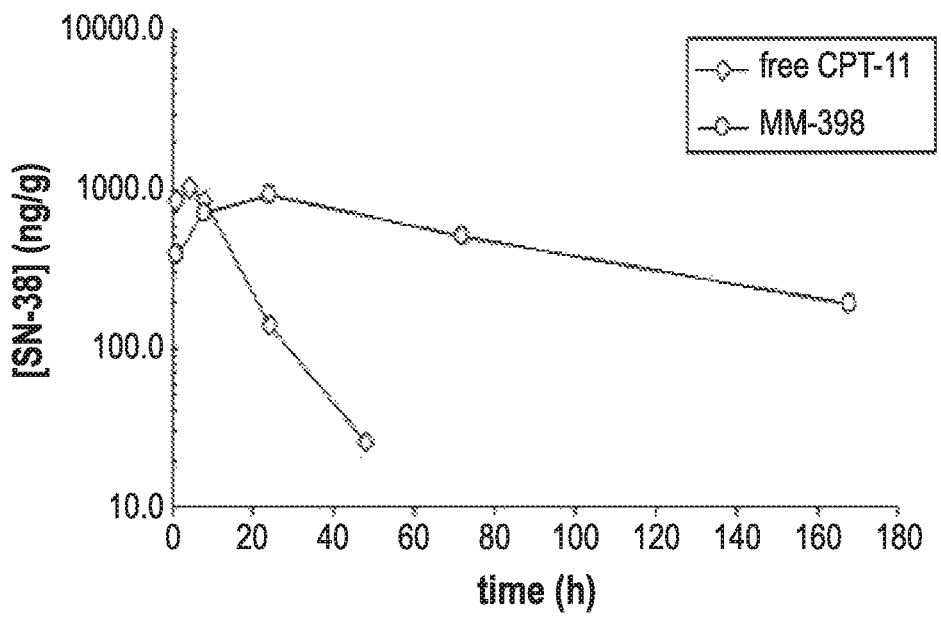
FIG. 2 is a graph showing accumulation of SN-38 in tumors following treatment with free irinotecan or liposomal irinotecan (MM-398).

As shown in FIG. 2, there was a 20-fold increase in the tumor $AUC_{SN-38}$ for MM-398 as compared to free irinotecan. The long duration of exposure allows for prolonged exposure of the slow proliferating cancer cells to the active metabolite as they progress through the cell cycle. In addition, this activity was also hypothesized to result from a reduction in intra-tumoral hypoxia, and the subsequent downstream effects on angiogenesis, metastasis, and the immunosuppressive environment in tumors.

Example 3: Effect of MM-398 on Carbonic Anhydrase IX Staining in a HT29 Xenograft Model To test whether MM-398 reduces markers of hypoxia, experiments were conducted in a human colon cancer cell (HT-29) model. Specifically, HT-29 cells were injected subcutaneously into nude mice, on day 13 either PBS control or 1.25, 2.5, 5, 10 or 20 mg/kg MM-398 was injected intravenously. MM-398 was dosed once a week for 4 weeks at the indicated doses. Tumors from both groups (n=5) were extracted 24 hours after the last dose. Frozen tumor sections were used for immunohistochemical staining of Carbonic Anhydrase IX (CAIX). Quantification of CAIX staining was performed using Definiens® (Definiens AG, Munich) software.

Figure 3:
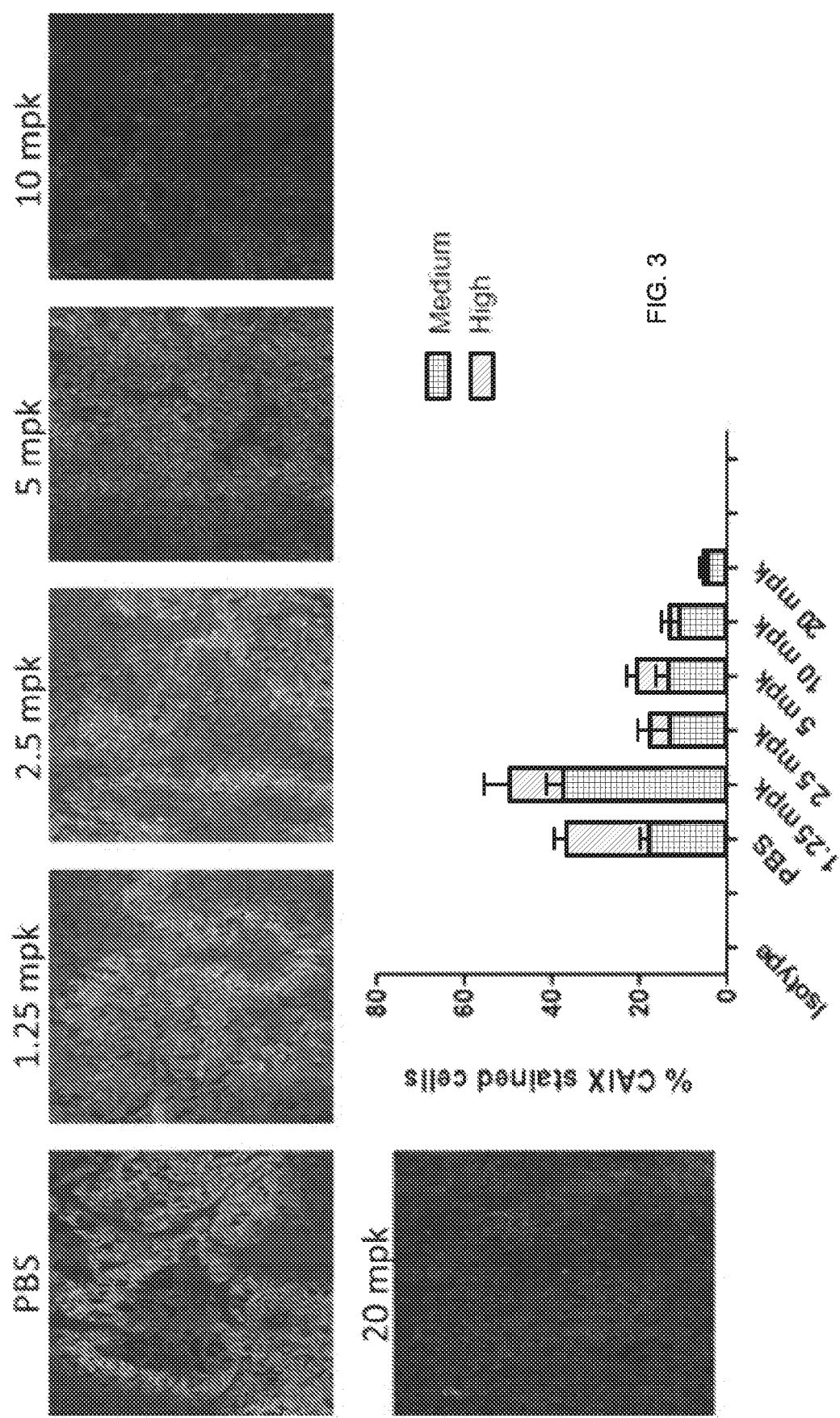
FIG. 3 is a graph showing the effect of MM-398 on Carbonic Anhydrase IX Staining in a HT29 Xenograft Model.

As shown in FIG. 3, MM-398 reduced markers of hypoxia. Specifically, the graphs in FIG. 3 show the percentage of cells that stained with medium (middle third) or high (top third) intensity for CAIX. Representative samples from each group are shown as well as the group average (mean+/−stdev). MM-398 treatment modifies the tumor microenvironment by decreasing the percentage of both medium and high CAIX positive cells in a dose-dependent manner. As hypoxia is a hallmark of resistant and aggressive disease, a reduction in hypoxia is expected to make tumor cells more sensitive to chemotherapies.

Example 4: MM-398 Increases Perfusion of Hoechst Stain

Figure 4:
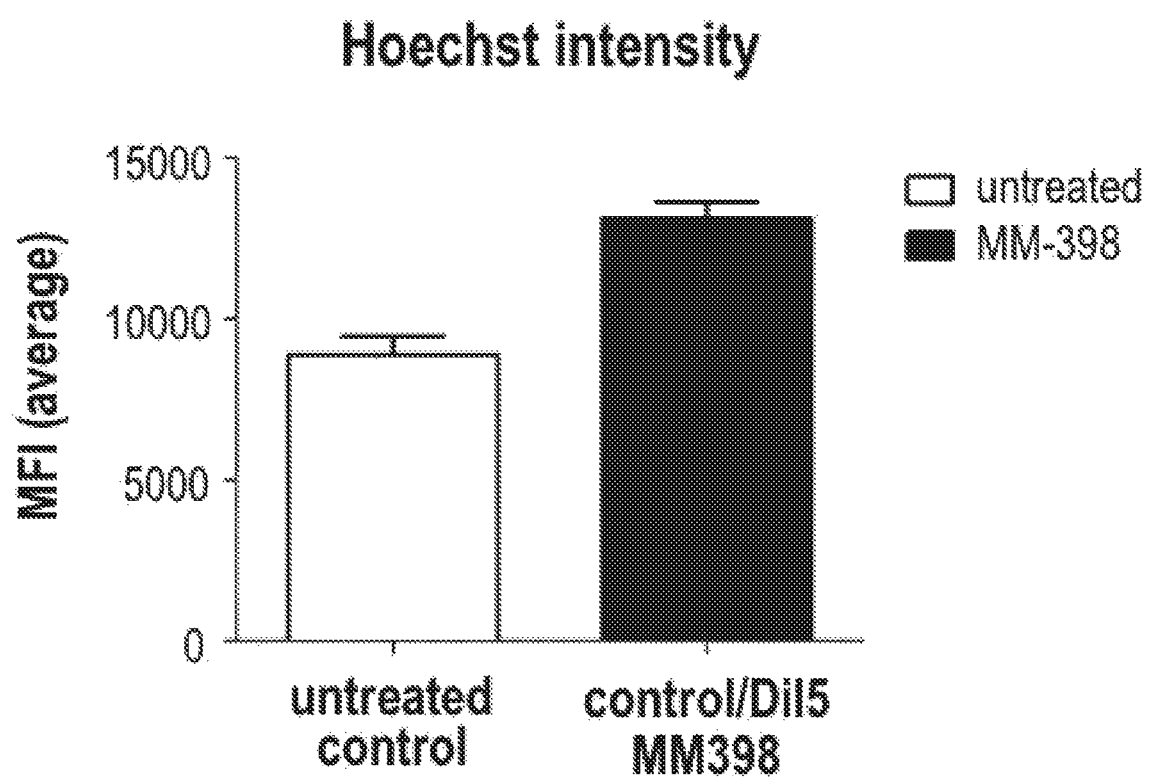
FIG. 4 shows the effect of MM-398 on perfusion of small molecule Hoechst stain.
Figure 7:
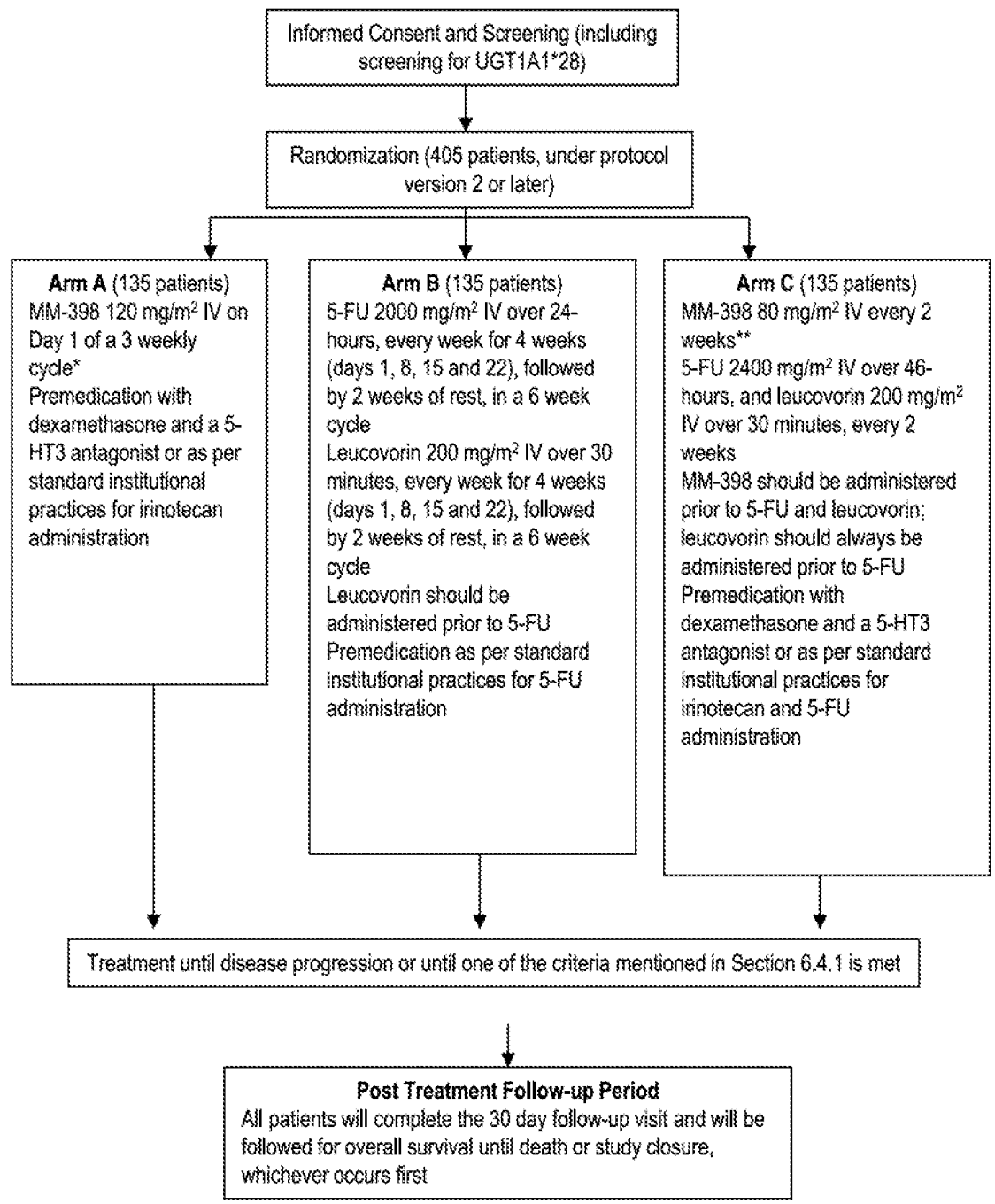
FIG. 7 is a schematic illustration of a Phase 3 study design. Patients who are homozygous for UGT1A1*28 allele and are randomized to Arm A, will receive the first cycle of therapy at a reduced dose of 80 mg/m$^2$. If the patient does not experience any drug related toxicity after the first administration of MM-398, from cycle 2 onwards, the dose may be increased in increments of 20 mg/m$^2$, up to a maximum of 120 mg/m$^2$. Patients who are homozygous for UGT1A1*28 allele and are randomized to Arm C, will receive the first cycle therapy at a reduced dose of 60 mg/m$^2$. If the patient does not experience any drug related toxicity after the first administration of MM-398, from cycle 2 onwards, the dose may be increased to 80 mg/m$^2$.

In addition to changing the chemosensitivity of tumor cells through modification of the tumor microenvironment, lowering hypoxia can indicate improved tumor vascularization, which can facilitate delivery of small molecule therapies. MM-398 treatment led to increased microvessel density 6 days after treatment as measured by CD31 (platelet endothelial cell adhesion molecule) staining in an HT29 xenograft study. To further assess the effect of MM-398 on small molecule tumor vascularization, a Hoechst 33342 perfusion experiment was conducted. Specifically, a primary pancreatic tumor was grown in NOD-SCID mice and given one dose of MM-398 (20 mg/kg). After 24 hours, Hoechst 33342 stain was administered 20 minutes prior to sacrificing the animal. As shown in FIG. 4, the increase in stain intensity in treated mice was statistically significant, p<0.001. These data indicate that MM-398 modifies the tumor microenvironment in a manner that should make tumors more susceptible to agents such as 5-FU/LV, through decreasing tumor hypoxia and increasing small molecule perfusion.

Example 5A: MM-398 (q3w) Pharmacokinetics in Humans (Phase I)

The pharmacokinetic profile of MM-398 single agent was investigated in a phase I clinical study (PEP0201) in patients at 60, 120 or 180 mg/m$^2$ dose levels and in a phase II clinical trial in gastric cancer patients (PEP0206) at 120 mg/m$^2$. Plasma levels of total irinotecan, SN-38 and encapsulated irinotecan were measured in these studies.

The peak serum concentrations of total irinotecan ($C_{max}$) ranged from 48-79 µg/ml for 120 mg/m$^2$ of MM-398, which was approximately 50 fold higher than 125 mg/m$^2$ free irinotecan. The total irinotecan half-life ($t_{1/2}$) for MM-398 ranged from 21 to 48 hours, which was approximately 2-3 fold higher than 125 mg/m$^2$ of free irinotecan. Overall, total irinotecan exposure at one week (AUC 0-T) ranged from 1200-3000 (µg*h/ml) at a dose of 120 mg/m$^2$ of MM-398, approximately 50-100 fold higher than 300 mg/m$^2$ of free irinotecan. In contrast, SN38 $C_{max}$ levels at 120 mg/m$^2$ of MM-398 ranged from 9 to 17 ng/ml, which was approximately 50% less than free irinotecan at 125 mg/m$^2$. Overall, exposure of SN38 at one week (AUC 0-T) ranged from 474 to 997 ng*/ml and was only 1-2 fold higher than achieved by free irinotecan at 300 mg/m$^2$. For both SN38 and total irinotecan, AUC increased less than proportionally with dose of MM-398. The PK parameters of encapsulated irinotecan almost matched that of total irinotecan indicates that most of irinotecan remained encapsulated in the liposomes during circulation. The MM-398 PK parameters were not significantly changed when combined with 5-FU/LV. FIGS. 5 and 6 summarize the PK findings in previous studies of MM 398.

Example 5B: MM-398 (q2w) Pharmacokinetics in Humans (Phase III)

The plasma pharmacokinetics of total irinotecan and total SN-38 were evaluated in patients with cancer who received MM-398, as a single agent or as part of combination chemotherapy, at doses between 50 and 150 mg/m² (free base) and 353 patients with cancer using population pharmacokinetic analysis. The pharmacokinetic parameters of total irinotecan and total SN-38 following the administration of MM-398 80 mg/m² (salt) as a single agent or part of combination chemotherapy are presented in Table 3. Summary of Mean (±Standard Deviation)

Direct measurement of irinotecan liposome showed that 95% of irinotecan remains liposome encapsulated, and the ratios between total and encapsulated forms did not change with time from 0 to 169.5 hours post-dose. The mean volume of distribution is summarized in Table 3.

In some embodiments, the liposomal irinotecan can be MM-398 or a product that is bioequivalent to MM-398. In some embodiments, the liposomal irinotecan can be characterized by the parameters in Table 4, including a $C_{max}$ and/or AUC value that is 80-125% of the corresponding value in Table 3. The pharmacokinetic parameters of total irinotecan for various alternative liposomal irinotecan formulations administering 70 mg/m² irinotecan free base once every two weeks is provided in Table 4.

TABLE 3

Total Irinotecan and Total SN-38 Pharmacokinetic Parameters in Patients with Solid Tumors.

| | Total Irinotecan | | | | | Total SN-38 | | |
| --- | --- | --- | --- | --- | --- | --- | --- | --- |
| Dose (mg/m²) (salt) | $C_{max}$ [µg/mL] (n = 25) | $AUC_{0-\infty}$ [h · µg/mL] (n = 23) | $t_{1/2}$ [h] (n = 23) | CL [L/h] (n = 23) | $V_d$ [L] (n = 23) | $C_{max}$ [ng/mL] (n = 25) | $AUC_{0-\infty}$ [h · ng/mL] (n = 13) | $t_{1/2}$ [h] (n = 13) |
| 80 | 37.2 (8.8) | 1364 (1048) | 25.8 (15.7) | 0.20 (0.17) | 4.1 (1.5) | 5.4 (3.4) | 620 (329) | 67.8 (44.5) |

$C_{max}$: Maximum plasma concentration
$AUC_{0-\infty}$: Area under the plasma concentration curve extrapolated to time infinity
$t_{1/2}$: Terminal elimination half-life
$V_d$: Volume of distribution The pharmacokinetic parameters of total irinotecan and total SN-38 following the administration of MM-398 80 mg/m² (salt) as a single agent or part of combination chemotherapy are presented in Table 3.

Over the dose range of 50 to 150 mg/m² (free base), the $C_{max}$ and AUC of total irinotecan increases with dose. Additionally, the $C_{max}$ of total SN-38 increases proportionally with dose; however, the AUC of total SN-38 increases less than proportionally with dose. The correlation of SN-38 $C_{max}$ with liposomal irinotecan dose had not previously been established. Higher plasma SN-38 $C_{max}$ was associated with increased likelihood of experiencing neutropenia.

The $C_{max}$ of SN-38 increases proportionally with liposomal irinotecan dose but the AUC of SN-38 increases less than proportionally with dose, enabling new methods of dosage adjustment. For example, the value of the parameter associated with adverse effects ($C_{max}$) decreases by a relatively greater extent than the value of the parameter associated with the effectiveness of treatment (AUC). Accordingly, when an adverse effect is seen, a reduction in the dosing of the liposomal irinotecan can be implemented that maximizes the difference between the reduction in $C_{max}$ and in AUC. The discovery means that in treatment regimens, a given SN-38 AUC can be achieved with a surprisingly low SN-38 $C_{max}$. Likewise, a given SN-38 $C_{max}$ can be achieved with a surprisingly high SN-38 AUC.

TABLE 4

Total Irinotecan Pharmacokinetic Parameters in Alternative Liposomal Irinotecan Formulations

| | Total Irinotecan | |
| --- | --- | --- |
| Dose (mg/m²) (salt) | $C_{max}$ [µg/mL] (n = 25) | $AUC_{0-\infty}$ [h · µg/mL] (n = 23) |
| 80 | 29.8-46.5 | 1091-1705 |

$C_{max}$: Maximum plasma concentration
$AUC_{0-\infty}$: Area under the plasma concentration curve extrapolated to time infinity
$t_{1/2}$: Terminal elimination half-life Plasma protein binding is <0.44% of the total irinotecan in MM-398.

The plasma clearance of total irinotecan from MM-398 80 mg/m² (salt) (equivalent to 70 mg/m² free base dose) is 0.077 L/h/m² with a terminal half live of 26.8 h. Following administration of irinotecan HCl 125 mg/m², the plasma clearance of irinotecan is 13.3 L/h/m² with a terminal half live of 10.4 h.

Example 6: Phase 1 Dose Escalation Study

A regimen combining 5-fluorouracil, leucovorin, and MM-398 was studied in a phase 1 trial of solid tumors in 16 subjects, of whom 5 were patients with pancreatic cancer. The objective tumor response rate, duration of response, and disease control rate were efficacy endpoints of the study. Among the 15 efficacy-evaluable patients, 2 (13.3%) had confirmed PR, 9 (60.0%) had SD, and 4 (26.7%) had PD. The overall disease control rate was 73.3%. Partial response was observed in one gastric cancer patient (at 80 mg/m² dose level) and one breast cancer patient (at 100 mg/m² dose level), with the duration of response of 142 and 76 days, respectively. Among the 6 patients who received the MTD dose of 80 mg/m², there were 1 PR, 4 SD and 1 PD. The tumor response rate and disease control rate were 16.7% and 83.3%, respectively. The main DLTs were grade 3 diarrhea, leucopenia, neutropenia and febrile neutropenia. The MTD for MM-398 was 80 mg/m².

In the phase 1 dose-escalation study of MM-398 in combination with 5-FU/LV in advanced solid tumors (PEP0203), a total of 401 episodes of AE were reported from the 16 treated subjects (safety population), of which 74 (18.4%) were of CTC grade 3 or above. Among all AEs, 231 (57.6%) were considered by the investigators to be treatment-related. The most common treatment-related AEs, included nausea (81.3%), diarrhea (75.0%), vomiting (68.8%), fatigue (43.8%), mucositis (43.8%), leucopenia (37.5%), neutropenia (37.5%), weight loss (37.5%), anemia (31.3%), and alopecia (31.3%). Acute cholinergic diarrhea was rarely observed. Table 5 provides the incidence of treatment-emergent adverse events by maximum CTC grade and by causality (incidence 20%), as seen in the PEP0203 study. Table 6 provides the incidence of grade 3 or higher treatment-emergent adverse events seen in the 5 pancreatic cancer patients treated in the PEP0203 study.

TABLE 5

Incidence of treatment-emergent adverse events by maximum CTC grade and by causality (incidence ≥ 20%) in the PEP0203 Study

| System organ class Preferred Term | Total (N = 16) | Severity (Grade)[1] | | | | Causality[2] | |
|---|---|---|---|---|---|---|---|
| | | I | II | III | IV | Yes | No |
| Blood and lymphatic system disorders | | | | | | | |
| Anemia | 7 (43.8%) | 3 | 2 | 2 | 0 | 5 | 2 |
| Leucopenia | 6 (37.5%) | 0 | 3 | 2 | 1 | 6 | 0 |
| Neutropenia | 6 (37.5%) | 0 | 2 | 3 | 1 | 6 | 0 |
| Gastrointestinal disorders | | | | | | | |
| Abdominal pain | 7 (43.8%) | 3 | 2 | 2 | 0 | 3 | 4 |
| Constipation | 6 (37.5%) | 3 | 3 | 0 | 0 | 0 | 6 |
| Diarrhea | 12 (75.0%) | 3 | 4 | 5 | 0 | 12 | 0 |
| Nausea | 13 (81.3%) | 6 | 6 | 1 | 0 | 13 | 0 |
| Vomiting | 12 (75.0%) | 3 | 8 | 1 | 0 | 11 | 1 |
| General disorders and administration site conditions | | | | | | | |
| Fatigue | 8 (50.0%) | 4 | 3 | 1 | 0 | 7 | 1 |
| Mucosal inflammation | 7 (43.8%) | 4 | 3 | 0 | 0 | 7 | 0 |
| Pyrexia | 7 (43.8%) | 3 | 4 | 0 | 0 | 2 | 5 |
| Infections and infestations | | | | | | | |
| Infection | 6 (37.5%) | 0 | 3 | 3 | 0 | 2 | 4 |
| Investigations | | | | | | | |
| ALT increased | 5 (31.3%) | 3 | 2 | 0 | 0 | 4 | 1 |
| AST increased | 4 (25.0%) | 3 | 1 | 0 | 0 | 1 | 3 |
| Weight decreased | 8 (50.0%) | 4 | 4 | 0 | 0 | 6 | 2 |
| Metabolism and nutrition disorders | | | | | | | |
| Anorexia | 4 (25.0%) | 1 | 2 | 1 | 0 | 3 | 1 |
| Hypoalbuminaemia | 4 (25.0%) | 0 | 3 | 1 | 0 | 0 | 4 |
| Hypocalcaemia | 5 (31.3%) | 1 | 4 | 0 | 0 | 0 | 5 |
| Hypokalaemia | 8 (50.0%) | 2 | 0 | 5 | 1 | 2 | 6 |
| Hyponatraemia | 4 (25.0%) | 2 | 0 | 0 | 2 | 0 | 4 |
| Nervous system disorders | | | | | | | |
| Dizziness | 4 (25.0%) | 4 | 0 | 0 | 0 | 1 | 3 |
| Psychiatric disorders | | | | | | | |
| Insomnia | 4 (25.0%) | 4 | 0 | 0 | 0 | 1 | 3 |
| Respiratory, thoracic and mediastinal disorders | | | | | | | |
| Cough | 5 (31.3%) | 3 | 1 | 1 | 0 | 0 | 5 |
| Skin and subcutaneous tissue disorders | | | | | | | |
| Alopecia | 5 (31.3%) | 5 | 0 | 0 | 0 | 5 | 0 |

[1]Severity grading used the highest grading ever rated for each subject if the subject had such adverse event reported
[2]Defined as subject ever experienced AE related to the study drug in causality or not

TABLE 6

Incidence of Grade 3 or higher treatment-emergent adverse events in pancreatic cancer patients in the PEP0203 Study

| Primary system organ class Preferred term | Overall N = 5 n (%) | 60 mg/m2 N = 1 n (%) | 80 mg/m2 N = 3 n (%) | 120 mg/m2 N = 1 n (%) |
|---|---|---|---|---|
| Any primary system organ class | | | | |
| Total | 3 (60.0) | 0 | 2 (66.7) | 1 (100.0) |
| Infections and infestations | | | | |
| Total | 3 (60.0) | 0 | 2 (66.7) | 1 (100.0) |
| Hepatitis viral | 1 (20.0) | 0 | 1 (33.3) | 0 |
| Infection | 1 (20.0) | 0 | 0 | 1 (100.0) |
| Pneumonia | 1 (20.0) | 0 | 1 (33.3) | 0 |
| Septic shock | 1 (20.0) | 0 | 1 (33.3) | 0 |
| Blood and lymphatic system disorders | | | | |
| Total | 2 (40.0) | 0 | 1 (33.3) | 1 (100.0) |
| Lymphopenia | 1 (20.0) | 0 | 0 | 1 (100.0) |
| Neutropenia | 1 (20.0) | 0 | 1 (33.3) | 0 |
| White blood cell disorder | 1 (20.0) | 0 | 0 | 1 (100.0) |
| Gastrointestinal disorders | | | | |
| Total | 2 (40.0) | 0 | 1 (33.3) | 1 (100.0) |
| Diarrhoea | 2 (40.0) | 0 | 1 (33.3) | 1 (100.0) |
| Abdominal pain | 1 (20.0) | 0 | 0 | 1 (100.0) |
| Gastrointestinal haemorrhage | 1 (20.0) | 0 | 1 (33.3) | 0 |
| Investigations | | | | |
| Total | 2 (40.0) | 0 | 1 (33.3) | 1 (100.0) |
| Blood bilirubin increased | 1 (20.0) | 0 | 1 (33.3) | 0 |
| Lipase increased | 1 (20.0) | 0 | 0 | 1 (100.0) |
| Neutrophil count decreased | 1 (20.0) | 0 | 0 | 1 (100.0) |
| White blood cell count decreased | 1 (20.0) | 0 | 0 | 1 (100.0) |
| Metabolism and nutrition disorders | | | | |
| Total | 2 (40.0) | 0 | 1 (33.3) | 1 (100.0) |
| Hypoalbuminaemia | 1 (20.0) | 0 | 1 (33.3) | 0 |
| Hypokalaemia | 1 (20.0) | 0 | 1 (33.3) | 0 |
| Hyponatraemia | 1 (20.0) | 0 | 0 | 1 (100.0) |
| Hypophosphataemia | 1 (20.0) | 0 | 0 | 1 (100.0) |
| Respiratory, thoracic and mediastinal disorders | | | | |
| Total | 2 (40.0) | 0 | 1 (33.3) | 1 (100.0) |
| Dyspnoea | 1 (20.0) | 0 | 0 | 1 (100.0) |
| Pleural effusion | 1 (20.0) | 0 | 1 (33.3) | 0 |

TABLE 6-continued

Incidence of Grade 3 or higher treatment-emergent adverse events in pancreatic cancer patients in the PEP0203 Study

| Primary system organ class<br>Preferred term | Overall<br>N = 5<br>n (%) | 60<br>mg/m2<br>N = 1<br>n (%) | 80<br>mg/m2<br>N = 3<br>n (%) | 120<br>mg/m2<br>N = 1<br>n (%) |
|---|---|---|---|---|
| General disorders and administration site conditions | | | | |
| Total | 1 (20.0) | 0 | 0 | 1 (100.0) |
| Death | 1 (20.0) | 0 | 0 | 1 (100.0) |

Example 7: Phase 3 NAPOLI-1 Clinical Trial

The efficacy of MM-398 was evaluated in NAPOLI-1 (also "Study 1"), a three-arm, randomized, open-label trial in patients with metastatic pancreatic adenocarcinoma with documented disease progression, after gemcitabine or gemcitabine-based therapy. NAPOLI-1 was an international randomized human Phase 3 clinical trial evaluating the use of the irinotecan liposome MM-398 in patients with a diagnosis of metastatic pancreatic cancer previously treated with a gemcitabine based therapy. The NAPOLI-1 trial is summarized below.

NAPOLI-1 was an open label, randomized, stratified by albumin (<4.0 g/dL vs ≥4.0 g/dL), Karnofsky Performance Status (KPS) (70 & 80 vs ≥90), and ethnicity (Caucasian vs East Asian vs others). The primary analysis compared each treatment arm to its corresponding 5-FU/LV control for OS by unstratified log-rank test; family-wise type I error rate was controlled at the 2-sided 0.05 level using the Bonferroni-Holm method. Primary analysis planned when at least 305 death events occurred to have 85% power to detect HR=0.67 in the MM-398 arm and 98% power to detect HR=0.50 in the MM-398+5-FU/LV arm. A supportive stratified analysis, accounting for the randomization strata, was performed.

Key eligibility criteria included Karnofsky Performance Status (KPS) ≥70, serum bilirubin within institution limits of normal, and albumin ≥3.0 g/dL. Patients were randomized to receive MM-398 plus 5-fluorouracil/leucovorin (MM-398/5-FU/LV), MM-398, or 5-fluorouracil/leucovorin (5-FU/LV). Randomization was stratified by ethnicity (White vs. East Asian vs. other), KPS (70-80 vs. 90-100), and baseline albumin level (≥4 g/dL vs. 3.0-3.9 g/dL). Patients randomized to MM-398/5-FU/LV received MM-398 80 mg/m$^2$ (salt) as an intravenous infusion over 90 minutes, followed by leucovorin 400 mg/m$^2$ intravenously over 30 minutes, followed by 5-fluorouracil 2400 mg/m$^2$ intravenously over 46 hours, every 2 weeks.

Patients randomized to MM-398 as a single agent received MM-398 120 mg/m$^2$ (salt) as an intravenous infusion over 90 minutes every 3 weeks. Patients randomized to 5-FU/LV received leucovorin 200 mg/m$^2$ intravenously over 30 minutes, followed by 5-fluorouracil 2000 mg/m$^2$ intravenously over 24 hours, administered on Days 1, 8, 15 and 22 of a 6-week cycle. Patients homozygous for the UGT1A1*28 allele initiated MM-398 at a reduced dose (60 mg/m$^2$ (salt) MM-398, if given with 5-FU/LV or 80 mg/m$^2$ (salt) MM-398 as a single agent). When MM-398 was withheld or discontinued for adverse reactions, 5-FU was also withheld or discontinued. When the dose of MM-398 was reduced for adverse reactions, the dose of 5-FU was reduced by 25%. Treatment continued until disease progression or unacceptable toxicity. The major efficacy outcome measure was overall survival (OS) with two pair-wise comparisons: MM-398 versus 5-FU/LV and MM-398/5-FU/LV versus 5-FU/LV. Additional efficacy outcome measures were progression-free survival (PFS) and objective response rate (ORR). Tumor status assessments were conducted at baseline and every 6 weeks thereafter. The trial was initiated as a two-arm study and amended after initiation to include a third arm (MM-398/5-FU/LV). The comparisons between the MM-398/5-FU/LV and the 5-FU/LV arms are limited to patients enrolled in the 5-FU/LV arm after this protocol amendment.

Four hundred seventeen patients were randomized to: MM-398/5-FU/LV (N=117), MM-398 (N=151), or 5-FU/LV (N=149). Baseline demographics and tumor characteristics for the 236 patients randomized to MM-398/5-FU/LV or 5-FU/LV (N=119) after the addition of the third arm to the study were a median age of 63 years (range 34-81 years) and with 41%≥65 years of age; 58% were men; 63% were White, 30% were Asian, 3% were Black or African American, and 5% were other. Mean baseline albumin level was 3.97 g/dL, and baseline KPS was 90-100 in 53% of patients. Disease characteristics included liver metastasis (67%) and lung metastasis (31%). A total of 13% of patients received gemcitabine in the neoadjuvant/adjuvant setting only, 55% of patients had 1 prior line of therapy for metastatic disease, and 33% of patients had 2 or more prior lines of therapy for metastatic disease. All patients received prior gemcitabine (alone or in combination with another agent); 54% received prior gemcitabine in combination with another agent, and 13% received prior gemcitabine in combination with nab-paclitaxel.

Figure 8:
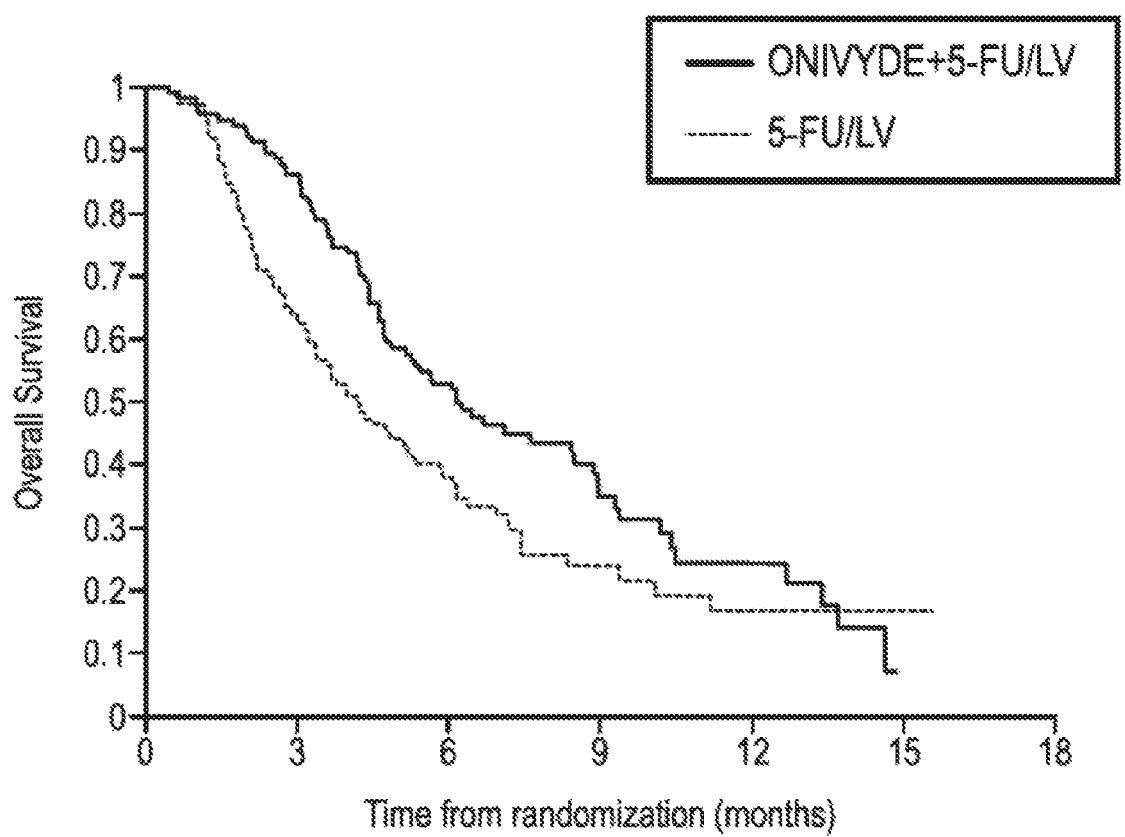
FIG. 8 is a graph providing the overall survival of patients in an assessment of the clinical efficacy and safety of the irinotecan liposome injection monotherapy or the irinotecan liposome injection in combination with 5-fluorouracil and leucovorin (the irinotecan liposome injection+5-FU/LV), compared to an active control arm of 5-FU/LV.
Figure 9:
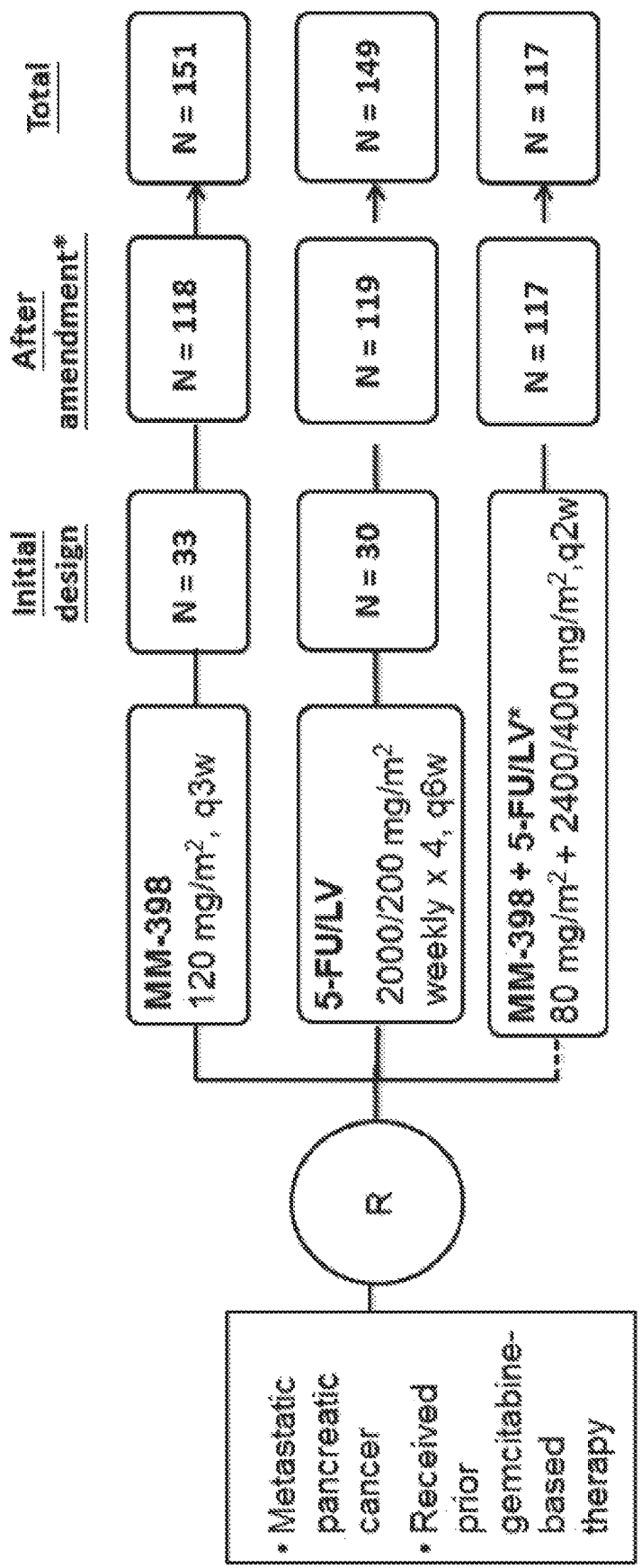
FIG. 9 is a flow-chart representation of the NAPOLI-1 study design.

NAPOLI-1 demonstrated a statistically significant improvement in overall survival for the MM-398/5-FU/LV arm over the 5-FU/LV arm as summarized in Table 7 and shown graphically in FIG. 8. There was no improvement in overall survival for the MM-398 arm over the 5-FU/LV arm (hazard ratio=1.00, p-value=0.97 (two-sided log-rank test)).

The OS and PFS benefits were maintained for MM-398+5-FU/LV compared with 5-FU/LV alone. Convergence of the OS curves at 20 months (with 19 [16%] patients surviving beyond 20 months) is likely a reason for the observed attenuation of the OS HR estimate and unstratified log-rank P value.

TABLE 7

Efficacy Results from Study 1†‡

| | MM-398/5-FU/LV (N = 117) | 5-FU/LV (N = 119) |
|---|---|---|
| Overall Survival | | |
| Number of Deaths, n (%) | 77 (66) | 86 (72) |
| Median Overall Survival (months) | 6.1 | 4.2 |
| (95% CI) | (4.8, 8.5) | (3.3, 5.3) |
| Hazard Ratio (95% CI) | 0.68 (0.50, 0.93) | |
| p-value (log-rank test) | 0.014 | |
| Progression-Free Survival | | |
| Death or Progression, n (%) | 83 (71) | 94 (79) |
| Median Progression-Free Survival (months) | 3.1 | 1.5 |
| (95% CI) | (2.7, 4.2) | (1.4, 1.8) |
| Hazard Ratio (95% CI) | 0.55 (0.41, 0.75) | |
| p-value (log rank test) | p < 0.001 | |

TABLE 7-continued

Efficacy Results from Study 1†‡

|  | MM-398/5-FU/LV (N = 117) | 5-FU/LV (N = 119) |
|---|---|---|
| Objective Response Rate | | |
| Confirmed complete or partial response n (%) | 9 (7.7) | 1 (0.8) |
| (95% CI) | (2.9, 12.5) | (0, 2.5) |

†5-FU/LV = 5-fluorouracil/leucovorin;
CI = confidence interval
‡The MM-398 dose in Study 1, 70 mg/m$^2$, is based on irinotecan as the free base (equivalent to 80 mg/m$^2$ of irinotecan as a hydrochloride trihydrate).

Table 7 sets out that the median overall survival of the MM-398/5-FU/LV is 6.1 months. Median overall survival is used to express survival rates. It is the amount of time after which, in the MM-398/5-FU/LV of Study 1 described herein (presented in table 7), 50% of the patients have died and 50% have survived in a study population. The expected lifetime in months from commencement of treatment with the MM-398/5-FU/LV treatment regimen as disclosed herein is defined by the parameter, $t_{surv}$. In some embodiments, the $t_{surv}$ of an individual being treated is at least ⅔ of the median overall survival rate (≥4.1 months (to one decimal place (dp))), such as at least ⅚ of the median overall survival (≥5.1 months (1dp)) or at least the median overall survival (≥6.1 months). In some embodiments, the $t_{surv}$ of an individual being treated is less than 2 times the median overall survival rate (<12.2 months (1dp)), such as less than 1.5 times the median overall survival (<9.15 months (2dp)) or less than 1.2 times the median overall survival (<7.32 months (1dp)). In some embodiments, the $t_{surv}$ of an individual being treated is at least ⅔ of the median overall survival rate and less than 2 times the median overall survival rate, such as less than 1.5 times the median overall survival or less than 1.2 times the median overall survival. In some embodiments, the $t_{surv}$ of an individual being treated is at least ⅚ of the median overall survival rate and less than 2 times the median overall survival rate, such as less than 1.5 times the median overall survival or less than 1.2 times the median overall survival. In some embodiments, the $t_{surv}$ of an individual being treated is at least the median overall survival rate and less than 2 times the median overall survival rate, such as less than 1.5 times the median overall survival or less than 1.2 times the median overall survival.

Figure 12:
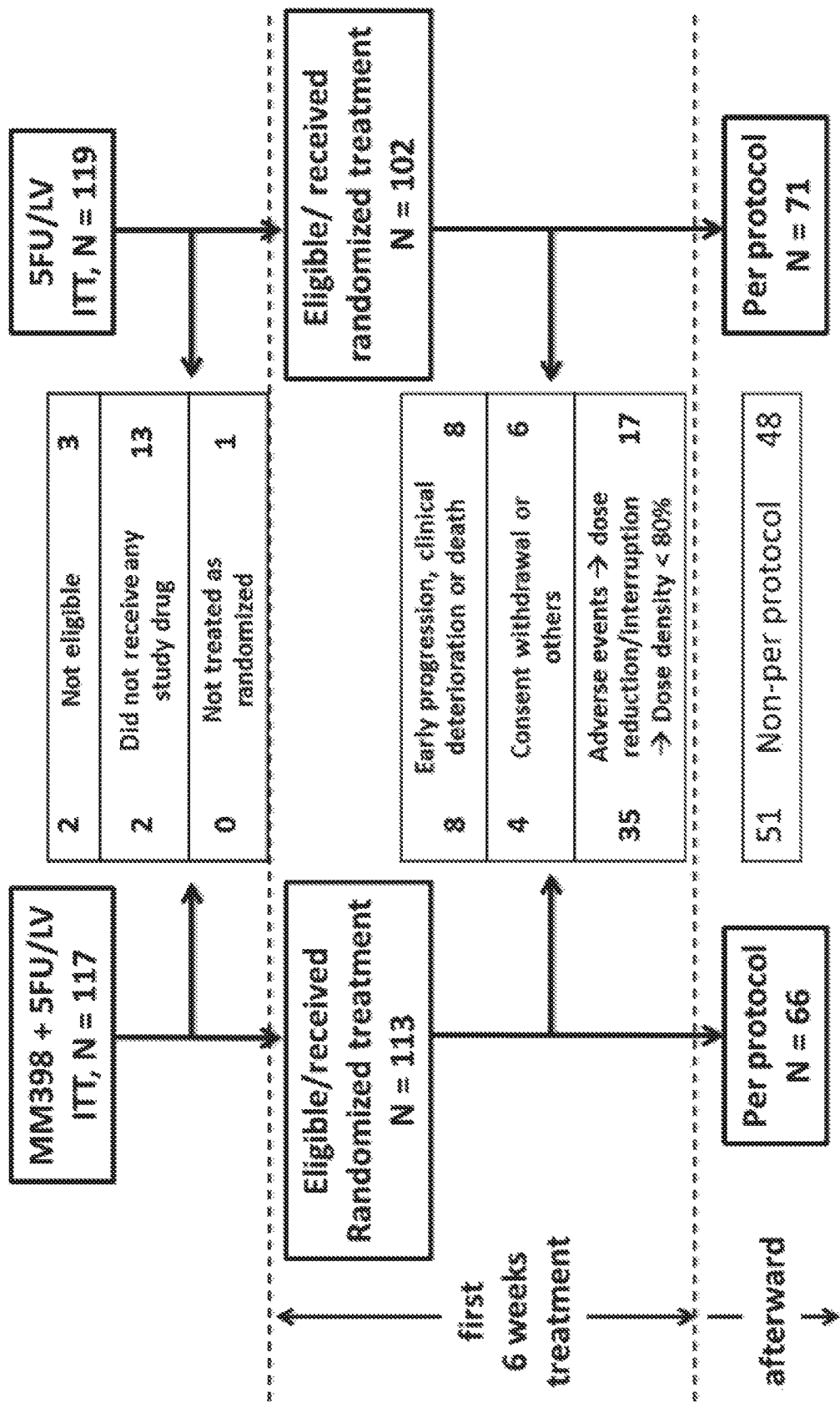
FIG. 12 is a flow chart explaining the ITT (all randomized patients) and PP (Per Protocol) populations. The Per Protocol population comprises eligible patients who received ≥80% dose density of the protocol defined treatment during the first 6 weeks of treatment.
Figure 13:
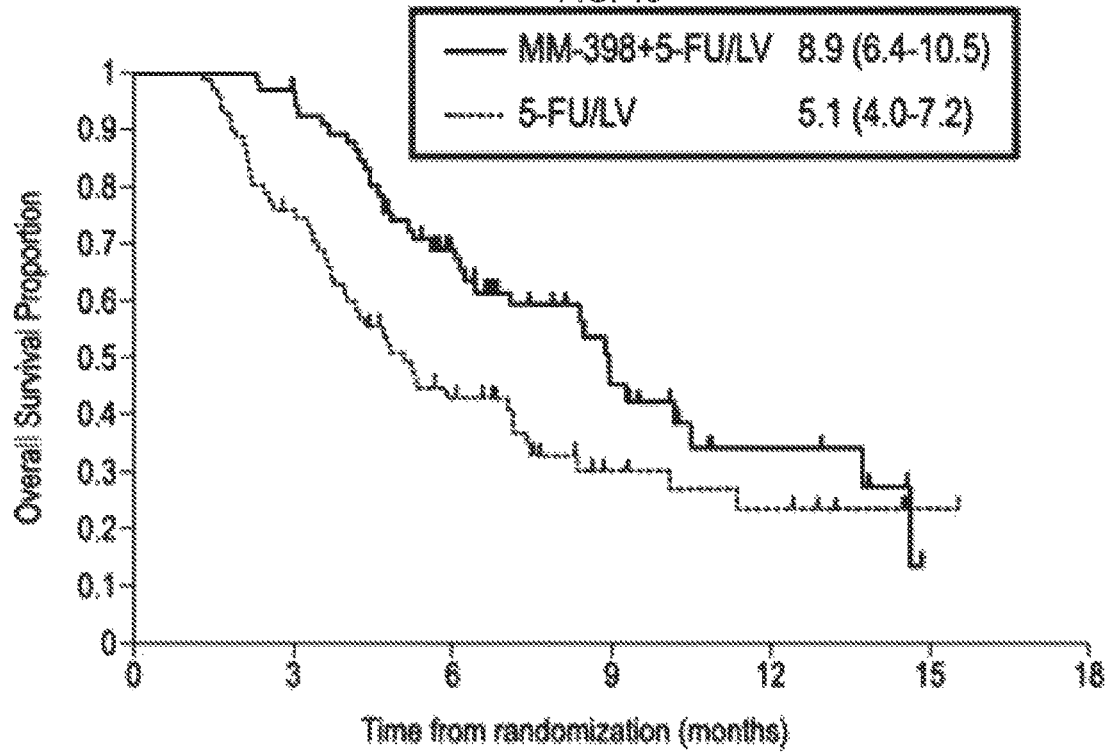
FIGS. 13 and 14 are graphical representations of overall survival (OS) for the Per Protocol (PP) patient population vs. the Non-Per Protocol (Non-PP) patient population. The results presented in the figures are a data cut from a protocol-defined primary analysis. Per protocol population was defined as patients who received at least 80% of the protocol defined treatment during the first 6 weeks of treatment and did not have protocol deviations related to inclusion/exclusion criteria, receiving prohibited therapies or not receiving treatment as randomized.
Figure 14:
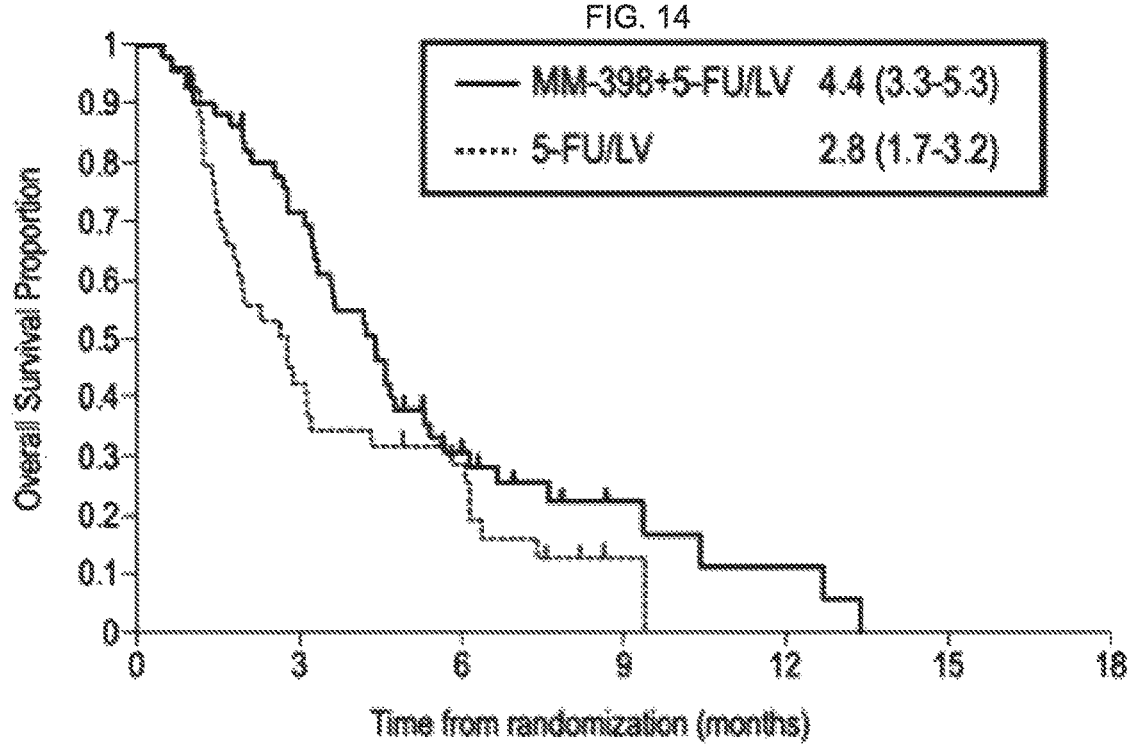

In NAPOLI-1, analysis of the ITT (intent to treat) patient group demonstrated statistically significant increase in overall survival (OS) of MM-398+5-FU/LV (MM-398 80 mg/m$^2$ (salt) q2w regimen) over 5-FU/LV alone (FIGS. 11A and 11B) of 6.1 months versus 4.2 months respectively. In comparison, MM-398, as a single agent (120 mg/m$^2$ q3w regimen), did not show a significant difference in OS. In the Per Protocol (PP) population (described in FIG. 12) of patients in the NAPOLI-1 human clinical trial (patients receiving 6 weeks of treatment), the MM-398+5-FU/LV combination regimen achieved a median OS of 8.9 months versus 5.1 months in the 5-FU/LV arm (stratified Hazard Ratio (HR): 0.47, p=0.0018; FIGS. 13 and 14). The observed patient safety profile was manageable, with most frequent being grade ≥3 adverse events including neutropenia, fatigue and GI effects, such as diarrhea and vomiting (FIG. 17).

The primary endpoint of the NAPOLI-1 study was overall survival; and the key secondary endpoints were Progression Free Survival (PFS), Objective Response Rate (ORR), Tumor Marker Response (CA19-9) and Safety. The study was amended to add the MM-398+5-FU/LV arm once safety data on the combination became available. Only those patients enrolled in the 5FU/LV arm after the amendment (N=119), were used as the control for the combination arm.

Key Inclusion Criteria for the NAPOLI-1 trial were: Adenocarcinoma of the exocrine pancreas; Metastatic disease, measurable or non-measurable; Progressed after prior gemcitabine or gemcitabine-containing therapy; KPS ≥70; Adequate bone marrow, hepatic (bilirubin within normal range for the institution and albumin ≥3 g/dL), and renal function.

Sixty six PP patients were in the MM398+5-FU/LV arm and 71 PP patients were in the 5-FU/LV arm of NAPOLI-1. The NAPOLI-1 study was well balanced. Patients in the MM-398+5FU/LV and 5FU/LV arms were consistent across the following patient characteristics: prognostic factors, demographics (age, sex, race), tumor and pre and post treatment characteristics. Post-study anticancer therapy was 31% in the MM-398+5-FU/LV arm and 38% in the 5-FU/LV arm.

Efficacy Analysis of NAPOLI-1 Clinical Trial (Phase III)

Figure 11A:
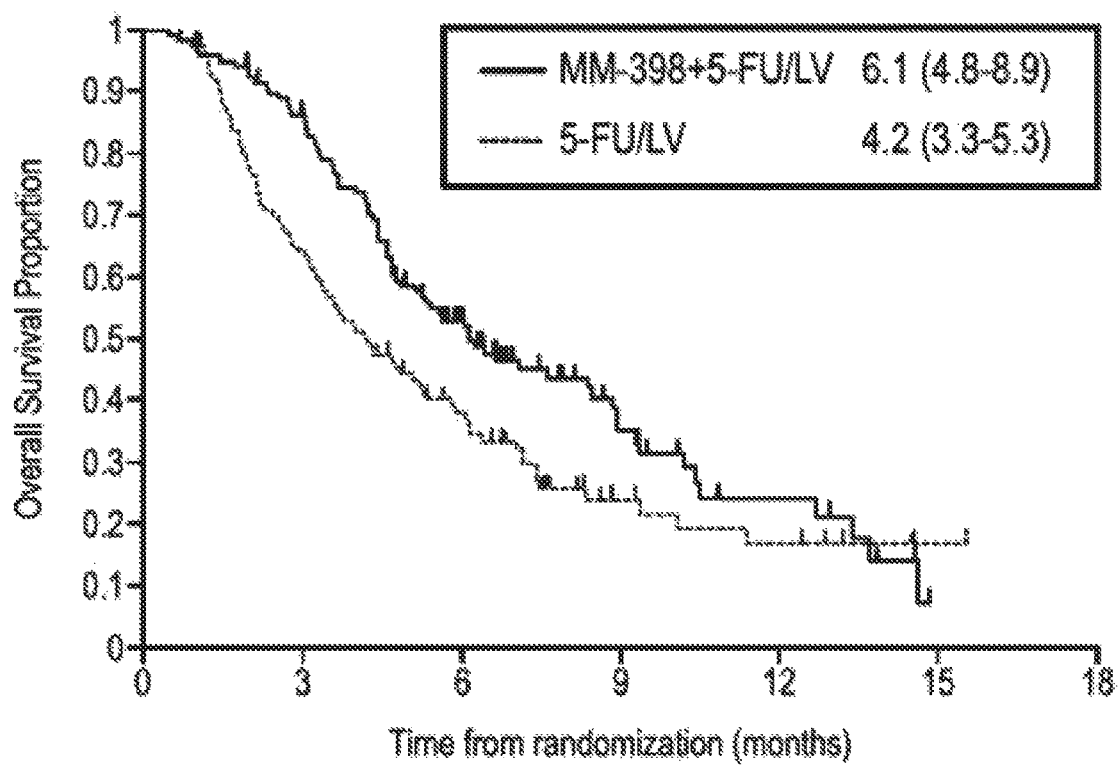
FIGS. 11A and 11B are graphical representations of overall survival (ITT population) in MM-398+5-FU/LV vs. MM-398 or 5-FU/LV alone. The data presented is the protocol-defined primary analysis data cut after 305 events. "" denotes un-stratified HR: 0.67 (0.49–0.92), p=0.0122; "*" denotes un-stratified HR: 0.99 (0.77–1.28), p=0.9416.
Figure 11B:
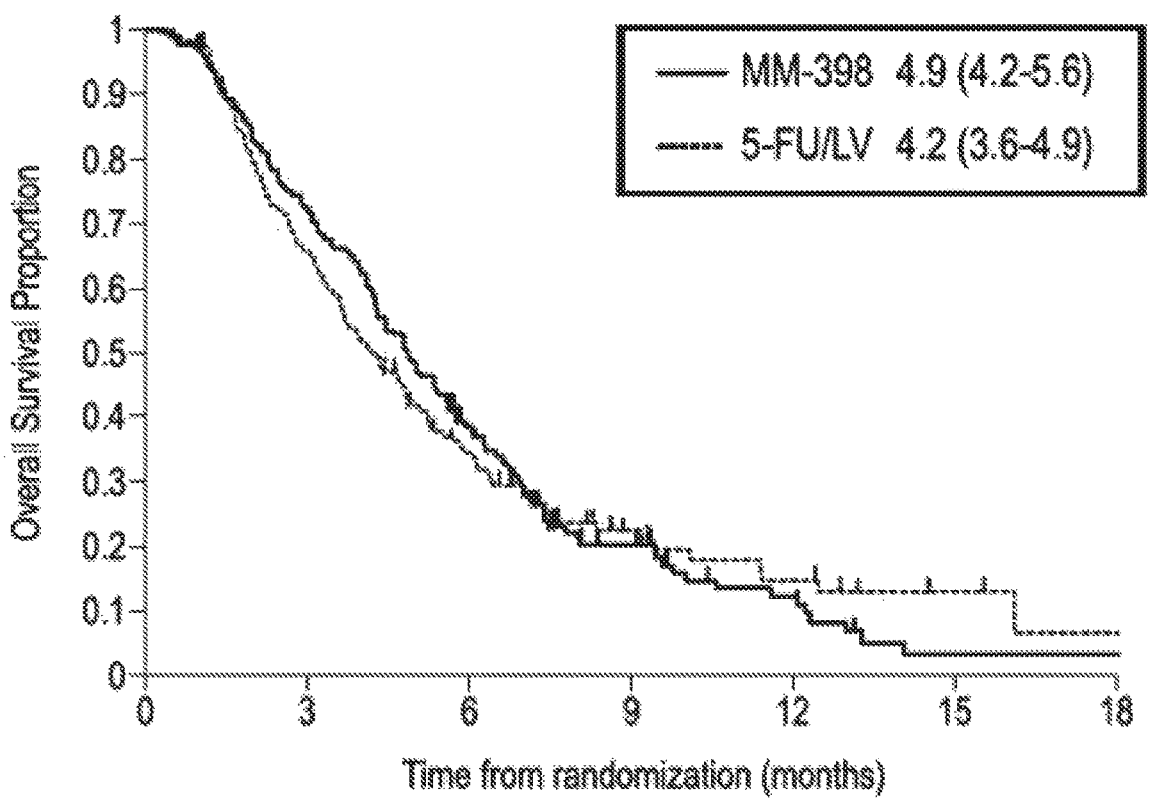

Overall Survival Results from the ITT patient group in the NAPOLI-1 clinical trial are shown in FIGS. 11A and 11B. FIG. 11A shows the median overall survival rate for the MM-398+5-FU/LV arm was 6.1 months (95% CI 4.8-8.9) and the 5-Fu/LV arm overall survival rate was 4.2 months (95% CI 3.3-5.3) and the stratified HR was 0.57 (95 CI 0.41-0.8), p=0.0009. FIG. 11B shows the median overall survival rate for the MM-398 arm was 4.9 months (95% CI 4.2-5.6) and the 5-FU/LV arm median OS was 4.2 months (95% CI 3.6-4.9) and the stratified HR was 0.93 (95 CI 0.71-1.21), p=035545.

The Per Protocol population comprises eligible patients who received ≥80% dose density of the protocol defined treatment during the first 6 weeks of treatment and did not have the following protocol violations: receipt of any prohibited therapies as defined in the protocol, not receiving treatment as randomized, or inclusion/exclusion criteria deviations.

Overall Survival Results for the PP and Non-PP populations are shown in FIGS. 13 and 14 respectively. FIG. 13 shows the median overall survival rate for the PP population; the median OS for the MM-398+5-FU/LV arm was 8.9 months (95% CI 6.4-10.5) and the median OS rate for the 5-Fu/LV arm was 5.1 months (95% CI 4.0-7.2) and the stratified HR was 0.47 (95 CI 0.29-0.77), p=0.0018. FIG. 14 shows the median overall survival rate for the Non-PP population; the median OS for the MM-398+5-FU/LV arm was 4.4 months (95% CI 3.3-5.3) and the median OS rate for the 5-Fu/LV arm was 2.8 months (95% CI 1.7-3.2) and the stratified HR was 0.56 (95 CI 0.33-0.97), p=0.365.

After 378 OS events, MM-398+5-FU/LV (n=117) retained an OS advantage relative to 5-FU/LV (n=119): 6.2 mo (95% confidence interval [CI], 4.8-8.4) vs 4.2 mo (95% CI, 3.3-5.3) with an unstratified HR of 0.75 (P=0.0417). In contrast, there was no OS advantage with MM-398 monotherapy (n=151) vs 5-FU/LV (n=149): 4.9 mo [95% CI, 4.2-5.6] vs 4.2 mo [95% CI, 3.6-4.9], HR=1.08; P=0.5. Six-month survival estimates were 53% (95% CI, 44-62%) for MM-398+5-FU/LV vs 38% (95% CI, 29-47%) for 5-FU/LV; 12-month survival estimates were 26% (95% CI, 18-35%) for MM-398+5-FU/LV vs 16% (95% CI, 10-24%) for 5-FU/LV. With events in nearly all patients, the OS curves converge at about 20 months with 19 patients (16.2%) surviving beyond 20 months. This is a reason for attenuation of the HR estimate and unstratified log rank p-value. The most common grade 3+ adverse events occurring at a ≥2% incidence in the MM-398-containing arms were neutropenia, diarrhea, vomiting, and fatigue. The median OS benefit for MM-398+5FU/LV over 5-FU/LV was maintained, with a similar safety profile. MM-398+5-FU/LV may be a new standard of care for patients with mPAC previously treated with gemcitabine-based therapy. The median overall survival (OS) increased significantly with MM-398+5-FU/LV relative to 5-FU/LV (6.1 vs 4.2 months; unstratified hazard ratio [HR]=0.67 [95% confidence interval (CI), 0.49-0.92]; P=0.012). The median OS did not differ between patients assigned MM-398 monotherapy and those allocated to 5-FU/LV (4.9 vs 4.2 months; unstratified HR=0.99 [95% CI, 0.77-1.28]; P=0.94). The median progression-free survival (PFS; 3.1 vs 1.5 months; unstratified HR=0.56 [95% CI, 0.41-0.75]; P=0.0001) and objective response rate (ORR; 16% vs 1%; P<0.0001) were also improved with MM-398+5-FU/LV compared with 5-FU/LV alone.

The objectives of the current descriptive analysis of the NAPOLI-1 trial are to evaluate the robustness of the previously observed OS treatment effect for MM-398+5-FU/LV versus 5-FU/LV control using data from longer follow-up, and to assess the long-term safety and tolerability of MM-398. A total of 76 sites in 14 countries enrolled 417 patients between January 2012 and September 2013. Patient demographics and baseline clinical characteristics were well balanced across treatment arms (Table 8).

Treatment Exposure

The mean duration of treatment exposure was 18.5 weeks (median, 8.7 weeks; range, 2-115 weeks) in the MM-398+5-FU/LV arm, 12.3 weeks (median, 8.9 weeks; range, 3-69 weeks) in the MM-398 arm, and 10.8 weeks (median, 6.0 weeks; range, 1-68 weeks) in the 5-FU/LV control arm. The mean relative dose intensity of MM-398 was 83% in the combination arm and 90% in the monotherapy arm.

TABLE 8

Patient Demographic and Baseline Clinical Characteristics

| Parameter | Nal-IRI + 5-FU/LV (n = 117) | 5-FU/LV combination control (n = 1119) | Nal-IRI Monotherapy (n = 151) | 5-FU/LV Monotherapy Control (n = 149) |
|---|---|---|---|---|
| Median age (IQR), y | 63 (57-70) | 62 (55-69) | 65 (58-70) | 63 (55-69) |
| KPS, % | | | | |
| 100 | 15 | 14 | 15 | 15 |
| 90 | 44 | 34 | 42 | 36 |
| 80 | 32 | 43 | 33 | 41 |
| 70 | 6 | 8 | 10 | 7 |
| 50-60 | 3 | 0 | 0 | 0 |
| Race, % | | | | |
| Caucasian | 62 | 64 | 59 | 62 |
| East Asian | 29 | 30 | 34 | 34 |
| Other | 9 | 6 | 7 | 5 |
| CA19-9 ≥ 40 U/mL, %[a] | 81 | 80 | 86 | 81 |
| Pancreatic head tumor, % | 65 | 58 | 66 | 54 |
| Prior lines of metastatic therapy, % | | | | |
| 0[b] | 13 | 13 | 11 | 13 |
| 1 | 53 | 56 | 57 | 58 |
| 2 | 34 | 31 | 32 | 30 | nal-IRI, nanoliposomal irinotecan; 5-FU, 5-flurouracil; LV, leucovorin; IQR, interquartile range; KPS, Karnofsky performance status; CA19-9, carbohydrate antigen 19-9.
[a]Includes only patients who had a measured CA19-9 value prior to treatment. Data were missing for 3 patients in the MM-398+5-FU/LV group and 5 patients each in the nal-IRI monotherapy and 5-FU/LV groups. [b]Patients received neoadjuvant, adjuvant, or locally advanced treatment, but had no previous therapy for metastatic disease.

Figure 22A:
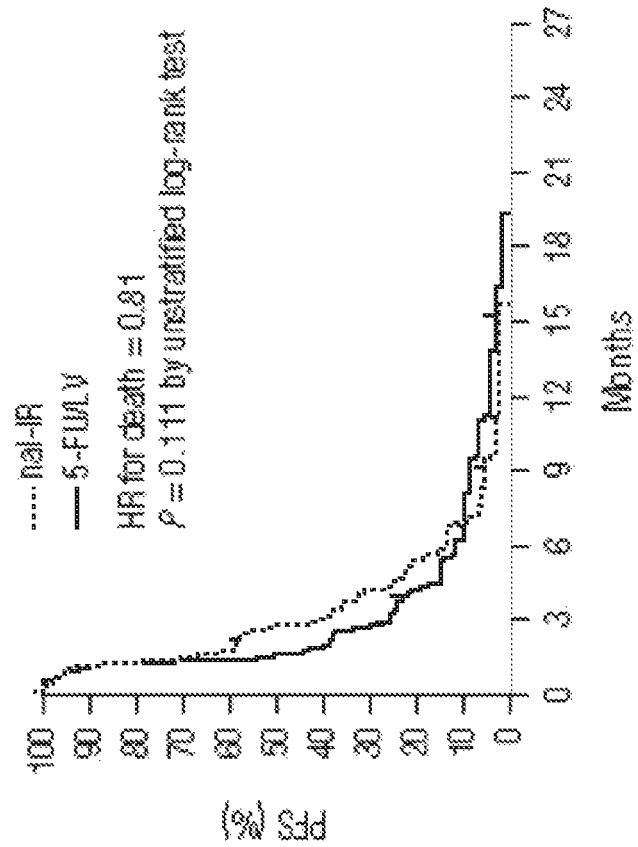
FIG. 22A is a graphical representation of the Progression Free Survival Rate (PFS) corresponding to treatment with MM-398+5-FU/LV vs. 5-FU/LV alone.
Figure 22B:
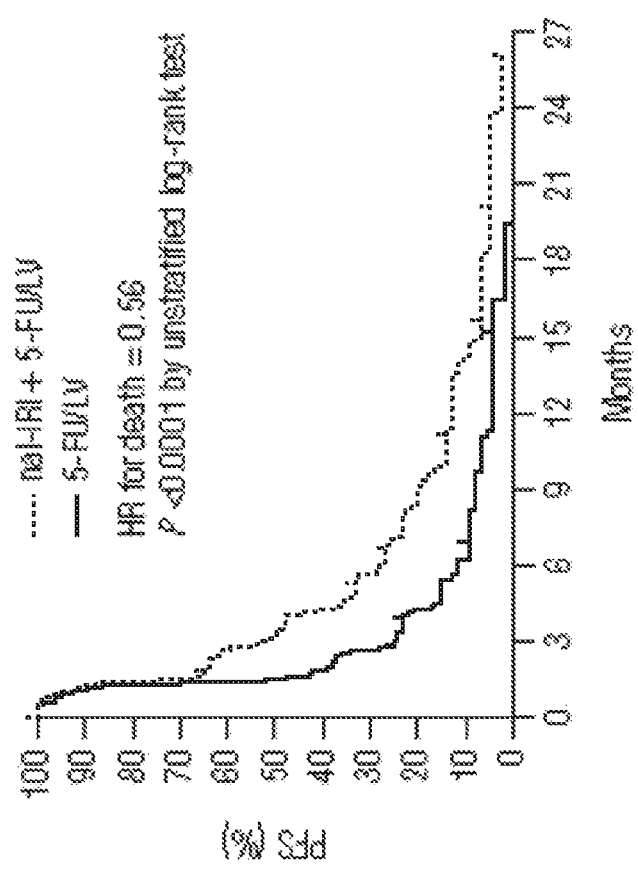
FIG. 22B is a graphical representation of the Progression Free Survival Rate (PFS) corresponding to treatment with MM-398 vs. 5-FU/LV alone.
Figure 23:
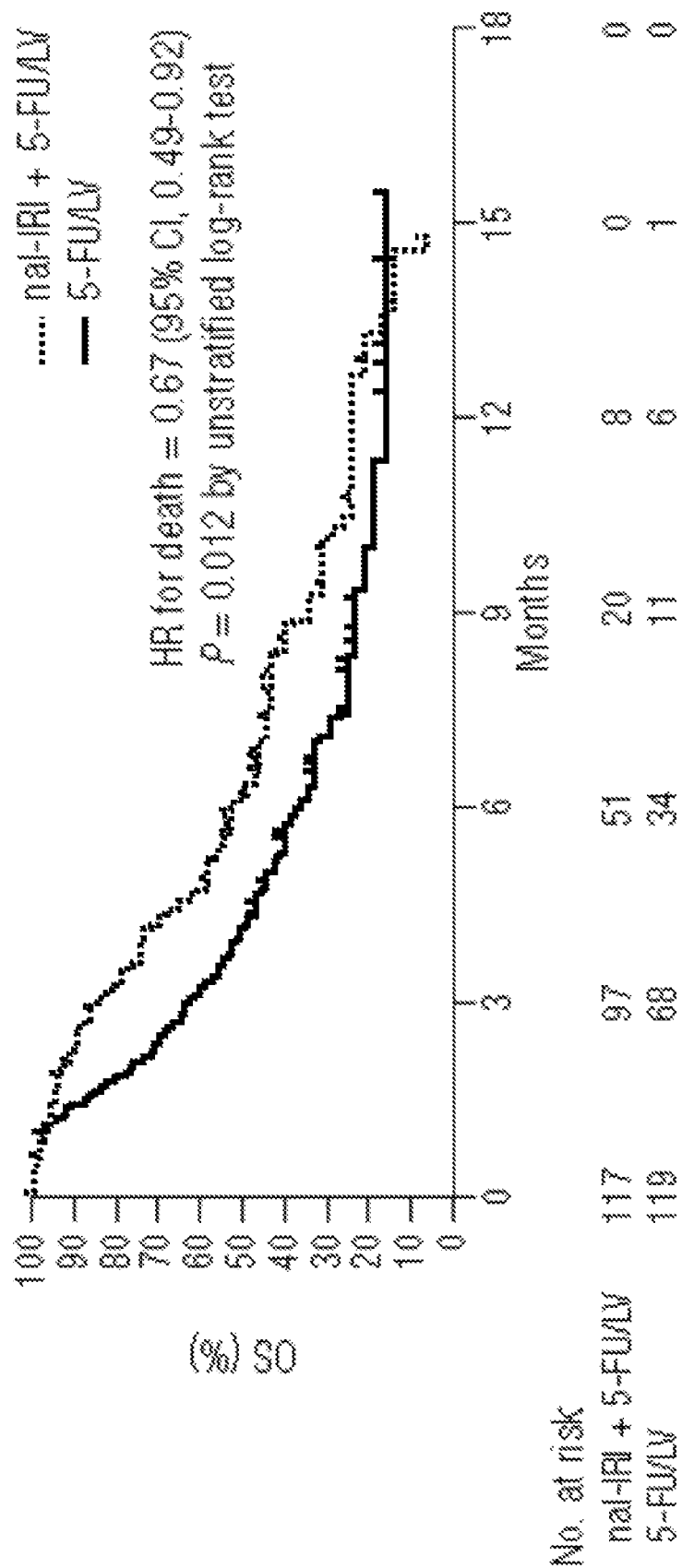
FIG. 23 is a Kaplan-Meier graph of Overall Survival (OS) in the NAPOLI-1 trial. OS, overall survival; CI, confidence interval; nal-IRI, nanoliposomal irinotecan; 5-FU, 5-fluorouracil; LV, leucovorin. OS analysis includes all patients randomized after implementation of a protocol amendment that added the nal-IRI+5-FU/LV combination arm.
Figure 24:
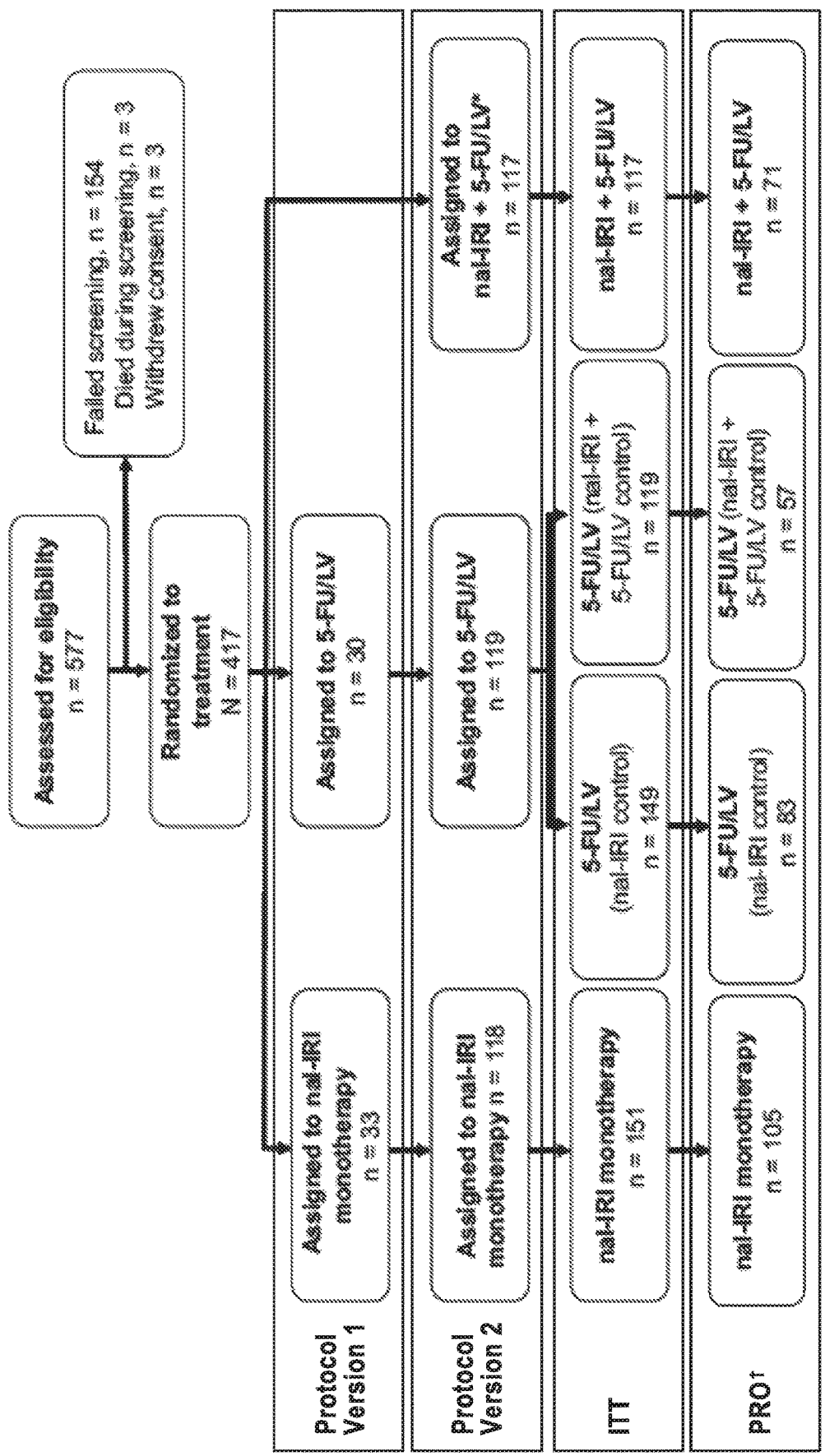
FIG. 24 is a trial profile.
Figure 26:
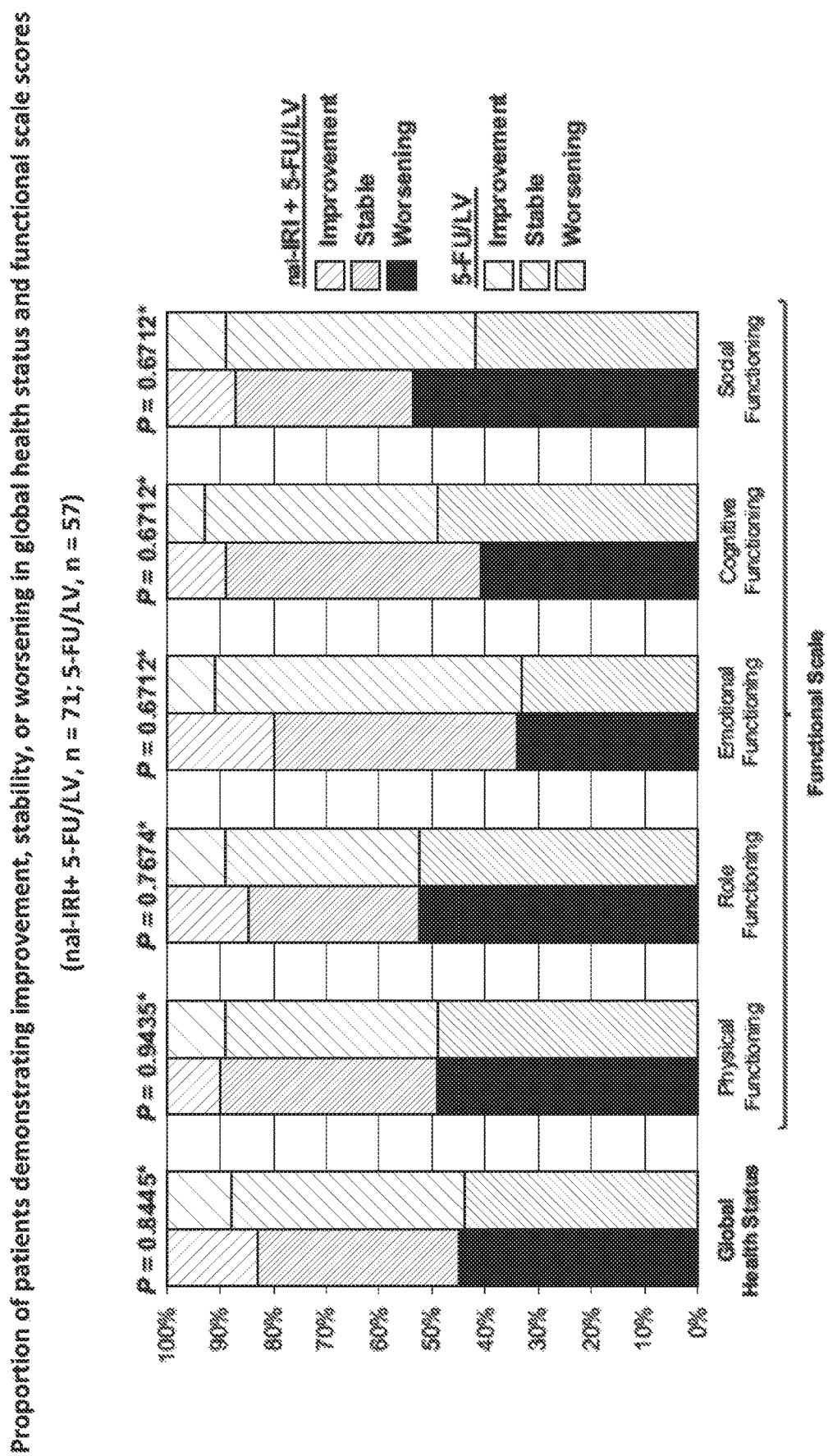
FIG. 26 is a graphical representation of the proportion of patients demonstrating improvement, stability, or worsening in global health status and functional scale scores (MM-398+5-FU/LV, n=71; 5-FU/LV, n=57).
Figure 27:
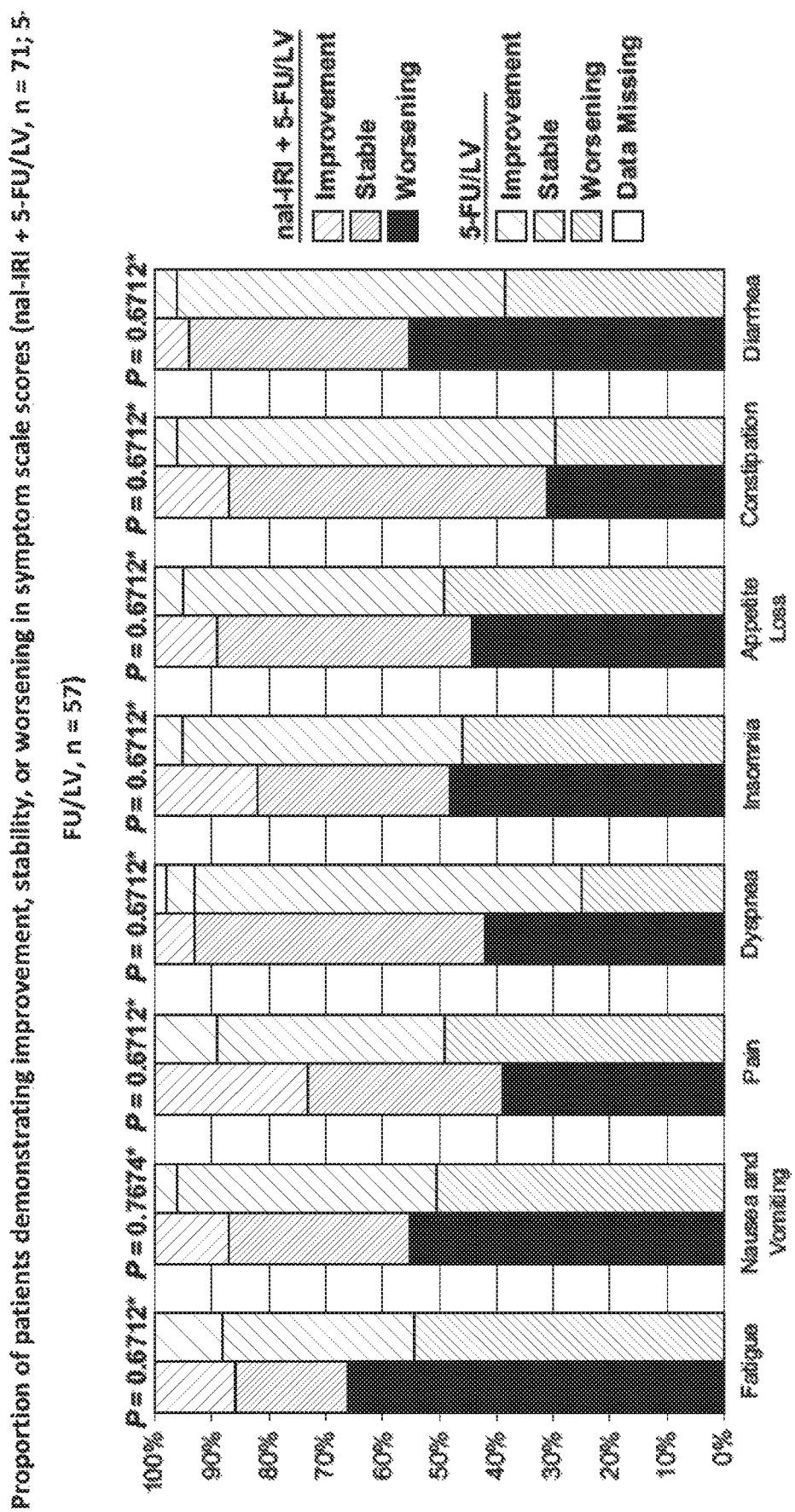
FIG. 27 is a graphical representation of the proportion of patients demonstrating improvement, stability, or worsening in symptom scale scores (MM-398+5-FU/LV, n=71; 5-FU/LV, n=57).
Figure 28:
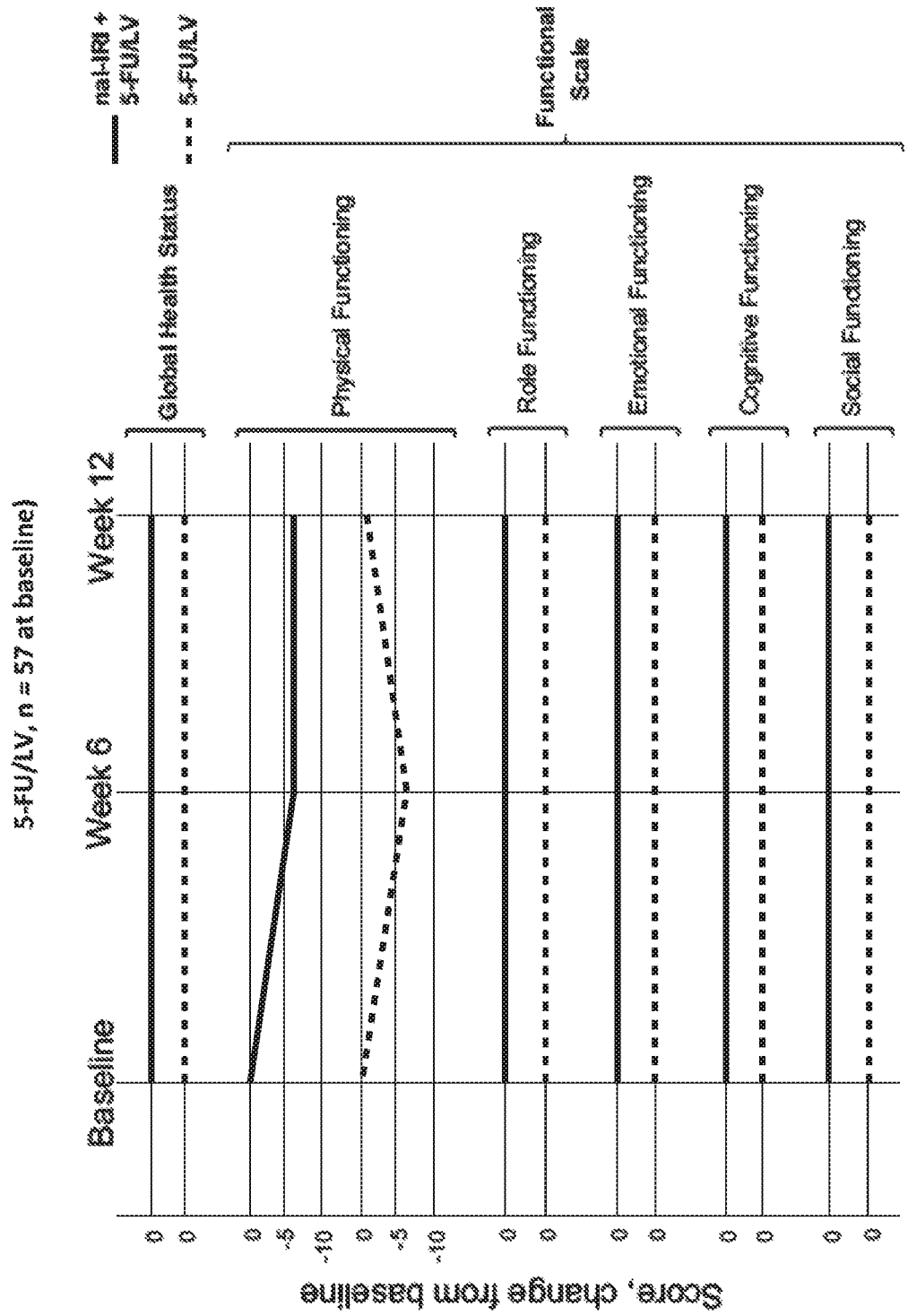
FIG. 28 is a graphical representation of the median change from baseline to week 12 in global health status and functional scale scores (MM-398+5-FU/LV, n=71 at baseline; 5-FU/LV, n=57 at baseline).
Figure 29:
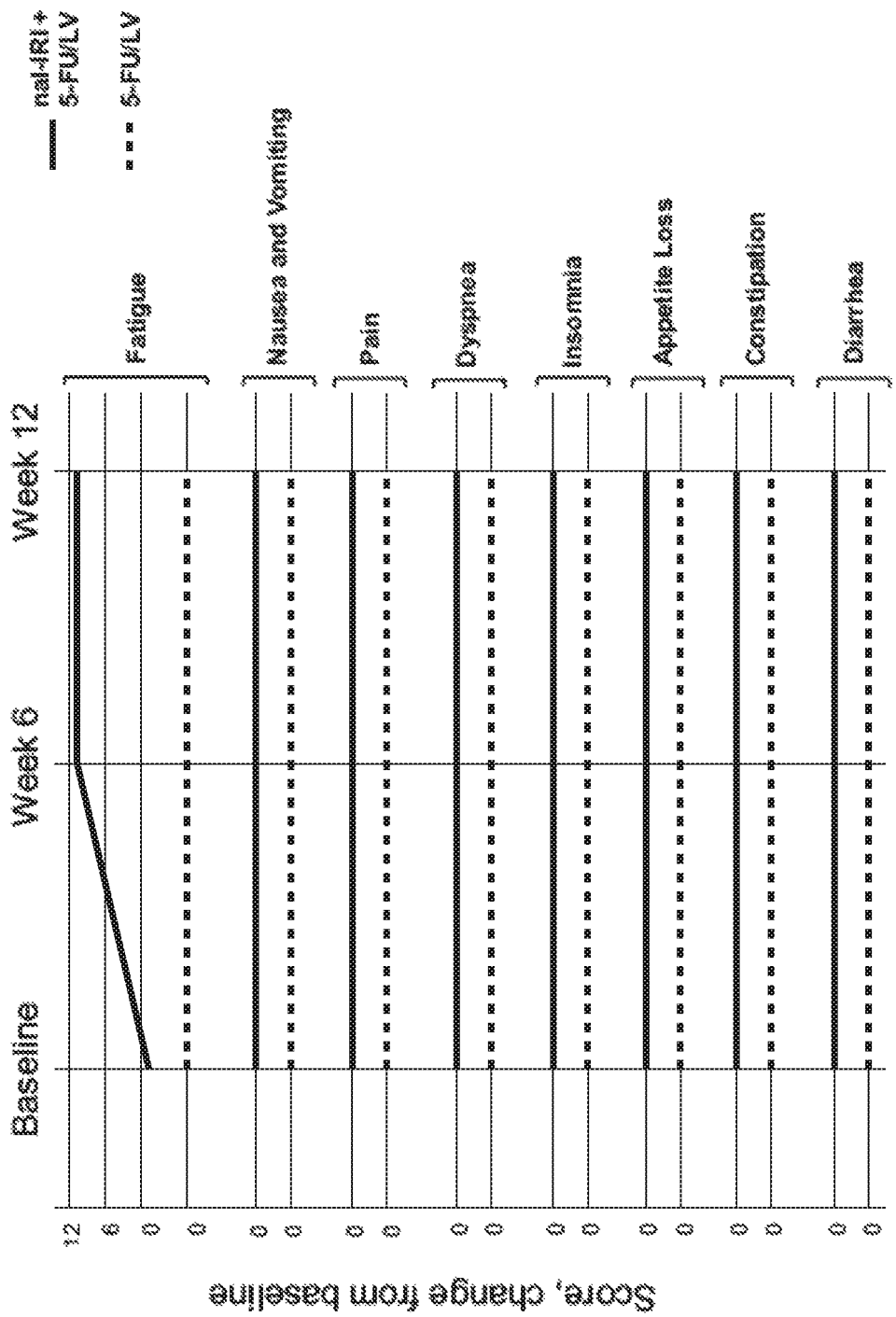
FIG. 29 is a graphical representation of the median change from baseline to week 12 in symptom scale scores (MM-398+5-FU/LV, n=71 at baseline; 5-FU/LV, n=57 at baseline).

After 378 events, MM-398+5-FU/LV retained an OS advantage relative to 5-FU/LV (Table 9 and FIG. 21A). With events in nearly all patients, the Kaplan-Meier OS curves converge at approximately 20 months, with 19 (16.2%) patients surviving beyond 20 months. No OS advantage was observed with MM-398 monotherapy versus 5-FU/LV (FIG. 21B). Median PFS was 3.1 months for MM-398+5-FU/LV versus 1.5 months for the 5-FU/LV combination control, and was 2.6 months for MM-398 monotherapy compared with 1.6 months for the 5-FU/LV monotherapy control (Table 9 and FIG. 22). ORR was higher than 5-FU/LV control for both MM-398+5-FU/LV (difference of 16% [95% CI, 9-24]) and MM-398 monotherapy (difference of 5% [95% CI, 1-9]; Table 9)

TABLE 9

Summary of the Updated Efficacy

| Endpoint | nal-IRI + 5-FU/LV (n = 117) | 5-FU/LV (n = 119) | Treatment effect[a] | nal-IRI (n = 151) | 5-FU/LV (n = 149) | Treatment effect[a] |
|---|---|---|---|---|---|---|
| Median OS (95% CI), months | 6.2 (4.8-8.4) | 4.2 (3.5-5.3) | HR 0.75 P = 0.042 | 4.9 (4.2-5.6) | 4.2 (3.6-4.9) | HR 1.08 P = 0.513 |
| OS rate at 6 months (95% CI), % | 53 (44-62) | 38 (29-47) | — | | | — |
| OS rate at 12 months (95% CI), % | 26 (18-35) | 16 (10-24) | — | | | — |
| Median PFS (95% CI), months | 3.1 (2.7-4.2) | 1.5 (1.4-1.8) | HR 0.56 P < 0.0001 | 2.7 (2.1-2.9) | 1.6 (1.4-1.8) | HR 0.81 P = 0.111 |
| ORR (95% CI), %[b] | 71 (10-24) | 1 (0-2) | P < 0.0001 | 6 (2-10) | 1 (0-2) | P = 0.020 |

TABLE 9-continued

Summary of the Updated Efficacy

| Endpoint | nal-IRI + 5-FU/LV (n = 117) | 5-FU/LV (n = 119) | Treatment effect[a] | nal-IRI (n = 151) | 5-FU/LV (n = 149) | Treatment effect[a] |
|---|---|---|---|---|---|---|
| Best overall response, % | | | | | | |
| Partial response[b] | 17 | 1 | — | 6 | 1 | — |
| Stable disease[c] | 33 | 22 | — | 36 | 24 | — |
| Progressive disease | 29 | 47 | — | 34 | 48 | — |
| Other[d] | 3 | 2 | — | 2 | 1 | — |
| Not evaluable | 19 | 29 | — | 23 | 27 | — | nal-IRI, nanoliposomal irinotecan; 5-FU, 5-flurouracil; LV, leucovorin; OS, overall survival; CI, confidence interval; HR, hazard ratio; PFS, progression-free survival; ORR, objective response rate.
[a]Unstratified HR and log-rank P value.
[b]Designation of response did not require confirmation and was based solely on the investigator's assessment using RECIST v1.1 criteria.
[c]Minimum duration for stable disease from baseline is 6 weeks from the date of randomization.
[d]Patients without measurable (target) disease at baseline may have a best overall-response of non-complete response/non-partial response.

After 382 events, median OS was improved with MM-398+5-FU/LV vs 5-FU/LV (6.2 vs 4.2 mo; HR 0.75; 95% CI 0.57-0.99; P=0.038), but not for MM-398 vs 5-FU/LV (4.9 vs 4.2 mo; HR 1.07; 95% CI 0.84-1.36; P=0.567). Kaplan-Meier estimates of OS for MM-398+5-FU/LV and 5-FU/LV, respectively, were 53% and 38% at 6 mo, and 26% and 16% at 12 mo. Median progression-free survival was longer for MM-398+5-FU/LV vs 5-FU/LV (3.1 vs 1.5 mo; HR 0.57; 95% CI 0.43-0.76; P<0.001), but not for MM-398 vs 5-FU/LV (2.7 vs 1.6 mo; HR 0.81; 95% CI 0.63-1.04; P=0.111). Response rates per RECIST v1.1 were higher for MM-398+5-FU/LV vs 5-FU/LV (17% vs 1%; P<0.001) and for MM-398 vs 5-FU/LV (6% vs 1%; P=0.020). Grade ≥3 treatment-emergent adverse events in ≥10% of pts in either MM-398 arm were neutropenia (28%, 15%, and 1% in the MM-398+5-FU/LV, MM-398, and 5-FU/LV arms, respectively), fatigue (14%, 6%, and 4%), diarrhea (13%, 21%, and 5%), vomiting (12%, 14%, and 4%), anemia (9%, 11%, and 7%), and hypokalemia (3%, 12%, and 2%).

Safety and Tolerability Analysis of NAPOLI-1 Clinical Trial (Phase III)

Safety profile was manageable, with most frequent being grade ≥3 adverse events including neutropenia, fatigue and GI effects, such as diarrhea and vomiting (FIG. 17). The safety data described below are derived from NAPOLI-1. Serum bilirubin within the institutional normal range, albumin ≥3 g/dL, and Karnofsky Performance Status (KPS) ≥70 were required for study entry. The median duration of exposure was 9 weeks in the MM-398/5-FU/LV arm, 9 weeks in the MM-398 monotherapy arm, and 6 weeks in the 5-FU/LV arm. Neutropenia, diarrhea, nausea, and vomiting typically first occur early during the course of treatment with MM-398+5-FU/LV and tend to decrease in incidence and severity thereafter.

The most common adverse reactions (≥20%) of MM-398 were diarrhea, fatigue/asthenia, vomiting, nausea, decreased appetite, stomatitis, and pyrexia. The most common laboratory abnormalities (≥10% Grade 3 or 4) were lymphopenia and neutropenia. The most common serious adverse reactions (≥2%) of MM-398 were vomiting, diarrhea, neutropenic fever or sepsis, nausea, pyrexia, anemia, pneumonia, sepsis, dehydration, septic shock, acute renal failure, thrombocytopenia and ileus.

The most common adverse reactions (≥20%) of patients receiving MM-398 were diarrhea, fatigue/asthenia, vomiting, nausea, decreased appetite, stomatitis, and pyrexia.

Severe (21%) or life-threatening (7%) neutropenia or neutropenic sepsis, of which 1% resulted in septic shock, occurred in patients receiving MM-398 in combination with 5-fluorouracil and leucovorin. In some embodiments, MM-398 is withheld from patients with an absolute neutrophil count below 1500/mm$^3$ or neutropenic fever. The blood cell counts of patients are preferably monitored periodically during treatment. Severe or life-threatening diarrhea occurred in 13% of patients receiving MM-398 in combination with 5FU and leucovorin.

Severe or life threatening neutropenia occurred in 27% of patients receiving MM-398/5-FU/LV compared to 2% of patients receiving 5-fluorouracil/leucovorin alone (5-FU/LV) in Study 1 described herein. The expected likelihood of severe or life threatening neutropenia (as a during treatment with MM-398/5-FU/LV in the protocol used in Study 1, is expressed by the parameter $P_{aen}$. In some embodiments, $P_{aen}$ is <50%. In some embodiments it is <45%, such as <40%, <35%, <30% or ≤27%.

In NAPOLI-1 study results, Grade 3 or 4 diarrhea occurred in 13% receiving MM-398/5-FU/LV compared to 4% receiving 5-FU/LV. The expected likelihood of Grade 3 or 4 diarrhea (as a %) during treatment with MM-398/5-FU/LV in the protocol used in Study 1, is expressed by the parameter $P_{aed}$. In some embodiments, $P_{aed}$ is <50%. In some embodiments it is <45%, such as <40%, <35%, <30%, <25%, <20%, <15% or ≤13%. In some embodiments, $t_{serv}$ is ≥6.1 months, $P_{aen}$ is P≤27% and $P_{aed}$ is <13%.

Adverse reactions led to permanent discontinuation of MM-398 in 11% of patients receiving MM-398/5-FU/LV; the most frequent adverse reactions resulting in discontinuation of MM-398 were diarrhea, vomiting, and sepsis. Dose reductions of MM-398 for adverse reactions occurred in 33% of patients receiving MM-398/5-FU/LV; the most frequent adverse reactions requiring dose reductions were neutropenia, diarrhea, nausea, and anemia. MM-398 was withheld or delayed for adverse reactions in 62% of patients receiving MM-398/5-FU/LV; the most frequent adverse reactions requiring interruption or delays were neutropenia, diarrhea, fatigue, vomiting, and thrombocytopenia.

Table 10 provides the frequency and severity of adverse reactions in Study 1 that occurred with higher incidence (≥5% difference for Grades 1-4 or ≥2% difference for Grades 3-4) in patients who received MM-398/5 FU/LV compared to patients who received 5-FU/LV arm.

TABLE 10

Adverse Reactions with Higher Incidence (≥5% Difference for Grades 1-4* or ≥2% Difference for Grades 3 and 4) in the MM-398/5-FU/LV.

| Adverse Reaction | MM-398/5-FU/LV N = 117 | | 5-FU/LV N = 134 | |
|---|---|---|---|---|
| | Grades 1-4 (%) | Grades 3-4 (%) | Grades 1-4 (%) | Grades 3-4 (%) |
| *Gastrointestinal disorders* | | | | |
| Diarrhea | 59 | 13 | 26 | 4 |
| Diarrhea, early† | 30 | 3 | 15 | 0 |
| Diarrhea, late‡ | 43 | 9 | 17 | 4 |
| Vomiting | 52 | 11 | 26 | 3 |
| Nausea | 51 | 8 | 34 | 4 |
| Stomatitis§ | 32 | 4 | 12 | 1 |
| *Infections and infestations* | | | | |
| Sepsis | 4 | 3 | 2 | 1 |
| Neutropenic fever/neutropenic sepsis♣ | 3 | 3 | 1 | 0 |
| Gastroenteritis | 3 | 3 | 0 | 0 |
| Device related infection | 3 | 3 | 0 | 0 |
| *General disorders and administration site conditions* | | | | |
| Fatigue/asthenia | 56 | 21 | 43 | 10 |
| Pyrexia | 23 | 2 | 11 | 1 |
| *Metabolism and nutrition disorders* | | | | |
| Decreased appetite | 44 | 4 | 32 | 2 |
| Weight loss | 17 | 2 | 7 | 0 |
| Dehydration | 8 | 4 | 7 | 2 |
| *Skin and subcutaneous tissue disorders* | | | | |
| Alopecia | 14 | 1 | 5 | 0 |

*NCI CTCAE v4.0
†Early diarrhea: onset within 24 hours of MM-398 administration
‡Late diarrhea: onset >1 day after MM-398 administration
§Includes stomatitis, aphthous stomatitis, mouth ulceration, mucosal inflammation.
♣Includes febrile neutropenia.

398 pts were treated with MM-398+5-FU/LV (n=117), MM-398 (n=147), or 5-FU/LV (n=134). In the MM-398+5-FU/LV arm, most first occurrences of neutropenia, diarrhea, nausea, and vomiting were during the first 6 wk of treatment, with incidence and severity generally decreasing thereafter (Table 11). Similarly, prevalence and severity were highest in the first 6 wk and tended to decrease over time. Similar trends were observed in the MM-398 and 5-FU/LV arms.

TABLE 11

| | | MM-398 + 5-FU/LV Period | | | MM-398 Period Incidence, % | | | 5-FU/LV Period | | |
|---|---|---|---|---|---|---|---|---|---|---|
| | | 1 | 2 | 3 | 1 | 2 | 3 | 1 | 2 | 3 |
| Neutropenia grade | | n = 117 | n = 73 | n = 34 | n = 147 | n = 95 | n = 43 | n = 134 | n = 111 | n = 43 |
| | 1 | 1 | 3 | 3 | 1 | 2 | 0 | 1 | 0 | 0 |
| | 2 | 8 | 3 | 3 | 8 | 3 | 0 | 1 | 2 | 2 |
| | 3 | 14 | 4 | 9 | 5 | 1 | 0 | 2 | 0 | 0 |
| | 4 | 7 | 0 | 0 | 6 | 2 | 0 | 0 | 0 | 0 |
| | 5 | 0 | 0 | 0 | 0 | 0 | 0 | 0 | 0 | 0 |
| Diarrhea grade | | n = 117 | n = 51 | n = 24 | n = 147 | n = 46 | n = 11 | n = 134 | n = 89 | n = 32 |
| | 1 | 21 | 4 | 0 | 25 | 11 | 18 | 15 | 5 | 6 |
| | 2 | 17 | 12 | 4 | 20 | 7 | 9 | 2 | 1 | 0 |
| | 3 | 12 | 0 | 4 | 16 | 4 | 0 | 2 | 1 | 3 |
| | 4 | 0 | 0 | 0 | 1 | 0 | 0 | 0 | 0 | 0 |
| | 5 | 0 | 0 | 0 | 1 | 0 | 0 | 0 | 0 | 0 |
| Nausea grade | | n = 117 | n = 56 | n = 28 | n = 147 | n = 53 | n = 25 | n = 134 | n = 87 | n = 26 |
| | 1 | 21 | 5 | 7 | 23 | 4 | 8 | 19 | 4 | 12 |
| | 2 | 16 | 0 | 7 | 27 | 4 | 8 | 5 | 4 | 4 |
| | 3 | 7 | 2 | 0 | 5 | 2 | 0 | 2 | 2 | 0 |
| | 4 | 0 | 0 | 0 | 0 | 0 | 0 | 0 | 0 | 0 |
| | 5 | 0 | 0 | 0 | 0 | 0 | 0 | 0 | 0 | 0 |
| Vomiting grade | | n = 117 | n = 61 | n = 35 | n = 147 | n = 61 | n = 28 | n = 134 | n = 89 | n = 29 |
| | 1 | 19 | 5 | 11 | 27 | 2 | 7 | 16 | 2 | 4 |
| | 2 | 14 | 0 | 9 | 10 | 3 | 4 | 5 | 1 | 4 |
| | 3 | 10 | 0 | 3 | 12 | 2 | 0 | 1 | 1 | 4 |
| | 4 | 0 | 0 | 0 | 0 | 0 | 0 | 0 | 0 | 0 |
| | 5 | 0 | 0 | 0 | 0 | 0 | 0 | 0 | 0 | 0 |

Cholinergic Reactions:

MM-398 can cause cholinergic reactions manifesting as rhinitis, increased salivation, flushing, bradycardia, miosis, lacrimation, diaphoresis, and intestinal hyperperistalsis with abdominal cramping and early onset diarrhea. In Study 1, Grade 1 or 2 cholinergic symptoms other than early diarrhea occurred in 12 (4.5%) MM-398-treated patients. Six of these 12 patients received atropine; in 1 of the 6 patients who received atropine, the atropine was administered for cholinergic symptoms other than diarrhea.

Infusion Reactions:

Infusion reactions, consisting of allergic reaction, rash, urticaria, periorbital edema, or pruritus, occurring on the day of MM-398 administration were reported in 3% of patients receiving MM-398 or MM-398/5-FU/LV.

Additional clinically significant adverse reactions occurring in <10% of MM-398/5-FU/LV-treated patients were:

Cardiovascular: Severe Hypotension

Laboratory abnormalities that occurred with higher incidence in the MM-398/5 FU/LV arm compared to the 5-FU/LV arm (≥5% difference) are summarized in the following table 12.

TABLE 12

Laboratory Abnormalities with Higher Incidence (≥5% Difference) in the MM-398/5-FU/LV Arm*#

|  | MM-398/5-FU/LV | | 5-FU/LV | |
|---|---|---|---|---|
| Laboratory abnormality | Grades 1-4 (%) | Grades 3-4 (%) | Grades 1-4 (%) | Grades 3-4 (%) |
| Hematology | | | | |
| Anemia | 97 | 6 | 86 | 5 |
| Decreased lymphocytes | 81 | 27 | 75 | 17 |
| Decreased leukocytes | 67 | 16 | 20 | 0 |
| Decreased neutrophil counts | 52 | 20 | 6 | 2 |
| Decreased platelet counts | 41 | 2 | 33 | 0 |
| Hepatic | | | | |
| Increased alanine aminotransferase (ALT) | 51 | 6 | 37 | 1 |
| Decreased albumin | 43 | 2 | 30 | 0 |
| Metabolic | | | | |
| Decreased magnesium | 35 | 0 | 21 | 0 |
| Decreased potassium | 32 | 2 | 19 | 2 |
| Decreased calcium | 32 | 1 | 20 | 0 |
| Decreased phosphate | 29 | 4 | 18 | 1 |
| Decreased sodium | 27 | 5 | 12 | 3 |
| Renal | | | | |
| Increased creatinine | 18 | 0 | 13 | 0 |

*NCI CTCAE v4.0, worst grade shown
Percent based on number of patients with a baseline and at least one post-baseline measurement.

Of the 264 patients who received MM-398 as a single agent or in combination with 5-FU and leucovorin in Study 1, 49% were ≥65 years old and 13% were ≥75 years old. No overall differences in safety and effectiveness were observed between these patients and younger patients.

The safety profiles of MM-398+5-FU/LV and MM-398 monotherapy described in the current updated analysis did not change appreciably from that reported in the primary analysis. The most frequently reported grade ≥3 TEAEs in the MM-398-containing arms were neutropenia, diarrhea, vomiting, and fatigue (Table 13). TEAEs led to dose delay, reduction, and/or discontinuation in 73% of patients in the MM-398+5-FU/LV arm, 56% of patients in the MM-398 monotherapy arm, and 37% of patients in the 5-FU/LV arm.

The most common reasons for dose reduction in the MM-398+5-FU/LV and MM-398 monotherapy arms were gastrointestinal events (12% and 17%, respectively) and neutropenia (18% and 10%). The rate of treatment discontinuation due to a TEAE was 12% with MM-398+5-FU/LV, 14% with MM-398, and 8% with 5-FU/LV; neutropenia, diarrhea, and vomiting were the most common reasons for discontinuation in the MM-398-containing arms. Grade ≥3 febrile neutropenia occurred in 2 (2%) patients receiving MM-398+5-FU/LV and 6 (4%) patients receiving MM-398; 1 and 5 patients, respectively, required a dose reduction but no patient discontinued treatment due to febrile neutropenia. No additional deaths due to treatment-related TEAEs have been reported since the primary analysis.

TABLE 13

Grade ≥3 TEAE (Treatment Emergent Adverse Event), %

| Grade ≥3 TEAE, % | nal-IRI + 5-FU/LV (n = 117) | nal-IRI monotherapy (n = 151) | 5-FU/LV (n = 134) |
|---|---|---|---|
| Any TEAE | 80 | 76 | 56 |
| Neutropenia | 28 | 15 | 2 |
| Fatigue | 14 | 6 | 4 |
| Diarrhea | 13 | 21 | 5 |
| Vomiting | 12 | 14 | 4 |
| Anemia | 9 | 11 | 7 |
| Asthenia | 8 | 7 | 7 |
| Nausea | 8 | 5 | 3 |
| White blood cell count | 8 | 3 | 0 |
| Abdominal pain | 7 | 8 | 7 |
| Decreased appetite | 5 | 9 | 2 |
| Hypokalemia | 3 | 12 | 2 |
| Hyponatremia | 3 | 6 | 2 |
| Hyperglycemia | 2 | 5 | 2 |

TEAE, treatment-emergent adverse event; MM-398, nano-liposomal irinotecan; 5-FU, 5-fluoruracil; LV, leucovorin. The tabel includes all grade ≥3 TEAEs reproted for ≥5% of patients in any treatment arm. "Neutropenia includes agranulocytosis, febrile neutropenia, granulocytopenia, neutropenia, neutropenic sepsis, decreased neutrophil count, and pancytopenia.

The most common grade ≥3 treatment-emergent adverse events (TEAEs) in the MM-398+5-FU/LV arm were neutropenia, fatigue, diarrhea, and vomiting. Based on NAPOLI-1, the MM-398+5-FU/LV regimen received regulatory approval from the US Food and Drug Administration for the treatment of patients with metastatic adenocarcinoma of the pancreas after disease progression following gemcitabine-based therapy. Here, we present results of a prespecified safety analysis by patient subgroup from NAPOLI-1.

TEAEs were graded by NCI CTCAE v4.0 and coded by MedDRA v14.1 for the following prespecified subgroups: sex, age (<65 vs ≥65 years), ethnicity (white vs Asian), UGT1A1*28 status, prior conventional irinotecan therapy (yes vs no), and prior 5-FU therapy (yes vs no). All TEAEs were followed until resolution or patient discontinuation. Analyses were performed on the safety population (ie, those who received ≥1 dose of study medication). Results herein are for the MM-398+5-FU/LV arm unless otherwise noted.

Overall, the incidence and severity of TEAEs were similar between men (n=67) and women (n=50). Patients aged ≥65 years (n=54) generally had a higher incidence of TEAEs than those <65 years (n=63) (eg, stomatitis: 20.4% vs 7.9%; anemia: 46.3% vs 30.2%), although the most common types of TEAEs were similar regardless of age. Overall, Asian (n=33) patients had a higher incidence of grade ≥3 TEAEs than white (n=73) patients (87.9% vs 69.9%), primarily because of an increased incidence of neutropenia (24.2% vs 12.3%) and decreased neutrophil counts (33.3% vs 1.4%); febrile neutropenia was reported in 3.0% of Asian patients and 0 white patients. Gastrointestinal disorders also occurred slightly more frequently in Asian patients than white patients (any grade: 100% vs 87.7%), although diarrhea was less frequent and less severe among Asian patients (any grade: 48.5% vs 61.6%; grade ≥3: 3.0% vs 19.2%). The UGT1A1 gene encodes an enzyme responsible for glucuronidation of the active metabolite of irinotecan, SN-38. Patients homozygous for the UGT1A1*28 allele (UGT1A1 7/7 genotype) may be at increased risk for neutropenia during irinotecan treatment due to reduced glucuronidation of SN-38. However, in this analysis, there were no differences in incidence, type, and severity of TEAEs between patients homozygous (n=7) for the UGT1A1*28 allele and those who were not (n=110). There were also no notable differences in the incidence or severity of TEAEs between patients with (n=12) and without (n=105) prior conventional irinotecan therapy, or between patients with (n=50) or without (n=67) prior 5-FU therapy.

Overall, the safety profile of MM-398+5-FU/LV was generally similar across patient subgroups, apart from an increased risk of grade ≥3 neutropenia/reduced neutrophil counts in Asian patients. The results of this prespecified subgroup analysis further support the tolerability profile of MM-398+5-FU/LV in patients with mPAC previously treated with gemcitabine-based therapy.

The median overall survival (OS) increased significantly with MM-398+5-FU/LV relative to 5-FU/LV (6.1 vs 4.2 months; unstratified hazard ratio [HR], 0.67 [95% confidence interval (CI), 0.49-0.92]; P=0.012), but did not differ significantly between MM-398 monotherapy and 5-FU/LV (4.9 vs 4.2 months; unstratified HR 0.99 [95% CI, 0.77-1.28]; P=0.94).

Adverse events that resulted in a dose reduction occurred in 39 (33%) patients in the MM-398+5-FU/LV arm, 46 (31%) patients in the MM-398 monotherapy arm, and 5 (4%) patients in the 5-FU/LV arm. Adverse events leading to treatment discontinuation occurred in 13 (11%) patients in the MM-398+5-FU/LV arm, 17 (12%) patients in the MM-398 monotherapy arm, and 10 (7%) patients in the 5-FU/LV arm.

Patients were initially randomized to MM-398 monotherapy (120 mg/m$^2$ irinotecan hydrochloride trihydrate salt equivalent to 100 mg/m$^2$ irinotecan free base every 3 weeks) or 5-FU/LV (200 mg/m$^2$ LV and 2000 mg/m$^2$ 5-FU, every week for the first 4 weeks of each 6-week cycle). Once safety data for the combination regimen became available from a concurrent study in metastatic colorectal cancer, the protocol was amended to include a third arm, MM-398+5-FU/LV (80 mg/m$^2$ irinotecan hydrochloride trihydrate salt [equivalent to 70 mg/m$^2$ irinotecan free base], 400 mg/m$^2$ LV, and 2400 mg/m$^2$ 5-FU over 46 hours, every 2 weeks).

The initial MM-398 dose in the MM-398+5-FU/LV arm was 60 mg/m$^2$ (salt) for patients homozygous for the UGT1A1*28 allele (TA7/TA7 genotype) and could be increased to the standard dose (80 mg/m$^2$ (salt)) in the absence of drug-related toxic effects. Randomization was stratified by baseline albumin levels (≥4.0 g/dL vs<4.0 g/dL) KPS (70 and 80 vs ≥90), and ethnicity (white vs east Asian vs all others).

TEAEs were graded by National Cancer Institute Common Terminology Criteria for Adverse Events, version 4.0, and coded by Medical Dictionary for Regulatory Activities, version 14.1. All TEAEs were followed until resolution or patient discontinuation. The safety analysis population included all patients who received ≥1 dose of study drug. The presence of the UGT1A1*28 allele was determined by genotype testing, and homozygous patients were identified (A7/TA7 genotype)

Eligibility Criteria:

Key Inclusion Criteria: Adults ≥18 years of age; Histologically or cytologically confirmed PDAC; Documented measurable or nonmeasurable distant metastatic disease (as defined by Response Evaluation Criteria in Solid Tumors, version 1.1); Disease progression after prior gemcitabine or gemcitabine-containing therapy in a neoadjuvant, adjuvant (only if distant metastases occurred within 6 months of completing adjuvant therapy), locally advanced, or metastatic setting; KPS score ≥70; Adequate hematologic (including absolute neutrophil count >1.5×109 cells/L), hepatic (including normal serum total bilirubin and albumin levels ≥30 g/L), and renal function.

Key Exclusion Criteria: Active central nervous system metastasis; Clinically significant gastrointestinal disorder; Severe arterial thromboembolic events <6 months before inclusion; New York Heart Association class III or IV congestive heart failure, ventricular arrhythmias, or uncontrolled blood pressure; Active infection or uncontrolled fever.

Of the 417 patients included in the intention-to-treat population, 398 (95%) received ≥1 dose of any study drug (safety analysis population).

Median duration of exposure to MM-398 in the MM-398 combination arm was 8.7 weeks (interquartile range [IQR], 5.4-22.0 weeks); mean dose intensity of MM-398 over 6 weeks was 167.5 mg/m$^2$ (standard deviation [SD], 52.05 mg/m$^2$). Median duration of exposure to 5-FU was 8.7 weeks (IQR, 5.4-22.0 weeks) in the MM-398 combination arm and 6.0 weeks (IQR, 5.9-12.1 weeks) in the control arm; mean dose intensities of 5-FU over 6 weeks were 5065.0 mg/m$^2$ (SD, 1539.1 mg/m$^2$) and 6718.0 mg/m$^2$ (SD, 1770.18 mg/m$^2$), respectively.

Incidence of any-grade and grade ≥3 TEAEs was similar between patients aged <65 years and those aged ≥65 years in each treatment arm. Grade ≥3 TEAEs of note (difference of ≥5% between subgroups): In the MM-398 combination arm, incidence of vomiting (14.3% vs 7.4%) was higher in patients <65 years; incidence of nausea (11.1% vs 4.8%) was higher in patients ≥65 years.

Incidence of any-grade TEAEs was similar between white and east Asian patients in each treatment arm, with the exception of diarrhea, which occurred less frequently in east Asians. Incidence of grade ≥3 TEAEs in the control arm was similar between white and east Asian patients (56.5% vs 54.5%), whereas the incidence of grade ≥3 TEAEs in the MM-398 combination arm was higher for east Asians compared with whites (87.9% vs 69.9%). Grade ≥3 TEAEs of note (difference of ≥5% between subgroups). In the MM-398 combination arm, incidence of diarrhea (19.2% vs 3.0%), fatigue (19.2% vs 0%), and vomiting (13.7% vs 6.1%) was higher in white patients; incidence of anemia (21.2% vs 5.5%), neutropenia (54.5% vs 17.8%), and white blood cell decrease (21.2% vs 2.7%) was higher in east Asian patients. In the control arm, incidence of abdominal pain (8.2% vs 2.3%) was higher in white patients; incidence of anemia (13.6% vs 3.5%) was higher in east Asian patients.

UGT1A1*28 Allele (TA7/TA7 Genotype): Although the low number of patients with the TA7/TA7 genotype makes comparison difficult the incidence of any-grade and grade ≥3 TEAEs appeared to be similar between patients with or without the TA7/TA7 genotype. In the MM-398 combination arm, 3 of the 7 patients with the TA7/TA7 genotype were able to escalate the MM-398 dose to 80 mg/m$^2$ without needing dose reduction. 1 patient escalated but required dose reduction back to 60 mg/m$^2$; 2 patients maintained the initial dose; 1 patient required dose reduction to 40 mg/m$^2$; 1 additional patient in the MM-398 combination arm with the TA7/TA7 genotype discontinued treatment (without dose reduction) because of grade 3 vomiting. Incidence of any-grade and grade ≥3 TEAEs was similar between patients with albumin levels ≥4.0 g/dL or <4.0 g/dL. Grade ≥3 TEAEs of note (difference of ≥5% between subgroups). In the MM-398 combination arm, incidence of diarrhea (17.6% vs 6.4%) and fatigue (16.2% vs 10.6%) was higher in patients with albumin levels ≥4.0 g/dL. In the control arm, incidence of diarrhea (8.1% vs 1.4%) was higher in patients with albumin levels <4.0 g/dL.

Karnofsky Performance Status: Incidence of any-grade TEAEs was similar between patients with KPS score of ≥90 or <90. Incidence of grade ≥3 TEAEs was similar between patients with KPS score of ≥90 or <90 in the MM-398 combination arm; incidence of grade ≥3 TEAEs was lower in patients with KPS score of ≥90 vs patients with KPS score of <90 in the control arm (40.9% vs 70.6%). Grade ≥3 TEAEs of note (difference of ≥5% between subgroups): In the MM-398 combination arm, incidence of decreased appetite (8.3% vs 1.4%) and abdominal pain (10.4% vs 4.3%) was higher in patients with KPS score <90; In the control arm, incidence of abdominal pain (8.8% vs 3.0%) was higher in patients with KPS score <90.

Patient Quality of Life Evaluation

Patients with mPDAC frequently experience a significant symptom burden. This in turn negatively impacts their QoL. QoL was a secondary endpoint of the study.

QoL was assessed using the European Organization for Research and Treatment of Cancer quality-of-life core questionnaire (EORTC-QLQ-C30), which includes functional scales (physical, role, cognitive, emotional, and social); symptom scales (appetite loss, constipation, diarrhea, dyspnea, fatigue, insomnia, nausea and vomiting, and pain); and a global health and quality-of-life scale. Patients were to complete the questionnaire at treatment start, every 6 weeks, and 30 days post-follow-up visit. The population analyzed included all patients who provided baseline and at ≥1 subsequent EORTC-QLQ-C30 assessment. Linear transformations were applied to the raw scores to produce reported scores in the 0-100 range. In the responder analysis, patients were classified as improved (≥10% increase in scale of breadth at a post-baseline time point and remained above baseline for ≥6 weeks), worsened (did not meet improvement criteria and died, or had ≥10% decrease from baseline in scale of breadth at a post-baseline time point), or stable (did not meet criteria for improvement or worsening) for each subscale. Pairwise treatment group comparisons on response classification were performed for each subscale using Cochran-Mantel-Haenszel testing adjusted for multiplicity with a Benjamini-Hochberg correction to control false discovery rate at 0.05 level for the 15 comparisons.

A total of 154 patients (MM-398+5-FU/LV, n=71; 5-FU/LV, n=83) comprised the population for this analysis of which 69% (49/71) of patients in the MM-398+5-FU group and 53% (44/83) in the 5-FU/LV group had evaluable data at 12 weeks. At baseline, median Global Health Status scores were near the midpoint of the scoring range, median Functional Scale scores were high, and Symptom Scale scores were low, with baseline values similar between groups. The observed median change in score at 12 weeks was 0 for both treatment groups for Global Health Status and for the following subscale scores: role functioning, emotional functioning, cognitive functioning, social functioning, nausea and vomiting, pain, dyspnea, insomnia, appetite loss, constipation, diarrhea, and financial difficulties. For subscale scores for which the median change was not 0 (MM-398+5-FU/LV: physical functioning and fatigue), the between-group differences were not substantial. Additionally, there were no significant differences in the proportion of patients classified as improved, worsened, or stable between the treatment groups. Across subscales, adjusted P values for the comparisons were >0.05 (NS).

In NAPOLI-1, evaluable MM-398+5-FU/LV-treated patients with data through 12 weeks tended to maintain baseline QoL over 12 weeks, and there were no significant differences versus the 5-FU/LV-treated patients in QoL response despite the addition of a second cytotoxic agent. These results are limited by the small number of patients and variability in QoL subscale scores.

The median overall survival (OS) increased significantly with MM-398+5-FU/V relative to 5-FU/LV (6.1 vs 4.2 months; unstratified hazard ratio [HR], 0.67 [95% confidence interval (CI), 0.49-0.92]; P=0.012), but did not differ significantly between MM-398 monotherapy and 5-FU/LV (4.9 vs 4.2 months; unstratified HR 0.99 [95% CI, 0.77-1.28]; P=0.94).

Median PFS was significantly longer with MM-398+5-FU/V compared with 5-FU/LV (3.1 vs 1.5 months; unstratified HR 0.56; 95% CI, 0.41-0.75; P=0.0001).

Median ORR was significantly higher with MM-398+5-FU/V compared with 5-FU/LV (16% vs 1%; P<0.0001).

MM-398+5-FU/LV exhibited a manageable safety profile; grade 3/4 adverse events (AEs) occurring more frequently with MM-398+5-FU/LV vs 5-FU/LV included neutropenia (27% vs 1%), fatigue (14% vs 4%), diarrhea (13% vs 4%), and vomiting (11% vs 3%). 71 patients (61% of the ITT population randomized under protocol version 2) in the MM-398+5-FU/LV arm and 57 patients (48% of the ITT population randomized under protocol version 2) in the 5-FU/LV arm provided baseline and ≥1 subsequent EORTC assessment (PRO population). Patient demographics and baseline characteristics were similar between the treatment arms. No substantial differences were identified in the proportion of patients exhibiting improved, stable, or worsening QoL in symptom scale scores between the MM-398+5-FU/LV and 5-FU/LV arms.

Baseline global health status and functional scale scores ranged from 58-83 and were similar between the treatment arms. Overall, there were no appreciable changes from baseline in global health status and functional scale scores between the MM-398+5-FU/LV and 5-FU/LV arms. The observed median change from baseline to week 6 in physical functioning score was 6.7 points in both arms; which corresponds to "a little" decrease. Baseline symptom scale scores ranged from 0-33 and were similar between the treatment arms. Overall, there were no appreciable changes from baseline in symptom scale scores between the MM-398+5-FU/LV and 5-FU/LV arms. The observed median change from baseline to week 6 in fatigue score was approximately 11 points in the MM-398+5-FU/LV arm, which corresponds to a "moderate" increase.

MM-398+5-FU/LV significantly improves OS in patients with mPDAC previously treated with gemcitabine-based therapy compared with 5-FU/LV. Global health status and functional scale scores were not significantly different between treatment arms at baseline, and showed no appreciable change over 12 weeks. Median symptom scale scores at baseline ranged from 0-33 (low levels of symptomatology), and showed no appreciable change over 12 weeks. MM-398+5-FU/LV provides a new treatment option that does not compromise QoL in patients with mPDAC previously treated with gemcitabine-based therapy.

Endnotes

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features set forth herein. The disclosure of each and every US, international, or other patent or patent application or publication referred to herein is hereby incorporated herein by reference in its entirety.

What is claimed is:

1. A method of treating metastatic adenocarcinoma of the pancreas in a human patient who has previously been treated with the antineoplastic agent gemcitabine, comprising intravenously administering to the patient once every two weeks, an antineoplastic therapy consisting of:
    a) irinotecan sucrose octasulfate salt liposome injection in an amount providing the equivalent of 70 mg/m$^2$ of irinotecan free base, the irinotecan sucrose octasulfate salt liposome injection comprising irinotecan sucrose octasulfate encapsulated in liposomes, wherein, following administration in patients, the irinotecan sucrose octasulfate salt liposome injection has a mean total SN-38 terminal elimination half-life in the plasma of 67.8±44.5 hours;
    b) 200 mg/m$^2$ of the (l) form of leucovorin or 400 mg/m$^2$ of the (l+d) racemic form of leucovorin; and
    c) 2,400 mg/m$^2$ of the antineoplastic agent 5-fluorouracil.

2. The method of claim 1, wherein the irinotecan sucrose octasulfate salt liposome injection is administered intravenously over 90 minutes, followed by intravenous administration of the leucovorin over 30 minutes, followed by intravenous administration of the 5-fluorouracil over 46 hours.

3. The method of claim 2, wherein the patient has metastatic adenocarcinoma of the pancreas that has progressed on gemcitabine-based therapy prior to the administration of the irinotecan sucrose octasulfate salt liposome injection.

4. The method of claim 3, wherein, following administration in patients, the irinotecan sucrose octasulfate salt liposome injection has an area under the plasma concentration curve extrapolated to time infinity (AUC$_{0-\infty}$) of the mean total SN-38 that increases less than proportionally with the dose of irinotecan sucrose octasulfate salt liposome injection.

5. The method of claim 3, wherein, following administration in patients, the irinotecan sucrose octasulfate salt liposome injection has a mean total SN-38 area under the plasma concentration curve extrapolated to time infinity (AUC$_{0-\infty}$) of 620±329 h·ng/mL.

6. The method of claim 3, wherein, following administration in patients, the irinotecan sucrose octasulfate salt liposome injection has a mean total SN-38 maximum plasma concentration of 5.4±3.4 nanograms/mL.

7. The method of claim 3, wherein the leucovorin is provided by administering 400 mg/m$^2$ of the (l+d) form of leucovorin.

8. The method of claim 2, further comprising premediating the human patient with an anti-emetic prior to administering the antineoplastic therapy.

9. The method of claim 1, wherein the irinotecan sucrose octasulfate salt liposome injection contains N-(methoxy-poly(ethyleneglycol) (M.W. 2000)-oxycarbonyl)-distearoylphosphatidylethanolamine.

10. The method of claim 1, wherein the sucrose octasulfate salt liposome injection comprises phosphatidylcholine, cholesterol, and N-(methoxy-poly(ethyleneglycol) (M.W. 2000)-oxycarbonyl)-distearoylphosphatidylethanolamine in a molar ratio of 3:2:0.015.

11. The method of claim 1, wherein the liposomes have an average size of from about 80 to about 140 nm as determined by volume-averaged mean of the liposome size distribution by quasi-elastic light scattering (QELS) using Gaussian model.

12. The method of claim 11, wherein the liposomes have an average size of about 110 nm as determined by volume-averaged mean of the liposome size distribution by quasi-elastic light scattering (QELS) using Gaussian model.

13. The method of claim 1, wherein the liposomes have been filtered through a 0.2 micron filter.

* * * * *